US012213999B2

(12) United States Patent
Evans et al.

(10) Patent No.: US 12,213,999 B2
(45) Date of Patent: Feb. 4, 2025

(54) COMPOSITIONS AND METHODS FOR TREATING TYPE 1 AND TYPE 2 DIABETES AND RELATED DISORDERS

(71) Applicant: SALK INSTITUTE FOR BIOLOGICAL STUDIES, La Jolla, CA (US)

(72) Inventors: Ronald M. Evans, La Jolla, CA (US); Eiji Yoshihara, La Jolla, CA (US); Michael R. Downes, La Jolla, CA (US); Ruth T. Yu, La Jolla, CA (US); Annette R. Atkins, La Jolla, CA (US)

(73) Assignee: SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 925 days.

(21) Appl. No.: 17/141,327

(22) Filed: Jan. 5, 2021

(65) Prior Publication Data

US 2021/0283187 A1 Sep. 16, 2021

Related U.S. Application Data

(60) Division of application No. 15/359,432, filed on Nov. 22, 2016, now Pat. No. 10,912,800, which is a division of application No. 14/793,391, filed on Jul. 7, 2015, now Pat. No. 9,546,379, which is a continuation of application No. PCT/US2015/022799, filed on Mar. 26, 2015.

(60) Provisional application No. 62/105,545, filed on Jan. 20, 2015, provisional application No. 62/065,537, filed on Oct. 17, 2014, provisional application No. 61/971,308, filed on Mar. 27, 2014.

(51) Int. Cl.

| | |
|---|---|
| *A61K 35/35* | (2015.01) |
| *A61K 35/12* | (2015.01) |
| *A61K 35/39* | (2015.01) |
| *A61K 35/51* | (2015.01) |
| *A61K 35/545* | (2015.01) |
| *A61K 48/00* | (2006.01) |
| *C07K 14/705* | (2006.01) |
| *C07K 14/72* | (2006.01) |
| *C12N 5/071* | (2010.01) |
| *C12N 15/85* | (2006.01) |
| *C12N 15/86* | (2006.01) |
| *A61K 38/00* | (2006.01) |

(52) U.S. Cl.

CPC .............. *A61K 35/39* (2013.01); *A61K 35/12* (2013.01); *A61K 35/35* (2013.01); *A61K 35/51* (2013.01); *A61K 35/545* (2013.01); *A61K 48/00* (2013.01); *C07K 14/70567* (2013.01); *C07K 14/721* (2013.01); *C12N 5/0676* (2013.01); *C12N 15/85* (2013.01); *C12N 15/86* (2013.01); *A61K 38/00* (2013.01); *C12N 2501/105* (2013.01); *C12N 2501/115* (2013.01); *C12N 2501/392* (2013.01); *C12N 2501/415* (2013.01); *C12N 2506/02* (2013.01); *C12N 2510/00* (2013.01); *C12N 2710/10032* (2013.01); *C12N 2710/10043* (2013.01)

(58) Field of Classification Search

CPC ...................................................... A61K 35/35

See application file for complete search history.

(56) References Cited

U.S. PATENT DOCUMENTS

| | | | |
|---|---|---|---|
| 4,683,202 | A | 7/1987 | Mullis |
| 5,399,346 | A | 3/1995 | Anderson et al. |
| 5,854,033 | A | 12/1998 | Lizardi |
| 5,942,435 | A | 8/1999 | Wheeler |
| 9,102,920 | B2 | 8/2015 | Feng et al. |
| 9,546,379 | B2 | 1/2017 | Evans et al. |
| 10,520,494 | B2 | 12/2019 | Lickert et al. |
| 10,912,800 | B2 | 2/2021 | Evans et al. |
| 10,920,199 | B2 | 2/2021 | Evans et al. |
| 2009/0281191 | A1 | 11/2009 | Rangwala et al. |
| 2010/0145470 | A1 | 6/2010 | Cohen et al. |
| 2011/0028401 | A1 | 2/2011 | Minchiotti et al. |
| 2011/0165570 | A1 | 7/2011 | Feng et al. |
| 2012/0039919 | A1 | 2/2012 | Yang et al. |
| 2012/0302491 | A1 | 11/2012 | Narkar et al. |
| 2013/0195811 | A1 | 8/2013 | Wang et al. |
| 2014/0289877 | A1 | 9/2014 | Taniguchi et al. |
| 2015/0203818 | A1 | 7/2015 | Mountford et al. |
| 2015/0368667 | A1 | 12/2015 | Evans et al. |

(Continued)

FOREIGN PATENT DOCUMENTS

| | | | |
|---|---|---|---|
| CA | 2937882 | A1 | 9/2015 |
| EP | 2878664 | A1 | 6/2015 |

(Continued)

OTHER PUBLICATIONS

2016, Yoshihara et al., Cell Metab., vol. 23(4), pp. 622-634 (Year: 2016).*

(Continued)

*Primary Examiner* — Anoop K Singh
*Assistant Examiner* — David A Montanari
(74) *Attorney, Agent, or Firm* — Greenberg Traurig LLP; Melissa Hunter-Ensor; Leslie Serunian

(57) ABSTRACT

The invention features compositions comprising in vitro generated beta cells capable of glucose-stimulated insulin secretion, methods of inducing beta cell maturation from embryonic or induced pluripotent stem cell-derived beta-like cells, and methods of using in vitro generated beta cells for the treatment of type 1 diabetes, type 2 diabetes, or a related disorder.

20 Claims, 68 Drawing Sheets

Specification includes a Sequence Listing.

(56) References Cited

U.S. PATENT DOCUMENTS

2016/0083693 A1 3/2016 Xu et al.
2017/0087189 A1 3/2017 Evans et al.
2018/0044642 A1 2/2018 Evans et al.
2019/0211310 A1 7/2019 Evans et al.
2021/0363490 A1 11/2021 Yoshihara et al.
2022/0220446 A1 7/2022 Evans et al.

FOREIGN PATENT DOCUMENTS

EP 2940127 A1 11/2015
JP 2009533017 A 9/2009
JP 2011522520 A 8/2011
JP 2016514481 A 5/2016
WO 2001015755 A2 3/2001
WO 2006063733 A1 6/2006
WO 2006063734 A2 6/2006
WO 2006063735 A1 6/2006
WO 2006063736 A1 6/2006
WO 2006119886 A1 11/2006
WO 2006119887 A1 11/2006
WO 2006119888 A2 11/2006
WO 2009136867 A1 11/2009
WO 2011160066 A1 12/2011
WO 2012044486 A1 4/2012
WO 2013159103 A1 10/2013
WO 2014017513 A1 1/2014
WO 2014104364 A1 7/2014
WO 2014145625 A1 9/2014
WO 2015148832 A1 10/2015
WO 2016015158 A1 2/2016
WO 2016100898 A1 6/2016
WO 2016100909 A1 6/2016
WO 2016100921 A1 6/2016
WO 2016100925 A1 6/2016
WO 2016100930 A1 6/2016
WO 2017205511 A1 11/2017
WO 2018156955 A1 8/2018

OTHER PUBLICATIONS

Akinci et al., "Reprogramming of various cell types to a beta-like state by Pdx1, Ngn3 and MafA," PLoS One, 2013, vol. 8, Iss. 11, e82424.
Brevini et al., "No shortcuts to pig embryonic stem cells," Theriogenology, 2010, vol. 74, Iss. 4, pp. 544-550.
Crunkhom, Sarah, "Human iPSC-derived β-like cells rescue diabetic mice," Nature Reviews Drug Discovery, Research Highlights, Published online May 20, 2016, vol. 15, p. 383; doi:10.1038/nrd.2016.99, one page.
Hickey et al., "Generation of islet-like cells from mouse gall bladder by direct ex vivo reprogramming," Stem Cell Research, 2013, vol. 11, No. 1, pp. 503-515.
Kapturczak et al., "Transduction of Human and Mouse Pancreatic Islet Cells Using a Bicistronic Recombinant Adeno-associated Viral Vector," Molecular Therapy, 2002, vol. 5, No. 2, pp. 154-160.
Kroon et al., "Pancreatic endoderm derived from human embryonic stem cells generates glucose-responsive insulin-secreting cells in vivo," Nature Biotechnology, 2008, vol. 26, No. 4, pp. 443-452.
Ludwig et al., "Transplantation of human islets without immunosuppression," Proceedings of the National Academy of Sciences of the United States of America, PNAS, 2013, vol. 110, No. 47, pp. 19054-19058.
Muñoz et al., "Conventional pluripotency markers are unspecific for bovine embryonic-derived cell-lines," Theriogenology, 2008, vol. 69, Iss. 9, pp. 1159-1164.
Nichols et al., "Adult tissue sources for new β cells," Translational Research, 2014, vol. 163, No. 4, pp. 418-431.
Pagliuca et al., "How to make a functional β-cell," Development, 2013, vol. 140, No. 12, pp. 2472-2483.
Pagliuca et al., "Generation of functional human pancreatic β cells in vitro," Cell, 2014, vol. 159, Iss. 2, pp. 482-439.
Paris et al., "Equine embryos and embryonic stem cells: Defining reliable markers of pluripotency," Theriogenology, 2010, vol. 74, Iss. 4, pp. 516-524.
Rezania et al., "Reversal of diabetes with insulin-producing cells derived in vitro from human pluripotent stem cells," Nature Biotechnology, Sep. 2014, vol. 32, pp. 1121-1133.
Yoshihara et al., "ERRγ Is Required for the Metabolic Maturation of Therapeutically Functional Glucose-Responsive β Cells," Cell Metabolism, Cell Press, Apr. 12, 2016, vol. 23, No. 4, pp. 622-634.
Communication pursuant to Article 94(3) dated Sep. 21, 2018 as received in corresponding European Patent Application No. 15768765.2 (5 pages).
Examination Report dated Jul. 11, 2020 as received in corresponding Australian Patent Application No. 2015235922 (3 pages).
Extended European Search Report dated Aug. 2, 2017 as received in corresponding European Patent Application No. 15768776.5 (7 pages).
Extended European Search Report dated Sep. 23, 2019 as received in corresponding European Patent Application No. 19175179.1 (13 pages).
Extended European Search Report dated Oct. 15, 2020 as received in corresponding European Patent Application No. 20179501.0 (12 pages).
International Search Report dated Jun. 2, 2015 as received in corresponding International Patent Application No. PCT/US2015/022799 (4 pages).
Written Opinion on the International Searching Authority dated Jun. 2, 2015 as received in corresponding International Patent Application No. PCT/US2015/022799 (4 pages).
Office Action mailed Oct. 26, 2016 as received in corresponding Canadian Patent Application No. 2,944,181.
Office Action dated May 29, 2017 as received in corresponding Canadian Patent Application No. 2,944,181 (3 pages).
Office Action dated Jul. 17, 2018 as received in corresponding Canadian Patent Application No. 2,944,181 (4 pages).
Office Action dated Dec. 15, 2018 as received in corresponding Canadian Patent Application No. 2,944,181 (3 pages).
Office Action (and English translation) dated Sep. 3, 2019 as received in corresponding Japanese Patent Application No. JP 2016-559335 (3 pages).
Translation of Japanese Office Action dated Mar. 26, 2019 as received in corresponding Japanese Patent Application No. 2016-559335 (3 pages).
Jaramillo et al., "Potential for Pancreatic Maturation of Differentiating Human Embryonic Stem Cells Is Sensitive to the Specific Pathway of Definitive Endoderm Commitment," PLoS One, Apr. 2014, vol. 9, No. 4, e94307, pp. 1-14.
Liu et al., "All mixed up: defining roles for β-cell subtypes in mature islets," Genes & Development, 2017, vol. 31, pp. 228-240.
Yoshihara et al., "Immune evasive human islet-like organoids ameliorate diabetes," Nature, Oct. 2020, vol. 586, No. 7830, pp. 606-611.
Wei et al., "Klf4 Organizes Long-Range Chromosomal Interactions with the Oct4 Locus in Reprogramming and Pluripotency," Cell Stem Cell, Jul. 3, 2013, vol. 13, pp. 36-47.
Wendeln et al., "Innate immune memory in the brain shapes neurological disease hallmarks," Nature, Apr. 2018, vol. 556, No. 7701, pp. 332-338.
Willert et al., "Wnt Proteins," Cold Spring Harbor Perspectives in Biology, 2012, vol. 4, a007864, pp. 1-14.
Wolff et al., "Direct Gene Transfer into Mouse Muscle in Vivo," Science, Mar. 23, 1990, vol. 247, pp. 1465-1468.
Wu et al., "Receptor-mediated gene delivery and expression in vivo," The Journal of Biological Chemistry, Oct. 15, 1988, vol. 263, No. 29, pp. 14621-14624.
Wu et al., "Targeting Genes: Delivery and Persistent Expression of a Foreign Gene Driven by Mammalian Regulatory Elements in Vivo," The Journal of Biological Chemistry, Oct. 15, 1989, vol. 264, No. 29, pp. 16985-16987.
Wulfing et al., "A Receptor/Cytoskeletal Movement Triggered by Costimulation During T Cell Activation," Science, Dec. 18, 1998, vol. 282, pp. 2266-2269.

(56) References Cited

OTHER PUBLICATIONS

Xu et al., "The role of pyruvate carboxylase in insulin secretion and proliferation in rat pancreatic beta cells," Diabetologia, 2008, vol. 51, pp. 2022-2030.
Yang et al., "Nuclear Receptor Expression Links the Circadian Clock to Metabolism," Cell, Aug. 25, 2006, vol. 126, pp. 801-810.
Yoshihara et al., "Disruption of TBP-2 ameliorates insulin sensitivity and secretion without affecting obesity," Nature Communications, 2010, vol. 1, Article No. 127, pp. 1-12.
Yu et al., "Human Induced Pluripotent Stem Cells Free of Vector and Transgene Sequences," Science, May 8, 2009, vol. 324, No. 5928, pp. 797-801.
Yu et al., "Induced Pluripotent Stem Cell Lines Derived from Human Somatic Cells," Science, Dec. 21, 2007, vol. 318, pp. 1917-1920.
Zhang et al., "Cardiac progenitor/stem cells on myocardial infarction or ischemic heart disease: what we have known from current research," Heart Failure Reviews, 2014, vol. 19, pp. 247-258.
Zhang et al., "Efficient Reprogramming of Naïve-Like Induced Pluripotent Stem Cells from Porcine Adipose-Derived Stem Cells with a Feeder-Independent and Serum-Free System," PLoS One, Jan. 2014, vol. 9, No. 1, e85089, pp. 1-13.
Zhang et al., "Esrb Activates Oct4 Transcription and Sustains Self-renewal and Pluripotency in Embryonic Stem Cells," The Journal of Biological Chemistry, Dec. 19, 2008, vol. 283, No. 51, pp. 35825-35833.
Zhang et al., "Metabolic Regulation in Pluripotent Stem Cells during Reprogramming and Self-Renewal," Cell Stem Cell, Nov. 2, 2012, vol. 11, pp. 589-595.
Zhao et al., "Overexpression of lactate dehydrogenase A attenuates glucose-induced insulin secretion in stable MIN-6 β-cell lines," FEBS Letters, 1998, vol. 430, pp. 213-216.
Zuckermann et al., "Discovery of Nanomolar Ligands for 7-Transmembrane G-Protein-Coupled Receptors from a Diverse N-(Substituted)glycine Peptoid Library," Journal of Medicinal Chemistry, 1994, vol. 37, pp. 2678-2685.
Ludwig et al., "Feeder-independent culture of human embryonic stem cells," Nature Methods, Aug. 2006, vol. 3, No. 8, pp. 637-646.
Mandel et al., "SERKAL Syndrome: An Autosomal-Recessive Disorder Caused by a Loss-of-Function Mutation in WNT4," The American Journal of Human Genetics, Jan. 2008, vol. 82, pp. 39-47.
Mangelsdorf et al., "The Nuclear Receptor Superfamily: The Second Decade," Cell, Dec. 15, 1995, vol. 83, No. 6, pp. 835-839.
Mao et al., "Automated genome annotation and pathway identification using the KEGG Orthology (KO) as a controlled vocabulary," Bioinformatics, 2005, vol. 21, No. 19, pp. 3787-3793.
Mao et al., "Lentiviral Vectors Mediate Long-Term and High Efficiency Transgene Expression in HEK 293T cells," International Journal of Medical Sciences, 2015, vol. 12, No. 5, pp. 407-415.
Martello et al., "Esrb Is a Pivotal Target of the Gsk3/Tcf3 Axis Regulating Embryonic Stem Cell Self-Renewal," Cell Stem Cell, Oct. 5, 2012, vol. 11, pp. 491-504.
Mathieu et al., "Investigating the real role of HIF-1 and HIF-2 in iron recycling by macrophages," Haematologica, 2014, vol. 99, pp. e112-e114.
Miller et al., "Improved Retroviral Vectors for Gene Transfer and Expression," Biotechniques, Oct. 1989, vol. 7, No. 9, pp. 980-990.
Miller, A. Dusty, "Retrovirus Packaging Cells," Human Gene Therapy, 1990, vol. 1, pp. 5-14.
Miyoshi et al., "Stable and efficient gene transfer into the retina using an HIV-based lentiviral vector," Proceedings of the National Academy of Sciences of the United States of America, Sep. 1997, vol. 94, pp. 10319-10323.
Morizane et al., "MHC matching improves engraftment of iPSC-derived neurons in non-human primates," Nature Communications, 2017, vol. 8, Article No. 385, pp. 1-12.
Naldini et al., "In Vivo Gene Delivery and Stable Transduction of Nondividing Cells by a Lentiviral Vector," Science, Apr. 12, 1996, vol. 272, pp. 263-267.
Narkar et al., "Exercise and PGC-1α-Independent Synchronization of Type I Muscle Metabolism and Vasculature by ERRγ," Cell Metabolism, Mar. 2, 2011, vol. 13, pp. 283-293.
Nemajerova et al., "Two-factor reprogramming of somatic cells to pluripotent stem cells reveals partial functional redundancy of Sox2 and Klf4," Cell Death and Differentiation, 2012, vol. 19, pp. 1268-1276.
Ono et al., "Plasmid DNAs directly injected into mouse brain with lipofectin can be incorporated and expressed by brain cells," Neuroscience Letters, 1990, vol. 117, pp. 259-263.
Osum et al., "Interferon-gamma drives programmed death-ligand 1 expression on islet β cells to limit T cell function during autoimmune diabetes," Scientific Reports, 2018, vol. 8, Article No. 8295, pp. 1-12.
Panopoulos et al., "The metabolome of induced pluripotent stem cells reveals metabolic changes occurring in somatic cell reprogramming," Cell Research, 2012, vol. 22, pp. 168-177.
Proksch et al., "Does the Human Skeletal Muscle Harbor the Murine Equivalents of Cardiac Precursor Cells?," Molecular Therapy, Apr. 2009, vol. 17, No. 4, pp. 733-741.
Raikwar et al., "Human iPS Cell-Derived Insulin Producing Cells Form Vascularized Organoids under the Kidney Capsules of Diabetic Mice," PLoS One, Jan. 28, 2015, vol. 10, No. 1, pp. e0116582, pp. 1-15.
Ravassard et al., "A genetically engineered human pancreatic β cell line exhibiting glucose-inducible insulin secretion," The Journal of Clinical Investigation, 2011, vol. 121, No. 9, pp. 3589-3597.
Roberts et al., "Identification of novel transcripts in annotated genomes using RNA-Seq," Bioinformatics, 2011, vol. 27, No. 17, pp. 2325-2329.
Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, vol. 323, No. 9, pp. 570-578.
Roska et al., "Dissection of the functions of antigen-presenting cells in the induction of T cell activation," The Journal of Immunology, Nov. 1985, vol. 135, No. 5, pp. 2953-2961.
Rossello et al., "Mammalian genes induce partially reprogrammed pluripotent stem cells in non-mammalian vertebrate and invertebrate species," eLife, 2013, vol. 2, Article No. e00036, pp. 1-24.
Russ et al., "Controlled induction of human pancreatic progenitors produces functional beta-like cells in vitro," The EMBO Journal, 2015, vol. 34, No. 13, pp. 1759-1772.
Saito et al., "Generation of Glucose-Responsive Functional Islets with a Three-Dimensional Structure from Mouse Fetal Pancreatic Cells and iPS Cells In Vitro," PLoS One, Dec. 2011, vol. 6, No. 12, e28209, pp. 1-7.
Schulz et al., "A Scalable System for Production of Functional Pancreatic Progenitors from Human Embryonic Stem Cells," PLoS One, May 2012, vol. 7, No. 5, e37004, pp. 1-17.
Shyh-Chang et al., "Influence of Threonine Metabolism on S-adenosylmethionine and Histone Methylation," Science, Jan. 11, 2013, vol. 339, No. 6116, pp. 222-226.
Si-Tayeb et al., "Generation of human induced pluripotent stem cells by simple transient transfection of plasmid DNA encoding reprogramming factors," BMC Developmental Biology, 2010, vol. 10, Article No. 81, pp. 1-10.
Sneddon et al., "Self-renewal of embryonic-stem-cell-derived progenitors by organ-matched mesenchyme," Nature, Nov. 29, 2012, vol. 491, No. 7426, pp. 765-768.
Soltanian et al., "Morphogenesis of Human Pluripotent Stem Cell Aggregates toward Pancreatic Progenitors in Suspension Culture," Cell Journal (Yakhteh), 2015, vol. 17, Suppl. 1, Ps-86, p. 59.
Subudhi et al., "Local expression of B7-H1 promotes organ-specific autoimmunity and transplant rejection," The Journal of Clinical Investigation, Mar. 2004, vol. 113, No. 5, pp. 694-700.
Sugii et al., "Human and mouse adipose-derived cells support feeder-independent induction of pluripotent stem cells," Proceedings of the National Academy of Sciences of the United States of America, Feb. 23, 2010, vol. 107, No. 8, pp. 3558-3563.

(56) References Cited

OTHER PUBLICATIONS

Sutton et al., "Isolation of Rat Pancreatic Islets by Ductal Injection of Collagenase," Transplantation, Dec. 1986, vol. 42, No. 6, pp. 689-691.
Taha et al., "Upregulation of Pluripotency Markers in Adipose Tissue-Derived Stem Cells by miR-302 and Leukemia Inhibitory Factor," BioMed Research International, 2014, vol. 2014, Article ID 941486, pp. 1-10.
Takahashi et al., "Induction of Pluripotent Stem Cells from Adult Human Fibroblasts by Defined Factors," Cell, Nov. 30, 2007, vol. 131, pp. 861-872.
Takahashi et al., "Induction of Pluripotent Stem Cells from Mouse Embryonic and Adult Fibroblast Cultures by Defined Factors," Cell, Aug. 25, 2006, vol. 126, pp. 663-676.
Takebe et al., "Vascularized and functional human liver from an iPSC-derived organ bud transplant," Nature, 2013, vol. 499, pp. 481-484.
Tang et al., "Desnutrin/ATGL Activates PPARδ to Promote Mitochondrial Function for Insulin Secretion in Islet β Cells," Cell Metabolism, Dec. 3, 2013, vol. 18, pp. 883-895.
Teta et al., "Very Slow Turnover of β-Cells in Aged Adult Mice," Diabetes , Sep. 2005, vol. 54, pp. 2557-2567.
Tolstoshev et al., "Gene expression using retroviral vectors," Current Opinion in Biotechnology, 1990, vol. 1, pp. 55-61.
Trapnell et al., "Differential analysis of gene regulation at transcript resolution with RNA-seq," Nature Biotechnology, 2013, vol. 31, pp. 46-53.
Tsonkova et al., "The EndoC-βH1 cell line is a valid model of human beta cells and applicable for screenings to identify novel drug target candidates," Molecular Metabolism, 2018, vol. 8, pp. 144-157.
Vaithilingam et al., "Co-encapsulation and co-transplantation of mesenchymal stem cells reduces pericapsular fibrosis and improves encapsulated islet survival and function when allografted," Scientific Reports, 2017, vol. 7, Article No. 10059, pp. 1-13.
Vegas et al., "Combinatorial hydrogel library enables identification of materials that mitigate the foreign body response in primates," Nature Biotechnology, Mar. 2016, vol. 34, No. 3, pp. 345-352.
Vegas et al., "Long term Glycemic Control Using Polymer Encapsulated, Human Stem-Cell Derived β-cells in Immune Competent mice," Nature Medicine, Mar. 2016, vol. 22, No. 3, pp. 306-311.
Vethe et al., "The Effect of Wnt Pathway Modulators on Human iPSC-Derived Pancreatic Beta Cell Maturation," Frontiers in Endocrinology, May 2019, vol. 10, Article 293, pp. 1-13.
Wei et al., "Klf4 Interacts Directly with Oct4 and Sox2 to Promote Reprogramming," Stem Cells, 2009, vol. 27, pp. 2969-2978.
Willert et al., "Wnt Proteins," Cold Spring Harbor Perspectives in Biology, 2012, vol. 4, No. a007864, pp. 1-14.
Alaynick et al., "ERRγ Directs and Maintains the Transition to Oxidative Metabolism in the Postnatal Heart," Cell Metabolism, Jul. 2007, vol. 6, pp. 13-24.
Anderson, W. French, "Prospects for Human Gene Therapy," Science, Oct. 26, 1984, vol. 226, No. 4673, pp. 401-409.
Anello et al., "Functional and morphological alterations of mitochondria in pancreatic beta cells from type 2 diabetic patients," Diabetologia, 2005, vol. 48, pp. 282-289.
Bader et al., "Identification of proliferative and mature β-cells in the islets of Langerhans," Nature, Jul. 21, 2016, vol. 535, pp. 430-434.
Baidal et al., "Bioengineering of an Intraabdominal Endocrine Pancreas," The New England Journal of Medicine, May 11, 2017, vol. 376, No. 19, pp. 1887-1889.
Barany, Francis, "Genetic disease detection and DNA amplification using cloned thermostable ligase," Proceedings of the National Academy of Sciences of the United States of America, Jan. 1991, vol. 88, pp. 189-193.
Bar-Ephraim et al., "Modelling cancer immunomodulation using epithelial organoid cultures," BioRxiv, 2018, pp. 1-13.
Blomer et al., "Highly efficient and sustained gene transfer in adult neurons with a lentivirus vector," Journal of Virology, Sep. 1997, vol. 71, No. 9, pp. 6641-6649.
Bosnak et al., "Somatostatin Therapy in the Management of Resistant Diabetic Ketoacidosis," Diabetes Care, Mar. 2002, vol. 25, No. 3, pp. 629-630.
Buenrostro et al., "ATAC-seq: A Method for Assaying Chromatin Accessibility Genome-Wide," Current Protocols in Molecular Biology, Jan. 5, 2015, vol. 109, pp. 21.29.1-21.29.9.
Buganim et al., "Single-Cell Expression Analyses during Cellular Reprogramming Reveal an Early Stochastic and a Late Hierarchic Phase," Cell, Sep. 14, 2012, vol. 150, pp. 1209-1222.
Buganim et al., "The Developmental Potential of iPSCs Is Greatly Influenced by Reprogramming Factor Selection," Cell Stem Cell, Sep. 4, 2014, vol. 15, pp. 295-309.
Burns et al., "High-Throughput Luminescent Reporter of Insulin Secretion for Discovering Regulators of Pancreatic Beta-Cell Function," Cell Metabolism, Jan. 6, 2015, vol. 21, pp. 126-137.
Carey et al., "Single-gene transgenic mouse strains for reprogramming adult somatic cells," Nature Methods, Jan. 2010, vol. 7, No. 1, pp. 56-59.
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy, Mar. 1, 1997, vol. 8, pp. 423-430.
Chen et al., "Integration of External Signaling Pathways with the Core Transcriptional Network in Embryonic Stem Cells," Cell, Jun. 13, 2008, vol. 133, pp. 1106-1117.
Chen et al., "PDGF signalling controls age-dependent proliferation in pancreatic β-cells," Nature, 2011, vol. 478, No. 7369, pp. 349-355.
Conrad et al., "Revealing transcription factors during human pancreatic β cell development," Trends in Endocrinology & Metabolism, Aug. 2014, vol. 25, No. 8, pp. 407-414.
D'Amour et al., "Production of pancreatic hormone-expressing endocrine cells from human embryonic stem cells," Nature Biotechnology, Nov. 2006, vol. 24, No. 11, pp. 1392-1401.
Ding et al., "Activation of CD4+ T cells by delivery of the B7 costimulatory signal on bystander antigen-presenting cells (transcostimulation)," European Journal of Immunology, 1994, vol. 24, pp. 859-866.
Dobin et al., "STAR: ultrafast universal RNA-seq aligner," Bioinformatics, 2013, vol. 29, No. 1, pp. 15-21.
Dor et al., "Adult pancreatic β-cells are formed by self-duplication rather than stem-cell differentiation," Nature, May 6, 2004, vol. 429, pp. 41-46.
Dufour et al., "Genome-wide Orchestration of Cardiac Functions by the Orphan Nuclear Receptors ERRβ and γ," Cell Metabolism, May 2007, vol. 5, pp. 345-356.
Felgner et al., "Lipofection: A highly efficient, lipid-mediated DNA-transfection procedure," Proceedings of the National Academy of Sciences of the United States of America, Nov. 1987, vol. 84, No. 21, pp. 7413-7417.
Feng et al., "Reprogramming of fibroblasts into induced pluripotent stem cells with orphan nuclear receptor Esrb," Nature Cell Biology, Feb. 2009, vol. 11, No. 2, pp. 197-203.
Festuccia et al., "Esrrb Is a Direct Nanog Target Gene that Can Substitute for Nanog Function in Pluripotent Cells," Cell Stem Cell, Oct. 5, 2012, vol. 11, pp. 477-490.
Folmes et al., "Somatic Oxidative Bioenergetics Transitions into Pluripotency-Dependent Glycolysis to Facilitate Nuclear Reprogramming," Cell Metabolism, Aug. 3, 2011, vol. 14, pp. 264-271.
Friedmann, Theodore, "Progress Toward Human Gene Therapy," Science, Jun. 16, 1989, vol. 244, No. 4910, pp. 1275-1281.
Guatelli et al., "Isothermal, in vitro amplification of nucleic acids by a multienzyme reaction modeled after retroviral replication," Proceedings of the National Academy of Sciences of the United States of America, Mar. 1990, vol. 87, pp. 1874-1878.
Hackenbrock, Charles R., "Ultrastructural Bases for Metabolically Linked Mechanical Activity in Mitochondria: I. Reversible Ultrastructural Changes with Change in Metabolic Steady State in Isolated Liver Mitochondria," The Journal of Cell Biology, 1966, vol. 30, pp. 269-297.
Hart et al., "Attenuation of FGF signalling in mouse β-cells leads to diabetes," Nature, Dec. 14, 2000, vol. 408, pp. 864-868.

(56) References Cited

OTHER PUBLICATIONS

Heinz et al., "Simple Combinations of Lineage-Determining Transcription Factors Prime cis-Regulatory Elements Required for Macrophage and B Cell Identities," Molecular Cell, May 28, 2010, vol. 38, No. 4, pp. 576-589.
Holmes et al., "Concise Review: Stem Cell Antigen-1: Expression, Function, and Enigma," Stem Cells, 2007, vol. 25, pp. 1339-1347.
Hirvatin et al., "Differentiated human stem cells resemble fetal, not adult, β cells," Proceedings of the National Academy of Sciences of the United States of America, Feb. 25, 2014, vol. 111, No. 8, pp. 3038-3043.
Hsiao et al., "Endogenous Cardiac Stem Cell Therapy for Ischemic Heart Failure," Journal of Clinical & Experimental Cardiology, 2013, vol. S11, No. 007, pp. 1-5.
Huang et al., "Enhanced Differentiation of Three-Gene-Reprogrammed Induced Pluripotent Stem Cells into Adipocytes via Adenoviral-Mediated PGC-1α Overexpression," International Journal of Molecular Sciences, 2011, vol. 12, pp. 7554-7568.
Huang et al., "Systematic and integrative analysis of large gene lists using DAVID bioinformatics resources," Nature Protocols, 2009, vol. 4, pp. 44-57.
Ishibashi et al., "ESAM is a novel human hematopoietic stem cell marker associated with a subset of human leukemias," Experimental Hematology, 2016, vol. 44, pp. 269-281.
Johnson, Larry G., "Gene Therapy for Cystic Fibrosis," Chest, Feb. 1995, vol. 107, No. 2, Supplement pp. 77S-83S.
Kawaguchi et al., "Generaltion of Naïve Bovine Induced Pluripotent Stem Cells Using PiggyBac Transposition of Doxycycline-Inducible Transcription Factors," PLoS One, Aug. 19, 2015, vol. 10, No. 8, e0135403, pp. 1-18.
Kawamura et al., "Linking the p53 tumor suppressor pathway to somatic cell reprogramming," Nature, Aug. 27, 2009, vol. 460, No. 7259, pp. 1140-1144.
Kida et al., "ERRs Mediate a Metabolic Switch Required for Somatic Cell Reprogramming to Pluripotency," Cell Stem Cell, May 7, 2015, vol. 16, pp. 547-555.
Kwoh et al., "Transcription-based amplification system and detection of amplified human immunodeficiency virus type 1 with a bead-based sandwich hybridization format," Proceedings of the National Academy of Sciences of the United States of America, Feb. 1989, vol. 86, pp. 1173-1177.
Le Gal La Salle et al., "An Adenovirus Vector for Gene Transfer into Neurons and Glia in the Brain," Science, Feb. 12, 1993, vol. 259, No. 5097, pp. 988-990.
Lee et al., "Decoding the Pluripotency Network: The Emergence of New Transcription Factors," Biomedicines, 2013, vol. 1, pp. 49-78.
Li et al., "Small Molecules Facilitate the Reprogramming of Mouse Fibroblasts into Pancreatic Lineages," Cell Stem Cell, Feb. 6, 2014, vol. 14, pp. 228-236.
Liu et al., "Cells that present both specific ligand and costimulatory activity are the most efficient inducers of clonal expansion of normal CD4 T cells," Proceedings of the National Academy of Sciences of the United States of America, May 1992, vol. 89, pp. 3845-3849.

* cited by examiner

FIG. 2A

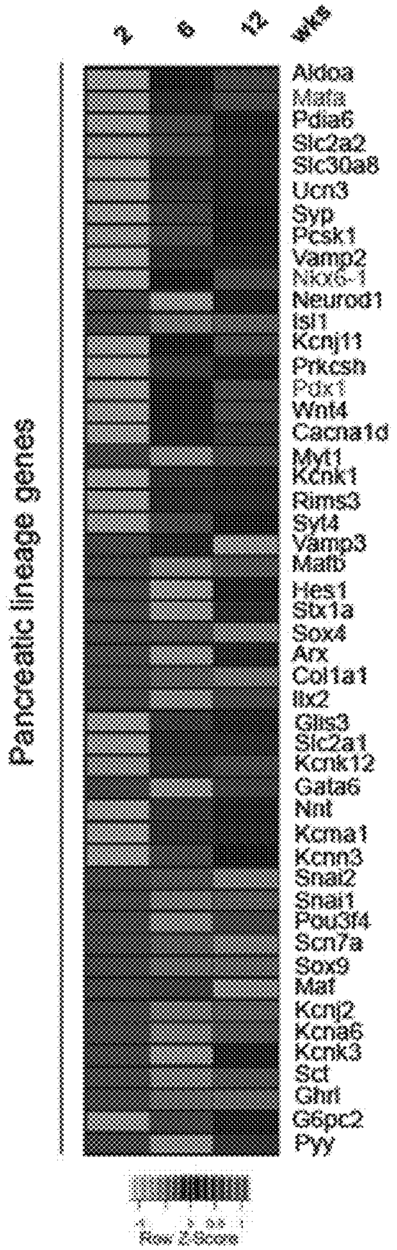

FIG. 2B

Enriched pathway in neonate islets

| GO Biological Function | Count | p value |
|---|---|---|
| cell adhesion | 114 | 1.40E-25 |
| vasculature development | 57 | 3.80E-15 |
| extracellular matrix organization | 31 | 5.40E-12 |
| regulation of cell proliferation | 84 | 5.70E-12 |
| cell motion | 65 | 8.50E-12 |
| regulation of cell migration | 26 | 2.50E-09 |
| response to hypoxia | 18 | 1.30E-06 |
| regulation of Wnt receptor signaling pathway | 9 | 5.00E-03 |

FIG. 2C

Enriched pathway in adult islets

| GO Biological Function | Count | p value |
|---|---|---|
| vesicle-mediated transport | 57 | 1.60E-08 |
| monosaccharide metabolic process | 26 | 3.90E-05 |
| oxidation reduction | 60 | 1.60E-04 |
| secretion | 27 | 1.60E-04 |
| cation transport | 49 | 1.70E-04 |
| generation of precursor metabolites and energy | 26 | 4.10E-03 |
| ATP biosynthetic process | 10 | 3.30E-02 |
| electron transport chain | 8 | 4.10E-01 |

FIG. 10A
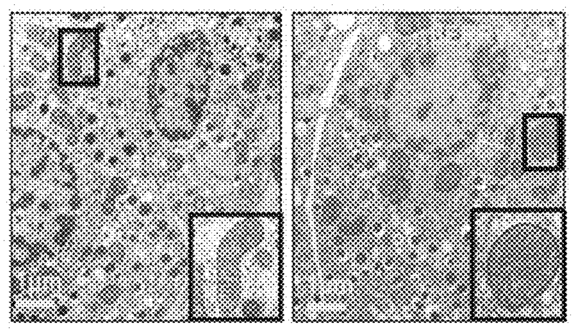
FIG. 10B
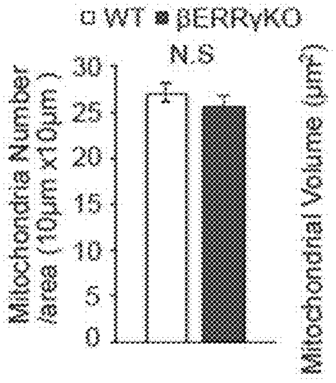
FIG. 10C
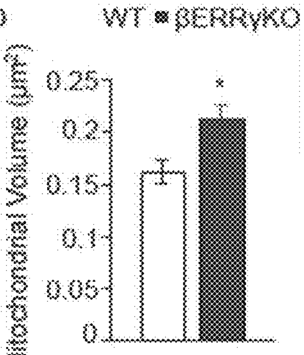
FIG. 10D
| GO Biological Function | Count | p-value |
|---|---|---|
| ATP biosynthetic process | 14 | 2.10E-07 |
| Ribonucleotide metabolic process | 16 | 1.00E-06 |
| Cation transport | 31 | 4.30E-05 |
| Oxidative phosphorylation | 13 | 2.40E-04 |
| Cellular amino acid derivative metabolic process | 6 | 3.60E-04 |
| Fructose metabolic process | 4 | 5.90E-04 |
| Electron transport chain | 11 | 7.60E-04 |
| Vesicle-mediated transport | 25 | 1.40E-03 |
| Generation of precursor metabolites and energy | 17 | 1.60E-03 |
| Secretion | 15 | 2.20E-03 |
FIG. 10E
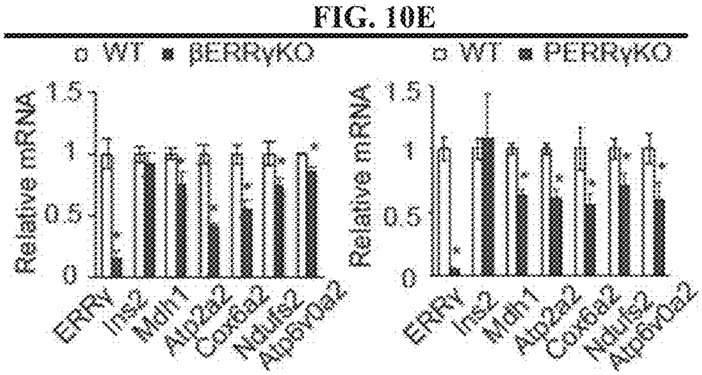
FIG. 10F
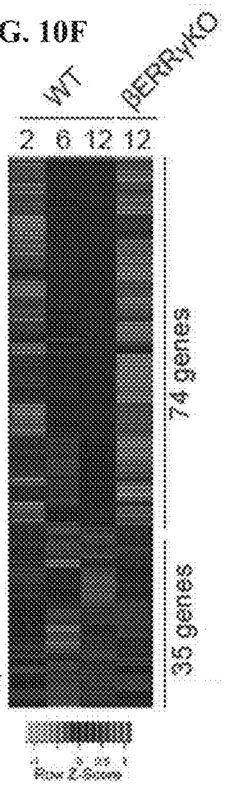
FIG. 10G
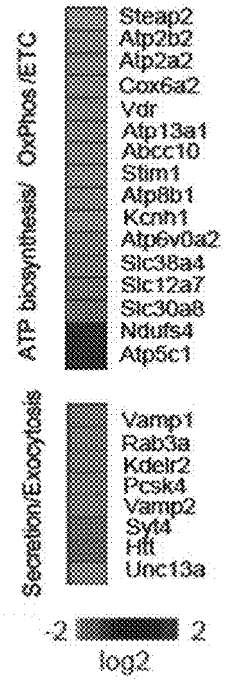

FIG. 13D

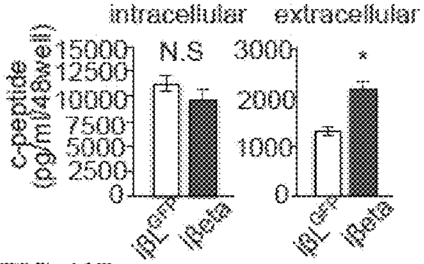

FIG. 13A

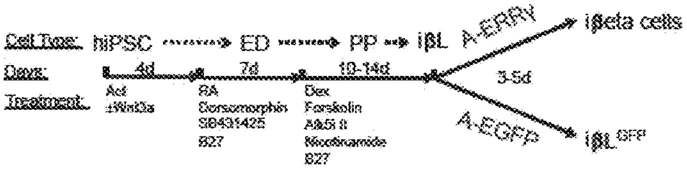

FIG. 13B

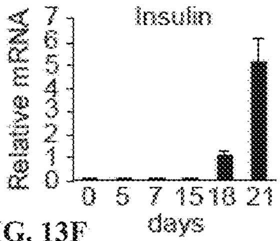

FIG. 13C

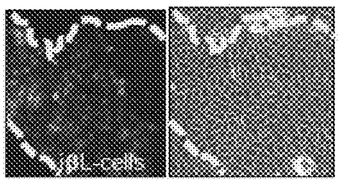

FIG. 13E

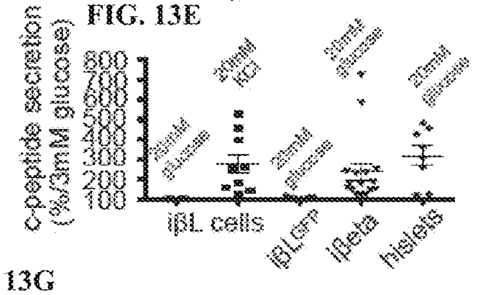

FIG. 13F

Up regulated pathways in iβeta

| GO Biological Function | Count | p-value |
|---|---|---|
| Cellular respiration | 45 | 8.40E-13 |
| Generation of precursor metabolites and energy | 96 | 8.30E-12 |
| Oxidation reduction | 159 | 2.80E-11 |
| Energy derivation by oxidation of organic compounds | 54 | 8.30E-11 |
| Extracellular structure organization | 54 | 1.30E-08 |
| Electron transport chain | 42 | 2.40E-08 |
| Cell adhesion | 159 | 3.10E-08 |
| Mitochondrion organization | 48 | 1.50E-07 |
| ATP synthesis coupled electron transport | 23 | 8.10E-06 |
| Cell morphogenesis involved in differentiation | 83 | 1.30E-05 |
| Blood vessel development | 81 | 5.80E-05 |
| Acetyl-CoA metabolic process | 15 | 5.90E-05 |

FIG. 13G

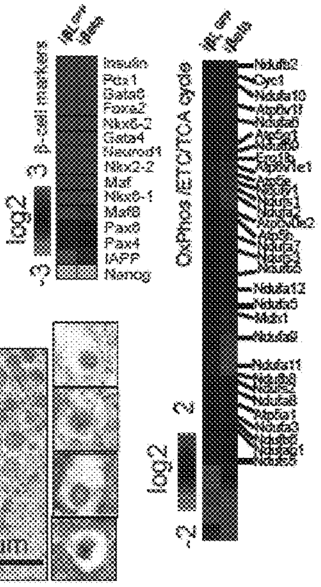

FIG. 13I

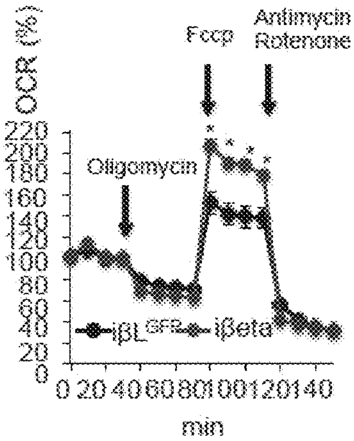

FIG. 13H

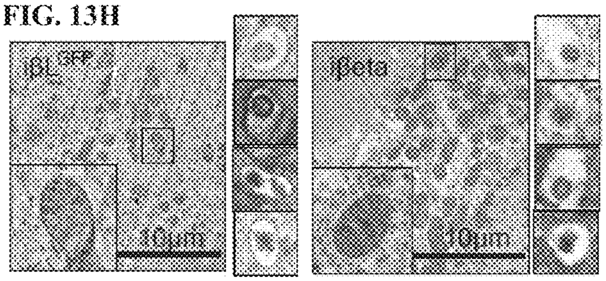

| GO Biological Function | Count | p-value |
|---|---|---|
| response to organic substance | 204 | 2.00E-17 |
| M phase of mitotic cell cycle | 75 | 2.60E-10 |
| nuclear division | 74 | 2.80E-10 |
| mitosis | 74 | 2.80E-10 |
| intracellular signaling cascade | 283 | 5.50E-10 |
| response to hormone stimulus | 106 | 7.80E-10 |
| cell cycle | 190 | 7.90E-10 |
| organelle fission | 75 | 8.20E-10 |
| regulation of apoptosis | 195 | 1.10E-09 |
| cell division | 89 | 2.00E-09 |

FIG. 22

| Upregulated genes | | | | | |
|---|---|---|---|---|---|
| | | | | | |
| Glucose Metabolism | | | | Fold Change | |
| GeneSymbol | Neonate (2w) | Adult (6w) | Adult (12w) | 6w/2w | 12w/2w |
| Pfkfb2 | 37.7099 | 54.782 | 46.543 | 1.452721964 | 1.234238224 |
| Gmds | 19.9336 | 30.0293 | 25.4075 | 1.506466469 | 1.274606694 |
| Aldoa | 208.264 | 289.021 | 379.322 | 1.387762647 | 1.821351746 |
| Agl | 4.35329 | 6.34823 | 5.41256 | 1.458260304 | 1.243326312 |
| Dhtkd1 | 0.603335 | 1.5811 | 1.58222 | 2.620600496 | 2.622456844 |
| Eno2 | 13.737 | 20.9828 | 28.1718 | 1.527465968 | 2.050797117 |
| Fuca2 | 7.41337 | 9.52024 | 9.27312 | 1.284198684 | 1.250864317 |
| Gale | 21.7878 | 44.4931 | 39.0093 | 2.042110723 | 1.790419409 |
| G6pc2 | 622.253 | 1592.85 | 961.201 | 2.559810881 | 1.544710913 |
| G6pdx | 7.94242 | 11.446 | 13.3024 | 1.441122479 | 1.674854767 |
| Gaa | 46.3268 | 58.6364 | 76.3732 | 1.265712287 | 1.648574907 |
| H6pd | 7.68641 | 10.9056 | 13.8097 | 1.418815806 | 1.796638483 |
| Man2b2 | 19.9192 | 25.8246 | 30.9794 | 1.29646773 | 1.555253223 |
| Ogdhl | 28.8813 | 42.5787 | 55.9294 | 1.474265355 | 1.936526403 |
| Pgm3 | 10.6326 | 14.8645 | 13.4281 | 1.398011775 | 1.262917819 |
| Phkb | 6.70959 | 9.64857 | 8.89935 | 1.438026765 | 1.326362714 |
| Ppp1r1a | 199.467 | 295.691 | 273.599 | 1.482405611 | 1.371650448 |
| Gnpda1 | 17.2946 | 27.557 | 29.5302 | 1.593387531 | 1.707480948 |
| Slc2a8 | 6.85597 | 10.6479 | 11.8803 | 1.553084392 | 1.732840138 |
| Slc37a4 | 47.2993 | 62.7977 | 58.2572 | 1.327666583 | 1.231671505 |
| Serp1 | 127.755 | 191.545 | 169.832 | 1.499315095 | 1.329356972 |

FIG. 22 (cont.)

| ATP biosynthesis/ETC/OxPhos | | | | Fold Change | |
|---|---|---|---|---|---|
| GeneSymbol | Neonate (2w) | Adult (6w) | Adult (12w) | 6w/2w | 12w/2w |
| Aldh3a2 | 21.5963 | 29.5792 | 27.6221 | 1.369642022 | 1.279020017 |
| Mdh1 | 94.9782 | 143.613 | 120.194 | 1.512062768 | 1.265490397 |
| Acaca | 3.19076 | 4.24441 | 4.25218 | 1.330219133 | 1.332654289 |
| Pcx | 29.9772 | 40.6599 | 42.6126 | 1.356360834 | 1.42150034 |
| Fh1 | 43.1449 | 85.4516 | 66.371 | 1.980572443 | 1.538327821 |
| Ero1lb | 219.545 | 609.117 | 439.823 | 2.774451707 | 2.003338723 |
| Ndufs2 | 91.9344 | 112.432 | 110.464 | 1.222958979 | 1.201552411 |
| Aifm3 | 0.960988 | 1.99052 | 1.94413 | 2.071326593 | 2.023053358 |
| Cyb5b | 42.5906 | 64.0062 | 56.6942 | 1.502824567 | 1.331143492 |
| Txn2 | 38.4321 | 50.3197 | 52.8945 | 1.309314349 | 1.376310428 |
| Uqcrq | 150.042 | 193.362 | 214.417 | 1.288719159 | 1.429046534 |
| Atp13a1 | 27.6532 | 36.187 | 37.45 | 1.308600813 | 1.354273646 |
| Atp2a2 | 192.267 | 316.151 | 275.459 | 1.644333141 | 1.432689957 |
| Atp2b2 | 6.49445 | 9.89005 | 9.80506 | 1.52284643 | 1.509759872 |
| Atp2a3 | 211.236 | 407.012 | 432.241 | 1.926811718 | 2.046246852 |
| Atp2c1 | 23.9265 | 32.6925 | 28.6935 | 1.366372014 | 1.199235158 |
| Atp6v0a2 | 14.9439 | 21.3178 | 22.3734 | 1.426521858 | 1.497159376 |
| Atp6ap1 | 92.8728 | 125.614 | 124.253 | 1.352538095 | 1.337883643 |
| Atp8a1 | 3.69179 | 5.34977 | 5.13048 | 1.449099217 | 1.389699847 |
| Atp8b1 | 23.268 | 30.7014 | 27.7501 | 1.319468798 | 1.192629362 |
| Atp9a | 33.102 | 43.4582 | 46.515 | 1.312857229 | 1.405202103 |

FIG. 22 (cont.)

| | | | | | |
|---|---|---|---|---|---|
| Cox6a2 | 6.13141 | 114.138 | 75.3329 | 18.61529404 | 12.2863909 |
| Esrrg | 1.53788 | 2.35801 | 2.82395 | 1.533286082 | 1.836261607 |
| Ppargc1a | 0.118166 | 0.355588 | 0.62384 | 3.009224312 | 5.279352775 |
| Acsf2 | 2.4742 | 5.16081 | 4.68377 | 2.085849972 | 1.893044216 |
| Acsl6 | 3.26485 | 5.32122 | 8.12907 | 1.629851295 | 2.489875492 |
| Acox3 | 4.76993 | 7.0344 | 7.25173 | 1.474738623 | 1.520301136 |
| Echdc2 | 34.3823 | 76.6522 | 82.1471 | 2.229408736 | 2.389226433 |
| Gpam | 3.44338 | 4.92714 | 5.06653 | 1.430902195 | 1.471382769 |
| Hadh | 296.111 | 435.348 | 415.18 | 1.470218938 | 1.402109344 |
| Pecr | 13.5074 | 23.3203 | 22.9962 | 1.726483261 | 1.702489006 |
| Pla2g15 | 9.40221 | 13.2277 | 18.3347 | 1.406871363 | 1.950041533 |
| Elovl6 | 3.504 | 5.82197 | 4.54522 | 1.661521119 | 1.297151826 |

FIG. 22 (cont.)

| Exsocytosis | | | | Fold Change | |
|---|---|---|---|---|---|
| GeneSymbol | Neonate (2w) | Adult (6w) | Adult (12w) | 6w/2w | 12w/2w |
| Rab3d | 32.9902 | 61.8632 | 52.5327 | 1.875199302 | 1.592372886 |
| Rapgef4 | 20.5435 | 27.5834 | 25.6863 | 1.3426826 | 1.25033709 |
| Exoc4 | 7.19042 | 11.1306 | 10.4225 | 1.547976335 | 1.449498082 |
| Exoc6b | 7.85047 | 10.2517 | 10.9596 | 1.305870859 | 1.396043804 |
| Glrb | 4.34541 | 12.9591 | 12.5052 | 2.982250236 | 2.877795191 |
| Myo5a | 1.66964 | 2.98675 | 3.22078 | 1.788858676 | 1.929026617 |
| Rims3 | 17.475 | 37.707 | 37.4407 | 2.15776824 | 2.142529328 |
| Scrn1 | 25.5082 | 33.267 | 34.2257 | 1.304168856 | 1.341752848 |
| Gnpda1 | 17.2946 | 27.557 | 29.5302 | 1.593387531 | 1.707480948 |
| Slc17a9 | 7.81311 | 20.2958 | 17.2675 | 2.597659575 | 2.210067438 |
| Sytl1 | 11.1931 | 22.102 | 24.0136 | 1.974609358 | 2.145393144 |
| Txlna | 30.1607 | 38.4949 | 36.8399 | 1.276326478 | 1.221453746 |
| Trim9 | 3.92438 | 7.40335 | 5.51138 | 1.886501817 | 1.404395089 |
| Vamp2 | 100.179 | 128.581 | 126.937 | 1.283512513 | 1.267101888 |
| Ucn3 | 247.285 | 442.515 | 411.311 | 1.789493904 | 1.66330752 |

FIG. 22 (cont.)

| Mitochondrial metabolic genes (Other) | | | | Fold Change | |
|---|---|---|---|---|---|
| GeneSymbol | Neonate (2w) | Adult (6w) | Adult (12w) | 6w/2w | 12w/2w |
| Abat | 23.1048 | 30.5479 | 31.5306 | 1.322145182 | 1.36467747 |
| Nt5dc3 | 10.0697 | 13.7555 | 12.9477 | 1.366028779 | 1.285807919 |
| Abcd1 | 10.136 | 13.5483 | 13.536 | 1.336651539 | 1.335438043 |
| Dhx32 | 24.5817 | 32.8138 | 33.8695 | 1.334887335 | 1.377833917 |
| Fastk | 35.3143 | 47.1708 | 53.7408 | 1.335742178 | 1.521785792 |
| Gmppb | 25.2035 | 44.0106 | 40.5427 | 1.746209852 | 1.608613883 |
| Hax1 | 41.4398 | 60.3515 | 64.4539 | 1.45636562 | 1.555362236 |
| Mosc2 | 16.6483 | 23.0555 | 22.912 | 1.384856111 | 1.376236613 |
| Mrs2 | 3.46279 | 7.21238 | 6.91378 | 2.082823388 | 1.996592343 |
| Asah2 | 6.7722 | 11.8547 | 11.1841 | 1.750494669 | 1.651472195 |
| Rexo2 | 37.5568 | 57.811 | 51.782 | 1.539295148 | 1.378764964 |
| 1300010F03Rik | 8.29433 | 12.0561 | 12.6006 | 1.453535126 | 1.519182381 |
| Akr1b10 | 9.37142 | 14.2408 | 13.2562 | 1.519598951 | 1.41453483 |
| 2510003E04Rik | 21.7387 | 27.7816 | 29.5011 | 1.277978904 | 1.35707747 |
| C030006K11Rik | 10.3964 | 14.5223 | 17.9569 | 1.396858528 | 1.727222885 |
| Adh1 | 60.0088 | 107.298 | 117.443 | 1.788037754 | 1.957096293 |
| Aldh1l2 | 0.387248 | 3.49173 | 8.47469 | 9.016779945 | 21.88439966 |
| Aldh18a1 | 18.2388 | 31.4031 | 33.7205 | 1.721774459 | 1.848833257 |
| Aass | 0.106617 | 1.10234 | 0.540396 | 10.33925171 | 5.068572554 |
| Nars | 32.1858 | 51.0155 | 48.7659 | 1.585031287 | 1.51513711 |
| Bzrap1 | 2.51025 | 3.53238 | 4.74241 | 1.407182552 | 1.889218205 |
| Bcat2 | 14.8615 | 22.1902 | 22.0952 | 1.493133264 | 1.486740908 |
| Bckdk | 18.1846 | 29.6469 | 30.1573 | 1.63033006 | 1.658397765 |

FIG. 22 (cont.)

| | | | | | |
|---|---|---|---|---|---|
| Ctsa | 29.341 | 36.8454 | 42.7121 | 1.255764971 | 1.455713848 |
| Ctsd | 125.962 | 167.671 | 180.308 | 1.331123672 | 1.431447579 |
| Ccdc56 | 117.726 | 152.499 | 164.3 | 1.295372305 | 1.395613543 |
| Chchd10 | 28.3093 | 39.7851 | 53.9212 | 1.405372086 | 1.904716825 |
| Cpox | 10.3978 | 15.3404 | 13.8884 | 1.475350555 | 1.33570563 |
| Cttnbp2 | 3.49976 | 6.96464 | 7.78121 | 1.990033602 | 2.223355316 |
| Cyb5r1 | 11.9782 | 20.1822 | 21.6318 | 1.684910922 | 1.805930774 |
| Dhtkd1 | 0.603335 | 1.5811 | 1.58222 | 2.620600496 | 2.622456844 |
| Gbas | 32.3254 | 44.2603 | 42.2963 | 1.369211209 | 1.308454033 |
| Gad1 | 30.2802 | 67.4267 | 59.3554 | 2.22675874 | 1.960205018 |
| Gcdh | 15.8671 | 22.8316 | 21.9393 | 1.438927088 | 1.382691229 |
| Gcat | 10.6494 | 16.6576 | 16.4309 | 1.56418202 | 1.542894435 |
| Golph3 | 45.1526 | 59.7686 | 56.8999 | 1.32370229 | 1.26016885 |
| Ghitm | 42.1443 | 62.0954 | 59.9798 | 1.473399724 | 1.423200765 |
| Hlcs | 3.95155 | 6.11196 | 6.61679 | 1.546724703 | 1.674479635 |
| Isoc2a | 21.0029 | 28.4431 | 28.7692 | 1.354246318 | 1.369772746 |
| Kif1b | 15.334 | 19.8252 | 19.3243 | 1.292891613 | 1.260225642 |
| Lactb2 | 7.47325 | 14.5084 | 11.1166 | 1.94137758 | 1.487518817 |
| Lgals12 | 8.33628 | 18.066 | 13.4589 | 2.167153694 | 1.614497114 |
| Mars | 13.4616 | 24.1704 | 32.2334 | 1.795507221 | 2.394470197 |
| Mccc1 | 5.2561 | 8.35979 | 7.46609 | 1.590492951 | 1.420461939 |
| Mthfd2 | 13.3934 | 21.738 | 26.7548 | 1.623038213 | 1.997610764 |
| Mthfd1l | 5.85093 | 13.0459 | 10.849 | 2.229713909 | 1.854235139 |
| Mthfd1 | 27.789 | 35.6276 | 33.2146 | 1.282075641 | 1.195242722 |
| Mrps12 | 63.7492 | 84.4915 | 97.0549 | 1.325373495 | 1.522448909 |
| Acad11 | 8.24031 | 11.6193 | 10.5315 | 1.410056175 | 1.278046578 |

FIG. 22 (cont.)

| | | | | | |
|---|---|---|---|---|---|
| Nnt | 6.81991 | 9.90222 | 9.4196 | 1.451957577 | 1.381191247 |
| Nudt9 | 10.8793 | 17.0676 | 17.0609 | 1.56881417 | 1.568198322 |
| Kcnj11 | 51.9616 | 65.0837 | 76.6179 | 1.252534564 | 1.474510023 |
| Bnip3 | 31.1634 | 45.5617 | 40.8214 | 1.462025966 | 1.309914836 |
| Prlr | 4.68508 | 23.5357 | 13.0972 | 5.023542821 | 2.795512563 |
| Pcca | 7.52779 | 11.183 | 10.4178 | 1.485562164 | 1.383912144 |
| Prkca | 8.11654 | 11.7662 | 10.2609 | 1.44965712 | 1.26419632 |
| Pycr1 | 2.0458 | 8.05935 | 9.92125 | 3.939461335 | 4.84956985 |
| Sars | 63.8287 | 91.7508 | 120.879 | 1.437453685 | 1.893803258 |
| Sfxn1 | 20.0193 | 24.8884 | 25.4109 | 1.243220292 | 1.269320106 |
| Ckb | 27.3359 | 56.6113 | 63.3398 | 2.070950655 | 2.317092175 |
| Fdps | 39.1556 | 53.1203 | 52.811 | 1.356646303 | 1.34874705 |
| Opa1 | 5.55503 | 7.38097 | 7.45101 | 1.328700295 | 1.341308688 |
| Slc25a16 | 7.01913 | 11.3239 | 10.5092 | 1.613291106 | 1.49722259 |
| Slc25a29 | 6.34608 | 10.0363 | 11.9508 | 1.581495979 | 1.883178277 |
| Slc25a35 | 3.19495 | 6.78362 | 6.8552 | 2.123231975 | 2.145636082 |
| Slc25a44 | 22.54 | 31.7154 | 33.7267 | 1.407071872 | 1.496304348 |
| Snph | 14.1499 | 18.768 | 21.7391 | 1.326369798 | 1.536343013 |
| Taz | 38.5911 | 51.9586 | 55.3254 | 1.346388157 | 1.43363107 |
| Tk2 | 13.6847 | 17.6197 | 21.075 | 1.287547407 | 1.540041068 |
| Tomm40l | 9.49607 | 12.9801 | 12.5657 | 1.366891777 | 1.323252672 |
| Tmem160 | 14.5571 | 22.9701 | 27.0187 | 1.577931044 | 1.856049625 |
| Tat | 13.9384 | 22.8455 | 22.7476 | 1.639033175 | 1.632009413 |
| Araf | 97.0924 | 130.922 | 144.543 | 1.348426859 | 1.488715904 |
| Yrdc | 26.3883 | 35.3824 | 35.7955 | 1.340836659 | 1.356491324 |

FIG. 22 (cont.)

| Down regulated genes | | | | | |
|---|---|---|---|---|---|
| Cell proliferation | | | | Fold Change | |
| GeneSymbol | Neonate (2w) | Adult (6w) | Adult (12w) | 6w/2w | 12w/2w |
| Pdgfra | 0.531488 | 0.118791 | 0.0599591 | -4.474143664 | -8.864175746 |
| Pdgfrb | 13.6993 | 6.18687 | 4.88494 | -2.214253734 | -2.804394732 |
| Pdgfb | 10.4681 | 4.98872 | 6.42143 | -2.098353886 | -1.630182062 |
| Btg1 | 41.035 | 31.668 | 23.0779 | -1.295787546 | -1.77810806 |
| Cd24a | 64.8127 | 29.3203 | 29.8714 | -2.210506032 | -2.169724218 |
| Cd81 | 94.7663 | 44.018 | 49.1501 | -2.152898814 | -1.928099841 |
| Cd9 | 30.7436 | 18.4787 | 21.5622 | -1.663731756 | -1.425809982 |
| H19 | 1.82006 | 0.0329267 | 0.0162366 | -55.27611331 | -112.0961285 |
| Hlx | 7.60966 | 4.06578 | 4.03268 | -1.871635947 | -1.886998225 |
| Jun | 372.527 | 101.106 | 149.548 | -3.684519217 | -2.491019606 |
| Klf10 | 12.8164 | 6.45046 | 8.4655 | -1.986897059 | -1.513956648 |
| Klf4 | 34.3161 | 6.84986 | 8.85161 | -5.009752024 | -3.876820149 |
| Marcksl1 | 15.5497 | 3.26489 | 3.62229 | -4.762702572 | -4.292781638 |
| Notch4 | 4.90875 | 3.172 | 2.88816 | -1.547525221 | -1.699611517 |
| Rasip1 | 6.0075 | 4.00161 | 4.17516 | -1.501270739 | -1.438867013 |
| Sox9 | 1.2451 | 0.222205 | 0.212415 | -5.603384262 | -5.861638773 |
| St8sia1 | 3.96032 | 1.9581 | 2.35817 | -2.022532046 | -1.679403945 |
| Tbx3 | 1.69627 | 0.646652 | 0.680807 | -2.623157432 | -2.491557813 |
| Tax1bp3 | 15.2751 | 9.80541 | 9.57771 | -1.557823691 | -1.594859314 |
| Adora2a | 4.87187 | 2.42642 | 2.51209 | -2.00784283 | -1.93936921 |
| Adrb2 | 4.87856 | 0.734998 | 0.465851 | -6.63751466 | -10.47236133 |
| Ager | 5.31734 | 1.71997 | 1.96309 | -3.091530666 | -2.708658289 |
| Agt | 25.4978 | 12.6647 | 15.5685 | -2.013296801 | -1.637781418 |
| Alox12 | 3.45361 | 2.07811 | 1.84056 | -1.661899514 | -1.876390881 |

FIG. 22 (cont.)

| | | | | | |
|---|---|---|---|---|---|
| Arx | 13.0418 | 4.15715 | 7.19812 | -3.137197359 | -1.811834201 |
| Axin2 | 4.10903 | 2.22812 | 2.8173 | -1.844169075 | -1.458499272 |
| Bmp2 | 1.05094 | 0.238734 | 0.172526 | -4.402137944 | -6.09148766 |
| Bmp7 | 1.3275 | 0.372687 | 0.233453 | -3.561970232 | -5.686369419 |
| Cdh5 | 18.5189 | 7.16264 | 6.95571 | -2.58548524 | -2.662402544 |
| Cav1 | 18.3551 | 8.97473 | 5.64167 | -2.045198017 | -3.253486999 |
| Cav2 | 10.1843 | 5.02247 | 3.94469 | -2.027747304 | -2.581774487 |
| Cdca7l | 1.08612 | 0.244845 | 0.300097 | -4.435949274 | -3.619229782 |
| Cxcl10 | 4.35437 | 1.15916 | 1.47927 | -3.756487456 | -2.9435938 |
| F2r | 5.75254 | 3.16496 | 3.21068 | -1.817571154 | -1.791688988 |
| Col18a1 | 4.0198 | 0.792091 | 1.04765 | -5.074921947 | -3.836968453 |
| Cdkn1a | 24.2714 | 8.78183 | 10.4379 | -2.763820297 | -2.325314479 |
| Crip2 | 27.4111 | 14.5057 | 14.2405 | -1.889677851 | -1.924869211 |
| Ddr2 | 1.08679 | 0.361669 | 0.377872 | -3.004929922 | -2.876079731 |
| Edn1 | 0.740122 | 0.12372 | 0.0686801 | -5.982234077 | -10.77636754 |
| Edn3 | 11.2901 | 2.53246 | 3.87548 | -4.458155311 | -2.913213331 |
| Fgfr1 | 7.52516 | 4.62295 | 5.30637 | -1.627783125 | -1.418137069 |
| Foxj1 | 0.980585 | 0.256675 | 0.41126 | -3.820337002 | -2.384343238 |
| Ghrl | 110.04 | 10.2291 | 11.8164 | -10.75754465 | -9.312480959 |
| Gpc3 | 3.94264 | 0.754122 | 0.830355 | -5.228119588 | -4.748137845 |
| Gas1 | 3.0356 | 0.647439 | 0.679422 | -4.688627037 | -4.467915375 |
| Hes1 | 14.7709 | 8.11106 | 10.6696 | -1.821081338 | -1.384391167 |
| Hhex | 15.1136 | 5.00465 | 6.96926 | -3.019911482 | -2.168609006 |
| Id4 | 6.54833 | 1.71555 | 1.85634 | -3.817044097 | -3.527548833 |
| Irs1 | 2.573 | 1.64952 | 1.60243 | -1.559847713 | -1.605686364 |
| Itgb1 | 54.5458 | 43.2508 | 34.1765 | -1.261151239 | -1.596003102 |
| Ifi30 | 43.99 | 31.6335 | 29.8529 | -1.39061438 | -1.473558683 |

FIG. 22 (cont.)

| | | | | | |
|---|---|---|---|---|---|
| Kitl | 4.24744 | 2.34546 | 1.12441 | -1.81091982 | -3.777483302 |
| Klb | 2.6044 | 0.698733 | 0.956334 | -3.727317874 | -2.723316331 |
| Lama5 | 6.73492 | 2.33844 | 2.4099 | -2.880091001 | -2.794688576 |
| Lif | 0.840135 | 0.145864 | 0.126611 | -5.759714529 | -6.635560891 |
| Ngfr | 1.39749 | 0.301977 | 0.441291 | -4.62780278 | -3.166821893 |
| Nos2 | 0.641683 | 0.115438 | 0.0481316 | -5.55868085 | -13.33184436 |
| Nos3 | 3.55446 | 2.14 | 2.29609 | -1.660962617 | -1.548049075 |
| Nfib | 2.15464 | 0.835071 | 0.746781 | -2.580187792 | -2.88523677 |
| Nfkbia | 53.2278 | 27.4873 | 27.7263 | -1.936450652 | -1.919758496 |
| Osr2 | 0.808182 | 0.149913 | 0.19969 | -5.391006784 | -4.047183134 |
| Prrx1 | 1.75091 | 0.452761 | 0.372544 | -3.86718379 | -4.699874377 |
| Pth1r | 1.47965 | 0.531786 | 0.46526 | -2.782416235 | -3.180264798 |
| Hmgn1 | 116.291 | 78.8928 | 67.6229 | -1.474038189 | -1.719698505 |
| Hmgb1 | 117.118 | 84.3609 | 76.6084 | -1.388297185 | -1.528787966 |
| Smo | 2.42184 | 0.658283 | 0.814555 | -3.679025586 | -2.973206229 |
| Npm1 | 152.428 | 113.284 | 101.791 | -1.345538646 | -1.497460483 |
| Ptgs1 | 3.14333 | 1.80873 | 1.52128 | -1.737865795 | -2.066240271 |
| Ptgs2 | 0.520124 | 0.12105 | 0.0748985 | -4.29676993 | -6.944384734 |
| Rbp4 | 400.562 | 101.114 | 127.715 | -3.961489012 | -3.136373958 |
| Sparc | 247.667 | 81.1192 | 49.9797 | -3.053124291 | -4.955351873 |
| Serpine1 | 7.87224 | 1.34745 | 1.69588 | -5.842324391 | -4.641979385 |
| Serpinf1 | 3.01085 | 1.20029 | 1.57869 | -2.508435461 | -1.907182537 |
| Ntn1 | 0.528705 | 0.164723 | 0.256271 | -3.209661067 | -2.063069953 |
| Fosl2 | 4.64055 | 2.60975 | 2.88402 | -1.778158827 | -1.609056109 |
| Spry1 | 9.53516 | 3.04521 | 4.03802 | -3.13119949 | -2.361345412 |
| Tesc | 9.5236 | 4.26839 | 5.46926 | -2.231192557 | -1.741295897 |

FIG. 22 (cont.)

| | | | | | |
|---|---|---|---|---|---|
| Timp2 | 11.2357 | 6.13705 | 7.58103 | -1.830798185 | -1.482080931 |
| Trp53 | 24.4568 | 18.547 | 17.9819 | -1.318639133 | -1.360078746 |
| Tgfb1 | 5.83957 | 3.06533 | 3.49215 | -1.905037957 | -1.672199075 |
| Tgfb2 | 2.0922 | 0.762483 | 0.758962 | -2.743930029 | -2.756659754 |
| Tgfbr2 | 10.2952 | 3.19674 | 2.98445 | -3.220530916 | -3.449613832 |
| Tgm2 | 4.74123 | 2.7551 | 2.47627 | -1.720892164 | -1.91466601 |
| Trim35 | 69.1413 | 42.9042 | 49.9599 | -1.611527543 | -1.383935917 |
| Erbb2 | 1.06949 | 0.364781 | 0.26529 | -2.93186871 | -4.0313996 |
| Mycn | 2.74882 | 0.505871 | 0.586729 | -5.433835899 | -4.684990856 |
| Ldha | 15.7742 | 6.80922 | 6.61999 | -2.316594265 | -2.382813267 |
| Hk1 | 3.25441 | 1.89346 | 2.32575 | -1.718763533 | -1.399294851 |

FIG. 23

| Pancreatic lineage gene list (Reference Hrvatin et al, PNAS, 2014) | | | | Fold Change | |
|---|---|---|---|---|---|
| Secretory | Neonate (2w) | Adult (6w) | Adult (12w) | 6w/2w | 12w/2w |
| Chga | Not Sig | | | Not Sig | |
| Chgb | Not Sig | | | Not Sig | |
| Gast | Not Sig | | | Not Sig | |
| gcg | Not Sig | | | Not Sig | |
| Ghrl | 110.04 | 10.2291 | 11.8164 | -10.75754465 | -9.312480959 |
| Gip | Not Sig | | | Not Sig | |
| Iapp | Not Sig | | | Not Sig | |
| Ins | No TEST | | | No TEST | |
| Nts | Not Sig | | | Not Sig | |
| Ppy | Not Sig | | | Not Sig | |
| Pyy | 7125.13 | 1677.32 | 3116.97 | -4.247925262 | -2.285915488 |
| Sct | 4.96306 | 0.0827237 | 0.651184 | -59.99562399 | -7.621593897 |
| Sst | Not Sig | | | Not Sig | |

FIG. 23 (cont.)

| | | | | Fold Change | |
|---|---|---|---|---|---|
| Transcription factors | Neonate (2w) | Adult (6w) | Adult (12w) | 6w/2w | 12w/2w |
| Alx3 | | Not Sig | | Not Sig | |
| Arx | 13.0418 | 4.15715 | 7.19812 | -3.137197359 | -1.811834201 |
| Cmip | | Not Sig | | Not Sig | |
| En1 | | Not Sig | | Not Sig | |
| Esr1 | | Not Sig | | Not Sig | |
| Foxa1 | | Not Sig | | Not Sig | |
| Foxa2 | | Not Sig | | Not Sig | |
| Foxa3 | | Not Sig | | Not Sig | |
| Foxo1 | | Not Sig | | Not Sig | |
| Gata4 | | Not Sig | | Not Sig | |
| Gata6 | 7.89917 | 3.83378 | 4.65043 | -2.060412961 | -1.698589163 |
| Glis3 | 3.21792 | 6.93969 | 6.3495 | 2.156576298 | 1.973169004 |
| Hes1 | 14.7709 | 8.11106 | 10.6696 | -1.821081338 | -1.384391167 |
| Hnf1a | | Not Sig | | Not Sig | |
| Hnf1b | | Not Sig | | Not Sig | |
| Hnf4a | | Not Sig | | Not Sig | |
| Insm1 | | Not Sig | | Not Sig | |
| Irx2 | 25.8712 | 7.11834 | 9.99981 | -3.634442862 | -2.587169156 |
| Isl1 | 100.86 | 69.0436 | 70.5751 | -1.460816064 | -1.429115935 |
| Lhx6 | | Not Sig | | Not Sig | |
| Lmx1a | | Not Sig | | Not Sig | |
| Lmx1b | | Not Sig | | Not Sig | |
| Maf | 0.944805 | 0.302423 | 0.122159 | -3.124117544 | -7.73422343 |
| Mafa | 108.602 | 175.383 | 330.609 | 1.614915011 | 3.044225705 |
| Mafb | 57.5913 | 14.4378 | 18.8427 | -3.988924905 | -3.056425035 |

FIG. 23 (cont.)

| | | | | | |
|---|---|---|---|---|---|
| Mlxipl | Not Sig | | | Not Sig | |
| Mnx1 | Not Sig | | | Not Sig | |
| Myt1 | 23.7294 | 17.6379 | 18.6202 | -1.345364244 | -1.274390178 |
| Nanog | Not Sig | | | Not Sig | |
| Neurod1 | 105.602 | 79.0341 | 88.6711 | -1.336157431 | -1.190940453 |
| Neurog3 | Not Sig | | | Not Sig | |
| Nkx2-2 | Not Sig | | | Not Sig | |
| Nkx6-1 | 78.5547 | 112.946 | 146.41 | 1.437800666 | 1.863796819 |
| Nkx6-2 | Not Sig | | | Not Sig | |
| Nkx6-3 | Not Sig | | | Not Sig | |
| Notch1 | Not Sig | | | Not Sig | |
| Onecut1 | Not Sig | | | Not Sig | |
| Onecut2 | Not Sig | | | Not Sig | |
| Onecut3 | Not Sig | | | Not Sig | |
| Pax2 | Not Sig | | | Not Sig | |
| Pax4 | Not Sig | | | Not Sig | |
| Pax6 | Not Sig | | | Not Sig | |
| Pbx1 | Not Sig | | | Not Sig | |
| Pdx1 | 76.8849 | 100.279 | 114.486 | 1.304274311 | 1.489057019 |
| Pou3f4 | 1.92511 | 0.349014 | 0.571939 | -5.515853232 | -3.365935878 |
| Prox1 | Not Sig | | | Not Sig | |
| Rfx2 | Not Sig | | | Not Sig | |
| Rfx3 | Not Sig | | | Not Sig | |
| Rfx6 | Not Sig | | | Not Sig | |
| Snai1 | 2.22422 | 0.608413 | 0.737025 | -3.655773299 | -3.017835216 |
| Snai2 | 2.12764 | 0.869592 | 0.687607 | -2.446710641 | -3.09426751 |
| Sox4 | 14.6178 | 8.04746 | 7.13493 | -1.816448917 | -2.04876572 |
| Sox9 | 1.2451 | 0.222205 | 0.212415 | -5.603384262 | -5.861638773 |

FIG. 23 (cont.)

| | | | | Fold Change | |
|---|---|---|---|---|---|
| Glucose processing, insulin secretion | Neonate (2w) | Adult (6w) | Adult (12w) | 6w/2w | 12w/2w |
| Acox2 | | Not Sig | | Not Sig | |
| Acss1 | | Not Sig | | Not Sig | |
| Aldoa | 208.264 | 289.021 | 379.322 | 1.387762647 | 1.821351746 |
| Atp5g3 | | Not Sig | | Not Sig | |
| Atp6v0e1 | | Not Sig | | Not Sig | |
| Cox4\|1 | | Not Sig | | Not Sig | |
| Gpi | | Not Sig | | Not Sig | |
| Nnt | 6.81991 | 9.90222 | 9.4196 | 1.451957577 | 1.381191247 |
| Pcsk1 | 71.8125 | 162.246 | 109.09 | 2.259300261 | 1.519094865 |
| Pcsk2 | | Not Sig | | Not Sig | |
| Pdia6 | 160.2 | 276.018 | 237.692 | 1.722958801 | 1.48372035 |
| Pdk3 | | Not Sig | | Not Sig | |
| Pgap1 | | Not Sig | | Not Sig | |
| Prkcsh | 51.4658 | 66.2942 | 63.5302 | 1.288121432 | 1.234415865 |
| Rims1 | | Not Sig | | Not Sig | |
| Rims2 | | Not Sig | | Not Sig | |
| Rims3 | 17.475 | 37.707 | 37.4407 | 2.15776824 | 2.142529328 |
| Rims4 | | Not Sig | | Not Sig | |
| Slc2a14 | | Not Sig | | Not Sig | |
| Slc30a8 | 359.411 | 504.51 | 497.351 | 1.403713298 | 1.383794597 |
| Snap25 | | Not Sig | | Not Sig | |
| Stx1a | 13.3614 | 7.97905 | 9.55851 | -1.674560255 | -1.39785385 |
| Stxbp1 | | Not Sig | | Not Sig | |

FIG. 23 (cont.)

| | | | | | |
|---|---|---|---|---|---|
| Syp | 88.7561 | 170.847 | 146.327 | 1.924904316 | 1.648641614 |
| Syt4 | 13.1072 | 33.2258 | 24.8161 | 2.534927368 | 1.893318176 |
| Syt7 | Not Sig | | | Not Sig | |
| Syt8 | Not Sig | | | Not Sig | |
| Vamp2 | 100.179 | 128.581 | 126.937 | 1.283512513 | 1.267101888 |
| Vamp3 | 45.4533 | 32.7204 | 26.5463 | -1.389142553 | -1.712227316 |
| G6pc2 | 622.253 | 1592.85 | 961.201 | 2.559810881 | 1.544710913 |
| Gck | Not Sig | | | Not Sig | |
| Slc2a1 | 3.25246 | 5.01674 | 5.00066 | 1.542444796 | 1.537500846 |
| Slc2a2 | 129.689 | 224.558 | 161.342 | 1.731511539 | 1.244068502 |
| Slc2a3 | Not Sig | | | Not Sig | |

FIG. 23 (cont.)

| | | | | Fold Change | |
|---|---|---|---|---|---|
| Membrane channels | Neonate (2w) | Adult (6w) | Adult (12w) | 6w/2w | 12w/2w |
| Abcc8 | | Not Sig | | Not Sig | |
| Cacna1a | | Not Sig | | Not Sig | |
| Cacna1b | | Not Sig | | Not Sig | |
| Cacna1c | | Not Sig | | Not Sig | |
| Cacna1d | 18.1147 | 22.4694 | 23.4498 | 1.240395922 | 1.294517712 |
| Hcn1 | | Not Sig | | Not Sig | |
| Hcn2 | | Not Sig | | Not Sig | |
| Hcn3 | | Not Sig | | Not Sig | |
| Hcn4 | | Not Sig | | Not Sig | |
| Kcna3 | | Not Sig | | Not Sig | |
| Kcna5 | | Not Sig | | Not Sig | |
| Kcna6 | 0.51181 | 0.0873796 | 0.138638 | -5.857316811 | -3.691700688 |
| Kcnj11 | 51.9616 | 65.0837 | 76.6179 | 1.252534564 | 1.474510023 |
| Kcnj2 | 0.865203 | 0.200627 | 0.24365 | -4.312495327 | -3.551007593 |
| Kcnj4 | | Not Sig | | Not Sig | |
| Kcnj6 | | Not Sig | | Not Sig | |
| Kcnk1 | 12.2431 | 16.1156 | 15.7287 | 1.31630061 | 1.284699137 |
| Kcnk12 | 3.67191 | 5.05525 | 9.65408 | 1.376735813 | 2.629171194 |
| Kcnk17 | | Not Sig | | Not Sig | |
| Kcnk3 | 5.48958 | 2.03482 | 3.24049 | -2.697820937 | -1.694058615 |
| Kcnma1 | 2.14507 | 3.78121 | 3.59991 | 1.762744339 | 1.678224953 |
| Kcnmb2 | | Not Sig | | Not Sig | |

FIG. 23 (cont.)

| | | | | | |
|---|---|---|---|---|---|
| Kcnn1 | | Not Sig | | Not Sig | |
| Kcnn3 | 2.04115 | 3.58122 | 2.78696 | 1.754510937 | 1.365387159 |
| Scn1a | | Not Sig | | Not Sig | |
| Scn2a | | Not Sig | | Not Sig | |
| Scn3a | | Not Sig | | Not Sig | |
| Scn4a | | Not Sig | | Not Sig | |
| Scn7a | 1.10103 | 0.434963 | 0.374819 | -2.531318756 | -2.937497832 |
| Cdh1 | | Not Sig | | Not Sig | |
| Cdh2 | | Not Sig | | Not Sig | |
| Dll3 | | Not Sig | | Not Sig | |
| Col1a1 | 16.4515 | 3.57139 | 2.69878 | -4.60646975 | -6.095902593 |
| Ctnnb1 | | Not Sig | | Not Sig | |
| Ffar1 | | Not Sig | | Not Sig | |
| Rap1a | | Not Sig | | Not Sig | |
| Ucn3 | 247.285 | 442.515 | 411.311 | 1.789493904 | 1.66330752 |
| Wnt2 | | Not Sig | | Not Sig | |
| Wnt3 | | Not Sig | | Not Sig | |
| Wnt4 | 52.0295 | 81.6961 | 119.019 | 1.570188066 | 2.28752919 |

FIG. 24

| | RPKM (Rawdata) | | | | | Fold Change | | |
|---|---|---|---|---|---|---|---|---|
| Down Regulated genes (232 genes) | Control | βERRγKO | Neonate (2w) | Adult (6w) | Adult (12w) | βERRγKO/Control | 6w/2w | 12w/2w |
| Abcc10 | 10.5964 | 6.08684 | 8.14412 | 12.0899 | 13.8155 | -1.740870468 | 1.484494335 | 1.696377264 |
| Acta2 | 6.82924 | 2.63057 | 10.1644 | 5.8978 | 5.40183 | -2.596106547 | -1.723422293 | -1.881658623 |
| AI846148 | 9.55391 | 7.62673 | | Not Sig | | -1.252687587 | Not Sig | Not Sig |
| Akap10 | 8.75722 | 7.20511 | | Not Sig | | -1.215417946 | Not Sig | Not Sig |
| Akr1c14 | 34.4546 | 10.6399 | 13.1848 | 27.3688 | 19.6361 | -3.23824472 | 2.075784236 | 1.489298283 |
| Aldh5a1 | 10.8607 | 8.65651 | | Not Sig | | -1.25462802 | Not Sig | Not Sig |
| Alg12 | 13.1805 | 9.9999 | | Not Sig | | -1.318063181 | Not Sig | Not Sig |
| Ampd2 | 57.2759 | 40.5954 | 56.0458 | 67.9467 | 79.3554 | -1.410896308 | 1.212342406 | 1.415902708 |
| Ankrd17 | 21.3869 | 14.8967 | | Not Sig | | -1.435680386 | Not Sig | Not Sig |
| Aoc2 | 5.52181 | 3.45452 | 7.65857 | 5.30485 | 6.06668 | -1.598430462 | -1.443692093 | -1.262398874 |
| Apc | 10.1517 | 8.36698 | | Not Sig | | -1.213305159 | Not Sig | Not Sig |
| Apoa2 | 9.35836 | 4.9446 | | Not Sig | | -1.892642479 | Not Sig | Not Sig |
| Aqp4 | 24.9948 | 17.9864 | 5.79211 | 4.07971 | 3.52998 | -1.389649958 | -1.419735717 | -1.640833659 |
| Arfip1 | 31.9213 | 26.3911 | 23.8157 | 23.977 | 19.4129 | -1.209547916 | -0.99327272 | -1.226797645 |
| Arl4a | 12.3934 | 9.13033 | 12.9713 | 7.82551 | 6.68627 | -1.357387959 | -1.657566088 | -1.939990458 |
| Ash1l | 16.7906 | 9.91607 | | Not Sig | | -1.693271629 | Not Sig | Not Sig |
| Atn1 | 33.2682 | 24.5834 | | Not Sig | | -1.353279042 | Not Sig | Not Sig |
| Atp13a1 | 25.9894 | 20.1073 | 27.6532 | 36.187 | 37.45 | -1.292535547 | 1.308600813 | 1.354273646 |
| Atp13a3 | 15.3782 | 9.14583 | | Not Sig | | -1.681443893 | Not Sig | Not Sig |
| Atp1a1 | 210.443 | 159.856 | | Not Sig | | -1.316453558 | Not Sig | Not Sig |
| Atp2a2 | 379.533 | 231.384 | 192.267 | 316.151 | 275.459 | -1.640273312 | 1.644333141 | 1.432689957 |
| Atp2b1 | 26.4986 | 20.1017 | 16.6586 | 16.5447 | 13.5513 | -1.318226817 | -1.00688438 | -1.229299034 |
| Atp2b2 | 13.5036 | 8.65262 | 6.49445 | 9.89005 | 9.80506 | -1.560637125 | 1.52284643 | 1.509759872 |
| Atp2b4 | 14.8401 | 7.04903 | | Not Sig | | -2.105268384 | Not Sig | Not Sig |
| Atp6v0a2 | 17.7913 | 12.9048 | 14.9439 | 21.3178 | 22.3734 | -1.378657554 | 1.426521858 | 1.497159376 |
| Atp6v1g2 | 5.31967 | 3.52944 | | Not Sig | | -1.507227776 | Not Sig | Not Sig |
| Atp7a | 9.32887 | 7.23493 | | Not Sig | | -1.289420907 | Not Sig | Not Sig |
| Atp8b1 | 54.1302 | 32.8376 | 23.268 | 30.7014 | 27.7501 | -1.648421322 | 1.319468798 | 1.192629362 |
| Atp8b2 | 20.3213 | 13.7527 | | Not Sig | | -1.477622576 | Not Sig | Not Sig |
| Azin1 | 30.2755 | 17.8333 | 25.2603 | 23.2344 | 15.394 | -1.697694762 | -1.087193988 | -1.64091854 |

FIG. 24 (cont.)

| | | | | | | | | |
|---|---|---|---|---|---|---|---|---|
| Bag3 | 16.2222 | 10.3267 | 11.3904 | 8.51332 | 9.20979 | -1.570898738 | -1.337950412 | -1.236770871 |
| Bcl6b | 10.1153 | 7.65302 | | Not Sig | | -1.321739653 | Not Sig | Not Sig |
| Bgn | 8.78822 | 6.53497 | 36.8229 | 15.1268 | 11.4858 | -1.344798828 | -2.434282201 | -3.205949956 |
| Bhlhe40 | 19.6124 | 14.7464 | 8.95951 | 12.1354 | 12.7278 | -1.329978842 | 1.354471394 | 1.420591081 |
| Btbd3 | 7.16663 | 6.74558 | 10.2177 | 6.64344 | 5.28646 | -1.06241865 | -1.538013439 | -1.932805696 |
| Cbs | 29.7177 | 9.02361 | 9.86534 | 34.1196 | 35.0921 | -3.293327172 | 3.4585326 | 3.557110044 |
| Cc2d2a | 6.66168 | 4.91946 | | Not Sig | | -1.354148626 | Not Sig | Not Sig |
| Ccdc21 | 10.1735 | 8.14017 | 7.41614 | 10.0861 | 9.72355 | -1.249789624 | 1.360020172 | 1.311133555 |
| Ccdc88a | 6.77078 | 4.55686 | 2.74659 | 3.07997 | 2.11347 | -1.485843322 | 1.121379602 | -1.299564224 |
| Cd200 | 78.5309 | 48.797 | 45.8187 | 42.2315 | 33.3644 | -1.609338689 | -1.084941335 | -1.373281102 |
| Cd44 | 20.0531 | 6.52421 | | Not Sig | | -3.073644165 | Not Sig | Not Sig |
| Cdr2 | 3.47573 | 2.98021 | 15.0685 | 19.7609 | 18.9908 | -1.166270162 | 1.311404586 | 1.260297973 |
| Chordc1 | 34.4765 | 21.9784 | 25.1345 | 21.2692 | 15.6157 | -1.568653769 | -1.18173227 | -1.609566014 |
| Cmtm4 | 40.4033 | 28.8151 | 5.2892 | 13.756 | 15.6383 | -1.402157202 | 2.600771383 | 2.956647508 |
| Cnot6l | 41.9159 | 24.3734 | 23.4086 | 16.9251 | 14.9377 | -1.719739552 | -1.383070115 | -1.567081947 |
| Cobll1 | 25.219 | 17.3003 | 10.4986 | 17.4989 | 15.7362 | -1.457720386 | 1.666784143 | 1.498885566 |
| Coq10b | 23.1223 | 10.5632 | 16.7237 | 22.6132 | 13.0291 | -2.188948425 | 1.352164892 | -1.28356525 |
| Cox6a2 | 74.4714 | 43.896 | 6.13141 | 114.138 | 75.3329 | -1.696541826 | 18.61529404 | 12.2863909 |
| Cpeb3 | 9.76127 | 6.54084 | 3.55995 | 4.96609 | 4.98111 | -1.492357251 | 1.394988694 | 1.399207854 |
| Cpsf6 | 16.578 | 12.2389 | 12.7357 | 11.6973 | 9.98974 | -1.354533496 | -1.088772623 | -1.274878025 |
| Creb3l2 | 59.9234 | 28.8467 | 22.7651 | 31.0149 | 31.9978 | -2.077305203 | 1.362388041 | 1.40556378 |
| Crem | 14.0465 | 10.7285 | 10.3687 | 15.0255 | 9.36021 | -1.309269702 | 1.449120912 | -1.107742241 |
| Dapl1 | 88.8508 | 5.96548 | 35.7354 | 172.158 | 73.1431 | -14.89415772 | 4.817575849 | 2.046796734 |
| Dclk2 | 5.31796 | 4.34352 | 5.78468 | 3.66585 | 5.03959 | -1.22434339 | -1.577991462 | -1.147847345 |
| Ddx17 | 234.865 | 153.128 | | Not Sig | | -1.533782195 | Not Sig | Not Sig |
| Dedd2 | 22.4428 | 15.3609 | 12.2471 | 12.5369 | 16.4331 | -1.461034184 | 1.023662745 | 1.3417952 |
| Dhx29 | 5.99701 | 4.74664 | | Not Sig | | -1.263422126 | Not Sig | Not Sig |
| Dicer1 | 18.8674 | 14.7474 | | Not Sig | | -1.279371279 | Not Sig | Not Sig |
| Dnajb4 | 29.3432 | 19.9257 | 22.2674 | 15.2485 | 14.9355 | -1.472630824 | -1.460301013 | -1.490904221 |
| Dock9 | 10.0157 | 7.35684 | 5.53722 | 7.20026 | 7.05981 | -1.361413324 | 1.300338437 | 1.274973723 |
| Dot1l | 8.18638 | 4.67969 | | Not Sig | | -1.749342371 | Not Sig | Not Sig |
| Dpp10 | 5.18384 | 3.21431 | 6.37429 | 3.60196 | 3.87444 | -1.612738037 | -1.645215825 | 0.607822989 |
| Dpp6 | 10.637 | 5.77372 | 7.44092 | 4.39645 | 6.23834 | -1.842313101 | -1.192772436 | 0.838382888 |

FIG. 24 (cont.)

| | | | | | | | | |
|---|---|---|---|---|---|---|---|---|
| Dst | 23.3098 | 18.0401 | | Not Sig | | -1.292110354 | Not Sig | Not Sig |
| Dusp23 | 17.7647 | 14.3334 | 8.35128 | 11.4137 | 12.1588 | -1.23939191 | 1.366700673 | 1.45592053 |
| Dusp7 | 10.0703 | 6.47747 | 8.33413 | 8.82493 | 11.4896 | -1.554665633 | 1.05889037 | 1.378620204 |
| Dync1h1 | 36.7345 | 19.8425 | | Not Sig | | -1.851304019 | Not Sig | Not Sig |
| Edem2 | 93.351 | 65.6615 | 44.5316 | 83.8463 | 85.0121 | -1.421700692 | 1.882849482 | 1.909028645 |
| Entpd7 | 6.45181 | 3.10136 | 3.33516 | 4.82393 | 4.34643 | -2.080316377 | 1.44638638 | 1.303214838 |
| Ero1lb | 547.722 | 294.549 | 219.545 | 609.117 | 439.823 | -1.859527617 | 2.774451707 | 2.003338723 |
| Etv1 | 14.959 | 6.93855 | 23.6924 | 8.91761 | 10.6033 | -2.15592595 | -2.15592595 | -0.631383904 |
| Etv6 | 4.91537 | 3.90005 | | Not Sig | | -1.260335124 | Not Sig | Not Sig |
| Flna | 6.85744 | 3.78155 | 9.39795 | 6.14238 | 5.7008 | -1.813393979 | -1.53001768 | -1.648531785 |
| Fmn2 | 18.4715 | 13.528 | 13.0491 | 16.5016 | 15.8222 | -1.365427262 | 1.264577634 | 1.21251274 |
| Fryl | 12.6812 | 7.46655 | 11.3402 | 8.70794 | 9.90838 | -1.698401538 | -1.302282744 | -1.144505964 |
| Gale | 22.1214 | 11.3679 | 21.7878 | 44.4931 | 39.0093 | -1.945953078 | 2.042110723 | 1.790419409 |
| Gbf1 | 41.2053 | 25.3624 | 26.4545 | 34.8225 | 36.0452 | -1.624660915 | 1.316316695 | 1.362535674 |
| Ggcx | 47.2195 | 26.9937 | 36.8305 | 47.194 | 54.0982 | -1.749278535 | 1.281383636 | 1.4688424 |
| Ghrl | 13.3409 | 8.18588 | 110.04 | 10.2291 | 11.8164 | -1.629745366 | -10.75754465 | -9.312480959 |
| Glb1l2 | 36.0785 | 28.751 | | Not Sig | | -1.2548607 | Not Sig | Not Sig |
| Golim4 | 58.6354 | 46.9225 | | Not Sig | | -1.249622249 | Not Sig | Not Sig |
| Gpaa1 | 19.4672 | 14.7197 | | Not Sig | | -1.322526954 | Not Sig | Not Sig |
| Gpd2 | 23.6451 | 13.7601 | | Not Sig | | -1.718381407 | Not Sig | Not Sig |
| Gtf3c1 | 22.0696 | 16.0199 | | Not Sig | | -1.377636565 | Not Sig | Not Sig |
| Hapln1 | 6.88949 | 2.31624 | 7.28724 | 5.25851 | 3.63403 | -2.974428384 | -1.385799399 | -2.005277887 |
| Heatr5a | 6.91175 | 4.32763 | 2.92978 | 5.25888 | 3.94703 | -1.597121288 | 1.794974367 | 1.347210371 |
| Heg1 | 9.5067 | 5.28057 | 3.01508 | 5.03306 | 5.80783 | -1.800317011 | 1.669295674 | 1.926260663 |
| Hipk3 | 37.0379 | 25.7662 | | Not Sig | | -1.437460704 | Not Sig | Not Sig |
| Hirip3 | 7.46513 | 6.00006 | 12.8783 | 12.1166 | 9.48265 | -1.244175892 | -1.06286417 | -1.358090829 |
| Hist2h4 | 11.7368 | 4.89546 | | Not Sig | | -2.397486651 | Not Sig | Not Sig |
| Hlcs | 9.31343 | 6.866 | 3.95155 | 6.11196 | 6.61679 | -1.356456452 | 1.546724703 | 1.674479635 |
| Hnrnpul1 | 40.7695 | 36.7235 | | Not Sig | | -1.110174684 | Not Sig | Not Sig |
| Hspa8 | 277.751 | 204.672 | 963.96 | 530.342 | 427.289 | -1.357054214 | -1.817619574 | -2.255990676 |
| Htt | 7.63898 | 5.31842 | 3.0463 | 4.42722 | 4.30668 | -1.436325074 | 1.453310573 | 1.41374126 |
| Insrr | 181.801 | 75.504 | 147.03 | 222.497 | 230.102 | -2.407832698 | 1.513276202 | 1.56500034 |
| Irs2 | 14.3674 | 9.40886 | 7.99556 | 5.28659 | 6.9565 | -1.527007523 | -1.512422942 | -1.149365342 |

FIG. 24 (cont.)

| | | | | | | | | |
|---|---|---|---|---|---|---|---|---|
| Kcnh1 | 7.45163 | 0.771805 | 0.57099 | 4.17233 | 3.38642 | -9.654809181 | 7.307185765 | 5.930786879 |
| Kcnk1 | 23.9009 | 19.195 | 12.2431 | 16.1156 | 15.7287 | -1.245162803 | 1.31630061 | 1.284699137 |
| Kctd12 | 24.0807 | 9.40936 | 21.6722 | 9.78209 | 9.36179 | -2.559228258 | -2.215497915 | -2.314963271 |
| Kdelr2 | 125.457 | 104.827 | 71.3835 | 105.455 | 104.141 | -1.196800443 | 1.477302178 | 1.458894562 |
| Klf5 | 11.6929 | 5.98691 | | Not Sig | | -1.953077631 | Not Sig | Not Sig |
| Klhl32 | 30.3228 | 24.219 | 17.1356 | 22.32 | 23.1639 | -1.252025269 | 1.302551413 | 1.351799762 |
| Lamc1 | 10.3072 | 6.54024 | 17.9191 | 7.89616 | 7.68308 | -1.575966631 | -2.26934358 | -2.332280804 |
| Leng8 | 57.007 | 31.4876 | 73.4413 | 97.7578 | 102.099 | -1.81045872 | 1.331101165 | 1.390212319 |
| Lphn1 | 22.9022 | 14.4188 | | Not Sig | | -1.588356867 | Not Sig | Not Sig |
| Lpin1 | 22.9022 | 14.4188 | 4.44964 | 8.77088 | 8.16146 | -1.588356867 | 1.971143733 | 1.834184339 |
| Lrp12 | 16.5245 | 13.4534 | | Not Sig | | -1.228276867 | Not Sig | Not Sig |
| Ltbp4 | 15.755 | 10.0186 | 47.051 | 16.3184 | 16.4466 | -1.57257501 | -2.883309638 | -2.860834458 |
| Lyst | 5.8847 | 2.86561 | 1.44857 | 2.14007 | 2.12463 | -2.053559277 | 1.477367335 | 1.466708547 |
| Mast2 | 14.3128 | 10.1895 | | Not Sig | | -1.404661662 | Not Sig | Not Sig |
| Mat2a | 30.0114 | 23.4371 | 35.4288 | 26.6205 | 23.8015 | -1.280508254 | -1.330884093 | -1.488511228 |
| Mdm1 | 54.3911 | 22.8402 | 41.4709 | 94.856 | 55.6663 | -2.38137582 | 2.287290606 | 1.342297852 |
| Mga | 11.742 | 8.10035 | 4.83545 | 4.19851 | 3.68013 | -1.449566994 | -1.151706201 | -1.313934562 |
| Mlxipl | 169.634 | 94.2782 | | Not Sig | | -1.799291883 | Not Sig | Not Sig |
| Muc4 | 24.6357 | 15.2069 | 9.17946 | 12.2218 | 11.5724 | -1.620034327 | 1.331429082 | 1.26068418 |
| Mycbp2 | 14.7441 | 9.93688 | | Not Sig | | -1.483775592 | Not Sig | Not Sig |
| Myst4 | 9.66941 | 7.5775 | | Not Sig | | -1.276068624 | Not Sig | Not Sig |
| Nbas | 22.7254 | 15.0478 | 9.1039 | 16.0545 | 16.4034 | -1.510214118 | 1.763474994 | 1.801799229 |
| Ncoa6 | 16.2235 | 12.4882 | | Not Sig | | -1.299106356 | Not Sig | Not Sig |
| Ndufa1 | 186.208 | 153.308 | | Not Sig | | -1.214600673 | Not Sig | Not Sig |
| Nfat5 | 17.1045 | 13.7658 | 13.6731 | 11.3093 | 10.1323 | -1.24253585 | -1.20901382 | -1.349456688 |
| Nfatc1 | 6.78037 | 4.39237 | | Not Sig | | -1.543670046 | Not Sig | Not Sig |
| Nid1 | 6.97378 | 5.46576 | 19.8738 | 6.88712 | 5.69746 | -1.275903077 | -2.885647411 | -3.488185964 |
| Nkx6-1 | 174.653 | 102.57 | 78.5547 | 112.946 | 146.41 | -1.702768841 | 1.437800666 | 1.863796819 |
| Nrxn1 | 9.58282 | 6.18284 | 2.41137 | 4.03316 | 4.50783 | -1.549905869 | 1.672559582 | 1.869406188 |
| Nupl1 | 15.3774 | 12.0289 | | Not Sig | | -1.278371256 | Not Sig | Not Sig |

FIG. 24 (cont.)

| | | | | | | | | |
|---|---|---|---|---|---|---|---|---|
| P2ry1 | 61.2153 | 14.2146 | 17.1896 | 33.3319 | 15.9 | -4.306508801 | 1.939073626 | -1.081106918 |
| P4ha1 | 16.45 | 12.5969 | | Not Sig | | -1.305876843 | Not Sig | Not Sig |
| P4ha2 | 9.06302 | 4.91674 | 5.14042 | 9.46845 | 10.5019 | -1.843298608 | 1.841960385 | 2.043004268 |
| Pak3 | 14.3961 | 9.93661 | 2.28697 | 1.36 | 0.910348 | -1.448793905 | -1.681595588 | -2.512193139 |
| Pard6b | 5.39453 | 4.36221 | | Not Sig | | -1.236650689 | Not Sig | Not Sig |
| Paxip1 | 42.42 | 20.0509 | 18.9612 | 30.6418 | 27.9967 | -2.115615758 | 1.616026412 | 1.476525747 |
| Pclo | 24.5875 | 12.0806 | | Not Sig | | -2.035287982 | Not Sig | Not Sig |
| Pcsk4 | 19.5661 | 14.2554 | 24.961 | 27.3442 | 34.6413 | -1.372539529 | 1.095476944 | 1.387816995 |
| Pcyt1b | 12.4937 | 9.92315 | | Not Sig | | -1.259045767 | Not Sig | Not Sig |
| Pdcd11 | 9.48462 | 7.74206 | 7.60111 | 9.56069 | 9.45598 | -1.225077047 | 1.257801821 | 1.244026201 |
| Pdpk1 | 23.5089 | 16.2788 | | Not Sig | | -1.444142074 | Not Sig | Not Sig |
| Pdxk | 9.8354 | 7.55818 | 6.27919 | 8.10402 | 8.19776 | -1.30129211 | 1.290615509 | 1.305544186 |
| Pdyn | 140.395 | 21.5689 | 1.42878 | 32.1131 | 51.1435 | -6.509140475 | 22.47588852 | 35.7952239 |
| Pfkfb2 | 59.1799 | 34.8997 | 37.7099 | 54.782 | 46.543 | -1.695713717 | 1.452721964 | 1.234238224 |
| Pfkfb3 | 7.44973 | 1.43805 | | Not Sig | | -5.180438789 | Not Sig | Not Sig |
| Pgbd5 | 14.8759 | 10.785 | | Not Sig | | -1.379313862 | Not Sig | Not Sig |
| Phactr1 | 69.0186 | 25.0224 | 32.8307 | 57.3759 | 49.2827 | -2.758272588 | 1.747629505 | 1.501116333 |
| Phf2 | 23.221 | 17.382 | | Not Sig | | -1.335922218 | Not Sig | Not Sig |
| Pik3c2a | 17.9164 | 11.548 | 7.26075 | 10.9783 | 8.82542 | -1.551472116 | 1.512006335 | 1.215497022 |
| Pkd1 | 26.1207 | 14.3124 | | Not Sig | | -1.825039826 | Not Sig | Not Sig |
| Pla2g6 | 22.8353 | 18.6452 | | Not Sig | | -1.22472808 | Not Sig | Not Sig |
| Plxna2 | 8.3447 | 6.01584 | | Not Sig | | -1.387121333 | Not Sig | Not Sig |
| Pold2 | 14.0076 | 9.95801 | 15.4229 | 18.3486 | 20.33 | -1.406666593 | 1.189698435 | 1.318169735 |
| Pon3 | 18.4778 | 12.8534 | | Not Sig | | -1.437580718 | Not Sig | Not Sig |
| Ppp1r10 | 27.208 | 15.9978 | | Not Sig | | -1.700733851 | Not Sig | Not Sig |
| Prkacb | 220.414 | 139.116 | 90.6106 | 136.046 | 109.011 | -1.584390005 | 1.501435814 | 1.203071164 |
| Prpf38b | 31.3057 | 25.6634 | 35.0402 | 28.4837 | 26.3318 | -1.219857852 | -1.230184281 | -1.330717991 |
| Prrc1 | 48.3924 | 30.2309 | 25.4511 | 37.5008 | 34.8428 | -1.600759488 | 1.473445156 | 1.369009591 |
| Ptprb | 7.08435 | 4.14687 | 5.21231 | 3.5707 | 3.23375 | -1.708360764 | -1.459744588 | -1.611846927 |
| Ptprr | 8.50349 | 6.68613 | | Not Sig | | -1.271810449 | Not Sig | Not Sig |

FIG. 24 (cont.)

| | | | | | | | | | |
|---|---|---|---|---|---|---|---|---|---|
| Rab3a | 94.907 | 69.9858 | 68.2508 | 80.0572 | 89.2382 | | -1.356089378 | 1.172985518 | 1.307504088 |
| Rab6 | 55.1448 | 36.779 | | Not Sig | | | -1.499355611 | Not Sig | Not Sig |
| Rasl10b | 6.78376 | 1.7977 | 0.498137 | 1.27922 | 1.67878 | | -3.773577349 | 2.568008399 | 3.370117056 |
| Rgmb | 17.2044 | 10.5916 | 8.22918 | 9.39357 | 11.399 | | -1.62434382 | 1.141495264 | 1.385192692 |
| Rgs16 | 71.7057 | 13.1007 | 41.2126 | 30.281 | 26.9749 | | -5.473425084 | -1.361005251 | -1.527812893 |
| Rgs7bp | 5.33898 | 1.45658 | 0.90067 | 1.44362 | 1.4088 | | -3.665421741 | 1.602829005 | 1.564168896 |
| Rhou | 7.46556 | 3.45829 | 6.94323 | 2.88437 | 4.12978 | | -2.158743194 | -2.407191172 | -1.68125905 |
| Rnf128 | 24.1546 | 16.7289 | 14.7398 | 21.1166 | 17.6548 | | -1.443884535 | 1.432624595 | 1.197763877 |
| Rnf214 | 12.2482 | 9.20299 | | Not Sig | | | -1.330893547 | Not Sig | Not Sig |
| Rpap1 | 8.71154 | 6.98598 | | Not Sig | | | -1.247003284 | Not Sig | Not Sig |
| Sec23a | 10.7347 | 8.19464 | | Not Sig | | | -1.309966027 | Not Sig | Not Sig |
| Sepn1 | 17.4655 | 14.1871 | | Not Sig | | | -1.231083167 | Not Sig | Not Sig |
| Serpina7 | 55.4226 | 4.50294 | 0.873253 | 2.69746 | 3.97375 | | -12.30809205 | 3.088978795 | 4.550513998 |
| Setd5 | 29.8269 | 23.5501 | | Not Sig | | | -1.266529654 | Not Sig | Not Sig |
| Sf1 | 43.6638 | 34.4152 | | Not Sig | | | -1.268735907 | Not Sig | Not Sig |
| Sgpp2 | 30.135 | 23.8692 | 19.9883 | 27.2282 | 26.9038 | | -1.262505656 | 1.362206891 | 1.345977397 |
| Shroom3 | 15.6599 | 10.0546 | | Not Sig | | | -1.557486126 | Not Sig | Not Sig |
| Slc12a7 | 24.8973 | 13.5932 | 23.6283 | 31.1346 | 33.1615 | | -1.831599623 | 1.317682609 | 1.403465336 |
| Slc22a17 | 56.3278 | 37.0979 | 62.633 | 63.2263 | 78.178 | | -1.518355486 | 1.009472642 | 1.248191848 |
| Slc2a2 | 255.322 | 174.578 | 129.689 | 224.558 | 161.342 | | -1.462509595 | 1.731511539 | 1.244068502 |
| Slc30a8 | 560.703 | 362.316 | 359.411 | 504.51 | 497.351 | | -1.547552413 | 1.403713298 | 1.383794597 |
| Slc35a3 | 11.0472 | 8.60696 | | Not Sig | | | -1.283519384 | Not Sig | Not Sig |
| Slc38a2 | 39.5828 | 28.0707 | | Not Sig | | | -1.410110899 | Not Sig | Not Sig |
| Slc38a4 | 105.447 | 66.8892 | 62.6131 | 86.7734 | 66.8933 | | -1.576442834 | 1.385866536 | 1.068359497 |
| Slc4a8 | 4.81502 | 2.98288 | | Not Sig | | | -1.614218473 | Not Sig | Not Sig |
| Slc6a17 | 22.0916 | 13.2049 | 8.88547 | 16.0417 | 17.0713 | | -1.672985028 | 1.805385646 | 1.921260215 |
| Slc7a2 | 87.8929 | 50.8452 | 65.3615 | 55.2795 | 51.7492 | | -1.728637118 | -1.182382257 | -1.26304368 |
| Slitrk6 | 41.5713 | 16.5625 | 18.3001 | 25.7992 | 16.9973 | | -2.509965283 | 1.409784646 | 0.928809132 |
| Sphkap | 72.7225 | 47.8869 | 24.2749 | 41.2012 | 29.1947 | | -1.518630356 | 1.697275787 | 1.202670248 |
| Spon2 | 22.8584 | 9.37844 | | Not Sig | | | -2.437334994 | Not Sig | Not Sig |
| Spp1 | 37.3284 | 17.6811 | 9.52709 | 15.2881 | 14.3416 | | -2.111203488 | 1.604697762 | 1.505349482 |
| Srebf2 | 34.4395 | 24.5506 | 28.9777 | 33.7997 | 38.0376 | | -1.402796673 | 1.166403821 | 1.312650762 |
| Srrm2 | 133.06 | 63.9805 | 66.948 | 99.77 | 87.6186 | | -2.079696157 | 1.490261098 | 1.308756049 |

FIG. 24 (cont.)

| | | | | | | | | |
|---|---|---|---|---|---|---|---|---|
| St18 | 33.0629 | 18.7359 | | Not Sig | | -1.764681707 | Not Sig | Not Sig |
| St6gal1 | 23.3175 | 15.5199 | 13.8251 | 12.6427 | 17.1631 | -1.502425918 | -1.093524326 | 1.241444908 |
| Stard13 | 13.0067 | 9.76504 | | Not Sig | | -1.33196587 | Not Sig | Not Sig |
| Steap2 | 9.35877 | 5.78986 | 3.56094 | 5.17222 | 4.18342 | -1.61640696 | 1.452487265 | 1.174807775 |
| Stim1 | 38.1765 | 26.6757 | 19.7857 | 29.9365 | 29.1152 | -1.431133953 | 1.513037194 | 1.471527416 |
| Stxbp6 | 14.4466 | 11.0765 | 5.50369 | 8.40917 | 8.91803 | -1.30425676 | 1.527914908 | 1.620372877 |
| Sult1d1 | 14.4305 | 6.87505 | 14.7663 | 16.3236 | 10.9147 | -2.098966553 | 1.105463115 | -1.352881893 |
| Syt4 | 57.6483 | 46.5599 | 13.1072 | 33.2258 | 24.8161 | -1.238153432 | 2.534927368 | 1.893318176 |
| Syt5 | 27.5254 | 20.3379 | 31.5767 | 33.6418 | 24.5242 | -1.353404235 | 1.065399488 | -1.287573091 |
| Tagln3 | 9.86072 | 1.22666 | 2.61309 | 1.68363 | 1.2522 | -8.038674123 | -1.552057162 | -2.086799233 |
| Tardbp | 33.5244 | 24.927 | | Not Sig | | -1.344903117 | Not Sig | Not Sig |
| Tmcc2 | 16.7354 | 13.6035 | 8.77062 | 11.3347 | 16.4608 | -1.230227515 | 1.292348774 | 1.876811445 |
| Tmco3 | 23.4165 | 18.1124 | 12.7881 | 19.3568 | 19.9871 | -1.292843577 | 1.513657228 | 1.562945238 |
| Tmem104 | 11.4836 | 8.798 | 5.95392 | 8.80184 | 9.32203 | -1.305251193 | 1.478326884 | 1.565696214 |
| Tmem131 | 16.3433 | 11.4033 | | Not Sig | | -1.433207931 | Not Sig | Not Sig |
| Tmem33 | 14.6397 | 11.2915 | | Not Sig | | -1.296523934 | Not Sig | Not Sig |
| Tmem39a | 36.623 | 27.8941 | 42.6131 | 51.475 | 54.1562 | -1.312929974 | 1.207961871 | 1.270881489 |
| Tmem63a | 35.005 | 26.8485 | | Not Sig | | -1.303797233 | Not Sig | Not Sig |
| Tmem65 | 77.7067 | 51.1461 | 50.6459 | 82.5934 | 59.7635 | -1.519308413 | 1.630801309 | 1.180026419 |
| Tmod2 | 44.6613 | 20.5982 | 11.8524 | 19.0237 | 14.9155 | -2.168213727 | 1.605050454 | 1.25843711 |
| Tnks | 15.1535 | 8.72498 | 1.77954 | 2.7647 | 2.55586 | -1.736794812 | 1.55360374 | 1.43624757 |
| Trim9 | 13.7408 | 4.52952 | 3.92438 | 7.40335 | 5.51138 | -3.033610625 | 1.886501817 | 1.404395089 |
| Try4 | 183.858 | 34.2336 | 5.93153 | 0.843135 | 15.5646 | -5.370688446 | -7.03508928 | 2.624044724 |
| Tsc22d2 | 5.13119 | 3.79644 | 3.66194 | 3.05974 | 2.778 | -1.351579374 | -1.196814108 | -1.318192945 |
| Tubb5 | 37.7928 | 30.0347 | 64.3536 | 43.3765 | 37.0859 | -1.258304561 | -1.483605178 | -1.735257874 |
| Uba1 | 86.9534 | 68.6018 | 73.2495 | 92.2258 | 86.235 | -1.267509016 | 1.259063884 | 1.177277661 |
| Ubr2 | 23.6416 | 17.1097 | 12.8175 | 17.8569 | 18.2887 | -1.381765899 | 1.393165594 | 1.426853911 |
| Unc13a | 14.3286 | 8.57029 | 13.5707 | 16.4524 | 18.6662 | -1.671892083 | 1.212347189 | 1.375478052 |
| Unc79 | 9.01601 | 5.63415 | 7.18126 | 9.19407 | 8.57949 | -1.60024316 | 1.280286468 | 1.194705386 |
| Unc80 | 26.4369 | 15.3145 | 12.8799 | 11.9871 | 10.6123 | -1.726265957 | -1.074480066 | -1.213676583 |

FIG. 24 (cont.)

| | | | | | | | | |
|---|---|---|---|---|---|---|---|---|
| Ush2a | 8.39914 | 2.1391 | 1.49209 | 2.94145 | 2.76603 | -3.9264831 | 1.971362317 | 1.853795683 |
| Usp19 | 38.0482 | 29.6726 | | Not Sig | | -1.282267142 | Not Sig | Not Sig |
| Vamp1 | 4.67594 | 3.38108 | 4.04843 | 5.4964 | 6.79806 | -1.382972305 | 1.357662106 | 1.679184276 |
| Vamp2 | 137.852 | 95.5901 | 100.179 | 128.581 | 126.937 | -1.442115868 | 1.283512513 | 1.267101888 |
| Vdr | 58.432 | 44.1524 | 34.5757 | 45.0657 | 41.863 | -1.323416168 | 1.303392267 | 1.210763629 |
| Vim | 8.41765 | 6.35639 | 25.7709 | 10.5881 | 11.9549 | -1.32428155 | -2.433949434 | -2.155676752 |
| Vsnl1 | 7.67847 | 2.87052 | 3.44083 | 5.02711 | 5.14014 | -2.674940429 | 1.461016673 | 1.493866306 |
| Xpo4 | 5.25172 | 3.35285 | | Not Sig | | -1.56634505 | Not Sig | Not Sig |
| Xpo6 | 20.1119 | 16.5183 | | Not Sig | | -1.217552654 | Not Sig | Not Sig |
| Yrdc | 30.2803 | 22.3198 | 26.3883 | 35.3824 | 35.7955 | -1.356656422 | 1.340836659 | 1.356491324 |
| Zfp398 | 8.78592 | 6.71862 | | Not Sig | | -1.307697116 | Not Sig | Not Sig |
| Zfp462 | 4.75445 | 3.12855 | 1.4719 | 2.40179 | 3.36528 | -1.519697623 | 1.631761669 | 2.286350975 |
| Zfp704 | 7.48129 | 5.61608 | 3.88342 | 3.15805 | 3.06466 | -1.332119557 | -1.229689207 | -1.267161773 |

FIG. 24 (cont.)

| | RPKM (Rawdata) | | | | | Fold Change | | |
|---|---|---|---|---|---|---|---|---|
| Up regulated genes (239 genes) | Control | βERRγKO | Neonate (2w) | Adult (6w) | Adult (12w) | βERRγKO/Control | 6w/2w | 12w/2w |
| 0610012G03Rik | 15.414 | 20.2099 | 9.90966 | 12.4086 | 15.4649 | 1.311139224 | 1.252172123 | 1.560588355 |
| 1110008P14Rik | 49.7967 | 60.7598 | | Not Sig | | 1.220157159 | Not Sig | Not Sig |
| 1110038D17Rik | 12.6637 | 15.4145 | Not Sig | | | 1.217219296 | Not Sig | Not Sig |
| 1110049F12Rik | 51.0528 | 61.9963 | 43.1638 | 55.1008 | 58.0915 | 1.214356509 | 1.276551184 | 1.345838411 |
| 1500031L02Rik | 14.3875 | 22.7395 | | Not Sig | | 1.58050391 | Not Sig | Not Sig |
| 1700021F05Rik | 9.99043 | 14.1638 | | Not Sig | | 1.417736774 | Not Sig | Not Sig |
| 1810030N24Rik | 13.5557 | 19.0271 | | Not Sig | | 1.403623568 | Not Sig | Not Sig |
| 1810063B05Rik | 16.3224 | 22.1608 | | Not Sig | | 1.357692496 | Not Sig | Not Sig |
| 2010007H12Rik | 11.4505 | 14.9327 | 10.6734 | 10.5537 | 16.7034 | 1.304108991 | -1.011341994 | 1.564955872 |
| 2310003F16Rik | 57.2244 | 71.9594 | | Not Sig | | 1.257495055 | Not Sig | Not Sig |
| 2310016M24Rik | 66.4634 | 90.9465 | | Not Sig | | 1.368369659 | Not Sig | Not Sig |
| 2700060E02Rik | 30.2383 | 39.2045 | 45.1204 | 42.5177 | 35.4304 | 1.296517992 | -1.061214506 | -1.273493949 |
| 6720456B07Rik | 74.6612 | 97.21 | | Not Sig | | 1.302014969 | Not Sig | Not Sig |
| 8430427H17Rik | 4.6787 | 6.68173 | 5.97985 | 3.87836 | 4.13252 | 1.428116785 | -1.541850163 | -1.44702264 |
| Acaa2 | 15.2081 | 27.7053 | | Not Sig | | 1.821746306 | Not Sig | Not Sig |
| Acadm | 10.8574 | 13.7045 | | Not Sig | | 1.262226684 | Not Sig | Not Sig |
| Adipor1 | 64.8056 | 80.9487 | | Not Sig | | 1.249100386 | Not Sig | Not Sig |
| Aes | 284.802 | 376.687 | | Not Sig | | 1.32262765 | Not Sig | Not Sig |
| Akr1a4 | 192.321 | 238.967 | | Not Sig | | 1.242542416 | Not Sig | Not Sig |
| Aldh4a1 | 7.89079 | 9.68966 | 7.29874 | 8.34643 | 10.1586 | 1.227970837 | 1.143543954 | 1.391829275 |
| Amigo2 | 35.9006 | 68.6703 | | Not Sig | | 1.912789758 | Not Sig | Not Sig |
| Anp32a | 32.4532 | 47.738 | 49.3267 | 33.3003 | 35.7332 | 1.470979749 | -1.481268938 | -1.380416531 |
| Arhgap12 | 9.1493 | 11.0534 | | Not Sig | | 1.208114282 | Not Sig | Not Sig |
| Arl1 | 98.6545 | 132.199 | 111.913 | 145.023 | 122.532 | 1.340019969 | 1.295854816 | 1.094886206 |
| Arl6ip1 | 42.1104 | 55.1235 | 43.9374 | 40.8066 | 32.03 | 1.309023424 | -1.076722883 | -1.371757727 |
| Arl8a | 35.8759 | 45.9363 | | Not Sig | | 1.280422233 | Not Sig | Not Sig |
| Atp5c1 | 85.5261 | 116.099 | 152.355 | 117.198 | 110.145 | 1.357468656 | -1.299979522 | -1.383222116 |
| Atp5h | 132.538 | 168.266 | | Not Sig | | 1.269567973 | Not Sig | Not Sig |
| Atp6v1d | 59.1313 | 100.511 | | Not Sig | | 1.69979351 | Not Sig | Not Sig |
| Aurkaip1 | 51.5984 | 83.3468 | 46.256 | 57.7979 | 64.2099 | 1.615298149 | 1.249522224 | 1.388142079 |

FIG. 24 (cont.)

| | | | | | | | | |
|---|---|---|---|---|---|---|---|---|
| Bbs4 | 8.5114 | 11.9368 | | Not Sig | | 1.402448481 | Not Sig | Not Sig |
| Bid | 2.10064 | 5.24085 | | Not Sig | | 2.494882512 | Not Sig | Not Sig |
| Blvrb | 4.70932 | 7.88923 | | Not Sig | | 1.675237614 | Not Sig | Not Sig |
| Bri3 | 18.8396 | 29.8974 | 29.3722 | 31.2104 | 39.3064 | 1.586944521 | 1.062582987 | 1.338217771 |
| Casp8 | 4.73385 | 6.33805 | | Not Sig | | 1.338878503 | Not Sig | Not Sig |
| Ccng1 | 35.1088 | 46.4276 | 16.4971 | 20.8704 | 17.2053 | 1.322392107 | 1.265095077 | 1.042928757 |
| Ccm4l | 18.643 | 23.248 | 9.41624 | 18.4849 | 15.5113 | 1.247009601 | 1.963087177 | 1.647292337 |
| Cd82 | 28.5858 | 46.2414 | 22.922 | 31.7105 | 46.6417 | 1.617635329 | 1.383408952 | 2.034800628 |
| Cdc42ep4 | 6.94762 | 9.69234 | 8.30772 | 5.91092 | 5.22996 | 1.395059027 | -1.405486794 | -1.588486336 |
| Cdkl2 | 9.64155 | 12.0715 | | Not Sig | | 1.252028979 | Not Sig | Not Sig |
| Cdkn1a | 15.9428 | 57.232 | 24.2714 | 8.78183 | 10.4379 | 3.589833655 | -2.763820297 | -2.325314479 |
| Cetn2 | 28.5594 | 39.4668 | | Not Sig | | 1.381919788 | Not Sig | Not Sig |
| Cfl1 | 184.353 | 238.97 | 294.504 | 234.24 | 241.133 | 1.296263147 | -1.25727459 | -1.221334284 |
| Chchd6 | 13.3895 | 20.6048 | 14.0201 | 17.9683 | 20.1529 | 1.538877479 | 1.281609974 | 1.43742912 |
| Chmp2a | 75.5396 | 108.388 | 109.616 | 94.4713 | 90.1247 | 1.434850065 | -1.160310062 | -1.216270345 |
| Chmp7 | 29.5262 | 39.2326 | | Not Sig | | 1.328738544 | Not Sig | Not Sig |
| Chrd | 2.68179 | 5.12149 | 1.84398 | 3.53611 | 4.31325 | 1.909728204 | 1.917650951 | 2.339098038 |
| Ckb | 48.9603 | 81.1341 | 27.3359 | 56.6113 | 63.3398 | 1.657140581 | 2.070950655 | 2.317092175 |
| Cldn23 | 1.5539 | 5.33319 | 3.49217 | 1.68867 | 1.8057 | 3.432132055 | -2.068000261 | -1.933970205 |
| Cldn3 | 30.1727 | 50.6158 | 17.1788 | 20.7923 | 25.598 | 1.677536316 | 1.210346474 | 1.49009244 |
| Clta | 100.727 | 156.754 | | Not Sig | | 1.556226235 | Not Sig | Not Sig |
| Cmc1 | 9.03762 | 12.2205 | | Not Sig | | 1.352181216 | Not Sig | Not Sig |
| Cmtm8 | 7.55813 | 17.3693 | | Not Sig | | 2.298094899 | Not Sig | Not Sig |
| Cops2 | 25.4079 | 31.6631 | | Not Sig | | 1.246191145 | Not Sig | Not Sig |
| Cops5 | 35.6146 | 44.1538 | 53.7895 | 45.2428 | 43.2127 | 1.239766837 | -1.188907406 | -1.244761378 |
| Coq2 | 26.9581 | 33.9121 | | Not Sig | | 1.257955865 | Not Sig | Not Sig |
| Cox5a | 38.0889 | 48.3497 | | Not Sig | | 1.26939082 | Not Sig | Not Sig |
| Cox6c | 137.571 | 188.96 | | Not Sig | | 1.373545297 | Not Sig | Not Sig |
| Cpt2 | 26.2337 | 34.1538 | | Not Sig | | 1.301905564 | Not Sig | Not Sig |
| Csde1 | 38.6778 | 48.4602 | | Not Sig | | 1.25292028 | Not Sig | Not Sig |
| Csrp1 | 17.866 | 24.0331 | | Not Sig | | 1.345186388 | Not Sig | Not Sig |
| Cstb | 67.6299 | 102.532 | | Not Sig | | 1.51607499 | Not Sig | Not Sig |

FIG. 24 (cont.)

| | | | | | | | | |
|---|---|---|---|---|---|---|---|---|
| Ctns | 12.9949 | 18.6975 | 10.2786 | 13.4476 | 14.6884 | 1.438833696 | 1.30831047 | 1.429027299 |
| Ctsf | 41.4721 | 60.1643 | | Not Sig | | 1.45071747 | Not Sig | Not Sig |
| Cuta | 57.0575 | 79.3167 | | Not Sig | | 1.39011874 | Not Sig | Not Sig |
| Cux2 | 6.00238 | 14.4749 | 5.82255 | 6.80048 | 8.41602 | 2.411526761 | 1.167955621 | 1.445418245 |
| Cyb5 | 47.2456 | 81.0195 | | Not Sig | | 1.714858103 | Not Sig | Not Sig |
| D16H22S680E | 8.03805 | 11.668 | 8.10718 | 10.7851 | 11.7187 | 1.451595847 | 1.33031461 | 1.445471792 |
| Dapp1 | 4.11862 | 12.5393 | 4.16605 | 6.65177 | 4.33129 | 3.04453919 | 1.596661106 | 1.03966347 |
| Dcxr | 4.03559 | 6.19052 | 3.35648 | 5.36649 | 7.27961 | 1.5339814 | 1.598844623 | 2.168822695 |
| Ddx25 | 11.6057 | 18.2594 | 5.59023 | 10.0139 | 12.7729 | 1.573313113 | 1.791321645 | 2.284861267 |
| Dpy30 | 34.5172 | 48.0583 | 58.6751 | 44.9789 | 43.723 | 1.392300071 | -1.304502778 | -1.341973332 |
| Dtnbp1 | 11.2386 | 16.7447 | | Not Sig | | 1.489927571 | Not Sig | Not Sig |
| Dusp26 | 20.9928 | 62.2294 | 15.3716 | 14.9974 | 21.7226 | 2.964321101 | -1.024950992 | 1.413164537 |
| Efna5 | 1.86885 | 5.87215 | 0.994186 | 1.33023 | 1.8584 | 3.142119485 | 1.338009185 | 1.869267924 |
| Egr1 | 68.4614 | 151.395 | 407.947 | 112.804 | 134.219 | 2.211392113 | -3.616423176 | -3.039413198 |
| Eif3i | 48.0435 | 69.8274 | | Not Sig | | 1.453420338 | Not Sig | Not Sig |
| Eif3k | 68.7309 | 92.7745 | 115.497 | 90.3131 | 108.245 | 1.349822278 | -1.278851019 | -1.066996166 |
| Elf3 | 7.62901 | 10.1936 | 13.074 | 8.37591 | 11.1494 | 1.336162884 | -1.560905024 | -1.172619154 |
| Emb | 142.937 | 201.057 | | Not Sig | | 1.406612703 | Not Sig | Not Sig |
| Enc1 | 6.32173 | 11.5325 | 7.09699 | 3.8183 | 4.01509 | 1.824263295 | -1.858677946 | -1.767579307 |
| Enpp5 | 74.4136 | 111.145 | 45.9972 | 63.7095 | 62.0501 | 1.493611383 | 1.385073439 | 1.34899733 |
| Fads1 | 13.1168 | 20.5959 | 12.2808 | 14.5953 | 15.4058 | 1.570192425 | 1.188464921 | 1.25446225 |
| Fam134b | 10.9794 | 17.5342 | | Not Sig | | 1.597008944 | Not Sig | Not Sig |
| Fbxo44 | 22.7789 | 32.5832 | 22.4087 | 27.0072 | 34.0368 | 1.430411477 | 1.205210476 | 1.518910066 |
| Fdxr | 5.38788 | 6.97467 | | Not Sig | | 1.294511014 | Not Sig | Not Sig |
| Fez2 | 7.21633 | 10.0224 | | Not Sig | | 1.388850011 | Not Sig | Not Sig |
| Gabarapl2 | 67.3287 | 84.7982 | | Not Sig | | 1.259465874 | Not Sig | Not Sig |
| Gad1 | 40.0143 | 54.9117 | 30.2802 | 67.4267 | 59.3554 | 1.372301902 | 2.22675874 | 1.960205018 |
| Gadd45b | 25.4839 | 39.6014 | 34.2172 | 13.9259 | 18.517 | 1.553977217 | -2.457090745 | -1.847880326 |
| Gadd45g | 64.5888 | 145.697 | 126.373 | 76.5327 | 102.538 | 2.255762609 | -1.651228821 | -1.232450409 |
| Gata6 | 3.7646 | 6.09771 | 7.89917 | 3.83378 | 4.65043 | 1.619749774 | -2.060412961 | -1.698589163 |
| Gclm | 29.9711 | 39.0637 | | Not Sig | | 1.303378922 | Not Sig | Not Sig |
| Gde1 | 106.43 | 137.766 | 77.4817 | 109.723 | 105.633 | 1.294428263 | 1.416115031 | 1.363328373 |
| Gdpd1 | 5.27276 | 9.59952 | 3.29087 | 3.93944 | 4.85448 | 1.82058732 | 1.197081623 | 1.475135754 |
| Ghitm | 55.6061 | 84.1214 | 42.1443 | 62.0954 | 59.9798 | 1.512808847 | 1.473399724 | 1.423200765 |
| Gkap1 | 8.66446 | 12.1002 | | Not Sig | | 1.396532502 | Not Sig | Not Sig |
| Glrx5 | 66.2952 | 80.4833 | | Not Sig | | 1.214013986 | Not Sig | Not Sig |
| Glt25d1 | 20.054 | 25.2541 | 21.1905 | 23.5373 | 25.5962 | 1.259304877 | 1.110747741 | 1.207909205 |

FIG. 24 (cont.)

| | | | | | | | | |
|---|---|---|---|---|---|---|---|---|
| Gnb2l1 | 251.048 | 340.801 | | Not Sig | | 1.357513304 | Not Sig | Not Sig |
| Gnb5 | 13.8412 | 19.2118 | | Not Sig | | 1.38801549 | Not Sig | Not Sig |
| Gnpda1 | 14.9176 | 24.3773 | 17.2946 | 27.557 | 29.5302 | 1.634130155 | 1.593387531 | 1.707480948 |
| Gnptg | 83.5342 | 106.333 | 82.1933 | 111.046 | 110.277 | 1.272927735 | 1.351034695 | 1.341678701 |
| Grn | 34.2002 | 46.7405 | 32.6402 | 38.4522 | 42.0027 | 1.366673294 | 1.178062634 | 1.286839541 |
| Gstm1 | 39.4713 | 53.5473 | 30.2107 | 31.1983 | 46.177 | 1.356613539 | 1.032690404 | 1.528498181 |
| Gsto1 | 10.4921 | 24.0014 | | Not Sig | | 2.287568742 | Not Sig | Not Sig |
| H2-T23 | 24.3026 | 36.2212 | 30.03 | 36.535 | 51.336 | 1.490424893 | 1.216616717 | 1.709490509 |
| H2afj | 21.8637 | 26.7422 | | Not Sig | | 1.223132407 | Not Sig | Not Sig |
| Hdac11 | 35.451 | 44.9124 | 26.2823 | 30.9792 | 36.5151 | 1.266886689 | 1.178709626 | 1.389341876 |
| Hexb | 22.2766 | 31.3515 | | Not Sig | | 1.407373657 | Not Sig | Not Sig |
| Hmgcl | 17.4611 | 23.1472 | | Not Sig | | 1.32564386 | Not Sig | Not Sig |
| Hn1 | 8.66415 | 11.324 | 20.3921 | 12.2235 | 13.2857 | 1.306994916 | -1.668270135 | -1.534890898 |
| Id2 | 9.45023 | 14.6508 | 23.3636 | 8.98573 | 9.84784 | 1.550311474 | -2.600078124 | -2.372459341 |
| Igtp | 5.32163 | 6.64187 | | Not Sig | | 1.248089401 | Not Sig | Not Sig |
| Kctd2 | 21.6909 | 31.9356 | 20.426 | 22.7974 | 25.8735 | 1.472304054 | 1.116097131 | 1.266694409 |
| Klhdc2 | 35.4319 | 44.4183 | | Not Sig | | 1.253624559 | Not Sig | Not Sig |
| Krt18 | 90.0098 | 148.298 | | Not Sig | | 1.647576153 | Not Sig | Not Sig |
| Krt8 | 52.1851 | 73.6404 | 91.3776 | 74.4854 | 79.615 | 1.411138428 | -1.226785383 | -1.147743516 |
| Lamp2 | 87.9182 | 132.811 | | Not Sig | | 1.510620099 | Not Sig | Not Sig |
| Laptm4b | 40.5371 | 69.6386 | | Not Sig | | 1.717897926 | Not Sig | Not Sig |
| Litaf | 3.35025 | 5.39367 | 6.84424 | 3.15962 | 4.35522 | 1.609930602 | -2.166159222 | -1.571502703 |
| Lyrm5 | 16.093 | 21.1698 | | Not Sig | | 1.315466352 | Not Sig | Not Sig |
| Mad2l2 | 7.10864 | 11.1008 | | Not Sig | | 1.561592653 | Not Sig | Not Sig |
| Map1lc3b | 67.911 | 98.372 | | Not Sig | | 1.448542946 | Not Sig | Not Sig |
| Mat2b | 36.655 | 44.9752 | 24.8411 | 31.1084 | 31.1071 | 1.226986769 | 1.252295591 | 1.252243258 |
| Mbp | 18.5342 | 25.8452 | 21.3244 | 14.1578 | 18.7075 | 1.394459971 | -1.506194465 | -1.139885073 |
| Mfsd1 | 20.9133 | 25.5732 | | Not Sig | | 1.222819928 | Not Sig | Not Sig |
| Mif | 44.9428 | 68.9505 | | Not Sig | | 1.534183451 | Not Sig | Not Sig |
| Minpp1 | 9.00822 | 13.8 | | Not Sig | | 1.531934167 | Not Sig | Not Sig |
| Mknk2 | 12.4038 | 15.1313 | | Not Sig | | 1.219892291 | Not Sig | Not Sig |
| Mlycd | 22.3319 | 32.3037 | 17.763 | 19.5042 | 26.275 | 1.446527165 | 1.098023982 | 1.479198334 |
| Mrpl20 | 42.5349 | 53.254 | | Not Sig | | 1.252007175 | Not Sig | Not Sig |
| Mrpl30 | 34.7462 | 59.4493 | | Not Sig | | 1.710958321 | Not Sig | Not Sig |
| Mrps15 | 16.2628 | 21.5697 | | Not Sig | | 1.326321421 | Not Sig | Not Sig |
| Mrps18a | 25.6963 | 39.0159 | | Not Sig | | 1.518346999 | Not Sig | Not Sig |
| Mrps24 | 17.2097 | 24.3844 | | Not Sig | | 1.41689861 | Not Sig | Not Sig |

FIG. 24 (cont.)

| | | | | | | | | |
|---|---|---|---|---|---|---|---|---|
| Mrps35 | 12.8342 | 16.0892 | | Not Sig | | 1.253619236 | Not Sig | Not Sig |
| Mtch2 | 25.2081 | 30.8086 | | Not Sig | | 1.222170651 | Not Sig | Not Sig |
| Naca | 69.544 | 109.03 | 207.869 | 175.012 | 173.15 | 1.567784424 | -1.187741412 | -1.200514005 |
| Nacc2 | 2.73609 | 5.3643 | | Not Sig | | 1.960571472 | Not Sig | Not Sig |
| Ndufb2 | 74.369 | 105.405 | | Not Sig | | 1.417324423 | Not Sig | Not Sig |
| Ndufb5 | 40.9798 | 53.892 | | Not Sig | | 1.315086945 | Not Sig | Not Sig |
| Ndufs4 | 17.093 | 23.1963 | 29.2463 | 21.9117 | 19.0936 | 1.357064295 | -1.334734411 | -1.531733146 |
| Ndufs7 | 52.1768 | 69.2865 | 84.3961 | 75.5645 | 110.027 | 1.327917772 | -1.116874988 | 1.303697683 |
| Npc2 | 52.833 | 78.3676 | | Not Sig | | 1.483307781 | Not Sig | Not Sig |
| Npm1 | 79.1478 | 123.376 | 152.428 | 113.284 | 101.791 | 1.558805172 | -1.345538646 | -1.497460483 |
| Nqo1 | 2.42708 | 6.28046 | | Not Sig | | 2.587660893 | Not Sig | Not Sig |
| Nudt10 | 2.96342 | 9.15731 | 4.88054 | 2.60977 | 2.76866 | 3.090115475 | -1.870103496 | -1.762780551 |
| Nudt11 | 3.87198 | 10.9082 | 8.46228 | 3.65891 | 4.84558 | 2.817214965 | -2.312787142 | -1.746391557 |
| Odc1 | 15.5376 | 33.2556 | 34.8959 | 34.7191 | 28.5353 | 2.140330553 | -1.005092298 | -1.222902861 |
| Pacsin1 | 8.37591 | 11.2387 | 6.30583 | 7.1368 | 9.12967 | 1.341788534 | 1.131778053 | 1.447814166 |
| Pcbd2 | 21.9023 | 34.041 | | Not Sig | | 1.554220333 | Not Sig | Not Sig |
| Pdzrn3 | 2.01234 | 5.04708 | 1.1604 | 0.307828 | 0.534963 | 2.508065237 | -3.76963759 | -2.169121977 |
| Pfdn4 | 10.2467 | 14.4678 | | Not Sig | | 1.411947261 | Not Sig | Not Sig |
| Pfkfb4 | 2.75876 | 5.27913 | | Not Sig | | 1.913587989 | Not Sig | Not Sig |
| Phax | 16.1564 | 21.5962 | | Not Sig | | 1.336696294 | Not Sig | Not Sig |
| Phlda3 | 6.04611 | 8.06462 | | Not Sig | | 1.333852676 | Not Sig | Not Sig |
| Pigx | 12.4658 | 19.8443 | | Not Sig | | 1.591899437 | Not Sig | Not Sig |
| Plekhg3 | 19.6081 | 24.1269 | 16.647 | 20.3359 | 20.9705 | 1.230455781 | 1.221595483 | 1.259716465 |
| Pomp | 62.5456 | 81.8451 | | Not Sig | | 1.30856687 | Not Sig | Not Sig |
| Prdx2 | 97.6562 | 143.546 | 177.934 | 140.784 | 149.248 | 1.469911793 | -1.263879418 | -1.192203581 |
| Prdx5 | 70.6539 | 91.4004 | | Not Sig | | 1.293635595 | Not Sig | Not Sig |
| Prr13 | 50.8138 | 71.351 | 53.169 | 51.6382 | 68.5461 | 1.404165797 | -1.02964472 | 1.289211759 |
| Psma5 | 19.0199 | 24.5024 | | Not Sig | | 1.288250727 | Not Sig | Not Sig |
| Psma7 | 69.8037 | 89.1599 | | Not Sig | | 1.277294757 | Not Sig | Not Sig |
| Psmb1 | 73.7119 | 101.582 | | Not Sig | | 1.378094989 | Not Sig | Not Sig |
| Psmb10 | 8.28877 | 12.4358 | 18.4903 | 12.8963 | 26.3852 | 1.500319106 | -1.433767825 | 1.426975225 |
| Psmb2 | 64.3792 | 80.2304 | | Not Sig | | 1.246216169 | Not Sig | Not Sig |
| Psmc3 | 23.7022 | 30.8104 | | Not Sig | | 1.299896212 | Not Sig | Not Sig |
| Psmc5 | 44.3386 | 56.0626 | | Not Sig | | 1.264419716 | Not Sig | Not Sig |
| Psme1 | 28.9942 | 38.1181 | 74.4021 | 50.3919 | 68.3722 | 1.314680177 | -1.476469433 | -1.088192277 |
| Ptp4a2 | 25.0353 | 30.1633 | 25.9664 | 23.4905 | 20.112 | 1.204830779 | -1.105400055 | -1.291089897 |
| Ptp4a3 | 16.8319 | 21.1035 | | Not Sig | | 1.253780025 | Not Sig | Not Sig |

FIG. 24 (cont.)

| | | | | | | | | |
|---|---|---|---|---|---|---|---|---|
| Pxmp4 | 8.39076 | 11.571 | | Not Sig | | 1.379016919 | Not Sig | Not Sig |
| Rab1b | 77.8716 | 103.027 | 78.5083 | 79.9579 | 98.6206 | 1.323036897 | 1.01846429 | 1.256180557 |
| Rab5c | 58.7537 | 71.5786 | | Not Sig | | 1.218282423 | Not Sig | Not Sig |
| Rab9 | 13.1632 | 16.8001 | | Not Sig | | 1.276292999 | Not Sig | Not Sig |
| Rabl5 | 24.5935 | 34.5439 | | Not Sig | | 1.40459471 | Not Sig | Not Sig |
| Ramp1 | 5.97082 | 12.077 | | Not Sig | | 2.022670253 | Not Sig | Not Sig |
| Rasd1 | 18.1781 | 51.6151 | 98.6563 | 28.9769 | 35.9795 | 2.83941116 | -3.404653362 | -2.742014203 |
| Rem2 | 3.83588 | 7.74937 | 13.8636 | 3.52187 | 5.19563 | 2.020232645 | -3.936431498 | -2.668319338 |
| Rhob | 58.7689 | 112.958 | 263.549 | 59.6716 | 86.1358 | 1.922071027 | -4.41665717 | -3.059691789 |
| Rnf208 | 6.25297 | 8.18801 | | Not Sig | | 1.309459345 | Not Sig | Not Sig |
| Rpl19 | 264.926 | 370.485 | 697.251 | 552.811 | 653.85 | 1.398447114 | -1.261282789 | -1.06637761 |
| Rpl27a | 69.7538 | 93.6708 | 344.931 | 269.806 | 286.373 | 1.342877377 | -1.278440806 | -1.204481568 |
| Rpl7a | 210.172 | 261.623 | | Not Sig | | 1.244804256 | Not Sig | Not Sig |
| Rpp25 | 2.08128 | 7.32085 | | Not Sig | | 3.517474823 | Not Sig | Not Sig |
| Rps27l | 108.863 | 131.783 | | Not Sig | | 1.210539853 | Not Sig | Not Sig |
| Rpusd4 | 7.63512 | 10.2137 | | Not Sig | | 1.337726192 | Not Sig | Not Sig |
| Rragd | 17.429 | 25.5474 | 6.70171 | 10.2626 | 11.8978 | 1.465798382 | 1.531340509 | 1.775337936 |
| Rsad2 | 3.00733 | 4.80839 | 6.41959 | 3.84519 | 3.49403 | 1.598890045 | -1.66951178 | -1.837302485 |
| S100a1 | 56.9619 | 109.358 | 50.6082 | 72.5743 | 70.0352 | 1.919844668 | 1.434042309 | 1.383870598 |
| S100a10 | 45.6801 | 85.4447 | | Not Sig | | 1.870501597 | Not Sig | Not Sig |
| S100a13 | 12.5873 | 19.6919 | | Not Sig | | 1.564426048 | Not Sig | Not Sig |
| Sdc4 | 23.8674 | 34.8079 | | Not Sig | | 1.458386753 | Not Sig | Not Sig |
| Sgk2 | 5.26712 | 15.0583 | | Not Sig | | 2.858924801 | Not Sig | Not Sig |
| Shc1 | 48.1788 | 62.7751 | | Not Sig | | 1.302961053 | Not Sig | Not Sig |
| Shfm1 | 118.271 | 167.732 | 218.248 | 179.758 | 171.414 | 1.418200573 | -1.214121207 | -1.273221557 |
| Siva1 | 8.98526 | 17.7128 | | Not Sig | | 1.971317469 | Not Sig | Not Sig |
| Slc25a17 | 27.117 | 35.4153 | | Not Sig | | 1.306018365 | Not Sig | Not Sig |
| Slc25a20 | 11.7883 | 16.6872 | | Not Sig | | 1.415573068 | Not Sig | Not Sig |
| Slc2a1 | 4.68126 | 12.0939 | 3.25246 | 5.01674 | 5.00066 | 2.583471117 | 1.542444796 | 1.537500846 |
| Slc30a1 | 6.32824 | 9.78096 | 4.73354 | 3.38877 | 3.52049 | 1.545605097 | -1.396831299 | -1.344568512 |
| Slc5a6 | 6.27985 | 10.3221 | 3.96094 | 6.67404 | 7.44959 | 1.643685757 | 1.68496367 | 1.880763152 |
| Slc6a8 | 7.60808 | 17.6387 | 8.22764 | 8.43459 | 10.8124 | 2.318416736 | 1.025153021 | 1.3141557 |
| Slc9a3r1 | 13.4058 | 17.1437 | 20.5515 | 12.5893 | 16.3182 | 1.278827075 | -1.632457722 | -1.259421995 |
| Smpdl3a | 19.3157 | 26.201 | | Not Sig | | 1.356461324 | Not Sig | Not Sig |
| Sord | 7.72501 | 10.7778 | 6.38437 | 8.95931 | 8.2555 | 1.39518266 | 1.403319356 | 1.293079818 |
| Spint1 | 76.9907 | 100.46 | 56.6128 | 64.8567 | 71.6634 | 1.304832921 | 1.145619012 | 1.265851539 |
| Ssbp3 | 24.1721 | 40.9142 | | Not Sig | | 1.692620831 | Not Sig | Not Sig |

FIG. 24 (cont.)

| | | | | | | | | |
|---|---|---|---|---|---|---|---|---|
| Ssx2ip | 10.6505 | 12.8446 | | Not Sig | | 1.206009108 | Not Sig | Not Sig |
| St14 | 7.37316 | 18.3657 | | Not Sig | | 2.490885862 | Not Sig | Not Sig |
| St3gal3 | 5.98218 | 15.8932 | | Not Sig | | 2.656757236 | Not Sig | Not Sig |
| Stmn3 | 18.8097 | 35.2233 | 8.10475 | 11.8947 | 19.9706 | 1.872613598 | 1.46762084 | 2.464061199 |
| Stx1a | 5.59863 | 7.30378 | 13.3614 | 7.97905 | 9.55851 | 1.304565581 | -1.674560255 | -1.39785385 |
| Stx3 | 16.0951 | 20.3471 | | Not Sig | | 1.264179781 | Not Sig | Not Sig |
| Sult2b1 | 4.57201 | 7.19306 | 3.09285 | 3.78921 | 6.62552 | 1.573281773 | 1.225151559 | 2.142205409 |
| Syf2 | 37.776 | 51.2416 | | Not Sig | | 1.356459127 | Not Sig | Not Sig |
| Tmem127 | 30.4613 | 38.7391 | | Not Sig | | 1.271748087 | Not Sig | Not Sig |
| Tmem130 | 17.7046 | 21.8711 | | Not Sig | | 1.23533432 | Not Sig | Not Sig |
| Tmem41a | 3.62871 | 7.5982 | | Not Sig | | 2.093912162 | Not Sig | Not Sig |
| Tmem50b | 31.9489 | 46.5608 | 26.1393 | 32.9376 | 30.6576 | 1.457352209 | 1.26007965 | 1.172854667 |
| Tmem51 | 15.818 | 23.3659 | | Not Sig | | 1.477171577 | Not Sig | Not Sig |
| Tmem53 | 5.01981 | 7.03624 | | Not Sig | | 1.401694486 | Not Sig | Not Sig |
| Tmem86a | 9.70081 | 16.9763 | 13.1208 | 9.0167 | 10.8678 | 1.749987888 | -1.455166524 | -1.207309667 |
| Tpi1 | 47.9123 | 73.6221 | | Not Sig | | 1.536601249 | Not Sig | Not Sig |
| Tpm1 | 33.5895 | 46.7296 | 62.1673 | 32.9659 | 30.6477 | 1.391196654 | -1.885806242 | -2.028449117 |
| Tppp3 | 4.32949 | 8.83074 | 18.5183 | 6.84144 | 10.9715 | 2.039672109 | -2.706783952 | -1.687854897 |
| Tprgl | 60.2616 | 75.3789 | | Not Sig | | 1.250861245 | Not Sig | Not Sig |
| Trappc3 | 35.5303 | 53.101 | | Not Sig | | 1.494527206 | Not Sig | Not Sig |
| Trp53inp1 | 21.8328 | 28.5832 | 10.8795 | 8.50772 | 7.2295 | 1.309186179 | -1.278779744 | -1.504875856 |
| Txnl4b | 5.243 | 7.39615 | | Not Sig | | 1.410671371 | Not Sig | Not Sig |
| Ubxn1 | 45.2238 | 64.6054 | | Not Sig | | 1.428570797 | Not Sig | Not Sig |
| Vti1b | 47.1532 | 71.8868 | 43.9218 | 48.2804 | 54.0538 | 1.524537041 | 1.099235459 | 1.230682713 |
| Wdr1 | 30.8276 | 47.8524 | | Not Sig | | 1.552258366 | Not Sig | Not Sig |
| Wipi1 | 17.9176 | 33.1587 | 11.6133 | 21.0858 | 17.1963 | 1.850621735 | 1.815659632 | 1.480741908 |
| Wsb1 | 8.08293 | 10.7259 | 17.8113 | 11.9675 | 10.6172 | 1.326981676 | -1.488305828 | -1.677589195 |
| Xpnpep1 | 10.0585 | 12.3088 | | Not Sig | | 1.223721231 | Not Sig | Not Sig |
| Yipf1 | 26.844 | 36.4942 | | Not Sig | | 1.359491879 | Not Sig | Not Sig |

FIG. 25

| | Log2 Fold change | |
|---|---|---|
| ETC/OxPhos/TCA | vs iPSC | vs iPSC |
| GeneSymbol | EGFP | ERRg |
| ACO2 | 1.59873 | 2.80003 |
| ALDH5A1 | 1.49639 | 3.37664 |
| ATP5A1 | Not Sig | 0.277102 |
| ATP5B | Not Sig | 0.846419 |
| ATP5E | 0.731179 | 1.25099 |
| ATP5G1 | 0.254222 | 1.05967 |
| ATP6V0E2 | Not Sig | 0.900001 |
| ATP6V1E1 | 0.626112 | 1.30561 |
| ATP6V1F | 0.45153 | 1.02396 |
| CYC1 | 0.603286 | 0.896287 |
| DLAT | 0.334244 | 0.961947 |
| DLD | 0.441694 | 0.921321 |
| DLST | Not Sig | 0.780315 |
| ENOX1 | 2.7392 | 4.74469 |
| ERO1LB | 0.672097 | 1.29379 |
| FDX1L | Not Sig | 0.434021 |
| FDXR | Not Sig | 3.67598 |
| FH | 0.241744 | 0.74715 |
| FXN | -0.948575 | Not Sig |
| GLRX | 0.501042 | 1.11671 |
| IDH3B | Not Sig | 1.14196 |
| IDH3G | 0.950187 | 1.75898 |
| MDH1 | -0.255856 | 1.10709 |
| NDUFA10 | 0.499061 | 0.948454 |
| NDUFA11 | Not Sig | 0.564872 |
| NDUFA12 | 0.25208 | 0.704452 |
| NDUFA2 | Not Sig | 0.914633 |
| NDUFA3 | -0.220469 | 0.553712 |
| NDUFA5 | Not Sig | 1.07434 |

FIG. 25 (cont.)

| | | |
|---|---|---|
| NDUFA6 | 0.379207 | 0.874344 |
| NDUFA7 | Not Sig | 0.75212 |
| NDUFA8 | Not Sig | 0.413066 |
| NDUFA9 | 0.755382 | 1.65441 |
| NDUFAB1 | -0.381263 | Not Sig |
| NDUFB2 | 0.597611 | 1.033 |
| NDUFB5 | 0.273809 | 0.774613 |
| NDUFB6 | -0.311921 | 0.189206 |
| NDUFB8 | Not Sig | 0.544258 |
| NDUFB9 | 0.263353 | 0.994521 |
| NDUFS1 | 0.379948 | 1.35876 |
| NDUFS2 | Not Sig | 0.50899 |
| NDUFS3 | Not Sig | 0.671524 |
| NDUFS5 | -0.917236 | -0.466569 |
| NDUFV1 | 0.551033 | 1.44145 |
| PDHB | -0.842791 | 0.669281 |
| SDHA | 0.790141 | 1.60913 |
| SDHB | 0.407439 | 1.09377 |
| SDHC | -0.273585 | 0.383452 |
| SLC1A3 | -0.511466 | 2.37408 |
| SLC25A12 | Not Sig | 0.839587 |
| SLC25A13 | Not Sig | 0.566767 |
| SNCA | Not Sig | 1.43413 |
| TMX4 | 2.1645 | 3.28654 |
| TXNRD3 | Not Sig | 1.52149 |
| UQCR10 | 0.592409 | 1.2018 |
| UQCRB | Not Sig | 0.632791 |
| UQCRC2 | 0.34232 | 0.837592 |
| UQCRFS1 | 0.309875 | 0.760593 |

FIG. 25 (cont.)

| Cell Cycle | vs iPSC | vs iPSC |
|---|---|---|
| GeneSymbol | EGFP | ERRg |
| CDC14A | -0.380578 | -1.03937 |
| CDC14B | -0.69238 | -1.25311 |
| CREBBP | 0 | -0.833229 |
| DBF4 | -1.1856 | -1.47334 |
| EP300 | -0.688392 | -1.09124 |
| E2F1 | -1.12537 | -1.97869 |
| E2F3 | -1.09357 | -1.52456 |
| E2F4 | -0.265279 | -0.470933 |
| MAD2L1 | -2.44662 | -3.14233 |
| RAD21 | -1.36874 | -2.20653 |
| SMAD3 | 2.08416 | 1.84569 |
| SMAD4 | -0.553343 | -0.94641 |
| TTK | -2.55557 | -3.36766 |
| ANAPC2 | 1.05548 | 0.704531 |
| BUB1 | -3.38933 | -3.70847 |
| BUB1B | -3.69111 | -4.09542 |
| ABL1 | -0.813672 | -1.13291 |
| CDK1 | -2.26848 | -2.6219 |
| CDC20 | -2.48852 | -2.90934 |
| CDC25B | 0.751421 | 0.343281 |
| CDC26 | -0.348854 | -1.21828 |
| CDC27 | 0.376144 | 0 |
| CCNA2 | -2.40664 | -3.15337 |
| CCNB1 | -2.51698 | -2.88801 |
| CCNB2 | -2.98725 | -3.35154 |
| CCND2 | -0.847802 | -0.899491 |
| CDKN1B | 0.42953 | -0.0322305 |

FIG. 25 (cont.)

| | | |
|---|---|---|
| CDKN2D | 1.98428 | 1.68098 |
| HDAC1 | 0 | -0.62393 |
| HDAC2 | -1.24824 | -1.43757 |
| MCM2 | -2.56831 | -3.01465 |
| MCM3 | -1.91484 | -2.34638 |
| MCM4 | -1.68462 | -2.42024 |
| MCM5 | -3.09236 | -3.60412 |
| MCM7 | -1.99523 | -2.8826 |
| PTTG1 | -2.75808 | -3.34462 |
| PLK1 | -2.78904 | -3.41241 |
| PCNA | -1.12241 | -1.77944 |
| CHEK2 | -2.99836 | -3.54351 |
| RB1 | 0.839276 | 0.601377 |
| RBL1 | -0.402046 | -0.853579 |
| STAG1 | 0.269041 | -0.287144 |
| STAG2 | -1.47451 | -1.94558 |
| SMC1A | -0.759328 | -1.12585 |
| SMC3 | -1.5107 | -1.83194 |
| TFDP1 | 0.237269 | -0.327076 |
| YWHAB | -0.166558 | -0.424803 |
| YWHAG | -0.0469328 | -0.429083 |
| YWHAQ | -0.599707 | -0.802293 |
| YWHAZ | 0.370218 | -0.281107 |

FIG. 25 (cont.)

| Beta Cell | vs iPSC | vs iPSC |
|---|---|---|
| GeneSymbol | EGFP | ERRg |
| INS | infinity | infinity |
| PDX1 | infinity | infinity |
| IAPP | -1.0251 | 1.54488 |
| FOXA2 | 7.08098 | 6.07311 |
| GATA4 | 7.10581 | 8.19732 |
| GATA6 | 9.68187 | 9.71362 |
| MAF | 4.1695 | 5.41346 |
| MAFA | No Test | No Test |
| MAFB | 2.32924 | 1.69467 |
| NEUROD1 | 5.23953 | 3.96233 |
| PAX4 | 1.00481 | 0.0836628 |
| PAX6 | 0.891676 | 0.309519 |
| NEUROD1 | 5.23953 | 3.96233 |
| NKX2-2 | 3.73834 | 3.46179 |
| NKX6-1 | 2.55188 | 2.40718 |
| NKX6-2 | 7.04707 | 5.21865 |
| NANOG | -9.38333 | -10.2497 |

FIG. 26

| IIDP Donor ID | Internal ID | Sex | Age (years) | Race | BMI | Cause of Death | Experiment | Collesponding Figures |
|---|---|---|---|---|---|---|---|---|
| 785 | #1 | Male | 50 | White | 28.99 | Cerebrobascular/stroke | cDNA library for qPCR | Data not shown |
| 790 | #2 | Female | 24 | Hispanic/Latino | 34.9 | Head trauma | cDNA library for qPCR | Data not shown |
| 794 | #3 | Female | 41 | White | 35.5 | Head trauma | cDNA library for qPCR | Data not shown |
| 807 | #4 | Female | 26 | White | 46.6 | Head trauma | cDNA library for qPCR | Data not shown |
| 821 | #5 | Male | 27 | Asian | 22.1 | Anoxia | cDNA library for qPCR | Data not shown |
| 824 | #6 | Female | 47 | White | 20.6 | Cerebrobascular/stroke | cDNA library for qPCR | Data not shown |
| 882 | #7 | Male | 50 | Hispanic/Latino | 25.7 | Cerebrobascular/stroke | cDNA library for qPCR | Data not shown |
| 915 | #8 | Male | 31 | White | 31.7 | Head trauma | cDNA library for qPCR | Data not shown |
| 937 | #9 | Male | 52 | White | 34.3 | Anoxia | glucose stimulated c-peptide secretion | Data not shown |
| 975 | #10 | Male | 54 | Black or African American | 23.3 | Cerebrobascular/stroke | glucose stimulated c-peptide secretion | Fig. 4e |
| 979 | #11 | Male | 53 | White | 27.2 | Cerebrobascular/stroke | cDNA library for qPCR | Expanded data Fig. 13g |
| 985 | #12 | Male | 40 | White | 38.91 | No info | cDNA library for qPCR | Data not shown |
| 1042 | #13 | Male | 37 | White | 26.3 | Anoxia | EM study human beta cell control/islets transplantation in NOD-SCID | Fig.5c, Extended data Fig.19b & 20 |
| 1050 | #14 | Male | 36 | White | 26 | Anoxia | islets transplantation in NOD-SCID | Fig.5c, Extended data Fig.19b & 20 |
| 1059 | #15 | Male | 32 | White | 23.1 | Anoxia | cDNA library for qPCR | Extended data Fig.16 |
| 1060 | #16 | Female | 47 | White | 25 | Cerebrobascular/stroke | cDNA library for qPCR | Extended data Fig.16 |
| 1061 | #17 | Male | 33 | Hispanic/Latino | 31.5 | Head trauma | cDNA library for qPCR | Extended data Fig.16 |
| 1082 | #18 | Female | 49 | White | 30.3 | Cerebrobascular/stroke | glucose stimulated c-peptide secretion | Fig. 4e |
| 1089 | #19 | Female | 51 | Hispanic/Latino | 25.4 | Cerebrovascular/stroke | EM study | Data not shown |

FIG. 27

| qPCR primers | | | | |
|---|---|---|---|---|
| NCBI or Primer bank ID | Genes | Species | Primers (Fw) | Primers (Rv) |
| NM_001243792.1 | ERRγ | mouse | gcaaggcattcttcaagagg | ggctgggcagctgtactcta |
| NM_001136069.2 | Ldha | mouse | ccgttacctgatgggagaga | gtaggcactgtccaccacct |
| NM_008618.3 | Mdh1 | mouse | gaagccctgaaagacgacag | tcgacacgaactctccctct |
| NM_009943.2 | Cox6a2 | mouse | ctctcgactgggtgaaggag | gaagagccagcacaaaggtc |
| L09192.1 | Pcx | mouse | cctctcagagcgagcagact | atagggaagccgaaggtgtt |
| NM_010886.2 | Ndufa4 | mouse | ctgcgtgtaggtaggcctgt | catggctctgggttgttctt |
| NM_153064.4 | Ndufs2 | mouse | gatccgagtgctctttggag | atgtcatccagaagcccaag |
| NM_001185083.1 | Ins2 | mouse | tttgtcaagcagcacctttg | tctacaatgccacgcttctg |
| NM_008814.3 | Pdx1 | mouse | gaaatccaccaaagctcacg | ttcaacatcactgccagctc |
| NM_001244202.1 | Pax6 | mouse | tggaaacaaacgccctagct | ggacagggaacacaccaacttt |
| NM_144955.2 | Nkx6-1 | mouse | tcaggtcaaggtctggttcc | cgatttgtgctttttcagca |
| NM_031250.5 | Ucn3 | mouse | atatgcacaggggagtggag | agtaggtgggcatcagcatc |
| NM_001039710.1 | Coq10b | mouse | ccccgttctggagagataca | tagcgagctgagagtgcaga |
| NM_023179.3 | Atp6v1g2 | mouse | ctggaagcctcagtgtcctc | tcacagtggctgaacaaagc |
| NM_001103157.1 | Steap2 | mouse | gcagagcaggagaaatggac | ctttctttcgggatgccata |
| NM_001177752.1 | Pfkfb3 | mouse | ccgacagaactggagaggag | agcggagacacgagacagat |
| NM_000207.2 | Insulin | human | agcctttgtgaaccaacacc | gctggtagagggagcagatg |
| NM_206594.2 | ERRγ | human | gctaacactgtcgcagtttga | cgaacagctggaatcaatgtg |
| NM_024865.2 | Nanog | human | ttccttcctccatggatctg | tctgctggaggctgaggtat |
| NM_001165923.2 | HNF1β | human | tcacagataccagcagcatcagt | gggcatcaccaggcttgta |
| NM_022454.3 | Sox17 | human | cctgggtttttgttgttgct | gaggaagctgttttgggaca |
| NG_012490.1 | Sox9 | human | acaggagtgctgggagagaa | acaaactctttccggtgtgg |
| NM_000209.3 | Pdx1 | human | ggatgaagtctaccaaagctcacgc | ccagatcttgatgtgtctctcggtc |
| NM_201589 | Mafa | human | cttcagcaaggaggaggtcatc | ctcgtatttctccttgtacaggtcc |
| NM_002500.4 | NeuroD | human | gttctcaggacgaggagcac | cttgggcttttgatcgtcat |
| NM_000162.3 | Gck | human | gctggaatcaatttcccaga | ctccccacacaggatgagtt |
| NM_000280.4 | Pax6 | human | ccgagagtagcgactccag | cttccggtctgcccgttc |
| NM_001275.3 | Chga | human | ctacgcgccttgtctcctac | agttgtgcccagtggatagg |
| NM_014232.2 | Vamp2 | human | tcccccagctggtatgtaag | ccacacacacactggtagcc |

FIG. 27 (cont.)

| | | | | |
|---|---|---|---|---|
| NM_002054.4 | Gcg | human | aggcagacccactcagtga | aacaatggcgacctcttctg |
| NM_001048.3 | Sst | human | gtacttcttggcagagctgctg | cagaagaaattcttgcagccag |
| 260099724c1 | Ldha | human | atggcaactctaaaggatcagc | ccaaccccaacaactgtaatct |
| NM_001199111 | Mdh1 | human | cccagtaatgggaagggatt | ccgtaacgtcctttggaaaa |
| 34147589c1 | Ndufa4 | human | atgatcggcttaatctgcctg | tccgggttgttctttctgtcc |
| NM_000920.3 | Pcx | human | ccagaggcaggtcttctttg | gggtgaggtcaccacagtct |
| NM_145230.3 | Atp6v0e2 | human | agtatcctgttccgcctcct | ctctcatcccagctctggtc |
| NM_001002.3 | U36B4 (RPLP0) | human/mouse | gtgctgatgggcaagaac | aggtcctccttggtgaac |
| | | | | |
| ChIP primers | | | | |
| Reference | Genes | Species | Primers (Fw) | Primers (Rv) |
| Dofour et al, Cell Metab, 2007 | Mdh1 | mouse | cgccagaggtcgccggaagaactacac | ccaggagcccacactcaccattattgc |
| Dofour et al, Cell Metab, 2007 | Atp2a2 | mouse | gtatgttttagacaaggtccaacgtgg | caaggtaattttgccaatataaagagg |
| Active Motif | EF1a | mouse | ChIP-IT Control Kit-Mouse No53011 | |
| | | | | |
| | | | | |
| Genotyping Primers | | | | |
| Reference | Genes | Animal model | Primers (Fw) | Primers (Rv) |
| - | ERRγ | ERRγ flox/flox | gttttaaaggcccttggtgatctcgc | ctgcaacccttggactgccagaac |
| - | Cre | Cre positive | gcattaccggtcgatgcaacgagtgatgag | gagtgaacgaacctggtcgaaatcagtgcg |
| - | FABP3 | internal control for Cre | tggacaggactggacctctgc | tagagctttgccacatcacag |
| - | Insulin GFP promoter | MIP-GFP | aagttcatctgcaccaccg | tccttgaagaagatggtgc |
| - | Insulin GFP promoter | internal control for MIPGFP | ctaggccacagaattgaaagatct | gtaggtggaaattctagcatcatcc |

FIG. 28

| Material | Dilution | Company | Catalog Number | STOCK solution | Final Concentration | Description to make stock solution | Expected effect |
|---|---|---|---|---|---|---|---|
| rh/m/r Activin A | 0.1% BSA PBS | R&D systems | 338-AC | 100ug/ml | 100ng/ml | 50ug rhActivin + 500ul 0.1%BSA PBS =100ug/ml | TGFb super family |
| rhWnt3a | 0.1% BSA PBS | R&D systems | 5036-WN | 25ug/ml | 25ng/ml | 10ug rhWnt3a + 400ul 0.1%BSA PBS = 25ug/ml | Wnt signaling |
| CHIR99021 | DMSO | Axon | Axon 1386 | 3mM | 3uM | 5mg CHIR99021 + 3.58ml DMSO = 3mM | GSK3β inhibitor |
| Wortmannin | DMSO | Invivo Gen | 10C22-MM | 100uM | 100nM | 5mg Wortmannin + 11.67ml DMSO = 1mM | PI3K Inhibitor |
| rhFGF10 | 0.1% BSA PBS | R&D systems | 345-FG | 50ug/ml | 50ng/ml | 25ug FGF10+500ul 0.1%BSA PBS = 50ug/ml | FGF10 signaling |
| rhFGF7/KGF | 0.1% BSA PBS | R&D systems | 251-KG/CF | 25ug/ml | 25-50ng/ml | 10ug FGF7+400ul 0.1%BSA PBS = 25ug/ml | FGF7 signaling |
| KAAD-cyclopamine | DMSO | STEMGENT | 04-0028 | 0.25mM | 0.25uM | 100ug KAAD-Cyc + DMSO 572ul 0.25mM | Hedgehog signaling inhibition |
| rhNoggin | 0.1% BSA PBS | R&D systems | 6057-NG | 50ug/ml | 50ng/ml | 25ug Noggin + 500ul 0.1%BSA PBS = 50ug/ml | BMP4 inhibition |
| rhFGF2 | 0.1% BSA PBS | Peprotech | 100-18B | 10ug/ml | 10ng/ml | 10ug rhFGF2 + 1ml 0.1%BSA PBS = 10ug/ml | FGF2 signaling |
| rhBMP4 | 0.1% BSA PBS | R&D systems | 314-BP | 10ug/ml | 10ng/ml | 10ug BMP4 + 1ml 0.1%BSA PBS =10ug/ml | BMP4 signaling |
| Forskolin | DMSO | SIGMA | F6886-25MG | 10mM | 10uM | 4.1mg Forskolin + 1ml DMSO = 10mM | adenylate cyclase activator |
| Dexametazon | DMSO | Sigma | D4902-100MG | 10mM | 10uM | 5mg Dex + 1.27ml DMSO = 10mM | Glucocorticoid receptor signaling |
| TGF-β RI kinase inhibitor II (ALK5i II) | DMSO | Calbiochem or Enzo | 616452 or ALX-270-445 | 10mM | 10uM | 5mg ALK5i II+ 1.738ml DMSO =10mM | TGFβRI inhibitor |
| Nicotinamide | H2O or PBS | SIGMA | 72340-100G | 1M | 10mM | 1.221g Nico + 10ml PBS =1M | Vitamin B3 |
| Exendin4 | H2O or PBS | SIGMA | E7144 | 1mg/ml | 1ug/ml | 1mg Ex4 + 1ml PBS = 1mg/ml | GLP1 analog |
| human GLP1 | 0.1% BSA PBS | Peprotech | 130-08 | 1mg/ml | 1ug/ml | 1mg GLP1 + 1ml 0.1%BSA PBS = 1mg/ml | GLP1 signaling/cAMP activation |
| human IGF2 | 0.1% BSA PBS | Prospec | cyt-265-b | 10ug/ml | 10ng/ml | 10ug IGF2 +1ml 0.1%BSA PBS = 1mg/ml | IGF2 signaling |
| B27 Supplement | - | GIBCO | 17504-044 | - | 1% | - | Growth supplement |
| N2 Supplement | - | GIBCO | 17502-048 | - | 1% | - | Growth supplement |
| Insulin-Transferrin-Selenium | - | GIBCO | 41400-045 | - | 1% | - | Growth supplement |
| Reserpine | DMSO | TOCRIS | 2742 | 0.63mM | 0.63uM | 1.92mg Reserpin + 5ml DMSO =0.63mM | VMAT inhibitor |
| Tetrabenazine (TBZ) | DMSO | TOCRIS | 2175 | 1.25mM | 1.25uM | 1.98mg TBZ + 5ml DMSO=1.25mM | VMAT inhibitor |
| dBu-cAMP | DMSO | ENZO | BML-CN125-0100 | 0.6mM | 0.6uM | 100mg cAMP + 3.39ml DMSO = 60mM | cAMP activation |
| R428 | DMSO | Selleckchem | S2841 | 2mM | 2uM | 1mg R428 + 0.9865ml DMSO = 2mM | Axl inhibitor |
| 3,3',5-Triiodo-L-thyronine sodium salt (T3) | DMSO | Sigma | T6397-100MG | 1mM | 1uM | 6.72mg T3 + 10ml DMSO = 1mM | Thyloid hormon |
| Stemolecule™ LDN-193189 | DMSO | Stemgent | 04-0074-10 | 100uM | 100nM | 10mg LDN-193189 + 2.28ml DMSO = 10mM | TGFβ/Smad inhibitor |
| SANT-1 | DMSO | Sigma | S4572-5MG | 0.25mM | 0.25uM | 5mg SANT-I +535ul DMSO=25mM | Hedgehog/Smoothened antagonist |
| N-acythyl cysteine | H2O | Sigma | A9165 | 100mM | 1mM | 0.16319g N-Cys + 10ml Milli Q water = 100mM | Anti oxidants |
| Gamma Secretase inhibitor XX (GSiXX) | DMSO | Millipore | 565789 | 100uM | 100nM | 1mg GSiXX + 2.25ml DMSO = 1mM | Notch inhibitor |
| Betacellulin (BTC) | 0.1% BSA PBS | Millipore EMD | 200496-10UG | 20ug/ml | 20ng/ml | 10ug BTC + 500ul 0.1%BSA PBS | EGFR ligand |
| Heparin | H2O | Sigma | H3149-10KU | 10mg/ml | 10ug/ml | 10mg Heparin + 1ml H2O | Enhance Growth hormone binding |

FIG. 28 (cont.)

| Days for differentiation | 0 day | 1~2 day | 3~4 day | 5~11 day | 11~21 day | 21 day~ |
|---|---|---|---|---|---|---|
| Virus or Reagents | Infection Human Insulin Reporter Lenti Virus | Atvivin A 100ng/ml | Atvivin 100ng/ml | Retinoic Acid 2uM | Forskolin 10uM | Forskolin 10uM |
| | (pGreenZeo System) | Wnt3a 25ng/ml | | SB431547 10uM | Dexametasone 10uM | Dexametasone 10uM |
| | 800g 1 hour spin fection | | | Dorsomorphin 1uM | AlkSi II 10uM | AlkSi II 10uM |
| | Chenge media to Fresh TeSR Media | | | B27 supplement 1% | Nicotinamide 10mM | Nicotinamide 10mM |
| | | | | | B27 supplement 1% | B27 supplement 1% |
| | Red; Essential small molecules | | | | | |
| | Blue; Additional small molecules | CHIR99021 3uM | | | | dBu-cAMP |
| | | Wortmannin 100nM | | | | T3 1uM |
| | | | | | | |
| | | | | | | |
| | Change media every day | Change media every day | Change media every day | Change media every other day | Change media every 2~3 days | Change media every 2~3 days |
| | | | | | | |
| | | | | | | |
| Base Midea | TESR media | Custam TESR media (w/o growth Factors) | | | | |

SEQUENCE LISTING

<160> NUMBER OF SEQ ID NOS: 96

<210> SEQ ID NO 1
<211> LENGTH: 458
<212> TYPE: PRT
<213> ORGANISM: Homo sapiens

<400> SEQUENCE: 1

Met Asp Ser Val Glu Leu Cys Leu Pro Glu Ser Phe Ser Leu His Tyr
1 5 10 15

Glu Glu Glu Leu Leu Cys Arg Met Ser Asn Lys Asp Arg His Ile Asp
20 25 30

Ser Ser Cys Ser Ser Phe Ile Lys Thr Glu Pro Ser Ser Pro Ala Ser
35 40 45

Leu Thr Asp Ser Val Asn His His Ser Pro Gly Gly Ser Ser Asp Ala
50 55 60

Ser Gly Ser Tyr Ser Ser Thr Met Asn Gly His Gln Asn Gly Leu Asp
65 70 75 80

Ser Pro Pro Leu Tyr Pro Ser Ala Pro Ile Leu Gly Gly Ser Gly Pro
85 90 95

Val Arg Lys Leu Tyr Asp Asp Cys Ser Ser Thr Ile Val Glu Asp Pro
100 105 110

Gln Thr Lys Cys Glu Tyr Met Leu Asn Ser Met Pro Lys Arg Leu Cys
115 120 125

Leu Val Cys Gly Asp Ile Ala Ser Gly Tyr His Tyr Gly Val Ala Ser
130 135 140

Cys Glu Ala Cys Lys Ala Phe Phe Lys Arg Thr Ile Gln Gly Asn Ile
145 150 155 160

Glu Tyr Ser Cys Pro Ala Thr Asn Glu Cys Glu Ile Thr Lys Arg Arg
165 170 175

Arg Lys Ser Cys Gln Ala Cys Arg Phe Met Lys Cys Leu Lys Val Gly
180 185 190

Met Leu Lys Glu Gly Val Arg Leu Asp Arg Val Arg Gly Gly Arg Gln
195 200 205

Lys Tyr Lys Arg Arg Ile Asp Ala Glu Asn Ser Pro Tyr Leu Asn Pro
210 215 220

Gln Leu Val Gln Pro Ala Lys Lys Pro Tyr Asn Lys Ile Val Ser His
225 230 235 240

Leu Leu Val Ala Glu Pro Glu Lys Ile Tyr Ala Met Pro Asp Pro Thr
245 250 255

Val Pro Asp Ser Asp Ile Lys Ala Leu Thr Thr Leu Cys Asp Leu Ala
260 265 270

Asp Arg Glu Leu Val Val Ile Ile Gly Trp Ala Lys His Ile Pro Gly
275 280 285

Phe Ser Thr Leu Ser Leu Ala Asp Gln Met Ser Leu Leu Gln Ser Ala
290 295 300

Trp Met Glu Ile Leu Ile Leu Gly Val Val Tyr Arg Ser Leu Ser Phe
305 310 315 320

Glu Asp Glu Leu Val Tyr Ala Asp Asp Tyr Ile Met Asp Glu Asp Gln
325 330 335

Ser Lys Leu Ala Gly Leu Leu Asp Leu Asn Asn Ala Ile Leu Gln Leu
340 345 350

Val Lys Lys Tyr Lys Ser Met Lys Leu Glu Lys Glu Glu Phe Val Thr
355 360 365

-continued

```
Leu Lys Ala Ile Ala Leu Ala Asn Ser Asp Ser Met His Ile Glu Asp
    370                 375                 380

Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Arg Ala Gly Lys
                405                 410                 415

Met Leu Met Thr Leu Pro Leu Leu Arg Gln Thr Ser Thr Lys Ala Val
            420                 425                 430

Gln His Phe Tyr Asn Ile Lys Leu Glu Gly Lys Val Pro Met His Lys
        435                 440                 445

Leu Phe Leu Glu Met Leu Glu Ala Lys Val
    450                 455


<210> SEQ ID NO 2
<211> LENGTH: 5260
<212> TYPE: DNA
<213> ORGANISM: Homo sapiens

<400> SEQUENCE: 2

aagctccaat cggggcttta agtccttgat taggagagtg tgagagcttt ggtcccaact      60

ggctgtgcct ataggcttgt cactaggaga acatttgtgt taattgcact gtgctctgtc     120

aaggaaactt tgatttatag ctggggtgca caaataatgg ttgccggtcg cacatggatt     180

cggtagaact ttgccttcct gaatcttttt ccctgcacta cgaggaagag cttctctgca     240

gaatgtcaaa caaagatcga cacattgatt ccagctgttc gtccttcatc aagacggaac     300

cttccagccc agcctccctg acggacagcg tcaaccacca cagccctggt ggctcttcag     360

acgccagtgg gagctacagt tcaaccatga atggccatca gaacggactt gactcgccac     420

ctctctaccc ttctgctcct atcctgggag gtagtgggcc tgtcaggaaa ctgtatgatg     480

actgctccag caccattgtt gaagatcccc agaccaagtg tgaatacatg ctcaactcga     540

tgcccaagag actgtgttta gtgtgtggtg acatcgcttc tgggtaccac tatggggtag     600

catcatgtga agcctgcaag gcattcttca agaggacaat tcaaggcaat atagaataca     660

gctgccctgc cacgaatgaa tgtgaaatca caaagcgcag acgtaaatcc tgccaggctt     720

gccgcttcat gaagtgttta aaagtgggca tgctgaaaga aggggtgcgt cttgacagag     780

tacgtggagg tcggcagaag tacaagcgca ggatagatgc ggagaacagc ccatacctga     840

accctcagct ggttcagcca gccaaaaagc catataacaa gattgtctca catttgttgg     900

tggctgaacc ggagaagatc tatgccatgc ctgaccctac tgtccccgac agtgacatca     960

aagccctcac tacactgtgt gacttggccg accgagagtt ggtggttatc attggatggg    1020

cgaagcatat tccaggcttc tccacgctgt ccctggcgga ccagatgagc cttctgcaga    1080

gtgcttggat ggaaattttg atccttggtg tcgtataccg gtctctttcg tttgaggatg    1140

aacttgtcta tgcagacgat tatataatgg acgaagacca gtccaaatta gcaggccttc    1200

ttgatctaaa taatgctatc ctgcagctgg taaagaaata caagagcatg aagctggaaa    1260

aagaagaatt tgtcaccctc aaagctatag ctcttgctaa ttcagactcc atgcacatag    1320

aagatgttga agccgttcag aagcttcagg atgtcttaca tgaagcgctg caggattatg    1380

aagctggcca gcacatggaa gaccctcgtc gagctggcaa gatgctgatg acactgccac    1440

tcctgaggca gacctctacc aaggccgtgc agcatttcta caacatcaaa ctagaaggca    1500

aagtcccaat gcacaaactt tttttggaaa tgttggaggc caaggtctga ctaaaagctc    1560

cctgggcctt cccatccttc atgttgaaaa agggaaaata aacccaagag tgatgtcgaa    1620
```

-continued

```
gaaacttaga gtttagttaa caacatcaaa aatcaacaga ctgcactgat aatttagcag   1680
caagactatg aagcagcttt cagattcctc cataggttcc tgatgagttt ctttctactt   1740
tctccatcat cttctttcct ctttcttccc acatttctct ttctctttat tttttctcct   1800
tttcttcttt cacctccctt atttctttgc ttctttcatt cctagttccc attctccttt   1860
atttcttcc  cgtctgcctg ccttctttct tttctttacc tactctcatt cctctctttt   1920
ctcatccttc cccttttttc taaatttgaa atagctttag tttaaaaaaa aatcctccct   1980
tccccctttc ctttcccttt ctttcctttt tccctttcct tttcccttc  ctttcctttc   2040
ctcttgacct tctttccatc tttctttttc ttccttctgc tgctgaactt ttaaaagagg   2100
tctctaactg aagagagatg gaagccagcc ctgccaaagg atggagatcc ataatatgga   2160
tgccagtgaa cttattgtga accatactgt ccccaatgac taaggaatca aagagagaga   2220
accaacgttc ctaaaagtac agtgcaacat atacaaattg actgagtgca gtattagatt   2280
tcatgggagc agcctctaat tagacaactt aagcaacgtt gcatcggctg cttcttatca   2340
ttgcttttcc atctagatca gttacagcca tttgattcct taattgtttt ttcaagtctt   2400
ccaggtattt gttagtttag ctactatgta actttttcag ggaatagttt aagctttatt   2460
cattcatgca atactaaaga gaaataagaa tactgcaatt ttgtgctggc tttgaacaat   2520
tacgaacaat aatgaaggac aaatgaatcc tgaaggaaga tttttaaaaa tgttttgttt   2580
cttcttacaa atggagattt ttttgtacca gctttaccac ttttcagcca tttattaata   2640
tgggaattta acttactcaa gcaatagttg aagggaaggt gcatattatc acggatgcaa   2700
tttatgttgt gtgccagtct ggtcccaaac atcaatttct taacatgagc tccagtttac   2760
ctaaatgttc actgacacaa aggatgagat tacacctaca gtgactctga gtagtcacat   2820
atataagcac tgcacatgag atatagatcc gtagaattgt caggagtgca cctctctact   2880
tgggaggtac aattgccata tgatttctag ctgccatggt ggttaggaat gtgatactgc   2940
ctgtttgcaa agtcacagac cttgcctcag aaggagctgt gagccagtat tcatttaaga   3000
ggcaataagg caaatgccag aattaaaaaa aaaaatcatc aaagacagaa aatgcctgac   3060
caaattctaa aacctaatcc atataagttt attcatttag gaatgttcgt ttaaattaat   3120
ctgcagtttt taccaagagc taagccaata tatgtgcttt tcaaccagta ttgtcacagc   3180
atgaaagtca agtcaggttc cagactgtta agaggtgtaa tctaatgaag aaatcaatta   3240
gatgccccga aatctacagt cgctgaataa ccaataaaca gtaacctcca tcaaatgcta   3300
taccaatgga ccagtgttag tagctgctcc ctgtattatg tgaacagtct tattctatgt   3360
acacagatgt aattaaaatt gtaatcctaa caaacaaaag aaatgtagtt cagcttttca   3420
atgtttcatg tttgctgtgc ttttctgaat tttatgttgc attcaaagac tgttgtcttg   3480
ttcttgtggt gtttggattc ttgtggtgtg tgcttttaga cacagggtag aattagagac   3540
aatattggat gtacaattcc tcaggagact acagtagtat attctattcc ttaccagtaa   3600
taaggttctt cctaataata attaagagat tgaaactcca aacaagtatt cattatgaac   3660
agatacacat caaaatcata ataatatttt caaaacaagg aataatttct ctaatggttt   3720
attatagaat accaatgtat agcttagaaa taaaactttg aatatttcaa gaatatagat   3780
aagtctaatt tttaaatgct gtatatatgg ctttcactca atcatctctc agatgttgtt   3840
attaactcgc tctgtgttgt tgcaaaactt tttggtgcag attcgtttcc aaaactattg   3900
ctactttgtg tgctttaaac aaaatacctt gggttgatga aacatcaacc cagtgctagg   3960
```

-continued

```
aatactgtgt atctatcatt agctatatgg gactatattg tagattgtgg tttctcagta   4020

gagaagtgac tgtagtgtga ttctagataa atcatcatta gcaattcatt cagatggtca   4080

ataacttgaa atttatagct gtgataggag ttcagaaatt ggcacatccc tttaaaaata   4140

acaacagaaa atacaactcc tgggaaaaaa ggtgctgatt ctataagatt atttatatat   4200

gtaagtgttt aaaaagatta ttttccagaa agtttgtgca gggtttaagt tgctactatt   4260

caactacact atatataaat aaaatatata caatatatac attgttttca ctgtatcaca   4320

ttaaagtact tgggcttcag aagtaagagc caaccaactg aaaacctgag atggagatat   4380

gttcaaagaa tgagatacaa ttttttagtt ttcagtttaa gtaactctca gcattacaaa   4440

agagtaagta tctcacaaat aggaaataaa actaaaacgt ggatttaaaa agaactgcac   4500

gggctttagg gtaaatgctc atcttaaacc tcactagagg gaagtcttct caagtttcaa   4560

gcaagaccat ttacttaatg tgaagttttg gaaagttata aaggtgtatg ttttagccat   4620

atgattttaa ttttaatttt gcttctttta ggttcgttct tatttaaagc aatatgattg   4680

tgtgactcct tgtagttaca cttgtgtttc aatcagatca gattgttgta tttattccac   4740

tattttgcat ttaaatgata acataaaaga tataaaaaat ttaaaactgc tatttttctt   4800

atagaagaga aaatgggtgt tggtgattgt attttaatta tttaagcgtc tctgtttacc   4860

tgcctaggaa aacattttat ggcagtctta tgtgcaaaga tcgtaaaagg acaaaaaatt   4920

taaactgctt ataataatcc aggagttgca ttatagccag tagtaaaaat aataataata   4980

ataataaaac catgtctata gctgtagatg ggcttcacat ctgtaaagca atcaattgta   5040

tatttttgtg atgtgtacca tactgtgtgc tccagcaaat gtccatttgt gtaaatgtat   5100

ttattttata ttgtatatat tgttaaatgc aaaaaggaga tatgattctg taactccaat   5160

cagttcagat gtgtaactca aattattatg cctttcagga tgatggtaga gcaatattaa   5220

acaagcttcc acttttgact gctaaaaaaa aaaaaaaaaa                         5260


<210> SEQ ID NO 3
<211> LENGTH: 283
<212> TYPE: PRT
<213> ORGANISM: Homo sapiens

<400> SEQUENCE: 3

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125

Ala Trp Lys Gly Gln Trp Ala Gly Gly Ala Tyr Ala Ala Glu Pro Glu
    130                 135                 140
```

-continued

```
Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
        195                 200                 205

Arg Gly Gly Gly Thr Ala Val Gly Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240

Pro Pro Pro Pro Gly Gly Ala Val Pro Pro Ala Ala Pro Val Ala Ala
                245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
        275                 280
```

<210> SEQ ID NO 4
<211> LENGTH: 2573
<212> TYPE: DNA
<213> ORGANISM: Homo sapiens

<400> SEQUENCE: 4

```
gggtggcgcc gggagtggga acgccacaca gtgccaaatc cccggctcca gctcccgact      60

cccggctccc ggctcccggc tcccggtgcc caatcccggg ccgcagccat gaacggcgag     120

gagcagtact acgcggccac gcagctttac aaggacccat gcgcgttcca gcgaggcccg     180

gcgccggagt tcagcgccag ccccccctgcg tgcctgtaca tgggccgcca gcccccgccg     240

ccgccgccgc acccgttccc tggcgccctg ggcgcgctgg agcagggcag ccccccggac     300

atctccccgt acgaggtgcc cccctcgcc gacgaccccg cggtggcgca ccttcaccac     360

cacctcccgg ctcagctcgc gctcccccac ccgcccgccg ggcccttccc ggagggagcc     420

gagccgggcg tcctggagga gcccaaccgc gtccagctgc ctttcccatg gatgaagtct     480

accaaagctc acgcgtggaa aggccagtgg gcaggcggcg cctacgctgc ggagccggag     540

gagaacaagc ggacgcgcac ggcctacacg cgcgcacagc tgctagagct ggagaaggag     600

ttcctattca acaagtacat ctcacggccg cgccgggtgg agctggctgt catgttgaac     660

ttgaccgaga gacacatcaa gatctggttc caaaaccgcc gcatgaagtg gaaaaaggag     720

gaggacaaga agcgcggcgg cgggacagct gtcgggggtg gcggggtcgc ggagcctgag     780

caggactgcg ccgtgacctc cggcgaggag cttctggcgc tgccgccgcc gccgcccccc     840

ggaggtgctg tgccgcccgc tgccccgtt gccgcccgag agggccgcct gccgcctggc     900

cttagcgcgt cgccacagcc ctccagcgtc gcgcctcggc ggccgcagga accacgatga     960

gaggcaggag ctgctcctgg ctgaggggct tcaaccactc gccgaggagg agcagagggc    1020

ctaggaggac cccgggcgtg gaccacccgc cctggcagtt gaatggggcg gcaattgcgg    1080

ggcccacctt agaccgaagg ggaaaacccg ctctctcagg cgcatgtgcc agttggggcc    1140

ccgcgggtag atgccggcag gccttccgga agaaaaagag ccattggttt ttgtagtatt    1200

ggggccctct tttagtgata ctggattggc gttgtttgtg gctgttgcgc acatccctgc    1260

cctcctacag cactccacct tgggacctgt ttagagaagc cggctcttca aagacaatgg    1320
```

-continued

```
aaactgtacc atacacattg gaaggctccc taacacacac agcggggaag ctgggccgag   1380
taccttaatc tgccataaag ccattcttac tcgggcgacc cctttaagtt tagaaataat   1440
tgaaaggaaa tgtttgagtt ttcaaagatc ccgtgaaatt gatgccagtg gaatacagtg   1500
agtcctcctc ttcctcctcc tcctcttccc cctccccttc ctcctcctcc tcttcttttc   1560
cctcctcttc ctcttcctcc tgctctcctt tcctcccccct cctcttttcc ctcctcttcc   1620
tcttcctcct gctctccttt cctccccctc ctctttctcc tcctcctcct cttcttcccc   1680
ctcctctccc tcctcctctt cttccccctc ctctccctcc tcctcttctt ctccctcctc   1740
ttcctcttcc tcctcttcca cgtgctctcc tttcctcccc ctcctcttgc tccccttctt   1800
ccccgtcctc ttcctcctcc tcctcttctt ctccctcctc ttcctcctcc tctttcttcc   1860
tgacctcttt ctttctcctc ctcctccttc tacctcccct tctcatccct cctcttcctc   1920
ttctctagct gcacacttca ctactgcaca tcttataact tgcacccctt tcttctgagg   1980
aagagaacat cttgcaaggc agggcgagca gcggcagggc tggcttagga gcagtgcaag   2040
agtccctgtg ctccagttcc acactgctgg cagggaaggc aaggggggac gggcctggat   2100
ctgggggtga gggagaaaga tggacccctg ggtgaccact aaaccaaaga tattcggaac   2160
tttctattta ggatgtggac gtaattcctg ttccgaggta gaggctgtgc tgaagacaag   2220
cacagtggcc tggtgcgcct tggaaaccaa caactattca cgagccagta tgaccttcac   2280
atctttagaa attatgaaaa cgtatgtgat tggagggttt ggaaaaccag ttatcttatt   2340
taacatttta aaaattacct aacagttatt tacaaacagg tctgtgcatc ccaggtctgt   2400
cttcttttca aggtctgggc cttgtgctcg ggttatgttt gtgggaaatg cttaataaat   2460
actgataata tgggaagaga tgaaaactga ttctcctcac tttgtttcaa acctttctgg   2520
cagtgggatg attcgaattc acttttaaaa ttaaattagc gtgttttgtt ttg          2573
```

<210> SEQ ID NO 5
<211> LENGTH: 341
<212> TYPE: PRT
<213> ORGANISM: Homo sapiens

<400> SEQUENCE: 5

```
Met Ala Trp Ser Ser Lys Ser Trp Leu Cys Leu Ile Ala Ser Ser Cys
1               5                   10                  15

Pro Arg Asp Thr Leu Leu Pro Ser Ala His His Ala Ser Pro Val Pro
            20                  25                  30

Ala Ser His Leu Thr Gln Val Ser Asn Gly Cys Val Ser Lys Ile Leu
        35                  40                  45

Gly Arg Tyr Tyr Arg Thr Gly Val Leu Glu Pro Lys Gly Ile Gly Gly
    50                  55                  60

Ser Lys Pro Arg Leu Ala Thr Pro Pro Val Val Ala Arg Ile Ala Gln
65                  70                  75                  80

Leu Lys Gly Glu Cys Pro Ala Leu Phe Ala Trp Glu Ile Gln Arg Gln
                85                  90                  95

Leu Cys Ala Glu Gly Leu Cys Thr Gln Asp Lys Thr Pro Ser Val Ser
            100                 105                 110

Ser Ile Asn Arg Val Leu Arg Ala Leu Gln Glu Asp Gln Gly Leu Pro
        115                 120                 125

Cys Thr Arg Leu Arg Ser Pro Ala Val Leu Ala Pro Ala Val Leu Thr
    130                 135                 140

Pro His Ser Gly Ser Glu Thr Pro Arg Gly Thr His Pro Gly Thr Gly
145                 150                 155                 160
```

```
His Arg Asn Arg Thr Ile Phe Ser Pro Ser Gln Ala Glu Ala Leu Glu
                165                 170                 175

Lys Glu Phe Gln Arg Gly Gln Tyr Pro Asp Ser Val Ala Arg Gly Lys
            180                 185                 190

Leu Ala Thr Ala Thr Ser Leu Pro Glu Asp Thr Val Arg Val Trp Phe
        195                 200                 205

Ser Asn Arg Arg Ala Lys Trp Arg Arg Gln Glu Lys Leu Lys Trp Glu
    210                 215                 220

Met Gln Leu Pro Gly Ala Ser Gln Gly Leu Thr Val Pro Arg Val Ala
225                 230                 235                 240

Pro Gly Ile Ile Ser Ala Gln Gln Ser Pro Gly Ser Val Pro Thr Ala
                245                 250                 255

Ala Leu Pro Ala Leu Glu Pro Leu Gly Pro Ser Cys Tyr Gln Leu Cys
            260                 265                 270

Trp Ala Thr Ala Pro Glu Arg Cys Leu Ser Asp Thr Pro Pro Lys Ala
        275                 280                 285

Cys Leu Lys Pro Cys Trp Gly His Leu Pro Pro Gln Pro Asn Ser Leu
    290                 295                 300

Asp Ser Gly Leu Leu Cys Leu Pro Cys Pro Ser Ser His Cys Pro Leu
305                 310                 315                 320

Ala Ser Leu Ser Gly Ser Gln Ala Leu Leu Trp Pro Gly Cys Pro Leu
                325                 330                 335

Leu Tyr Gly Leu Glu
            340
```

<210> SEQ ID NO 6
<211> LENGTH: 1613
<212> TYPE: DNA
<213> ORGANISM: Homo sapiens

<400> SEQUENCE: 6

```
gggcagcaag gatgcagtct cccaggagag gatgcactcg gtggtgggaa gccaggctgg     60

aggggcctga gtgaccctct ccacaggcgg gcagggcagt gggagaggtg gtgtgtggat    120

acctctgtct cacgcccagg gatcagcagc atgaaccagc ttggggggct ctttgtgaat    180

ggccggcccc tgcctctgga tacccggcag cagattgtgc ggctagcagt cagtggaatg    240

cggccctgtg acatctcacg gatccttaag gtaatgggcc agcaccttta cccagtgatg    300

gggacaggaa gcagggagaa agggctcctc tgaaggcaag agcctggggc tgttgcaggc    360

tctgagggct tctgggactt gggtcacttc ctgggagatc ctctcggagg ttgaaaaggg    420

gagcctcagg ccctcaaagc tgaggctgga ctcccgactt catggcctgg tccagtaagt    480

cttggctttg tcttatagcc tcctcctgtc ccagggacac tctccttcct tctgcccatc    540

atgcctcacc tgtccctgct tctcacctga ctcaggtatc taatggctgt gtgagcaaga    600

tcctagggcg ttactaccgc acaggtgtct tggagccaaa gggcattggg ggaagcaagc    660

cacggctggc tacacccccct gtggtggctc gaattgccca gctgaagggt gagtgtccag    720

ccctctttgc ctgggaaatc caacgccagc tttgtgctga agggctttgc acccaggaca    780

agactcccag tgtctcctcc atcaaccgag tcctgcgggc attacaggag gaccagggac    840

taccgtgcac acggctcagg tcaccagctg ttttggctcc agctgtcctc actccccata    900

gtggctctga gactccccgg ggtacccacc cagggaccgg ccaccggaat cggactatct    960

tctccccaag ccaagcagag gcactggaga aagagttcca gcgtgggcag tatcctgatt   1020
```

-continued cagtggcccg tggaaagctg gctactgcca cctctctgcc tgaggacacg gtgagggtct 1080
ggttttccaa cagaagagcc aaatggcgtc ggcaagagaa gctcaagtgg gaaatgcagc 1140
tgccaggtgc ttcccagggg ctgactgtac caagggttgc cccaggaatc atctctgcac 1200
agcagtcccc tggcagtgtg cccacagcag ccctgcctgc cctggaacca ctgggtccct 1260
cctgctatca gctgtgctgg gcaacagcac cagaaaggtg tctgagtgac accccaccta 1320
aagcctgtct caagccctgc tggggccact tgccccccaca gccgaattcc ctggactcag 1380
gactgctttg ccttccttgc ccttcctccc actgtcccct ggccagtctt agtggctctc 1440
aggccctgct ctggcctggc tgcccactac tgtatggctt ggaatgaggc aggagtggga 1500
aggagatggc atagagaaga tctaatacca tcctgcccat tgtccttacc gtcctgccca 1560
tacagactgt ggctccttcc tccttcctgt gattgctccc tcctgtgtgg acg 1613

<210> SEQ ID NO 7
<211> LENGTH: 798
<212> TYPE: PRT
<213> ORGANISM: Homo sapiens

<400> SEQUENCE: 7

Met Ala Trp Asp Met Cys Asn Gln Asp Ser Glu Ser Val Trp Ser Asp
1 5 10 15

Ile Glu Cys Ala Ala Leu Val Gly Glu Asp Gln Pro Leu Cys Pro Asp
20 25 30

Leu Pro Glu Leu Asp Leu Ser Glu Leu Asp Val Asn Asp Leu Asp Thr
35 40 45

Asp Ser Phe Leu Gly Gly Leu Lys Trp Cys Ser Asp Gln Ser Glu Ile
50 55 60

Ile Ser Asn Gln Tyr Asn Asn Glu Pro Ser Asn Ile Phe Glu Lys Ile
65 70 75 80

Asp Glu Glu Asn Glu Ala Asn Leu Leu Ala Val Leu Thr Glu Thr Leu
85 90 95

Asp Ser Leu Pro Val Asp Glu Asp Gly Leu Pro Ser Phe Asp Ala Leu
100 105 110

Thr Asp Gly Asp Val Thr Thr Asp Asn Glu Ala Ser Pro Ser Ser Met
115 120 125

Pro Asp Gly Thr Pro Pro Pro Gln Glu Ala Glu Glu Pro Ser Leu Leu
130 135 140

Lys Lys Leu Leu Leu Ala Pro Ala Asn Thr Gln Leu Ser Tyr Asn Glu
145 150 155 160

Cys Ser Gly Leu Ser Thr Gln Asn His Ala Asn His Asn His Arg Ile
165 170 175

Arg Thr Asn Pro Ala Ile Val Lys Thr Glu Asn Ser Trp Ser Asn Lys
180 185 190

Ala Lys Ser Ile Cys Gln Gln Gln Lys Pro Gln Arg Arg Pro Cys Ser
195 200 205

Glu Leu Leu Lys Tyr Leu Thr Thr Asn Asp Asp Pro Pro His Thr Lys
210 215 220

Pro Thr Glu Asn Arg Asn Ser Ser Arg Asp Lys Cys Thr Ser Lys Lys
225 230 235 240

Lys Ser His Thr Gln Ser Gln Ser Gln His Leu Gln Ala Lys Pro Thr
245 250 255

Thr Leu Ser Leu Pro Leu Thr Pro Glu Ser Pro Asn Asp Pro Lys Gly
260 265 270

-continued

```
Ser Pro Phe Glu Asn Lys Thr Ile Glu Arg Thr Leu Ser Val Glu Leu
        275                 280                 285

Ser Gly Thr Ala Gly Leu Thr Pro Pro Thr Thr Pro Pro His Lys Ala
    290                 295                 300

Asn Gln Asp Asn Pro Phe Arg Ala Ser Pro Lys Leu Lys Ser Ser Cys
305                 310                 315                 320

Lys Thr Val Val Pro Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
    370                 375                 380

Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
                405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
        435                 440                 445

Thr Arg Lys Gln Leu Gln Asp Gln Glu Ile Arg Ala Glu Leu Asn Lys
    450                 455                 460

His Phe Gly His Pro Ser Gln Ala Val Phe Asp Asp Glu Ala Asp Lys
465                 470                 475                 480

Thr Gly Glu Leu Arg Asp Ser Asp Phe Ser Asn Glu Gln Phe Ser Lys
                485                 490                 495

Leu Pro Met Phe Ile Asn Ser Gly Leu Ala Met Asp Gly Leu Phe Asp
            500                 505                 510

Asp Ser Glu Asp Glu Ser Asp Lys Leu Ser Tyr Pro Trp Asp Gly Thr
        515                 520                 525

Gln Ser Tyr Ser Leu Phe Asn Val Ser Pro Ser Cys Ser Ser Phe Asn
    530                 535                 540

Ser Pro Cys Arg Asp Ser Val Ser Pro Pro Lys Ser Leu Phe Ser Gln
545                 550                 555                 560

Arg Pro Gln Arg Met Arg Ser Arg Ser Arg Ser Phe Ser Arg His Arg
                565                 570                 575

Ser Cys Ser Arg Ser Pro Tyr Ser Arg Ser Arg Ser Arg Ser Pro Gly
            580                 585                 590

Ser Arg Ser Ser Ser Arg Ser Cys Tyr Tyr Tyr Glu Ser Ser His Tyr
        595                 600                 605

Arg His Arg Thr His Arg Asn Ser Pro Leu Tyr Val Arg Ser Arg Ser
    610                 615                 620

Arg Ser Pro Tyr Ser Arg Arg Pro Arg Tyr Asp Ser Tyr Glu Glu Tyr
625                 630                 635                 640

Gln His Glu Arg Leu Lys Arg Glu Glu Tyr Arg Arg Glu Tyr Glu Lys
                645                 650                 655

Arg Glu Ser Glu Arg Ala Lys Gln Arg Glu Arg Gln Arg Gln Lys Ala
            660                 665                 670

Ile Glu Glu Arg Arg Val Ile Tyr Val Gly Lys Ile Arg Pro Asp Thr
        675                 680                 685

Thr Arg Thr Glu Leu Arg Asp Arg Phe Glu Val Phe Gly Glu Ile Glu
```

-continued

```
    690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
                725                 730                 735

Thr Leu Arg Arg Ser Asn Glu Thr Asp Phe Glu Leu Tyr Phe Cys Gly
            740                 745                 750

Arg Lys Gln Phe Phe Lys Ser Asn Tyr Ala Asp Leu Asp Ser Asn Ser
        755                 760                 765

Asp Asp Phe Asp Pro Ala Ser Thr Lys Ser Lys Tyr Asp Ser Leu Asp
    770                 775                 780

Phe Asp Ser Leu Leu Lys Glu Ala Gln Arg Ser Leu Arg Arg
785                 790                 795


<210> SEQ ID NO 8
<211> LENGTH: 6318
<212> TYPE: DNA
<213> ORGANISM: Homo sapiens

<400> SEQUENCE: 8

tagtaagaca ggtgccttca gttcactctc agtaaggggc tggttgcctg catgagtgtg     60

tgctctgtgt cactgtggat tggagttgaa aaagcttgac tggcgtcatt caggagctgg    120

atggcgtggg acatgtgcaa ccaggactct gagtctgtat ggagtgacat cgagtgtgct    180

gctctggttg gtgaagacca gcctctttgc ccagatcttc ctgaacttga tctttctgaa    240

ctagatgtga acgacttgga tacagacagc tttctgggtg gactcaagtg gtgcagtgac    300

caatcagaaa taatatccaa tcagtacaac aatgagcctt caaacatatt tgagaagata    360

gatgaagaga atgaggcaaa cttgctagca gtcctcacag agacactaga cagtctccct    420

gtggatgaag acggattgcc ctcatttgat gcgctgacag atggagacgt gaccactgac    480

aatgaggcta gtccttcctc catgcctgac ggcacccctc caccccagga ggcagaagag    540

ccgtctctac ttaagaagct cttactggca ccagccaaca ctcagctaag ttataatgaa    600

tgcagtggtc tcagtaccca gaaccatgca aatcacaatc acaggatcag aacaaaccct    660

gcaattgtta agactgagaa ttcatggagc aataaagcga agagtatttg tcaacagcaa    720

aagccacaaa gacgtccctg ctcggagctt ctcaaatatc tgaccacaaa cgatgaccct    780

cctcacacca aacccacaga gaacagaaac agcagcagag acaaatgcac ctccaaaaag    840

aagtcccaca cacagtcgca gtcacaacac ttacaagcca aaccaacaac tttatctctt    900

cctctgaccc cagagtcacc aaatgacccc aagggttccc catttgagaa caagactatt    960

gaacgcacct taagtgtgga actctctgga actgcaggcc taactccacc caccactcct   1020

cctcataaag ccaaccaaga taacccttttt agggcttctc caaagctgaa gtcctcttgc   1080

aagactgtgg tgccaccacc atcaaagaag cccaggtaca gtgagtcttc tggtacacaa   1140

ggcaataact ccaccaagaa agggccggag caatccgagt tgtatgcaca actcagcaag   1200

tcctcagtcc tcactggtgg acacgaggaa aggaagacca agcggcccag tctgcggctg   1260

tttggtgacc atgactattg ccagtcaatt aattccaaaa cagaaatact cattaatata   1320

tcacaggagc tccaagactc tagacaacta gaaaataaag atgtctcctc tgattggcag   1380

gggcagattt gttcttccac agattcagac cagtgctacc tgagagagac tttggaggca   1440

agcaagcagg tctctccttg cagcacaaga aaacagctcc aagaccagga aatccgagcc   1500

gagctgaaca agcacttcgg tcatcccagt caagctgttt ttgacgacga agcagacaag   1560
```

-continued accggtgaac tgagggacag tgatttcagt aatgaacaat tctccaaact acctatgttt 1620
ataaattcag gactagccat ggatggcctg tttgatgaca gcgaagatga aagtgataaa 1680
ctgagctacc cttgggatgg cacgcaatcc tattcattgt tcaatgtgtc tccttcttgt 1740
tcttctttta actctccatg tagagattct gtgtcaccac ccaaatcctt attttctcaa 1800
agaccccaaa ggatgcgctc tcgttcaagg tccttttctc gacacaggtc gtgttcccga 1860
tcaccatatt ccaggtcaag atcaaggtct ccaggcagta gatcctcttc aagatcctgc 1920
tattactatg agtcaagcca ctacagacac cgcacgcacc gaaattctcc cttgtatgtg 1980
agatcacgtt caagatcgcc ctacagccgt cggcccaggt atgacagcta cgaggaatat 2040
cagcacgaga ggctgaagag ggaagaatat cgcagagagt atgagaagcg agagtctgag 2100
agggccaagc aaagggagag gcagaggcag aaggcaattg aagagcgccg tgtgatttat 2160
gtcggtaaaa tcagacctga cacaacacgg acagaactga gggaccgttt tgaagttttt 2220
ggtgaaattg aggagtgcac agtaaatctg cgggatgatg gagacagcta tggtttcatt 2280
acctaccgtt atacctgtga tgcttttgct gctcttgaaa atggatacac tttgcgcagg 2340
tcaaacgaaa ctgactttga gctgtacttt tgtggacgca agcaattttt caagtctaac 2400
tatgcagacc tagattcaaa ctcagatgac tttgaccctg cttccaccaa gagcaagtat 2460
gactctctgg attttgatag tttactgaaa gaagctcaga gaagcttgcg caggtaacat 2520
gttccctagc tgaggatgac agagggatgg cgaatacctc atgggacagc gcgtccttcc 2580
ctaaagacta ttgcaagtca tacttaggaa tttctcctac tttacactct ctgtacaaaa 2640
acaaaacaaa acaacaacaa tacaacaaga acaacaacaa caataacaac aatggtttac 2700
atgaacacag ctgctgaaga ggcaagagac agaatgatat ccagtaagca catgtttatt 2760
catgggtgtc agctttgctt ttcctggagt ctcttggtga tggagtgtgc gtgtgtgcat 2820
gtatgtgtgt gtgtatgtat gtgtgtggtg tgtgtgcttg gtttagggga agtatgtgtg 2880
ggtacatgtg aggactgggg gcacctgacc agaatgcgca agggcaaacc atttcaaatg 2940
gcagcagttc catgaagaca cgcttaaaac ctagaacttc aaaatgttcg tattctattc 3000
aaaaggaaat atatatatat atatatatat atatatatat atatataaat taaaaaggaa 3060
agaaaactaa caaccaacca accaaccaac caaccacaaa ccaccctaaa atgacagccg 3120
ctgatgtctg ggcatcagcc tttgtactct gttttttttaa gaaagtgcag aatcaacttg 3180
aagcaagctt tctctcataa cgtaatgatt atatgacaat cctgaagaaa ccacaggttc 3240
catagaacta atatcctgtc tctctctctc tctctctctc tctctttttt ttttcttttt 3300
ccttttgcca tggaatctgg gtgggagagg atactgcggg caccagaatg ctaaagtttc 3360
ctaacatttt gaagtttctg tagttcatcc ttaatcctga cacccatgta aatgtccaaa 3420
atgttgatct tccactgcaa atttcaaaag ccttgtcaat ggtcaagcgt gcagcttgtt 3480
cagcggttct ttctgaggag cggacaccgg gttacattac taatgagagt tgggtagaac 3540
tctctgagat gtgttcagat agtgtaattg ctacattctc tgatgtagtt aagtatttac 3600
agatgttaaa tggagtattt ttattttatg tatatactat acaacaatgt tctttttttgt 3660 tacagctatg cactgtaaat gcagccttct tttcaaaact gctaaatttt tcttaatcaa 3720
gaatattcaa atgtaattat gaggtgaaac aattattgta cactaacata tttagaagct 3780
gaacttactg cttatatata tttgattgta aaaacaaaaa gacagtgtgt gtgtctgttg 3840
agtgcaacaa gagcaaaatg atgctttccg cacatccatc ccttaggtga gcttcaatct 3900

-continued

```
aagcatcttg tcaagaaata tcctagtccc ctaaaggtat taaccacttc tgcgatattt   3960
ttccacattt tcttgtcgct tgtttttctt tgaagtttta tacactggat ttgttagggg   4020
aatgaaattt tctcatctaa aatttttcta gaagatatca tgattttatg taaagtctct   4080
caatgggtaa ccattaagaa atgtttttat tttctctatc aacagtagtt ttgaaactag   4140
aagtcaaaaa tctttttaaa atgctgtttt gttttaattt ttgtgatttt aatttgatac   4200
aaaatgctga ggtaataatt atagtatgat ttttacaata attaatgtgt gtctgaagac   4260
tatctttgaa gccagtattt ctttcccttg gcagagtatg acgatggtat ttatctgtat   4320
tttttacagt tatgcatcct gtataaatac tgatatttca ttcctttgtt tactaaagag   4380
acatatttat cagttgcaga tagcctattt attataaatt atgagatgat gaaaataata   4440
aagccagtgg aaattttcta cctaggatgc atgacaattg tcaggttgga gtgtaagtgc   4500
ttcatttggg aaattcagct tttgcagaag cagtgtttct acttgcacta gcatggcctc   4560
tgacgtgacc atggtgttgt tcttgatgac attgcttctg ctaaatttaa taaaaacttc   4620
agaaaaacct ccattttgat catcaggatt tcatctgagt gtggagtccc tggaatggaa   4680
ttcagtaaca tttggagtgt gtattcaagt ttctaaattg agattcgatt actgtttggc   4740
tgacatgact tttctggaag acatgataca cctactactc aattgttctt ttcctttctc   4800
tcgcccaaca cgatcttgta agatggattt cacccccagg ccaatgcagc taattttgat   4860
agctgcattc atttatcacc agcatattgt gttctgagtg aatccactgt ttgtcctgtc   4920
ggatgcttgc ttgatttttt ggcttcttat ttctaagtag atagaaagca ataaaaatac   4980
tatgaaatga aagaacttgt tcacaggttc tgcgttacaa cagtaacaca tctttaatcc   5040
gcctaattct tgttgttctg taggttaaat gcaggtattt taactgtgtg aacgccaaac   5100
taaagtttac agtctttctt tctgaatttt gagtatcttc tgttgtagaa taataataaa   5160
aagactatta agagcaataa attattttta agaaatcgag atttagtaaa tcctattatg   5220
tgttcaagga ccacatgtgt tctctatttt gcctttaaat ttttgtgaac caattttaaa   5280
tacattctcc tttttgccct ggattgttga catgagtgga atacttggtt tcttttctta   5340
cttatcaaaa gacagcacta cagatatcat attgaggatt aatttatccc ccctaccccc   5400
agcctgacaa atattgttac catgaagata gttttcctca atggacttca aattgcatct   5460
agaattagtg gagcttttgt atcttctgca gacactgtgg gtagcccatc aaaatgtaag   5520
ctgtgctcct ctcattttta tttttatttt tttgggagag aatatttcaa atgaacacgt   5580
gcaccccatc atcactggag gcaaatttca gcatagatct gtaggatttt tagaagaccg   5640
tgggccattg ccttcatgcc gtggtaagta ccacatctac aattttggta accgaactgg   5700
tgctttagta atgtggattt ttttcttttt taaaagagat gtagcagaat aattcttcca   5760
gtgcaacaaa atcaattttt tgctaaacga ctccgagaac aacagttggg ctgtcaacat   5820
tcaaagcagc agagagggaa ctttgcacta ttggggtatg atgtttgggt cagttgataa   5880
aaggaaacct tttcatgcct ttagatgtga gcttccagta ggtaatgatt atgtgtcctt   5940
tcttgatggc tgtaatgaga acttcaatca ctgtagtcta agacctgatc tatagatgac   6000
ctagaatagc catgtactat aatgtgatga ttctaaattt gtacctatgt gacagacatt   6060
ttcaataatg tgaactgctg atttgatgga gctactttaa gatttgtagg tgaaagtgta   6120
atactgttgg ttgaactatg ctgaagaggg aaagtgagcg attagttgag cccttgccgg   6180
gcctttttc cacctgccaa ttctacatgt attgttgtgg ttttattcat tgtatgaaaa   6240
ttcctgtgat ttttttaaa tgtgcagtac acatcagcct cactgagcta ataaagggaa   6300
```

acgaatgttt caaatcta 6318

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gcaaggcatt cttcaagagg 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ccgttacctg atgggagaga 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gaagccctga aagacgacag 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ctctcgactg ggtgaaggag 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cctctcagag cgagcagact 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14

-continued

```
ctgcgtgtag gtaggcctgt                                                20


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

gatccgagtg ctctttggag                                                20


<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

tttgtcaagc agcacctttg                                                20


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

gaaatccacc aaagctcacg                                                20


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

tggaaacaaa cgccctagct                                                20


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

tcaggtcaag gtctggttcc                                                20


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

atatgcacag gggagtggag                                                20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
ccccgttctg gagagataca 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
ctggaagcct cagtgtcctc 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
gcagagcagg agaaatggac 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
ccgacagaac tggagaggag 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
agcctttgtg aaccaacacc 20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gctaacactg tcgcagtttg a 21

-continued

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
ttccttcctc catggatctg 20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
tcacagatac cagcagcatc agt 23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
cctgggtttt tgttgttgct 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
acaggagtgc tgggagagaa 20

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
ggatgaagtc taccaaagct cacgc 25

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
cttcagcaag gaggaggtca tc 22

```
<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

gttctcagga cgaggagcac                                                20


<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

gctggaatca atttcccaga                                                20


<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

ccgagagtag cgactccag                                                 19


<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

ctacgcgcct tgtctcctac                                                20


<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

tcccccagct ggtatgtaag                                                20


<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

aggcagaccc actcagtga                                                 19


<210> SEQ ID NO 39
```

<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
gtacttcttg gcagagctgc tg 22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
atggcaactc taaaggatca gc 22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
cccagtaatg ggaagggatt 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
atgatcggct taatctgcct g 21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ccagaggcag gtcttctttg 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
agtatcctgt tccgcctcct 20

<210> SEQ ID NO 45
<211> LENGTH: 18

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
gtgctgatgg gcaagaac 18

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
ggctgggcag ctgtactcta 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
gtaggcactg tccaccacct 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
tcgacacgaa ctctccctct 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
gaagagccag cacaaaggtc 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
atagggaagc cgaaggtgtt 20

<210> SEQ ID NO 51
<211> LENGTH: 20
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 51
catggctctg ggttgttctt 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
atgtcatcca gaagcccaag 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tctacaatgc cacgcttctg 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttcaacatca ctgccagctc 20

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggacagggaa cacaccaact tt 22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgatttgtgc tttttcagca 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
agtaggtggg catcagcatc 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tagcgagctg agagtgcaga 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tcacagtggc tgaacaaagc 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ctttctttcg ggatgccata 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
agcggagaca cgagacagat 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gctggtagag ggagcagatg 20

<210> SEQ ID NO 63
<211> LENGTH: 21
<212> TYPE: DNA
<213> ORGANISM: Artificial Sequence
<220> FEATURE:

-continued

<223> OTHER INFORMATION: Description of Artificial Sequence: Synthetic primer

<400> SEQUENCE: 63
cgaacagctg gaatcaatgt g 21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tctgctggag gctgaggtat 20

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gggcatcacc aggcttgta 19

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gaggaagctg ttttgggaca 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
acaaactctt tccggtgtgg 20

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ccagatcttg atgtgtctct cggtc 25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ctcgtatttc tccttgtaca ggtcc 25

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
cttgggcttt tgatcgtcat 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
ctccccacac aggatgagtt 20

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
cttccggtct gcccgttc 18

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
agttgtgccc agtggatagg 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
ccacacacac actggtagcc 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
aacaatggcg acctcttctg 20

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
cagaagaaat tcttgcagcc ag 22

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
ccaaccccaa caactgtaat ct 22

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
ccgtaacgtc ctttggaaaa 20

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
tccgggttgt tctttctgtc c 21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gggtgaggtc accacagtct 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
ctctcatccc agctctggtc 20

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
aggtcctcct tggtgaac 18

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
cgccagaggt cgccggaaga actacac 27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
gtatgtttta gacaaggtcc aacgtgg 27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
ccaggagccc acactcacca ttattgc 27

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
caaggtaatt ttgccaatat aaagagg 27

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
gttttaaagg cccttggtga tctcgc 26

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 88
gcattaccgg tcgatgcaac gagtgatgag 30

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 89
tggacaggac tggacctctg c 21

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
aagttcatct gcaccaccg 19

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
ctaggccaca gaattgaaag atct 24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
ctgcaaccct tggactgcca gaac 24

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93

-continued

```
gagtgaacga acctggtcga aatcagtgcg                                        30


<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

tagagctttg ccacatcaca g                                                 21


<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

tccttgaaga agatggtgc                                                    19


<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

gtaggtggaa attctagcat catcc                                             25
```

COMPOSITIONS AND METHODS FOR TREATING TYPE 1 AND TYPE 2 DIABETES AND RELATED DISORDERS

CROSS REFERENCE TO RELATED APPLICATIONS

This application is a divisional of application U.S. Ser. No. 15/359,432, filed on Nov. 22, 2016, now U.S. Pat. No. 10,912,800, issued on Feb. 9, 2021, which is a divisional of application U.S. Ser. No. 14/793,391, filed on Jul. 7, 2015, now U.S. Pat. No. 9,546,379, issued on Jan. 17, 2017, which is a continuation of PCT/US2015/022799, filed on Mar. 26, 2015, which claims the benefit of and priority to U.S. Provisional Application Nos. 61/971,308, filed on Mar. 27, 2014; 62/065,537, filed on Oct. 17, 2014; and 62/105,545, filed on Jan. 20, 2015, the contents of all of which are incorporated herein by reference in their entireties.

STATEMENT OF RIGHTS TO INVENTIONS MADE UNDER FEDERALLY SPONSORED RESEARCH

This invention was made with U.S. government support under DK057978, DK090962, HL088093, HL105278, and ES010337 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. The ASCII copy, created on Aug. 3, 2015, is named 365550.1002US1 (00018) SL.txt and is 57,529 bytes in size.

BACKGROUND OF THE INVENTION

Beta cell dysfunction is associated with type 1 and type 2 diabetes. Type 1 diabetes is usually diagnosed in children and young adults and results from autoimmune destruction of insulin-producing pancreatic β cells. The defect in insulin production causes a dramatic rise of glucose levels in the blood and urine leading to polyuria (frequent urination), polydipsia (increased thirst), polyphagia (increased hunger), and weight loss. Type 1 diabetes is fatal unless treated with insulin injections, which is therapeutic, but not curative. The generation and production of insulin-secreting β cells has long been a major goal in regenerative medicine to cure type 1 and certain types of type 2 diabetes. To date no method exists for the production of fully “functional” β cells: that is, in vitro generated cells that can secrete insulin properly in response to physiologic levels of glucose. The production of such cells represents the best hope of curing diabetes. Accordingly, methods for obtaining fully functional beta cells and using such cells for the treatment of diabetes are urgently required.

SUMMARY OF THE INVENTION

As described below, the present invention features compositions comprising in vitro generated beta cells capable of glucose-stimulated insulin secretion, methods of inducing beta cell maturation from embryonic or induced pluripotent stem cell-derived beta-like cells, methods of transplanting these cells in a subject (e.g., human) to restore glucose homeostasis, and methods of using in vitro generated beta cells for the treatment of type 1 diabetes, type 2 diabetes, or a related disorder.

In one aspect, the invention generally provides a method for reprogramming a beta-like cell to a functional beta cell, the method involving expressing recombinant estrogen related receptor (ERR) gamma in a beta-like cell, thereby reprogramming the beta-like cell to a functional beta cell.

In another aspect, the invention provides a method for generating a cell capable of glucose-stimulated insulin secretion, the method involving expressing recombinant estrogen-related receptor (ERR) gamma in a beta-like cell, thereby generating a cell capable of glucose-stimulated insulin secretion.

In yet another aspect, the invention provides a method of ameliorating hyperglycemia in a subject in need thereof, the method involving administering to the subject a beta-like cell expressing recombinant estrogen-related receptor (ERR) gamma, thereby ameliorating hyperglycemia in the subject.

In still another aspect, the invention provides a method of treating type 1 or type 2 diabetes in a subject in need thereof, the method involving administering to the subject a beta-like cell expressing recombinant estrogen-related receptor (ERR) gamma, thereby treating type 1 or type 2 diabetes in the subject.

In another aspect, the invention provides an expression vector containing a beta cell-specific promoter operably linked to a nucleic acid sequence encoding an ERRgamma polypeptide. In one embodiment, the promoter is selected from the group consisting of Insulin, Insulin II, Pdx1, Mafa, Nkx6-1, Pax4 and NeuroD1 promoters. In another embodiment, the expression vector is a viral vector (e.g., a lentiviral vector or adeno associated viral vector (AAV)).

In another aspect, the invention provides a method of ameliorating hyperglycemia in a subject in need thereof, the method involving contacting a beta-like cell with an AAV vector encoding ERRgamma, thereby causing the cell to be capable of glucose-stimulated insulin secretion and administering the cell to the subject, thereby ameliorating hyperglycemia in the subject. In one embodiment, the beta-like cell is derived from the subject or is not derived from the subject.

In another aspect, the invention provides a host cell containing the expression vector of a previous aspect. In one embodiment, the cell is an embryonic stem cell, neonate stem cell, adult stem cell, induced pluripotent stem cell, adipocyte-derived stem cell, human umbilical vein endothelial cell (Huvec), or a progenitor or stem cell thereof.

In another aspect, the invention generally provides a tissue containing the host cell of any previous aspect. In one embodiment, the tissue is a pancreatic tissue.

In another aspect, the invention generally provides an organ containing the host cell of any previous aspect.

In another aspect, the invention generally provides a matrix containing the host cell of any previous aspect.

In another aspect, the invention generally provides a cellular composition containing an effective amount of a host cell of the invention in a pharmaceutically acceptable excipient. In another aspect, the invention generally provides a packaged pharmaceutical containing a host cell of a previous aspect; and instructions for using the cell to ameliorate hyperglycemia in a subject.

In another aspect, the invention generally provides a kit for treating hyperglycemia, the kit containing an effective amount of a host cell of any previous aspect, and instructions for use thereof. In one embodiment, the hyperglycemia is related to type 1 or type 2 diabetes.

In another aspect, the invention generally provides a method for generating a cell capable of glucose-stimulated insulin secretion, the method involving expressing recombinant estrogen-related receptor (ERR) gamma and Pdx1 or ERRgamma, Pdx1, and PGC-1alpha in an human adipose-derived stem cell (hADSC), thereby generating a cell capable of glucose-stimulated insulin secretion. In one embodiment, the invention generally involves expressing Pax4 in the hADSC.

In various embodiments of any of the above aspects or any other aspect of the invention delineated herein, the beta-like cell expresses one or more beta cell transcription factors that is any one or more of Nkx2.2, NeuroD1, Foxa2, Pax6, HNF4a, Pdx1, MafA, and Nkx6-1. In other embodiments of the above aspects, the beta-like cell expresses one or more beta cell markers that is Insulin 1, Insulin 2, glucagon and somatostatin. In other embodiments of the above aspects, the beta-like cell is an embryonic stem cell, induced pluripotent stem cell, adipocyte-derived stem cell, human umbilical vein endothelial cell (Huvec), or a progenitor or stem cell thereof. In other embodiments of the above aspects, the beta-like cell is modified to express ERRgamma in vitro or in vivo. In other embodiments of the above aspects, the beta-like cell is transduced with a viral vector encoding ERRgamma. In other embodiments of the above aspects, the reprogrammed cell expresses insulin. In other embodiments of the above aspects, the reprogrammed cell secretes insulin in response to glucose stimulation. In other embodiments of the above aspects, the beta-like cell is obtained by contacting an embryonic stem cell or induced pluripotent stem cell in culture with one or more of activin A, wingless-type MMTV integration site family member 3A (Wnt3a), insulin growth factor (IGF)-2, extendin (Ex)-4, fibroblast growth factor (FGF)-2, nicotinamide, and/or B27. In other embodiments of the above aspects, the beta-like cell is treated with 50 ng/ml Activin A each day for 1-3, 1-5, or 1-6 days (e.g., 1, 2, 3, 4, 5, or 6 days). In other embodiments of the above aspects, the beta-like cell is treated with 25 ng/ml Wnt3a on day 0. In other embodiments of the above aspects, the beta-like cell is treated with 50 ng/ml IGF-2, Ex-4 50 ng/ml, 10 ng/ml FGF-2, 10 mM nicotinamide, and 1% B27 on day 3. In other embodiments of the above aspects, the obtained beta cell expresses one or more mRNA that is Pdx1, insulin, Mafa, Pax6, NeuroD, GCK, CHGA, VAMP2, PC1/3, Glut2, Nkx6.1, GCG, SST, and U36B4. In other embodiments of the above aspects, the beta-like cells is obtained by expressing in the embryonic stem cell or induced pluripotent stem cell one or more transcription factors that is Oct4, Nanog, Sox17, FoxA2, Pdx1, Nkx6.1, and Ngn3. In other embodiments of the above aspects, the beta cell expresses one or more polypeptides that is insulin, Pdx1, Mafa, Pax6, Glut2, NeuroD1, GCK (glucokinase; hexokinase 4), GCG (glucagon), SST (somatostatin), CHGA (chromogranin A; parathyroid secretory protein 1) and VAMP2 (vesicle-associated membrane protein 2 (synaptobrevin 2)). In still other embodiments of the above aspects, the method reduces blood glucose level in the subject. In other embodiments of the above aspects, the method normalizes blood glucose level in the subject. In other embodiments of the above aspects, the subject is a veterinary or human subject.

The invention provides compositions comprising in vitro generated beta-like cells capable of glucose-stimulated insulin secretion and methods of using such cells for the treatment of subjects having or at risk of developing type 1 or type 2 diabetes or a related metabolic disorder. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "beta-like cell" is meant a cell that expresses at least one pancreatic islet beta cell transcription factor or at least one beta cell marker. Beta-like cells may be derived from embryonic stem cells or induced pluripotent stem cells. If desired, an embryonic stem cell or induced pluripotent stem cell can be induced to become a beta-like cell, for example, by culturing the cell as described herein below, or by recombinantly expressing in the cell (e.g., hADSC) one or more proteins of the invention. (e.g., ERRgamma; ERRgamma and Pdx1; ERRgamma, Pdx1, and PGC-1alpha). If desired, Pax4 is also expressed in combination with ERRgamma; ERRgamma and Pdx1; ERRgamma, Pdx1, and PGC-1alpha. In one embodiment, a beta-like cell or a descendent thereof expresses insulin and/or is capable of glucose-stimulated insulin secretion.

By "glucose-stimulated insulin secretion" is meant secretes insulin in response to physiologic levels of glucose. A physiological level of glucose would be about 20 mM glucose. By "estrogen-related receptor (ERR) gamma polypeptide" is meant a protein having at least 85% amino acid sequence identity to a human estrogen-related receptor gamma sequence provided at NCBI Ref No. P62508 or a fragment thereof having transcriptional regulatory activity. The sequence of ERRgamma also termed "ERR3" is provided below:

```
                                                        (SEQ ID NO: 1)
        10         20         30         40         50         60
MDSVELCLPE SFSLHYEEEL LCRMSNKDRH IDSSCSSFIK TEPSSPASLT DSVNHHSPGG

        70         80         90        100        110        120
SSDASGSYSS TMNGHQNGLD SPPLYPSAPI LGGSGPVRKL YDDCSSTIVE DPQTKCEYML

       130        140        150        160        170        180
NSMPKRLCLV CGDIASGYHY GVASCEACKA FFKRTIQGNI EYSCPATNEC EITKRRRKSC
```

-continued

```
       190        200        210        220        230        240
QACRFMKCLK VGMLKEGVRL DRVRGGRQKY KRRIDAENSP YLNPQLVQPA KKPYNKIVSH

       250        260        270        280        290        300
LLVAEPEKIY AMPDPTVPDS DIKALTTLCD LADRELVVII GWAKHIPGFS TLSLADQMSL

       310        320        330        340        350        360
LQSAWMEILI LGVVYRSLSF EDELVYADDY IMDEDQSKLA GLLDLNNAIL QLVKKYKSMK

       370        380        390        400        410        420
LEKEEFVTLK AIALANSDSM HIEDVEAVQK LQDVLHEALQ DYEAGQHMED PRRAGKMLMT

       430        440        450
LPLLRQTSTK AVQHFYNIKL EGKVPMHKLF LEMLEAKV
```

By "ERRgamma polynucleotide" is meant any nucleic acid sequence encoding an ERRgamma polypeptide or fragment thereof. An exemplary ERRgamma nucleic acid sequence is provided at NCBI Ref: NM_001438.3:

```
                                                        (SEQ ID NO: 2)
aagctccaat cggggcttta agtccttgat taggagagtg tgagagcttt ggtcccaact   61

ggctgtgcct ataggcttgt cactaggaga acatttgtgt taattgcact gtgctctgtc  121

aaggaaactt tgatttatag ctggggtgca caaataatgg ttgccggtcg cacatggatt  181

cggtagaact ttgccttcct gaatcttttt ccctgcacta cgaggaagag cttctctgca  241

gaatgtcaaa caaagatcga cacattgatt ccagctgttc gtccttcatc aagacggaac  301

cttccagccc agcctccctg acggacagcg tcaaccacca cagccctggt ggctcttcag  361

acgccagtgg gagctacagt tcaaccatga atggccatca gaacggactt gactcgccac  421

ctctctaccc ttctgctcct atcctgggag gtagtgggcc tgtcaggaaa ctgtatgatg  481

actgctccag caccattgtt gaagatcccc agaccaagtg tgaatacatg ctcaactcga  541

tgcccaagag actgtgttta gtgtgtggtg acatcgcttc tgggtaccac tatggggtag  601

catcatgtga agcctgcaag gcattcttca agaggacaat tcaaggcaat atagaataca  661

gctgccctgc cacgaatgaa tgtgaaatca caaagcgcag acgtaaatcc tgccaggctt  721

gccgcttcat gaagtgttta aaagtgggca tgctgaaaga aggggtgcgt cttgacagag  781

tacgtggagg tcggcagaag tacaagcgca ggatagatgc ggagaacagc ccatacctga  841

accctcagct ggttcagcca gccaaaaagc catataacaa gattgtctca catttgttgg  901

tggctgaacc ggagaagatc tatgccatgc ctgaccctac tgtccccgac agtgacatca  961

aagccctcac tacactgtgt gacttggccg accgagagtt ggtggttatc attggatggg 1021

cgaagcatat tccaggcttc tccacgctgt ccctggcgga ccagatgagc cttctgcaga 1081

gtgcttggat ggaaattttg atccttggtg tcgtataccg gtctctttcg tttgaggatg 1141

aacttgtcta tgcagacgat tatataatgg acgaagacca gtccaaatta gcaggccttc 1201

ttgatctaaa taatgctatc ctgcagctgg taaagaaata caagagcatg aagctggaaa 1261

aagaagaatt tgtcaccctc aaagctatag ctcttgctaa ttcagactcc atgcacatag 1321

aagatgttga agccgttcag aagcttcagg atgtcttaca tgaagcgctg caggattatg 1381

aagctggcca gcacatggaa gaccctcgtc gagctggcaa gatgctgatg acactgccac 1441

tcctgaggca gacctctacc aaggccgtgc agcatttcta caacatcaaa ctagaaggca 1501

aagtcccaat gcacaaactt tttttggaaa tgttggaggc caaggtctga ctaaaagctc 1561

cctgggcctt cccatccttc atgttgaaaa agggaaaata aacccaagag tgatgtcgaa 1621

gaaacttaga gtttagttaa caacatcaaa aatcaacaga ctgcactgat aatttagcag 1681

caagactatg aagcagcttt cagattcctc cataggttcc tgatgagttt ctttctactt 1741
```

-continued

```
tctccatcat cttctttcct ctttcttccc acatttctct ttctctttat tttttctcct 1801
tttcttcttt cacctccctt atttctttgc ttctttcatt cctagttccc attctccttt 1861
attttcttcc cgtctgcctg ccttctttct tttctttacc tactctcatt cctctctttt 1921
ctcatccttc ccctttttc taaatttgaa atagctttag tttaaaaaaa aatcctccct 1981
tccccctttc ctttcccttt ctttcctttt tccctttcct tttccctttc ctttcctttc 2041
ctcttgacct tctttccatc tttcttttc ttccttctgc tgctgaactt ttaaaagagg 2101
tctctaactg aagagagatg gaagccagcc ctgccaaagg atggagatcc ataatatgga 2161
tgccagtgaa cttattgtga accatactgt ccccaatgac taaggaatca aagagagaga 2221
accaacgttc ctaaaagtac agtgcaacat atacaaattg actgagtgca gtattagatt 2281
tcatgggagc agcctctaat tagacaactt aagcaacgtt gcatcggctg cttcttatca 2341
ttgcttttcc atctagatca gttacagcca tttgattcct taattgtttt ttcaagtctt 2401
ccaggtattt gttagtttag ctactatgta actttttcag ggaatagttt aagctttatt 2461
cattcatgca atactaaaga gaaataagaa tactgcaatt ttgtgctggc tttgaacaat 2521
tacgaacaat aatgaaggac aaatgaatcc tgaaggaaga tttttaaaaa tgttttgttt 2581
cttcttacaa atggagattt ttttgtacca gctttaccac ttttcagcca tttattaata 2641
tgggaattta acttactcaa gcaatagttg aagggaaggt gcatattatc acggatgcaa 2701
tttatgttgt gtgccagtct ggtcccaaac atcaatttct taacatgagc tccagtttac 2761
ctaaatgttc actgacacaa aggatgagat tacacctaca gtgactctga gtagtcacat 2821
atataagcac tgcacatgag atatagatcc gtagaattgt caggagtgca cctctctact 2881
tgggaggtac aattgccata tgatttctag ctgccatggt ggttaggaat gtgatactgc 2941
ctgtttgcaa agtcacagac cttgcctcag aaggagctgt gagccagtat tcatttaaga 3001
ggcaataagg caaatgccag aattaaaaaa aaaaatcatc aaagacagaa aatgcctgac 3061
caaattctaa aacctaatcc atataagttt attcatttag gaatgttcgt ttaaattaat 3121
ctgcagtttt taccaagagc taagccaata tatgtgcttt tcaaccagta ttgtcacagc 3181
atgaaagtca agtcaggttc cagactgtta agaggtgtaa tctaatgaag aaatcaatta 3241
gatgccccga aatctacagt cgctgaataa ccaataaaca gtaacctcca tcaaatgcta 3301
taccaatgga ccagtgttag tagctgctcc ctgtattatg tgaacagtct tattctatgt 3361
acacagatgt aattaaaatt gtaatcctaa caaacaaaag aaatgtagtt cagcttttca 3421
atgtttcatg tttgctgtgc ttttctgaat tttatgttgc attcaaagac tgttgtcttg 3481
ttcttgtggt gtttggattc ttgtggtgtg tgcttttaga cacagggtag aattagagac 3541
aatattggat gtacaattcc tcaggagact acagtagtat attctattcc ttaccagtaa 3601
taaggttctt cctaataata attaagagat tgaaactcca aacaagtatt cattatgaac 3661
agatacacat caaaatcata ataatatttt caaaacaagg aataatttct ctaatggttt 3721
attatagaat accaatgtat agcttagaaa taaaactttg aatatttcaa gaatatagat 3781
aagtctaatt tttaaatgct gtatatatgg ctttcactca atcatctctc agatgttgtt 3841
attaactcgc tctgtgttgt tgcaaaactt tttggtgcag attcgtttcc aaaactattg 3901
ctactttgtg tgctttaaac aaaatacctt gggttgatga aacatcaacc cagtgctagg 3961
aatactgtgt atctatcatt agctatatgg gactatattg tagattgtgg tttctcagta 4021
gagaagtgac tgtagtgtga ttctagataa atcatcatta gcaattcatt cagatggtca 4081
ataacttgaa atttatagct gtgataggag ttcagaaatt ggcacatccc tttaaaaata 4141
acaacagaaa atacaactcc tgggaaaaaa ggtgctgatt ctataagatt atttatatat 4201
```

-continued

```
gtaagtgttt aaaaagatta ttttccagaa agtttgtgca gggtttaagt tgctactatt 4261

caactacact atatataaat aaaatatata caatatatac attgttttca ctgtatcaca 4321

ttaaagtact tgggcttcag aagtaagagc caaccaactg aaaacctgag atggagatat 4381

gttcaaagaa tgagatacaa ttttttagtt ttcagtttaa gtaactctca gcattacaaa 4441

agagtaagta tctcacaaat aggaaataaa actaaaacgt ggatttaaaa agaactgcac 4501

gggctttagg gtaaatgctc atcttaaacc tcactagagg gaagtcttct caagtttcaa 4561

gcaagaccat ttacttaatg tgaagttttg gaaagttata aaggtgtatg ttttagccat 4621

atgattttaa ttttaatttt gcttctttta ggttcgttct tatttaaagc aatatgattg 4681

tgtgactcct tgtagttaca cttgtgtttc aatcagatca gattgttgta tttattccac 4741

tattttgcat ttaaatgata acataaaaga tataaaaaat ttaaaactgc tatttttctt 4801

atagaagaga aaatgggtgt tggtgattgt attttaatta tttaagcgtc tctgtttacc 4861

tgcctaggaa aacattttat ggcagtctta tgtgcaaaga tcgtaaaagg acaaaaaatt 4921

taaactgctt ataataatcc aggagttgca ttatagccag tagtaaaaat aataataata 4981

ataataaaac catgtctata gctgtagatg ggcttcacat ctgtaaagca atcaattgta 5041

tatttttgtg atgtgtacca tactgtgtgc tccagcaaat gtccatttgt gtaaatgtat 5101

ttattttata ttgtatatat tgttaaatgc aaaaaggaga tatgattctg taactccaat 5161

cagttcagat gtgtaactca aattattatg cctttcagga tgatggtaga gcaatattaa 5221

acaagcttcc acttttgact gctaaaaaaa aaaaaaaaaa
```

By “Pancreatic and Duodenal Homeobox-1 (Pdx-1) polypeptide” is meant a protein or fragment thereof having at least 85% homology to the sequence provided at NCBI Reference Sequence: NP_000200.1 and having DNA binding or transcriptional regulation activity. An exemplary human PDX1 amino acid sequence is provided below:

```
                                                     (SEQ ID NO: 3)
mngeeqyyaa tqlykdpcaf qrgpapefsa sppaclymgr qppppphpf pgalgaleqg  61

sppdispyev ppladdpava hlhhhlpaql alphppagpf pegaepgvle epnrvqlpfp 121

wmkstkahaw kgqwaggaya aepeenkrtr taytraqlle lekeflfnky isrprrvela 181

vmlnlterhi kiwfqnrrmk wkkeedkkrg ggtavggggv aepeqdcavt sgeellalpp 241

ppppggavpp aapvaaregr lppglsaspq pssvaprrpq epr
```

By “Pancreatic and Duodenal Homeobox-1 (Pdx-1)” nucleic acid sequence is meant a nucleic acid sequence encoding a PDX-1 polypeptide. Exemplary pdx-1 nucleic acid sequences include NM_000209:

```
                                                     (SEQ ID NO: 4)
gggtggcgcc gggagtggga acgccacaca gtgccaaatc cccggctcca gctcccgact  61

cccggctccc ggctcccggc tcccggtgcc caatcccggg ccgcagccat gaacggcgag 121

gagcagtact acgcggccac gcagctttac aaggacccat gcgcgttcca gcgaggcccg 181

gcgccggagt tcagcgccag ccccccctgcg tgcctgtaca tgggccgcca gccccccgccg 241

ccgccgccgc acccgttccc tggcgccctg ggcgcgctgg agcagggcag ccccccggac 301

atctccccgt acgaggtgcc ccccctcgcc gacgaccccg cggtggcgca ccttcaccac 361

cacctcccgg ctcagctcgc gctcccccac ccgcccgccg ggcccttccc ggagggagcc 421
```

-continued

```
gagccgggcg tcctggagga gcccaaccgc gtccagctgc ctttcccatg gatgaagtct  481
accaaagctc acgcgtggaa aggccagtgg gcaggcggcg cctacgctgc ggagccggag  541
gagaacaagc ggacgcgcac ggcctacacg cgcgcacagc tgctagagct ggagaaggag  601
ttcctattca acaagtacat ctcacggccg cgccgggtgg agctggctgt catgttgaac  661
ttgaccgaga gacacatcaa gatctggttc caaaaccgcc gcatgaagtg gaaaaaggag  721
gaggacaaga agcgcggcgg cgggacagct gtcgggggtg gcggggtcgc ggagcctgag  781
caggactgcg ccgtgacctc cggcgaggag cttctggcgc tgccgccgcc gccgcccccc  841
ggaggtgctg tgccgcccgc tgcccccgtt gccgcccgag agggccgcct gccgcctggc  901
cttagcgcgt cgccacagcc ctccagcgtc gcgcctcggc ggccgcagga accacgatga  961
gaggcaggag ctgctcctgg ctgaggggct tcaaccactc gccgaggagg agcagagggc 1021
ctaggaggac cccgggcgtg gaccacccgc cctggcagtt gaatggggcg gcaattgcgg 1081
ggcccacctt agaccgaagg ggaaaacccg ctctctcagg cgcatgtgcc agttggggcc 1141
ccgcgggtag atgccggcag gccttccgga agaaaaagag ccattggttt ttgtagtatt 1201
ggggccctct tttagtgata ctggattggc gttgtttgtg gctgttgcgc acatccctgc 1261
cctcctacag cactccacct tgggacctgt ttagagaagc cggctcttca aagacaatgg 1321
aaactgtacc atacacattg gaaggctccc taacacacac agcggggaag ctgggccgag 1381
taccttaatc tgccataaag ccattcttac tcgggcgacc cctttaagtt tagaaataat 1441
tgaaaggaaa tgtttgagtt ttcaaagatc ccgtgaaatt gatgccagtg gaatacagtg 1501
agtcctcctc ttcctcctcc tcctcttccc cctcccttc ctcctcctcc tcttcttttc 1561
cctcctcttc ctcttcctcc tgctctcctt tcctccccct cctcttttcc ctcctcttcc 1621
tcttcctcct gctctccttt cctccccctc ctctttctcc tcctcctcct cttcttcccc 1681
ctcctctccc tcctcctctt cttccccctc ctctccctcc tcctcttctt ctccctcctc 1741
ttcctcttcc tcctcttcca cgtgctctcc tttcctcccc ctcctcttgc tccccttctt 1801
ccccgtcctc ttcctcctcc tcctcttctt ctccctcctc ttcctcctcc tctttcttcc 1861
tgacctcttt ctttctcctc ctcctccttc tacctcccct tctcatccct cctcttcctc 1921
ttctctagct gcacacttca ctactgcaca tcttataact tgcacccctt tcttctgagg 1981
aagagaacat cttgcaaggc agggcgagca gcggcagggc tggcttagga gcagtgcaag 2041
agtccctgtg ctccagttcc acactgctgg cagggaaggc aagggggggac gggcctggat 2101
ctgggggtga gggagaaaga tggacccctg ggtgaccact aaaccaaaga tattcggaac 2161
tttctattta ggatgtggac gtaattcctg ttccgaggta gaggctgtgc tgaagacaag 2221
cacagtggcc tggtgcgcct tggaaaccaa caactattca cgagccagta tgaccttcac 2281
atctttagaa attatgaaaa cgtatgtgat tggagggttt ggaaaaccag ttatcttatt 2341
taacatttta aaaattacct aacagttatt tacaaacagg tctgtgcatc ccaggtctgt 2401
cttcttttca aggtctgggc cttgtgctcg ggttatgttt gtgggaaatg cttaataaat 2461
actgataata tgggaagaga tgaaaactga ttctcctcac tttgtttcaa acctttctgg 2521
cagtgggatg attcgaattc acttttaaaa ttaaattagc gtgttttgtt ttg
```

By "Pax4 polypeptide" is meant a protein or fragment thereof having at least 85% homology to the sequence provided at GenBank Accession No. AAI07151 and having DNA binding or transcriptional regulation activity.

(SEQ ID NO: 5)

```
mawsskswlc liasscprdt llpsahhasp vpashltqvs ngcvskilgr yyrtgvlepk  61

giggskprla tppvvariaq lkgecpalfa weiqrqlcae glctqdktps vssinrvlra 121

lqedqglpct rlrspavlap avltphsgse tprgthpgtg hrnrtifsps qaealekefq 181

rgqypdsvar gklatatslp edtvrvwfsn rrakwrrqek lkwemqlpga sqgltvprva 241

pgiisaqqsp gsvptaalpa leplgpscyq lcwataperc lsdtppkacl kpcwghlppq 301

pnsldsgllc lpcpsshcpl aslsgsqall wpgcpllygl e
```

By "Pax4 nucleic acid molecule" is meant a polynucleotide or fragment thereof that encodes a Pax4 polypeptide. Exemplary Pax4 polypeptides include BC107150, which sequence is provided below:

(SEQ ID NO: 6)

```
gggcagcaag gatgcagtct cccaggagag gatgcactcg gtggtgggaa gccaggctgg   61

aggggcctga gtgaccctct ccacaggcgg gcagggcagt gggagaggtg gtgtgtggat  121

acctctgtct cacgcccagg gatcagcagc atgaaccagc ttggggggct ctttgtgaat  181

ggccggcccc tgcctctgga tacccggcag cagattgtgc ggctagcagt cagtggaatg  241

cggccctgtg acatctcacg gatccttaag gtaatgggcc agcaccttta cccagtgatg  301

gggacaggaa gcagggagaa agggctcctc tgaaggcaag agcctggggc tgttgcaggc  361

tctgagggct tctgggactt gggtcacttc ctgggagatc ctctcggagg ttgaaaaggg  421

gagcctcagg ccctcaaagc tgaggctgga ctcccgactt catggcctgg tccagtaagt  481

cttggctttg tcttatagcc tcctcctgtc ccagggacac tctccttcct tctgcccatc  541

atgcctcacc tgtccctgct tctcacctga ctcaggtatc taatggctgt gtgagcaaga  601

tcctagggcg ttactaccgc acaggtgtct tggagccaaa gggcattggg ggaagcaagc  661

cacggctggc tacacccccct gtggtggctc gaattgccca gctgaagggt gagtgtccag  721

ccctctttgc ctgggaaatc caacgccagc tttgtgctga agggctttgc acccaggaca  781

agactcccag tgtctcctcc atcaaccgag tcctgcgggc attacaggag gaccagggac  841

taccgtgcac acggctcagg tcaccagctg ttttggctcc agctgtcctc actccccata  901

gtggctctga gactccccgg ggtacccacc cagggaccgg ccaccggaat cggactatct  961

tctccccaag ccaagcagag gcactggaga aagagttcca gcgtgggcag tatcctgatt 1021

cagtggcccg tggaaagctg gctactgcca cctctctgcc tgaggacacg gtgagggtct 1081

ggttttccaa cagaagagcc aaatggcgtc ggcaagagaa gctcaagtgg gaaatgcagc 1141

tgccaggtgc ttcccagggg ctgactgtac caagggttgc cccaggaatc atctctgcac 1201

agcagtcccc tggcagtgtg cccacagcag ccctgcctgc cctggaacca ctgggtccct 1261

cctgctatca gctgtgctgg gcaacagcac cagaaaggtg tctgagtgac accccaccta 1321

aagcctgtct caagccctgc tggggccact tgcccccaca gccgaattcc ctggactcag 1381

gactgctttg ccttccttgc ccttcctccc actgtcccct ggccagtctt agtggctctc 1441

aggccctgct ctggcctggc tgcccactac tgtatggctt ggaatgaggc aggagtggga 1501

aggagatggc atagagaaga tctaatacca tcctgcccat tgtccttacc gtcctgccca 1561

tacagactgt ggctccttcc tccttcctgt gattgctccc tcctgtgtgg acg
```

By "PGC1 alpha polypeptide" is meant a protein or fragment thereof having at least 85% homology to the sequence provided at NCBI Ref: NP_037393.1 or UniProt Ref: Q9UBK2." An exemplary amino acid sequence is provided below.

```
>sp|Q9UBK2|PRGC1_HUMAN Peroxisome proliferator-
activated receptor gamma coactivator 1-alpha
OS = Homo sapiens GN = PPARGC1A PE = 1 SV = 1
                                    (SEQ ID NO: 7)
MAWDMCNQDSESVWSDIECAALVGEDQPLCPDLPELDLSELDVNDLDTDS

FLGGLKWCSDQSEIISNQYNNEPSNIFEKIDEENEANLLAVLTETLDSLP

VDEDGLPSFDALTDGDVTTDNEASPSSMPDGTPPPQEAEEPSLLKKLLLA

PANTQLSYNECSGLSTQNHANHNHRIRTNPAIVKTENSWSNKAKSICQQQ

KPQRRPCSELLKYLTTNDDPPHTKPTENRNSSRDKCTSKKKSHTQSQSQH

LQAKPTTLSLPLTPESPNDPKGSPFENKTIERTLSVELSGTAGLTPPTTP
```

-continued

```
PHKANQDNPFRASPKLKSSCKTVVPPPSKKPRYSESSGTQGNNSTKKGPE

QSELYAQLSKSSVLTGGHEERKTKRPSLRLFGDHDYCQSINSKTEILINI

SQELQDSRQLENKDVSSDWQGQICSSTDSDQCYLRETLEASKQVSPCSTR

KQLQDQEIRAELNKHFGHPSQAVEDDEADKTGELRDSDFSNEQFSKLPMF

INSGLAMDGLFDDSEDESDKLSYPWDGTQSYSLFNVSPSCSSFNSPCRDS

VSPPKSLFSQRPQRMRSRSRSFSRHRSCSRSPYSRSRSRSPGSRSSSRSC

YYYESSHYRHRTHRNSPLYVRSRSRSPYSRRPRYDSYEEYQHERLKREEY

RREYEKRESERAKQRERQRQKAIEERRVIYVGKIRPDTTRTELRDRFEVF

GEIEECTVNLRDDGDSYGFITYRYTCDAFAALENGYTLRRSNETDFELYF

CGRKQFFKSNYADLDSNSDDFDPASTKSKYDSLDFDSLLKEAQRSLRR
```

By "PGC1 alpha polynucleotide" is meant a nucleic acid molecule encoding a PGC1 alpha polypeptide. An exemplary PGC1 alpha polynucleotide sequence is provided below:

```
                                                            (SEQ ID NO: 8)
tagtaagaca ggtgccttca gttcactctc agtaaggggc tggttgcctg catgagtgtg   61

tgctctgtgt cactgtggat tggagttgaa aaagcttgac tggcgtcatt caggagctgg  121

atggcgtggg acatgtgcaa ccaggactct gagtctgtat ggagtgacat cgagtgtgct  181

gctctggttg gtgaagacca gcctctttgc ccagatcttc ctgaacttga tctttctgaa  241

ctagatgtga acgacttgga tacagacagc tttctgggtg gactcaagtg gtgcagtgac  301

caatcagaaa taatatccaa tcagtacaac aatgagcctt caaacatatt tgagaagata  361

gatgaagaga atgaggcaaa cttgctagca gtcctcacag agacactaga cagtctccct  421

gtggatgaag acggattgcc ctcatttgat gcgctgacag atggagacgt gaccactgac  481

aatgaggcta gtccttcctc catgcctgac ggcacccctc caccccagga ggcagaagag  541

ccgtctctac ttaagaagct cttactggca ccagccaaca ctcagctaag ttataatgaa  601

tgcagtggtc tcagtaccca gaaccatgca aatcacaatc acaggatcag aacaaaccct  661

gcaattgtta agactgagaa ttcatggagc aataaagcga agagtatttg tcaacagcaa  721

aagccacaaa gacgtccctg ctcggagctt ctcaaatatc tgaccacaaa cgatgaccct  781

cctcacacca aacccacaga gaacagaaac agcagcagag acaaatgcac ctccaaaaag  841

aagtcccaca cacagtcgca gtcacaacac ttacaagcca aaccaacaac tttatctctt  901

cctctgaccc cagagtcacc aaatgacccc aagggttccc catttgagaa caagactatt  961

gaacgcacct taagtgtgga actctctgga actgcaggcc taactccacc caccactcct 1021

cctcataaag ccaaccaaga taaccctttt agggcttctc caaagctgaa gtcctcttgc 1081

aagactgtgg tgccaccacc atcaaagaag cccaggtaca gtgagtcttc tggtacacaa 1141

ggcaataact ccaccaagaa agggccggag caatccgagt tgtatgcaca actcagcaag 1201

tcctcagtcc tcactggtgg acacgaggaa aggaagacca agcggcccag tctgcggctg 1261

tttggtgacc atgactattg ccagtcaatt aattccaaaa cagaaatact cattaatata 1321

tcacaggagc tccaagactc tagacaacta gaaaataaag atgtctcctc tgattggcag 1381

gggcagattt gttcttccac agattcagac cagtgctacc tgagagagac tttggaggca 1441

agcaagcagg tctctccttg cagcacaaga aaacagctcc aagaccagga aatccgagcc 1501

gagctgaaca agcacttcgg tcatcccagt caagctgttt ttgacgacga agcagacaag 1561

accggtgaac tgagggacag tgatttcagt aatgaacaat tctccaaact acctatgttt 1621
```

-continued

```
ataaattcag gactagccat ggatggcctg tttgatgaca gcgaagatga aagtgataaa 1681
ctgagctacc cttgggatgg cacgcaatcc tattcattgt tcaatgtgtc tccttcttgt 1741
tcttctttta actctccatg tagagattct gtgtcaccac ccaaatcctt attttctcaa 1801
agaccccaaa ggatgcgctc tcgttcaagg tccttttctc gacacaggtc gtgttcccga 1861
tcaccatatt ccaggtcaag atcaaggtct ccaggcagta gatcctcttc aagatcctgc 1921
tattactatg agtcaagcca ctacagacac cgcacgcacc gaaattctcc cttgtatgtg 1981
agatcacgtt caagatcgcc ctacagccgt cggcccaggt atgacagcta cgaggaatat 2041
cagcacgaga ggctgaagag ggaagaatat cgcagagagt atgagaagcg agagtctgag 2101
agggccaagc aaagggagag gcagaggcag aaggcaattg aagagcgccg tgtgatttat 2161
gtcggtaaaa tcagacctga cacaacacgg acagaactga gggaccgttt tgaagttttt 2221
ggtgaaattg aggagtgcac agtaaatctg cgggatgatg gagacagcta tggtttcatt 2281
acctaccgtt atacctgtga tgcttttgct gctcttgaaa atggatacac tttgcgcagg 2341
tcaaacgaaa ctgactttga gctgtacttt tgtggacgca agcaattttt caagtctaac 2401
tatgcagacc tagattcaaa ctcagatgac tttgaccctg cttccaccaa gagcaagtat 2461
gactctctgg attttgatag tttactgaaa gaagctcaga gaagcttgcg caggtaacat 2521
gttccctagc tgaggatgac agagggatgg cgaatacctc atgggacagc gcgtccttcc 2581
ctaaagacta ttgcaagtca tacttaggaa tttctcctac tttacactct ctgtacaaaa 2641
acaaaacaaa acaacaacaa tacaacaaga acaacaacaa caataacaac aatggtttac 2701
atgaacacag ctgctgaaga ggcaagagac agaatgatat ccagtaagca catgtttatt 2761
catgggtgtc agctttgctt ttcctggagt ctcttggtga tggagtgtgc gtgtgtgcat 2821
gtatgtgtgt gtgtatgtat gtgtgtggtg tgtgtgcttg gtttagggga agtatgtgtg 2881
ggtacatgtg aggactgggg gcacctgacc agaatgcgca agggcaaacc atttcaaatg 2941
gcagcagttc catgaagaca cgcttaaaac ctagaacttc aaaatgttcg tattctattc 3001
aaaaggaaat atatatatat atatatatat atatatatat atatataaat taaaaaggaa 3061
agaaaactaa caaccaacca accaaccaac caaccacaaa ccaccctaaa atgacagccg 3121
ctgatgtctg ggcatcagcc tttgtactct gtttttttaa gaaagtgcag aatcaacttg 3181
aagcaagctt tctctcataa cgtaatgatt atatgacaat cctgaagaaa ccacaggttc 3241
catagaacta atatcctgtc tctctctctc tctctctctc tctcttttttt ttttcttttt 3301
ccttttgcca tggaatctgg gtgggagagg atactgcggg caccagaatg ctaaagtttc 3361
ctaacatttt gaagtttctg tagttcatcc ttaatcctga cacccatgta aatgtccaaa 3421
atgttgatct tccactgcaa atttcaaaag ccttgtcaat ggtcaagcgt gcagcttgtt 3481
cagcggttct ttctgaggag cggacaccgg gttacattac taatgagagt tgggtagaac 3541
tctctgagat gtgttcagat agtgtaattg ctacattctc tgatgtagtt aagtatttac 3601
agatgttaaa tggagtattt ttattttatg tatatactat acaacaatgt tctttttttgt 3661
tacagctatg cactgtaaat gcagccttct tttcaaaact gctaaatttt tcttaatcaa 3721
gaatattcaa atgtaattat gaggtgaaac aattattgta cactaacata tttagaagct 3781
gaacttactg cttatatata tttgattgta aaaacaaaaa gacagtgtgt gtgtctgttg 3841
agtgcaacaa gagcaaaatg atgctttccg cacatccatc ccttaggtga gcttcaatct 3901
aagcatcttg tcaagaaata tcctagtccc ctaaaggtat taaccacttc tgcgatattt 3961
ttccacattt tcttgtcgct tgtttttctt tgaagtttta tacactggat ttgttagggg 4021
```

-continued

```
aatgaaattt tctcatctaa aatttttcta gaagatatca tgattttatg taaagtctct 4081
caatgggtaa ccattaagaa atgtttttat tttctctatc aacagtagtt ttgaaactag 4141
aagtcaaaaa tctttttaaa atgctgtttt gttttaattt ttgtgatttt aatttgatac 4201
aaaatgctga ggtaataatt atagtatgat ttttacaata attaatgtgt gtctgaagac 4261
tatctttgaa gccagtattt ctttcccttg gcagagtatg acgatggtat ttatctgtat 4321
tttttacagt tatgcatcct gtataaatac tgatatttca ttcctttgtt tactaaagag 4381
acatatttat cagttgcaga tagcctattt attataaatt atgagatgat gaaaataata 4441
aagccagtgg aaattttcta cctaggatgc atgacaattg tcaggttgga gtgtaagtgc 4501
ttcatttggg aaattcagct tttgcagaag cagtgtttct acttgcacta gcatggcctc 4561
tgacgtgacc atggtgttgt tcttgatgac attgcttctg ctaaatttaa taaaaacttc 4621
agaaaaacct ccattttgat catcaggatt tcatctgagt gtggagtccc tggaatggaa 4681
ttcagtaaca tttggagtgt gtattcaagt ttctaaattg agattcgatt actgtttggc 4741
tgacatgact tttctggaag acatgataca cctactactc aattgttctt ttcctttctc 4801
tcgcccaaca cgatcttgta agatggattt cacccccagg ccaatgcagc taattttgat 4861
agctgcattc atttatcacc agcatattgt gttctgagtg aatccactgt ttgtcctgtc 4921
ggatgcttgc ttgatttttt ggcttcttat ttctaagtag atagaaagca ataaaaatac 4981
tatgaaatga aagaacttgt tcacaggttc tgcgttacaa cagtaacaca tctttaatcc 5041
gcctaattct tgttgttctg taggttaaat gcaggtattt taactgtgtg aacgccaaac 5101
taaagtttac agtctttctt tctgaatttt gagtatcttc tgttgtagaa taataataaa 5161
aagactatta agagcaataa attattttta agaaatcgag atttagtaaa tcctattatg 5221
tgttcaagga ccacatgtgt tctctatttt gcctttaaat ttttgtgaac caattttaaa 5281
tacattctcc tttttgccct ggattgttga catgagtgga atacttggtt tcttttctta 5341
cttatcaaaa gacagcacta cagatatcat attgaggatt aatttatccc ccctaccccc 5401
agcctgacaa atattgttac catgaagata gttttcctca atggacttca aattgcatct 5461
agaattagtg gagcttttgt atcttctgca gacactgtgg gtagcccatc aaaatgtaag 5521
ctgtgctcct ctcattttta tttttatttt tttgggagag aatatttcaa atgaacacgt 5581
gcaccccatc atcactggag gcaaatttca gcatagatct gtaggatttt tagaagaccg 5641
tgggccattg ccttcatgcc gtggtaagta ccacatctac aattttggta accgaactgg 5701
tgctttagta atgtggattt ttttcttttt taaaagagat gtagcagaat aattcttcca 5761
gtgcaacaaa atcaattttt tgctaaacga ctccgagaac aacagttggg ctgtcaacat 5821
tcaaagcagc agagagggaa ctttgcacta ttggggtatg atgtttgggt cagttgataa 5881
aaggaaacct tttcatgcct ttagatgtga gcttccagta ggtaatgatt atgtgtcctt 5941
tcttgatggc tgtaatgaga acttcaatca ctgtagtcta agacctgatc tatagatgac 6001
ctagaatagc catgtactat aatgtgatga ttctaaattt gtacctatgt gacagacatt 6061
ttcaataatg tgaactgctg atttgatgga gctactttaa gatttgtagg tgaaagtgta 6121
atactgttgg ttgaactatg ctgaagaggg aaagtgagcg attagttgag cccttgccgg 6181
gcctttttcc cacctgccaa ttctacatgt attgttgtgg ttttattcat tgtatgaaaa 6241
ttcctgtgat ttttttaaa tgtgcagtac acatcagcct cactgagcta ataaagggaa 6301
acgaatgttt caaatcta
```

By "exogenous" is meant a nucleic acid molecule or polypeptide that is not endogenously present in the cell. The term "exogenous" would therefore encompass any recombinant nucleic acid molecule or polypeptide expressed in a cell, such as foreign, heterologous, and over-expressed nucleic acid molecules and polypeptides.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels.

By "analog" is meant a structurally related polypeptide or nucleic acid molecule having the function of a reference polypeptide or nucleic acid molecule.

By "an effective amount" is meant the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "functional beta cell" is meant a beta cell capable of glucose-stimulated insulin secretion.

By "fusion protein" is meant a protein that combines at least two amino acid sequences that are not naturally contiguous.

By "increases or decreases" is meant a positive or negative alteration. Such alterations are by 5%, 10%, 25%, 50%, 75%, 85%, 90% or even by 100% of a reference value.

By "isolated cell" is meant a cell that is separated from the molecular and/or cellular components that naturally accompany the cell.

By "isolated nucleic acid molecule" is meant a nucleic acid (e.g., a DNA) that is free of the genes, which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In one embodiment, the preparation is at least 75%, 85%, 90%, 95%, or at least 99%, by weight, a polypeptide of the invention. An isolated polypeptide of the invention may be obtained, for example, by extraction from a natural source, by expression from a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "matrix" is meant a natural or artificial material in which a cell is embedded. In particular embodiment, the matrix comprises a component of the extracellular matrix (e.g., proteoglycans, heparan sulfate, integrin, chondroitin sulfate, keratan sulfate, hyaluronic acid, collagen, elastin, fibronectin, laminin. In other embodiments, the matrix comprises a supportive cell type (e.g., fibroblast, osteoblast, chondrocyte).

The terms "isolated," "purified," or "biologically pure" refer to material (e.g., a cell) that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "naturally occurs" is meant is endogenously expressed in a cell of an organism.

By "negative" is meant that a cell expresses an undetectable level of a marker or a reduced level of marker, such that the cell can be distinguished in a negative selection from a population of unselected cells.

By "obtaining" as in "obtaining the polypeptide" is meant synthesizing, purchasing, or otherwise acquiring the polypeptide.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "polypeptide" is meant any chain of amino acids, regardless of length or post-translational modification.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant polypeptide of the invention, or an RNA molecule).

By "positive" is meant that a cell expresses a detectable level of a marker.

As used herein, "obtaining" as in "obtaining an agent" includes synthesizing, purchasing, or otherwise acquiring the agent.

By "Beta cell transcription factor" is meant any transcription factor expressed in a pancreatic tissue. Exemplary pancreatic transcription factors include, but are not limited to, ERRgamma, Pdx-1, Ngn3, Pax4, NeuroD1, Nkx2.2 (human C075092, AAH75092), Nkx6.1 (human P78426, NM_006168) Isl1 (human NM_002202, NP_002193), Pax6 (human NP_000271, BC011953), MafA (v-maf musculoaponeurotic fibrosarcoma oncogene homolog A) (human NP_963883, NM_201589)), and MafB (v-maf musculoaponeurotic fibrosarcoma oncogene homolog B) (human NP_005452, NM_005461).

By "promoter" is meant a polynucleotide sufficient to direct transcription. Exemplary promoters include nucleic acid sequences of lengths 100, 250, 300, 400, 500, 750, 900, 1000, 1250, and 1500 nucleotides that are upstream (e.g., immediately upstream) of the translation start site.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "regenerate" is meant capable of contributing at least one cell to the repair or de novo construction of a tissue or organ.

By "reprogramming" is meant altering a cell such that at least one protein product is produced in the reprogrammed cell that is not produced in the cell prior to reprogramming (or in a corresponding control cell). Typically, the reprogrammed cell has an altered transcriptional or translational profile, such that the reprogrammed cell expresses a set of proteins not expressed in the cell prior to reprogramming (or in a corresponding control cell).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By "preventing" a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a graph showing glucose-stimulated insulin secretion from mouse neonatal (<14 days) and adult (>12 weeks) pancreatic islets after sequential perfusion with 3 mM and 20 mM glucose (10 islets per assay, n=6). FIGS. 1B and 1C are heatmaps of transcriptional changes in C57BL/6J islets during postnatal maturation. FIG. 1B shows the Row Z-score of downregulated, and FIG. 1C of upregulated genes. FIG. 1D is a graph depicting relative ERR-gamma (ERRγ) expression in isolated islets measured by qPCR. FIG. 1E shows relative ERRgamma expression in murine heart, liver, white adipose (WAT), whole pancreas and isolated islets (n=4). X-gal staining indicating ERR-gamma expression in islets from $ERRgamma^{-/-}$ mice (top panel). FIG. 1F shows relative expression of Ldha and selected mitochondrial metabolic genes during postnatal islet maturation, as measured by qPCR. (n=3, data represent the mean±s.e.m., *p<0.01 Student's unpaired t-test. 2 wks, 2 weeks; 6 wks, 6 weeks; 12 wks, 12 weeks).

FIGS. 2A-2C show transcriptional changes between neonatal and adult islets. FIG. 2A is a heatmap of expression changes in pancreatic lineage genes in islets from 2, 6, and 12 week old C57BL/6J mice. FIG. 2B is a table showing biological pathways enriched in neonatal (2 week old) islets, determined by gene ontology (GO). FIG. 2C is a table showing biological pathways enriched in adult (12 week old) islets, determined by gene ontology (GO).

FIG. 3A is a bar graph showing relative expression of cell type-specific markers in FACS-sorted cell populations from mouse insulin promoter GFP (MIP-GFP) islets at 2 and 12 weeks (n=3). FIG. 3B is a bar graph showing relative expression of ERRgamma and the proliferative marker PdgfRβ in FACS-sorted cell populations from mouse insulin promoter GFP (MIP-GFP) islets at 2 and 12 weeks (n=3).

FIG. 4A is a bar graph showing relative expression of ERRgamma in isolated islets and tissues from $ERR\gamma^{lox/lox}$ (WT) and βERRγKO mice, measured by qPCR. FIG. 4B is a bar graph depicting developmental changes in body weight of WT, βERRγKO, and WT (RIP-Cre) mice. FIG. 4C is a line graph depicting developmental changes in ad lib fed blood glucose levels in male mice. FIG. 4D is a line graph depicting developmental changes in ad lib fed blood glucose levels in female mice.

FIG. 5A is a line graph depicting results of an intra-peritoneal glucose tolerance test (IP-GTT) of $ERR\gamma^{lox/lox}$ (WT) and βERRγKO mice on normal chow diet (NCD; WT n=8, βERRγKO n=6). FIG. 5B is a line graph depicting results of an intra-peritoneal glucose tolerance test (IP-GTT) of $ERR\gamma^{lox/lox}$ (WT) and βERRγKO mice on high fat diet (HFD; WT n=7, βERRγKO n=9). FIG. 5C is a line graph showing results of an intra-peritoneal insulin tolerance test (IP-ITT) of $ERR\gamma^{lox/lox}$ (WT) and βERRγKO mice on NCD (WT n=4, βERRγKO n=5). FIG. 5D is a line graph depicting glucose-stimulated insulin secretion of NCD fed mice (WT n=4, βERRγKO n=12). FIG. 5E is a line graph depicting glucose-stimulated insulin secretion of HFD fed mice (4 weeks HFD, WT n=6, βERRγKO n=6). FIG. 5F depicts images showing isolated islets from HFD-fed WT (top panel) and βERRγKO (bottom panel) mice stained for insulin (green) and glucagon (red). FIG. 5G is a bar graph showing insulin content of isolated islets (WT n=17 and βERRγKO n=19). FIG. 5H is a bar graph showing relative ERRγ and Insulin 2 (Ins2) expression in adenoviral-EGFP (Ad-EGFP) and adenoviral-Cre (Ad-Cre) infected $ERR\gamma^{lox/lox}$ islets. FIG. 5I is a bar graph depicting an ex vivo GSIS assay of adenoviral-EGFP (Ad-EGFP) and adenoviral-Cre (Ad-Cre) infected $ERR\gamma^{lox/lox}$ islets. FIG. 5J is a line graph showing oxygen consumption (OCR) in adenoviral-EGFP (Ad-EGFP) and adenoviral-Cre (Ad-Cre) infected $ERR\gamma^{lox/lox}$ islets. FIG. 5K is a bar graph showing that ERRγ deletion disrupted insulin secretion in response to nutrients. The graph depicts data for ex vivo insulin secretion from $ERR\gamma^{lox/lox}$ (WT) and βERRγKO islets in response to nutrients (glucose, leucine and glutamine) and KCl.

FIG. 6A is a line graph showing results of an intra-peritoneal glucose tolerance test (IP-GTT) on $ERR\gamma^{lox/lox}$ (WT, n=8), βERRγKO (n=6), and RIP-Cre (WT (RIP-Cre), n=3) mice fed a normal chow diet (NCD). FIG. 6B is a line graph showing results of an intra-peritoneal glucose tolerance test (IP-GTT) after 4 weeks on a high fat diet (HFD). FIG. 6C is a line graph depicting an intra-peritoneal insulin tolerance test (IP-ITT) of WT and βERRγKO mice fed a normal chow diet (NCD; WT, n=4, βERRγKO, n=5) and after 4 weeks on a high fat diet (HFD; WT, n=8, βERRγKO, n=8). FIG. 6D depicts a line graph (left panel) and a bar graph (right panel) depicting in vivo glucose-stimulated insulin secretion (GSIS) under normal chow diet (NCD; WT n=4, βERRγKO n=12, WT(RIP-Cre), n=5). FIG. 6E depicts a line graph (left panel) and a bar graph (right panel) depicting in vivo glucose-stimulated insulin secretion (GSIS) after 4 weeks high fat diet (HFD; WT n=6, βERRγKO n=6, and WT(RIP-Cre), n=6), respectively. Bar graph indicates area under the curve (AUC). FIG. 6F is a graph showing ERRgamma expression in isolated islets from WT and Tamoxifen-induced beta cell-specific ERRgammaKO βERRγKO ER; $ERR\gamma^{lox/lox}$×RIP-creER). FIG. 6G is a line graph showing results of IP-GTT of WT (n=9) and βERRγKO ER (n=11) mice after tamoxifen (Tam) treatment. Data are shown as mean s.e.m.

FIG. 7A is a bar graph showing body weights of 16 week old male $ERRgamma^{lox/lox}$ (WT) and pancreatic-specific ERRgammaKO (βERRγKO; $ERR\gamma^{lox/lox}$×PDX1-Cre) mice. FIG. 7B is a line graph showing an intra-peritoneal glucose tolerance test (IP-GTT) of 16 week old male WT and βERRγKO mice fed a normal chow diet (NCD, n=6-10). Data are mean±s.e.m. *p<0.01 Student's unpaired t-test. FIG. 7C is a bar graph showing body weights of 16 week old female $ERR\gamma^{lox/lox}$ (WT) and pancreatic-specific ERRgammaKO (βERRγKO; $ERR\gamma^{lox/lox}$×PDX1-Cre) mice. FIG. 7D is a line graph showing results of an intra-peritoneal glucose tolerance test (IP-GTT) of 16 week old female WT and βERRγKO mice fed a normal chow diet (NCD, n=6-10). Data are mean±s.e.m. *p<0.01 Student's unpaired t-test.

FIG. 8A depicts images of immunostaining (insulin, green and glucagon, red) of islets from $ERR\gamma^{lox/lox}$ (WT) and βERRγKO mice fed a normal chow diet (NCD) or high fat diet (HFD). FIG. 8B depicts images of hematoxylin and eosin (H&E) staining of islets from $ERR\gamma^{lox/lox}$ (WT) and βERRγKO mice fed a normal chow diet (NCD) or high fat diet (HFD). FIG. 8C is a bar graph showing insulin content of islets from WT and βERRγKO mice fed a normal chow diet (NCD). FIG. 8D is a bar graph showing insulin content of islets from WT and βERRγKO mice fed a high fat diet (HFD). FIG. 8E is a bar graph showing the average area of islet sizes from FIG. 8D (WT, n=5; βERRγKO, n=5). FIG. 8F is a bar graph showing the frequency distribution of islet sizes of FIG. 8D (WT, n=5; βERRγKO, n=5). Data are mean±s.e.m. *p<0.01 Student's unpaired t-test.

FIG. 9A is a bar graph of relative ERRgamma expression in INS-1 cells transfected with scrambled (Control) or ERRgamma-targeted siRNA. FIG. 9B is a bar graph of glucose stimulated insulin secretion (GSIS) in INS-1 cells transfected with scrambled (Control) or ERRgamma-targeted siRNA. FIG. 9C is a bar graph of cellular ATP levels in INS-1 cells transfected with scrambled (Control) or ERRgamma-targeted siRNA. FIG. 9D is a scatter graph of cellular bioenergetics in INS-1 cells transfected with scrambled (Control) or ERRgamma-targeted siRNA. *p<0.01 Student's unpaired t-test.

FIGS. 10A-10H show that islet ERRgamma knockout disrupted islet functional maturation. FIG. 10A depicts two electron microscopy images showing mitochondrial morphology in beta cells from ERRγ$^{lox/lox}$ (WT) and βERRγKO (ERRγ$^{lox/lox}$xRIP-Cre) islets (n=8). FIG. 10B is a bar graph depicting mitochondria number in beta cells from ERRγ$^{lox/lox}$ (WT) and βERRγKO (ERRγ$^{lox/lox}$xRIP-Cre) islets (n=8). FIG. 10C is a bar graph depicting mitochondrial volume in beta cells from ERRγ$^{lox/lox}$ (WT) and βERRγKO (ERRγ$^{lox/lox}$xRIP-Cre) islets (n=8). FIG. 10D is a table of dysregulated biological function categories in βERRγKO islets, identified by Gene Ontology (GO). FIG. 10E depicts two sets of bar graphs showing relative expression of metabolic genes in βERRγKO (left panel) and pancreatic ERRγKO (ERRγ$^{lox/lox}$xPDX1-Cre, βERRγKO, right panel) islets, as measured by qPCR. FIG. 10F is a heatmap of gene expression levels (Row Z-score) during functional maturation of islets, compared to βERRγKO islets. FIG. 10G is a heatmap of expression changes in selected metabolic and secretion/exocytosis pathway genes in βERRγKO islets. FIG. 10H shows altered gene expression in ERRγKO islets. FIG. 10H depicts a heatmap of 471 hierarchally-clustered genes whose expression changed (Row Z-score) in βERRγKO islets, compared to postnatal developmental changes in WT mice.

FIG. 12A depicts a schematic of the ERR response element identified in 140 down- and 149 up-regulated genes in βERRγKO islets. FIG. 12B is a bar graph depicting a ChIP assay for indicated genes in mouse insulinoma cell line (MIN-6 cells). *p<0.01 Student's unpaired t-test.

FIGS. 13A-13K show that ERRgamma promotes maturation of human iPSC-derived beta-like cells. FIG. 13A is a schematic summarizing a protocol for iPSC-derived beta-like cell generation (ED, endoderm; PP, pancreatic progenitors; iβL, iPSC-derived beta-like cells; iβeta, ERRgamma expressing iPSC-derived beta-like cells). FIG. 13B is a bar graph showing relative expression of human insulin during iPSC differentiation. FIG. 13C depicts two images of human insulin reporter-driven GFP expression (left panel) and phase contrast image (right panel) of day 22 beta-like (iβL) cells. FIG. 13D depicts two bar graphs of intracellular (left) and extracellular (right) c-peptide concentrations of iβL cells after adenoviral infection: Ad-EGFP infected, iβL$^{GFP}$ cells, open bars, Ad-ERRγ infected, iβeta cells, red bars. FIG. 13E is a scatter graph showing induced c-peptide secretion in iβL cells, iβL$^{GFP}$ cells, iβeta cells, and human islets. FIG. 13F is a table showing functional annotation of upregulated gene categories in iβeta cells identified by Gene Ontology (GO). FIG. 13G depicts two heatmaps of expression changes in known beta cell maker genes (left) and metabolic genes (right) in iβLG$^{FP}$ and iβeta cells (log 2 ratio relative to undifferentiated iPSC). FIG. 13H depicts two electron microscopy images showing mitochondrial morphology and insulin granules (right panels) in iβL$^{GFP}$ and iβeta cells. FIG. 13I is a line graph depicting oxidative capacity of iβL$^{GFP}$ and iβeta cells, as measured by oxygen consumption rate (OCR). FIG. 13J has four line graphs showing that β cell marker expression was independent of ERRγ. The graphs show Nkx6-1 and MafA expression in undifferentiated iPSCs, iβL and iβeta (ERRγ expressing) cells. FIG. 13K has 11 scatter graphs showing that ERRγ induced the expression of metabolic genes. Expression of metabolic genes in iβL$^{GFP}$ cells and iβeta cells, compared to human islets, as determined by qPCR.

FIG. 15A depicts images of immunohistochemical staining for PDX1, c-peptide and PC1/3 (red, left panels), compared to human insulin reporter GFP expression (green, middle panels) and nuclear staining (DAPI blue, right panels) in iPSC-derived beta-like (iβL) cells. FIG. 15B shows human insulin reporter-driven GFP expression (top panels) and phase contrast image (bottom panels) of day 30 β-like (iβL) cells. FIG. 15C is a scatter graph showing percentage of iβL cells expressing human insulin reporter-driven GFP, as measured by FACS (n=8). The representative FACS analysis is shown to the right. FIG. 15D has two graphs showing representative FACS analyses of insulin (GFP) and glucagon expression in iPSCs and iβL cells. FIG. 15E depicts representative electron microscopy analyses of iβL cells (day 22) and mouse primary (3 cells (selected mitochondria and insulin granules are indicated by arrows). FIG. 15F is a bar graph depicting glucose and potassium-stimulated c-peptide secretion from iβL cells. FIG. 15G is a bar graph showing relative ERRgamma expression in human islets, beta-like cells with adenoviral EGFP expression (iβL$^{GFP}$ cells) and beta-like-cells with adenoviral ERRgamma expression (iβeta cells). FIG. 15H is a set of 6 graphs of representative FACS analyses showing increased (3 cell marker expression in iβL cells. Co-expression of Insulin (GFP reporter) and Nkx6-1 or MafA in iPSCs and iβL cells, as measured by FACS. IgG is shown as a negative control.

FIG. 18A is a line graph showing acute effects on ad lib fed blood glucose levels in STZ-induced hyperglycemic NOD-SCID mice after mock transplantation (n=3), transplantation of iβeta cells (n=5) and mouse islets (200 islets/mice, n=5). FIG. 18B is a line graph depicting chronic effects on ad lib fed blood glucose levels after mock transplantation (n=3), transplantation of iβL$^{GFP}$ cells (n=14/12; 2 mice died at 2 weeks), iβeta cells (n=13), mouse islets (200 islets/mice, n=5) and human islets (500 islets/mice, n=2). (n=4) and iβeta cell transplantation (n=4) into STZ-NOD-SCID mice. FIG. 18C is a bar graph showing human c-peptide levels before and 15 minutes after a glucose challenge after the indicated transplantation. FIG. 18D depicts 4 line graphs showing oxygen consumption ($VO_2$), carbon dioxide production ($VCO_2$), Respiratory Exchange Ratio (RER), and ambulatory motion (X-beam breaks) of mock (n=4) and iβeta cell transplanted (n=4) STZ-NOD-SCID mice after 60 days. FIG. 18E is a schematic depicting the functional maturation of adult beta and iβeta cells.

FIG. 19A is a line graph showing ad lib fed blood glucose levels in STZ-induced hyperglycemic NOD-SCID mice after mock transplantation (n=3), transplantation of $i\beta L^{GFP}$ (n=8), iβeta cells (n=7) and mouse islets (200 islets/mice, n=5) at 6 days after transplantation. FIG. 19B is a line graph showing ad lib fed blood glucose levels in STZ-induced hyperglycemic NOD-SCID mice after mock transplantation (n=3), transplantation of $i\beta L^{GFP}$ cells (n=14/12; 2 mice died at 2 weeks), iβeta cells (n=13), mouse islets (200 islets/mice, n=5) and human islets (n=2, #13 & #14 human islets) for 8 weeks after transplantation.

FIG. 21 has six images of representative IHC of kidneys 2 months post-transplantation, stained for Insulin (Red) and DAPI (Blue).

FIG. 22 presents a gene list related to FIGS. 1B and 1C.

FIG. 23 presents a gene list for pancreatic lineage-specific gene expression in neonatal and adult islets.

FIG. 24 presents a gene list related to FIGS. 10D-10F.

FIG. 25 presents a list of representative up-regulated and down-regulated pathways in iβeta cells.

FIG. 26 presents additional information regarding human islets.

FIG. 27 presents primer information (qPCR primers "Primers (Fw)" disclosed as SEQ ID NOS 9-45, respectively, in order of appearance; qPCR primers "Primers (Rv)" disclosed as SEQ ID NOS 46-82, respectively, in order of appearance; ChIP primers "Primers (Fw)" disclosed as SEQ ID NOS 83-84, respectively, in order of appearance; ChIP primers "Primers (Rv)" disclosed as SEQ ID NOS 85-86, respectively, in order of appearance; Genotyping Primers "Primers (Fw)" disclosed as SEQ ID NOS 87-91, respectively, in order of appearance; and Genotyping Primers "Primers (Rv)" disclosed as SEQ ID NOS 92-96, respectively, in order of appearance).

FIG. 28 presents a stepwise differentiation protocol and small molecule information for insulin-producing cells.

DETAILED DESCRIPTION OF THE INVENTION

Figure 1A:
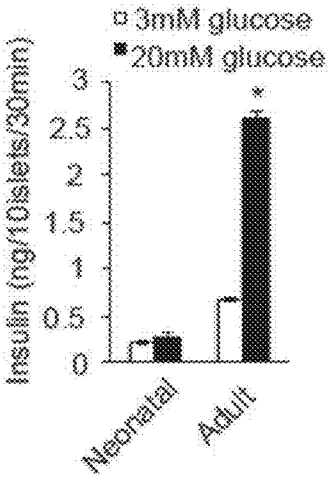
FIGS. 1A-1F show that islets acquire oxidative features postnatally.
Figure 1B:
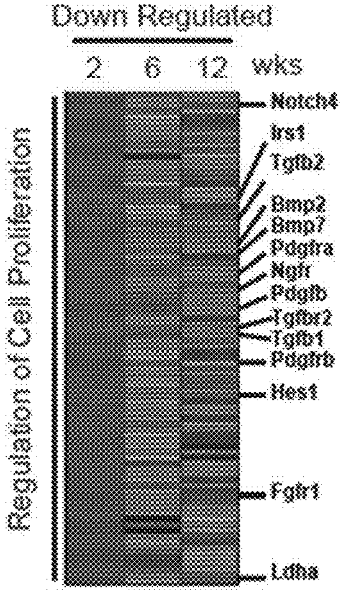

The invention features compositions comprising in vitro generated beta cells capable of glucose-stimulated insulin secretion, methods of inducing beta cell maturation from embryonic or induced pluripotent stem cell-derived beta-like cells or human adipose-derived stem cells (ADSCs), and methods of using in vitro generated beta cells for the treatment of type 1 diabetes, type 2 diabetes, or a related disorder.

The invention is based, at least in part, on the discovery that the orphan nuclear receptor, estrogen related receptor (ERR) gamma regulates beta cell metabolism and insulin secretion. As reported in greater detail below, expression of ERRgamma and ERRgamma target mitochondrial genes are increased during islet development after birth. Beta cell-specific ERRgamma knockout mice showed impaired glucose tolerance with reduced insulin secretion. Genome-wide transcriptome analysis revealed that ERRgamma deletion disrupted the gene regulatory network involved in energy metabolism, which is enhanced during beta cell maturation.

In addition, human iPSC-derived insulin-positive beta-like cells showed activated insulin promoter activity and insulin gene expression, as well as expression of other beta cell markers, but the cells were not glucose-responsive, and showed little expression of ERRgamma or mitochondrial genes. Forced ERRgamma expression significantly increased glucose-stimulated c-peptide secretion and also increased mitochondrial activity in iPSC-derived beta-cell-like-cells. Importantly, overexpression of ERRγ in human iPSC-derived β-like cells yielded functional, glucose-responsive β cells (iPSC-derived β ERRγ transplantable active cells, iβeta cells). Furthermore, transplantation of these iβeta cells was able to restore glucose homeostasis in a type 1 diabetic mouse model. These results revealed a significant role for ERRgamma in acquiring glucose-stimulated insulin secretion function, which is associated with beta cell maturation.

Beta Cell Maturation

Juvenile/neonatal human and rodent beta cells have poor glucose-stimulated insulin secretion (GSIS) function. During the course of beta cell maturation, the neonatal cell develops the ability to secrete insulin in response to glucose stimulation. During the course of development, beta cells acquire the ability to robustly secrete insulin in response to glucose. Therefore, beta cells acquire insulin secretion during the functional beta cell maturation period. Fully functional beta cells are long lived and tightly regulate whole body glucose homeostasis by regulating insulin production and secretion in response to nutrition intake (e.g., intake of amino acids, free fatty acids and glucose). Since insulin promotes lipid synthesis and glucose uptake in peripheral tissues, such as liver, skeletal muscle and adipose, it is not surprising that loss of beta cell function leads to both type 1 and type 2 diabetes.

Functional beta cells are considered highly metabolic cells because of their high demand for mitochondrial ATP production to facilitate insulin secretion in response to food intake in the form of glucose, amino acids and fatty acids. Beta cell glucose metabolism has the following special features: (1) glucose transportation is not limiting. This results in the rapid equalization of extracellular and intracellular glucose concentration. This equalization is carried out by Glut-2 in rodents and Glut-1 in Humans; (2) Glycolysis is controlled by glucokinase (GK), a hexokinase isoform with a low affinity for glucose. (3) glucose stimulation of beta cells reveals that glycolysis is tightly correlated with mitochondrial metabolism resulting in the quantitative flux of pyruvate (product made by glycolysis) into mitochondria. This is facilitated by low levels of lactate dehydrogenase (LDH) and monocarboxylate transporter (MCT) resulting in the conversion of glucose carbons to pyruvate, which is primarily used in the citric acid cycle and enhanced oxidative phosphorylation. Thus, glucose-stimulated insulin secretion is associated with increased oxidative ATP production in response to glucose.

Estrogen-Related Receptors

Nuclear Receptors are a specialized family of ligand-dependent transcription factors that play central roles in controlling development, growth and metabolism. They are defined by a conserved zinc-finger DNA binding domain and a C-terminal ligand-binding domain (LBD) that can impart multiple regulatory functions. Estrogen-related receptors are orphan nuclear receptors within the family of nuclear receptors, represented by three paralogs in mammals, ERRα (NR3B1, Esrra), ERRβ (NR3B2, Esrrb) and ERRγ(NR3B3, Esrrg). Although they have no known natural ligands, ERRβ plays an essential role in embryonic stem cell maintenance. ERRα and ERRγ are known to regulate metabolic genes involved in processing, such as the oxidative tricarboxylic acid (TCA) pathway, the electron transport complex (ETC), and oxidative phosphorylation (OXPHOS). ERRα and ERRγ are important mitochondrial metabolic regulators. Genetic studies in mice have shown the differential roles of ERRα and ERRγ. Mice having a whole body ERRα knockout (ERRαKO) have no significant developmental defects, but the mice are lean and resistant to high fat diet-induced obesity. In contrast, mice with whole body ERRγ knockout (ERRγKO) mice have significant developmental defects that are lethal in the first week after birth. These defects are associated with the failure of ERRγKO mice to undergo a fetal to postnatal metabolic switch in the heart associated with increased postnatal carbohydrate utilization.

Although it is well known that beta cells have high mitochondrial metabolic activity which allows them to secrete insulin in response to glucose and other forms of nutrition, the transcriptional network that regulates beta cell metabolism and insulin secretion is poorly understood. Furthermore, insulin-producing beta-like-cells derived from human pluripotent stem cells do not secrete insulin in response to glucose. To date, no one has produced glucose responsive beta-like-cells.

As reported in more detail below, the present invention identifies a metabolic regulatory pathway for fetal/neonate to adult beta cell maturation. The expression of ERRgamma and related genes increased during this period. Beta cell-specific ERRgamma deficient WERRγKO) mice exhibited glucose intolerance with reduced glucose-stimulated insulin secretion (GSIS) in Normal Chow Diet (NCD) and High Fat Diet (HFD) conditions. Disrupted regulation of genes involved in the ATP biosynthesis pathway and OxPhos is seen in βERRγKO islets. Significantly, ERRgamma overexpression increased ATP production in response to glucose in beta-like-cells and caused beta-like-cells to increase their mitochondrial metabolic activity and to exhibit glucose stimulated insulin secretion, which are two hallmarks of functional beta cells. Beta-like cells were generated from human induced pluripotent stem cells (hiPSC) and directly from human adipose-derived stem cells (hADSC). These results suggest that metabolic maturation through ERRgamma signaling is likely the transcriptional pathway responsible for the metabolic maturation of beta cells. These results provide for the production of functional, glucose responsive human beta cells from hiPSC, hADSC and other stem cells by over-expression of ERRgamma in such cells.

ERR Gamma Overexpression

The invention provides methods for reprogramming a beta-like cell by over-expressing ERR gamma in a beta-like cell and inducing the beta-like cell to become capable of glucose-stimulated insulin secretion. Typically, over-expression of ERRgamma is also associated with increased mitochondrial metabolic activity.

Transducing viral (e.g., retroviral, adenoviral, and adeno-associated viral) vectors can be used to express ERRgamma in a cell, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an ERRgamma polypeptide, variant, or fragment thereof, can be cloned into a retroviral vector and expression can be driven from its endogenous promoter, from the retroviral long terminal repeat, or from a promoter specific for a target cell type of interest, such as a pancreatic islet beta cell. Exemplary promoters useful in the methods of the invention include, but are not limited to, the human insulin promoter, insulin II promoter, as well as other promoters such as Pdx1, Mafa, Nkx6-1 Pax4 and NeuroD1 expressed in a pancreatic tissue, such as a islet beta cell.

Other viral vectors that can be used in the methods of the invention include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). In one embodiment, an adeno-associated viral vector (e.g., serotype 2) is used to administer a polynucleotide to a beta-like cell, including a beta-like cell derived from a pluripotent stem cell, induced pluripotent stem cell, embryonic stem cell or other cell-type capable of giving rise to beta-like cells.

Non-viral approaches can also be employed for the introduction of an ERRgamma polynucleotide into a beta-like cell derived from a pluripotent stem cell, induced pluripotent stem cell, embryonic stem cell or other cell-type capable of giving rise to beta-like cells. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). In one embodiment, the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell (e.g., a beta-like cell derived from a pluripotent stem cell, induced pluripotent stem cell, embryonic stem cell or other cell-type capable of giving rise to beta-like cells). Transplantation of an ERRgamma polynucleotide can also be accomplished by transferring a normal nucleic acid into a cultivatable cell type ex vivo (e.g., an autologous or heterologous primary cell or progeny thereof), after which the cell (or its descendants) are injected into a targeted tissue (e.g., pancreatic tissue) or delivered via a canula. Human islets can survive in subcutaneous skin or fat and kidney with or without immune reaction protective devices such as Theracyte (Theracyte Inc, US). Cells can be transplanted using similar methods for human islet transplantation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types (e.g., pancreatic cells, beta cells) can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Beta-Like Cells

Cells useful in the methods of the invention include virtually any cell type that expresses markers that are typically expressed in a beta cell or beta cell progenitor. In particular embodiments, cells useful in the invention can be induced to acquire glucose-stimulated insulin secretion by over-expression of ERRgamma.

In particular embodiments, cells useful in the invention include, but are not limited to, adult or embryonic stem cells or other multi- or pluripotent stem cells that express or that can be induced to express one or more pancreatic islet beta cell markers, endocrine markers or beta cell transcription factors. Exemplary beta cell transcription factors include Pdx1, Mafa, Math, Nkx6.1, NeuroD1, Foxa2, Hnf4a, Nkx2.2, Pax6 and HNF4a. In particular embodiments, the beta cell transcription factor is a factor expressed at higher levels in an adult islet cell relative to a neonatal islet cell. Beta cell transcription factors expressed at increased levels in an adult islet include Pdx1, MafA and Nkx6-1 compared with neonatal islets. In other embodiments, a beta-like cell expresses a beta cell marker including, but not limited to, Insulin 1, Insulin 2, α-cell marker glucagon and δ-cell marker, somatostatin. In other embodiments, the beta-like cell expresses an endocrine marker including, but not limited to, Insulin1, Insulin2, Glucagon and Somatostatin.

In particular embodiments, human induced pluripotent stem cells are derived from Huvec (iPSC) or from Embryonic stem cells (HUES). Cells of the invention may be maintained, for example, on matrigel (BD) coated dishes in virtually any culture media that supports growth or maintenance of the cells (e.g., complete TeSR Media). For pancreatic differentiation, hPC are infected with a human insulin reporter lentivirus (pGreenZero *lenti* reporter human insulin, System biosciences) or using any other standard transfection method.

In one embodiment, pancreatic differentiation is induced by treating the cells with Activin (e.g., 50-100 ng/ml human Activin (Sigma), Wnt3a (e.g, 25 ng/ml recombinant human Wnt3a (Sigma)) in custom TESR (TeSR without FGF2 and TGFβ) for 2 days and then with Activin (e.g., 100 ng/ml human Activin) in custom TESR for extra 2 days (Stage 1).

Subsequently, the medium was replaced with culture media (e.g., DMEM) supplemented with 2% BSA, 1% NEAA, 1% Glutamax (Base Media) with 1 μM dorsomorphin (Calbiochem), 2 μM Retinoic Acid (Sigma), optionally 50 ng/ml recombinant human FGF10 (R & D systems), and 10 μM SB431542 for 7 days (Stage 2). Then, the media was replaced with base media containing, for example, 10 μM Forskolin (Sigma), 10 μM dexamethasone (Stemgent), 5 μM TGFβ RI Kinase inhibitor II (Calbiochem), 10 mM Nicotinamide (Sigma) for 10 days (stage 1). Media were replaced every day (stage 1), every day or every other day (stage 2) and every other day (stage 3). These treatment methods result in the production of beta-like cells that may be modified to over-express ERRgamma. In one embodiment, beta-like cells are transduced, for example, with an Adenoviral ERRgamma purchased from Welgen, Inc.

The invention is not limited to beta-like cells produced using such methods, but encompasses virtually any beta-like cell known in the art. Methods for producing beta-like cells are known in the art and described herein, for example, where an embryonic stem cell or induced pluripotent stem cell is recombinantly modified to express any one or more of Oct4, Nanog, Sox17, FoxA2, Pdx1, Nkx6.1, and/or Ngn3. Beta-like cells generated by such methods express one or more of the following markers: insulin, Pdx1, Mafa, Pax6, Glut2, NeuroD1, glucokinase, glucagon, somatostatin, chromogranin A, and Vamp2. See also, Pagliuca et al., Dev. 140:2472-2483, 2013, which is incorporated herein by reference in its entirety.

As reported in detail below, the present studies determined the expression of nuclear receptor (NR) family members and their co-activators during the normal 10-12 week maturation process of fetal glycolytic (non-functional) beta cells to mature oxidative glucose-responsive beta cells. This led to the identification of a number of nuclear receptors whose expression increased during the normal physiological maturation of functional beta cells, including ERRgamma, ERRalpha, FXR, VDR and their co-activators PGC-1alpha and PGC-1beta.

Utilizing this knowledge, combinations of these receptors and co-activators were expressed in combination with Pdx1 (Pancreatic and duodenal homeobox 1, a known master regulatory transcription factor in pancreatic development and beta-cells) in human adipose-derived stem cells (hADSC). This approach led to the development of a novel 2-factor protocol in which forced expression of Pdx1 in concert with ERRgamma facilitated direct reprogramming of hADSC into "functional" glucose-responsive beta cells. Furthermore, a 3-factor protocol, which included expression of PGC-1alpha with Pdx1 and ERRgamma, resulted in increased glucose responsiveness in the hADSC-derived beta cell. Notably, stably enhanced expression of ERRgamma, with Pdx1 in combination with other beta cell maturation genes such as Pax4 also produced functional glucose-responsive beta cells. However, in the absence of ERRgamma, these beta cell maturation gene combinations failed to produce functional glucose-responsive beta cells. Together these results identify ERRgamma as an important competence factor. These findings have potential medicinal and commercial value in being able to produce large amounts of immunologically compatible and functional pancreatic beta cells for the treatment of type 1 and insulin-dependent type 2 diabetes.

ERRgamma Polypeptide Analogs

The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring ERRgamma amino acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also provides fragments of any one of the polypeptides or peptide domains of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Methods of analog design are well known in the art, and synthesis of analogs can be carried out according to such methods by modifying the chemical structures such that the resultant analogs increase the reprogramming or regenerative activity of a reference ERRgamma polypeptide. These chemical modifications include, but are not limited to, substituting alternative R groups and varying the degree of saturation at specific carbon atoms of a reference fusion polypeptide. Preferably, the ERRgamma protein analogs are relatively resistant to in vivo degradation, resulting in a more prolonged therapeutic effect upon administration. Assays for measuring functional activity include, but are not limited to, those described in the Examples below.

Therapeutic Methods

The invention provides for the treatment of type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production). For example, the invention provides compositions for the treatment of diabetic patients who lack sufficient levels of insulin due to a decrease in the number or activity of insulin-producing pancreatic cells. Many diseases associated with a deficiency in cell number are characterized by beta cell loss or an increase in beta cell death. Methods of the invention ameliorate such type 1 diabetes, type 2 diabetes, and related diseases, disorders, by generating cells (e.g., insulin-expressing cells) that can supplement the deficiency. Such cells are generated from the reprogramming of a cell to a cell type of interest (e.g., the reprogramming of a beta-like cell, embryonic stem cell, induced pluripotent cell) or by promoting the regeneration of a beta cell, pancreatic tissue, or organ. In general, the invention provides a method for reprogramming a cell that involves contacting the cell (e.g., a beta-like cell, such as derived from an induced pluripotent stem cell, or stem cell derived from adipocytes, endothelial cells, pancreatic cells, and their progenitor cells or stem cells) with a polynucleotide encoding an ERRgamma, thereby reprogramming the cell. In particular embodiments, expression of ERRgamma in the beta-like cell alters the expression level of at least one, two, three, four, five or more polypeptides in the cell, and or increases mitochondrial metabolic activity.

In one embodiment, the polypeptide is administered to beta-like cells in vitro and then the cells containing the polypeptide (or nucleic acid molecules encoding them) are administered to a patient to ameliorate, for example, type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production). Administration may be by any means sufficient to increase the number of insulin-secreting beta cells in the subject. In various embodiments, ERRgamma-expressing cells are administered by local injection to a site of disease or injury, by sustained infusion, or by micro-injection under surgical conditions (Wolff et al., Science 247:1465, 1990). In other embodiments, the fusion polypeptides are administered systemically to a tissue or organ of a patient having a deficiency in cell number that can be ameliorated by cell regeneration or reprogramming.

In another approach ERRgamma is introduced into a cultivatable cell type ex vivo (e.g., an autologous or heterologous primary cell or progeny thereof), after which the cell (or its descendants) are injected into a target tissue at the site of disease or injury. In some embodiments, the cells are present in a cellular matrix that provides for their survival, proliferation, or biological activity. Another therapeutic approach included in the invention involves administration of an ERRgamma fusion polypeptide (e.g., ERRgamma fused to a detectable moiety).

In other embodiments, therapeutic polypeptides of the invention are produced in a cell transduced with a viral (e.g., retroviral, adenoviral, and adeno-associated viral) vector that is used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a nucleic acid molecule, or a portion thereof, that encodes a ERRgamma protein of the invention can be cloned into a retroviral vector and expression can be driven from its endogenous promoter, from the retroviral long terminal repeat, or from a promoter specific for a target cell type of interest (e.g., a cell of the central nervous system). Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer the gene of interest systemically or to a cell at the site that requires cell reprogramming or an increase in regeneration.

Selected cells of the invention may be employed in therapeutic or prophylactic methods following isolation. Accordingly, the present invention provides methods of treating, for example, type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production) or symptoms thereof which comprise administering a therapeutically effective amount of a pharmaceutical composition comprising a cell expressing ERRgamma to a subject (e.g., a mammal such as a human). Thus, one embodiment is a method of treating a subject suffering from or susceptible to type 1 diabetes, type 2 diabetes, pre-diabetes, or a symptom thereof. The method includes the step of administering to the mammal a therapeutic amount of a cell herein sufficient to treat the disease or disorder or symptom thereof, under conditions such that the disease or disorder is treated.

The methods herein include administering to the subject (including a subject identified as in need of such treatment) an effective amount of a cellular composition described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of a cellular composition described herein, to subjects, particularly humans, suffering from, having susceptibility to, or at risk of having type 1 diabetes, type 2 diabetes, pre-diabetes, or another metabolic disease or disorder associated with a deficiency in beta cell number (e.g., a reduction in the number of pancreatic cells) or an insufficient level of beta cell biological activity (e.g., a deficiency in glucose-stimulated insulin secretion, a deficiency in insulin production). Determination of those subjects "at risk" can be made by any objective or subjective determination by a diagnostic test or opinion of a subject or health care provider (e.g., genetic test, enzyme or protein marker, Marker (as defined herein), family history, and the like).

In one embodiment, the invention provides a method of monitoring treatment progress in connection with type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production). The method includes the step of determining a level of diagnostic marker (Marker) (e.g., any target delineated herein in a subject suffering from or susceptible to a disorder or symptoms thereof associated with a defect in beta cell number or activity, in which the subject has been administered a therapeutic amount of a cellular composition described herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In some embodiments, it may be desirable to maintain the selected cells in culture for hours, days, or even weeks prior to administering them to a subject. Media and reagents for tissue culture are well known in the art (see, for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Examples of suitable media for incubating/transporting beta-like cells expressing ERRgamma include, but are not limited to, Dulbecco's Modified Eagle Medium (DMEM), RPMI media, Hanks' Balanced Salt Solution (HBSS) phosphate buffered saline (PBS), and L-15 medium. Examples of appropriate media for culturing cells of the invention include, but are not limited to, Dulbecco's Modified Eagle Medium (DMEM), DMEM-F12, RPMI media, EpiL1fe medium, and Medium 171. The media may be supplemented with fetal calf serum (FCS) or fetal bovine serum (FBS) as well as antibiotics, growth factors, amino acids, inhibitors or the like, which is well within the general knowledge of the skilled artisan.

Formulations

Compositions of the invention comprising purified cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified beta-like cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the genetically modified beta-like cells or their progenitors or descendants.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the genetically modified cells as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of genetically modified beta-like cells of the invention is the quantity of cells necessary to achieve an optimal effect. The quantity of cells to be administered will vary for the subject being treated. In a one embodiment, between $10^4$ to $10^8$, between $10^5$ to $10^7$, or between $10^6$ and $10^7$ genetically modified beta-like cells of the invention are administered to a human subject. In preferred embodiments, at least about $1\times10^7$, $2\times10^7$, $3\times10^7$, $4\times10^7$, and $5\times10^7$ genetically modified beta-like cells of the invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions to be administered in the methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Administration of ERRgamma Cells

Compositions comprising an ERRgamma expressing beta-like cell of the invention or their progenitors/descendants can be provided systemically or directly to a subject for the treatment or prevention of type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production). In one embodiment, cells of the invention are directly injected into an organ of interest (e.g., pancreas). Alternatively, compositions comprising beta-like cells of the invention are provided indirectly to the organ of interest, for example, by administration into the circulatory system (e.g., the pancreatic vasculature). Expansion and differentiation agents can be provided prior to, during or after administration of the cells to increase production of cells having insulin-producing potential in vitro or in vivo. The cells can be administered in any physiologically acceptable vehicle, normally intravascularly, although they may also be introduced into another convenient site where the cells may find an appropriate site for regeneration and differentiation.

In one approach, at least 100,000, 250,000, or 500,000 cells are injected. In other embodiments, 750,000, or 1,000,000 cells are injected. In other embodiments, at least about $1\times10^5$ cells will be administered, $1\times10^6$, $1\times10^7$, or even as many as $1\times10^8$ to $1\times10^{10}$, or more are administered. Selected cells of the invention can comprise a purified population of cells that expresses ERRgamma. Preferable ranges of purity in populations comprising selected cells are about 50 to about 55%, about 55 to about 60%, and about 65 to about 70%. More preferably the purity is at least about 70%, 75%, or 80% pure, more preferably at least about 85%, 90%, or 95% pure. In some embodiments, the population is at least about 95% to about 100% selected cells. Dosages can be readily adjusted by those skilled in the art (e.g., a decrease in purity may require an increase in dosage). The cells can be introduced by injection, catheter, or the like.

Compositions of the invention include pharmaceutical compositions comprising genetically modified beta-like cells or their progenitors and a pharmaceutically acceptable carrier. Administration can be autologous or heterologous. For example, beta-like cells, or progenitors can be obtained from one subject, and administered to the same subject or a different, compatible subject.

Selected cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a selected cell), it will generally be formulated in a unit dosage injectable form (solution, suspension, emulsion).

Accordingly, the invention also relates to a method of treating a subject having, for example, type 1 diabetes, type 2 diabetes, pre-diabetes, or another metabolic disease or disorder associated with a deficiency in beta cell number (e.g., a reduction in the number of pancreatic cells) or an insufficient level of beta cell biological activity (e.g., a deficiency in glucose-stimulated insulin secretion, a deficiency in insulin production). This method comprises administering to the subject an effective amount either of a stem/progenitor cell isolated as explained herein or of a cellular extract derived from such a cell.

In another pharmaceutical use, stem/progenitor cells of the present invention can be genetically modified prior to their administration to a subject. For this purpose, the cells can be transformed with a nucleic acid encoding the protein that is to be produced in the cells. The nucleic acid can be introduced into cells of the invention using any of the various methods that are well known to the skilled person, for example, using a viral vector and/or a lipid containing transfection composition such as IBAfect (IBA GmbH, Goettingen, Germany), Fugene (Roche), GenePorter (Gene Therapy Systems), Lipofectamine (Invitrogen), Superfect (Qiagen), Metafecten (Biontex) or those ones described in the PCT application WO 01/015755). In a related embodiment, the cells of the invention, after being transformed with a nucleic acid encoding a polypeptide of choice, can be used to recombinantly produce this polypeptide.

Methods of Treatment

Provided herein are methods for treating or preventing type 1 diabetes, type 2 diabetes, pre-diabetes, and the treatment of other metabolic diseases or disorders associated with a deficiency in beta cell number (e.g., a reduction in the number of beta cells) or an insufficient level of beta cell biological activity (e.g., a deficiency in glucose stimulated insulin secretion, a deficiency in insulin production) in a subject. In particular embodiments, the invention provides methods for treating or preventing type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production). Patients having diabetes or a metabolic disorder are generally identified by a reduction in beta cell activity or function, for example, by monitoring serum sugar levels in the blood.

In general, the methods comprise administering selected cells of the invention in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of beta-like cells administered.

Suitable human subjects for therapy typically comprise two treatment groups that can be distinguished by clinical criteria. The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Kits

The invention provides kits for the treatment or prevention of type 1 diabetes, type 2 diabetes, pre-diabetes, and the treatment of other metabolic diseases or disorders associated with a deficiency in beta cell number (e.g., a reduction in the number of pancreatic cells) or an insufficient level of beta cell biological activity (e.g., a deficiency in glucose-stimulated insulin secretion, a deficiency in insulin production). In one embodiment, the kit includes a therapeutic or prophylactic composition containing an effective amount of a cell (e.g., a beta-like cell) that expresses ERRgamma in unit dosage form. In some embodiments, the kit comprises a sterile container which contains a therapeutic or prophylactic cellular composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired a cell of the invention is provided together with instructions for administering the cell to a subject having or at risk of developing type 1 diabetes, type 2 diabetes, pre-diabetes, or a metabolic disease or disorder associated with a deficiency in beta cell number (e.g., a reduction in the number of pancreatic cells) or an insufficient level of beta cell biological activity (e.g., a deficiency in glucose-stimulated insulin secretion, a deficiency in insulin production). The instructions will generally include information about the use of the composition for the treatment or prevention of type 1 diabetes, type 2 diabetes, pre-diabetes, or a metabolic disease or disorder associated with a deficiency in beta cell number (e.g., a reduction in the number of pancreatic cells) or an insufficient level of beta cell biological activity (e.g., a deficiency in glucose-stimulated insulin secretion, a deficiency in insulin production). In other embodiments, the instructions include at least one of the following: description of the cells; dosage schedule and administration for treatment or prevention of type 1 diabetes, type 2 diabetes, pre-diabetes or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, “Molecular Cloning: A Laboratory Manual”, second edition (Sambrook, 1989); “Oligonucleotide Synthesis” (Gait, 1984); “Animal Cell Culture” (Freshney, 1987); “Methods in Enzymology” “Handbook of Experimental Immunology” (Weir, 1996); “Gene Transfer Vectors for Mammalian Cells” (Miller and Calos, 1987); “Current Protocols in Molecular Biology” (Ausubel, 1987); “PCR: The Polymerase Chain Reaction”, (Mullis, 1994); “Current Protocols in Immunology” (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Postnatal Islets Acquired Oxidative Features

Beta cells are known to functionally mature postnatally, including acquiring the ability to robustly secrete insulin in response to glucose. Consistent with an immature phenotype, islets isolated from 2-week-old neonatal mice were unable to secrete insulin in response to a glucose challenge (FIG. 1A). To identify important pathways required for glucose-stimulated insulin secretion (GSIS), the transcriptomes of isolated islets during postnatal maturation were compared. Consistent with beta cell terminal differentiation being essentially completed postnatally, and the fact that adult β cells were formed by self-duplication rather than stem cell differentiation_ENREF_13 (Dor et al., 2004, Adult pancreatic beta-cells are formed by self-duplication rather than stem-cell differentiation. Nature 429, 41-46), the expression of genes known to regulate pancreatic endocrine development in rodents and humans were largely unchanged postnatally (FIG. 2A, FIG. 23, Conrad et al., 2014, Trends in endocrinology and metabolism: TEM, 25(8): 407-414).

Figure 1C:
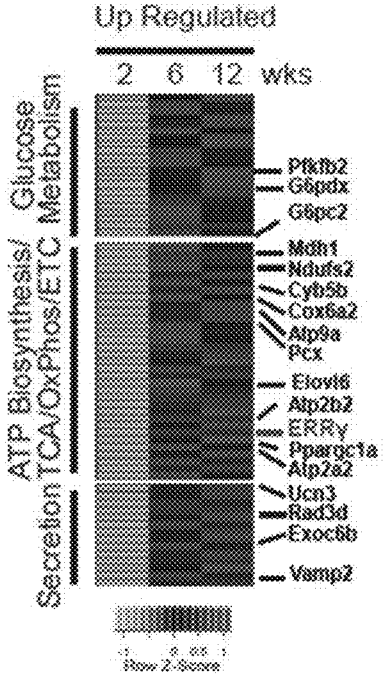
Figure 1D:
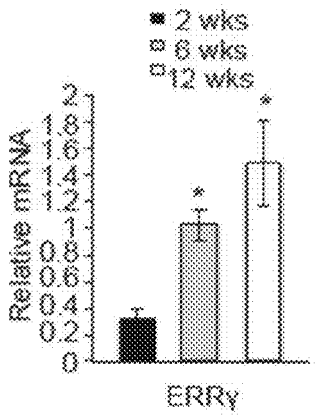
Figure 1E:
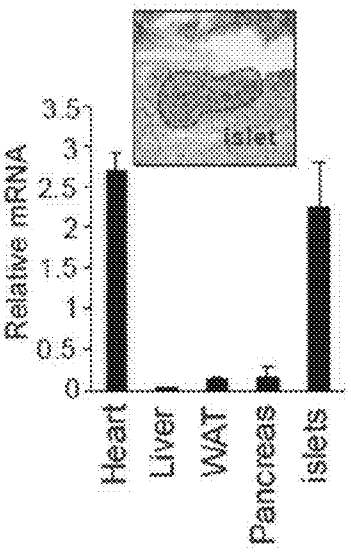
Figure 1F:
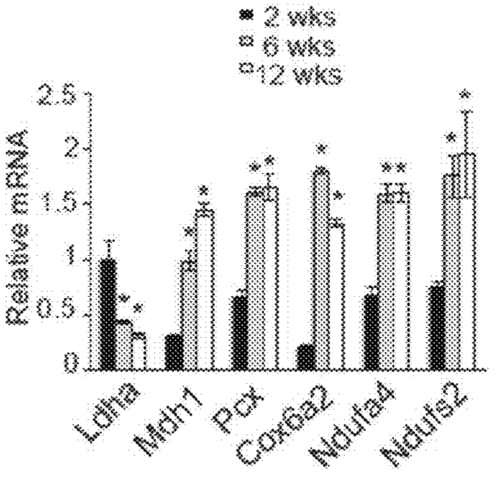
Figure 3A:
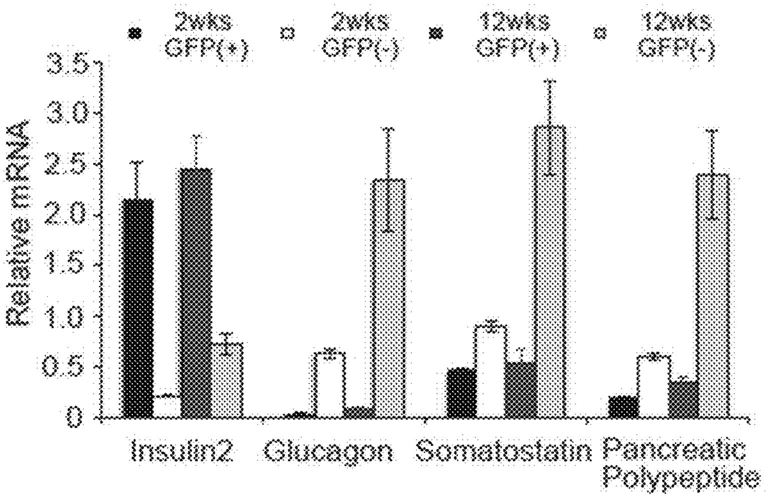
FIGS. 3A and 3B show that ERRgamma is induced during postnatal beta cell development.
Figure 3B:
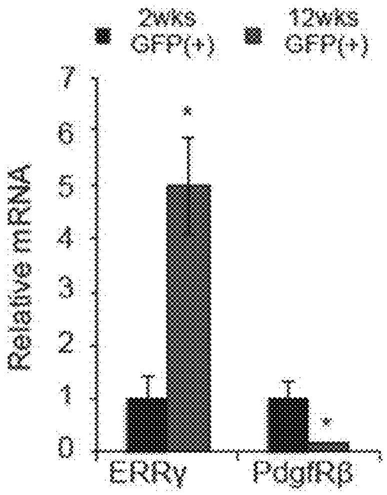

Increased Pdx1, MafA and Nkx6.1, and decreased MafB expression were observed with maturation (FIG. 2A), in agreement with these genes being required for adult beta cell function (Conrad et al., 2014, Trends in endocrinology and metabolism: TEM, 25(8): 407-414). Functional analyses of the transcriptomes revealed that genes involved in cell proliferation were down-regulated during islet maturation, including known positive beta cell proliferation regulators Pdgfra, Pdgfrβ, Pdgfβ and Fgfr1 (FIG. 1B, FIG. 22, and FIG. 2B and FIG. 2C), in line with the observed decline in clonal beta cell expansion in adult islets (Chen et al., 2011, Nature 478, 349-355; Hart et al., 2000, Nature 408, 864-868; Teta et al., 2005, Diabetes 54, 2557-2567; Dor et al., 2004, Nature 429, 41-46). In contrast, up-regulated genes were associated with metabolic pathways, particularly glucose metabolism and ATP biosynthesis pathways, including electron transport chain (ETC), Oxidative Phosphorylation (OxPhos) and ion channel-related exocytosis. Without being bound to a particular theory, induction of metabolic genes may be important for GSIS, given the high mitochondrial activity of adult beta cells. Consistent with this hypothesis, mitochondria genes known to regulate GSIS, including malate dehydrogenase (Mdh1), pyruvate carboxylase (Pcx), and components of OxPhos including Cox6a2, Ndufa4 and Ndufs2 (Xu et al., 2008, Diabetologia 51, 2022-2030; Zhao et al., 1998, FEBS letters 430, 213-216), were more highly expressed, while lactate dehydrogenase (Ldha), a suppressor of GSIS, had reduced expression in adult compared to neonatal beta cells (FIG. 1C and FIG. 1F, FIG. 22). Without being bound to a particular theory, these results indicate that an important metabolic transition occurs in islet beta cells during postnatal functional maturation. Of particular note, expression of ERRgamma, a known mitochondrial gene regulator, was progressively induced during islet maturation (FIG. 1C and FIG. 1D). This induction of ERRgamma expression was similarly observed in beta cells isolated from mouse insulin-GFP (MIP-GFP) mice, where ERRgamma expression was ~5 fold higher in adult compared to neonatal beta cells (FIG. 3A and FIG. 3B). These findings, combined with the predominant expression of ERRgamma in endocrine islets compared to exocrine cells and the positive staining of islets in ERRgamma-LacZ knock-in mice (Alaynick et al., 2007, Cell metabolism 6, 13-24), indicate a specific role for ERRgamma in orchestrating a metabolic transition in endocrine cells required for GSIS (FIG. 1E).

Example 2: ERRgamma was Required for Glucose-Stimulated Insulin Secretion

Figure 4A:
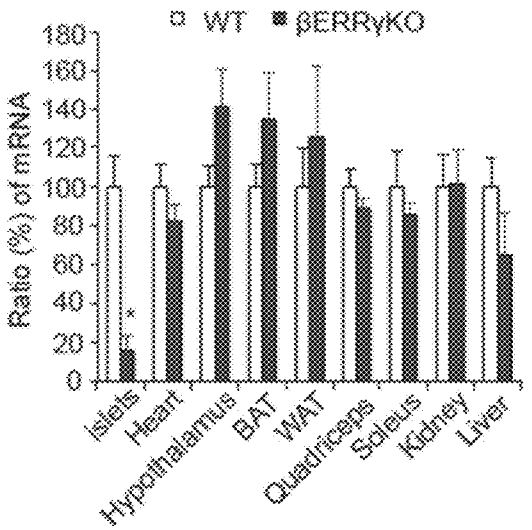
FIGS. 4A-4D show phenotyping of beta cell-specific ERRgamma knockout mice.
Figure 4B:
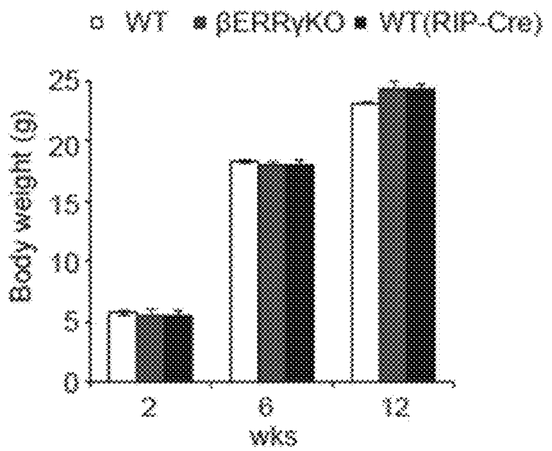
Figure 4C:
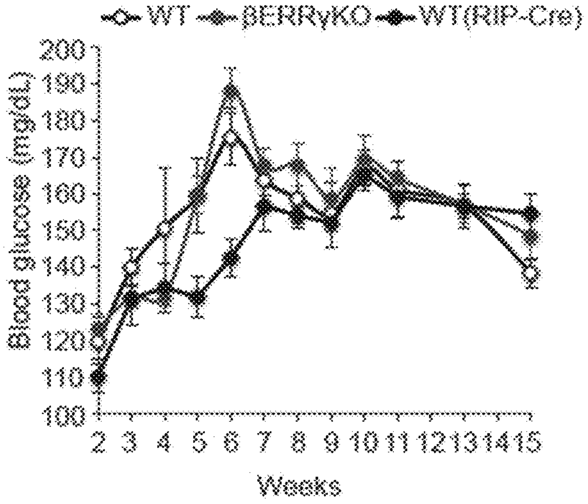
Figure 4D:
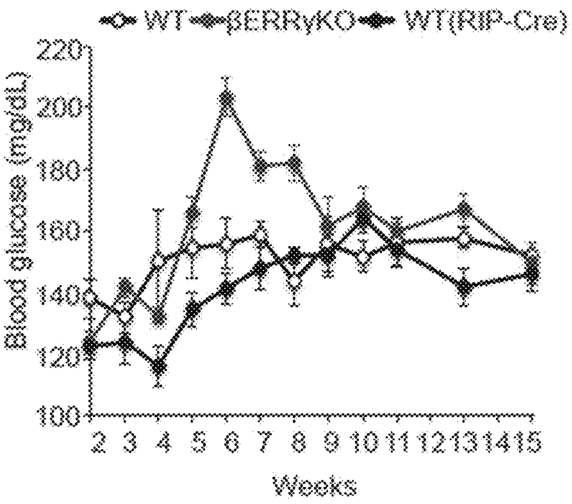
Figure 5A:
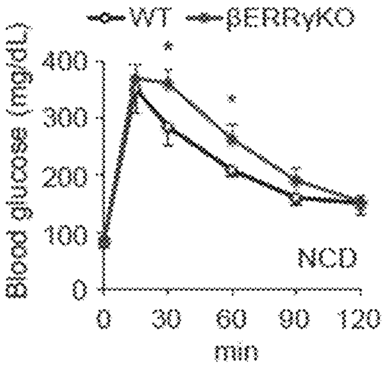
FIGS. 5A-5K show beta cell-specific ERRgamma deleted mice were glucose intolerant.
Figure 5B:
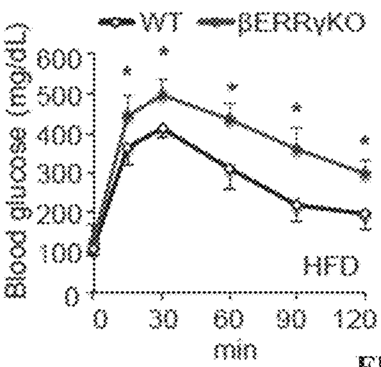
Figure 5C:
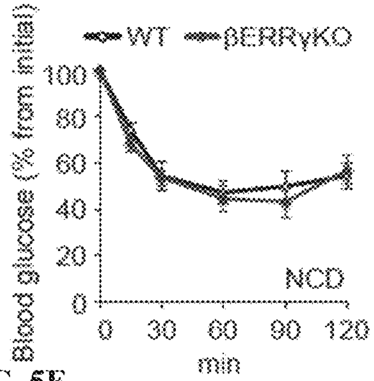
Figure 5D:
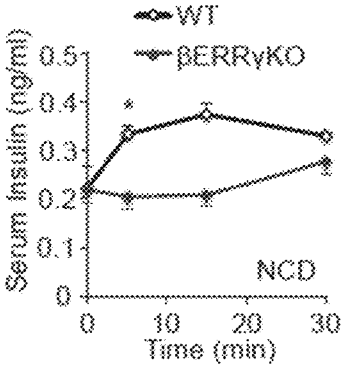
Figure 5E:
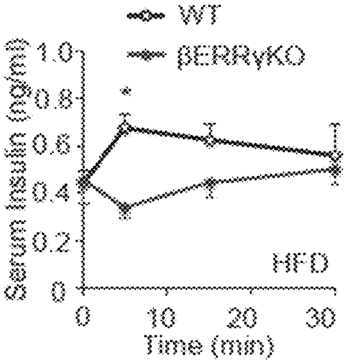
Figure 5F:
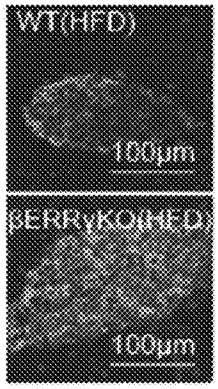
Figure 5G:
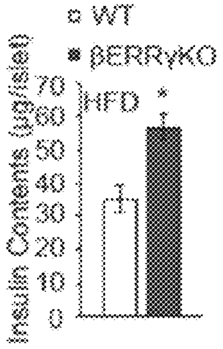
Figure 6A:
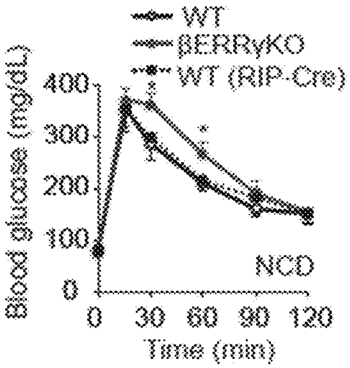
FIGS. 6A-6G show that beta cell-specific ERRgamma deletion caused glucose intolerance (extended data relating to FIGS. 5A-5J).
Figure 6B:
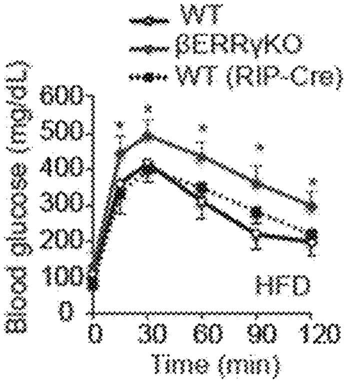
Figure 6C:
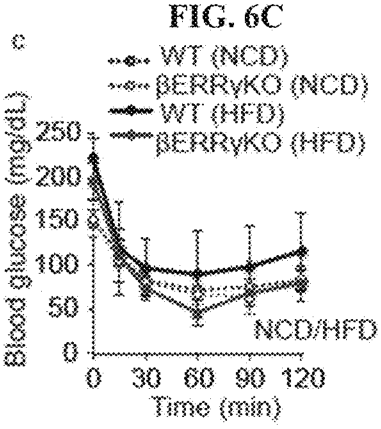
Figure 6D:
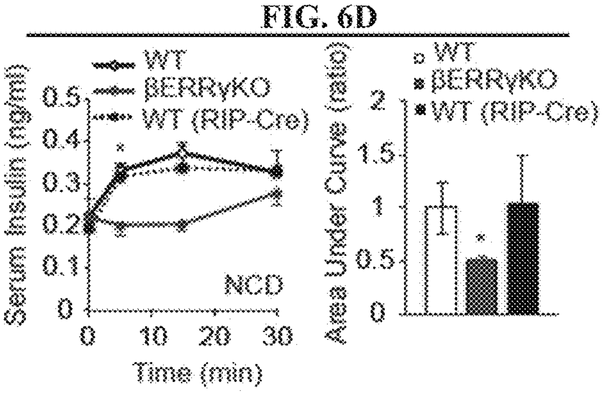
Figure 6E:
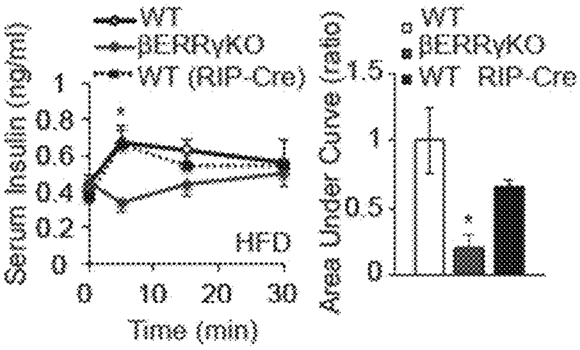

To investigate the role of ERRgamma in the functional maturation of pancreatic beta cells, beta cell-specific ERRgamma knockout (betaERRgammaKO) mice were generated by crossing ERRgamma$^{lox/lox}$ mice with rat insulin 2 promoter (RIP)-Cre mice. βERRgammaKO mice were born at the expected Mendelian frequency and exhibited normal body weights and life expectancies (FIG. 4A and FIG. 4B). The RIP-Cre recombinase selectively decreased ERRgamma expression by 80% in βERRgammaKO compared to wild-type ERRgamma$^{lox/lox}$ islets without significantly affecting hypothalamic ERRgamma expression (FIG. 4A and FIG. 4B), in agreement with recent similar reports (Tang et al., 2003, Cell metabolism 18, 883-895). Monitoring ad lib fed blood glucose levels of βERRgammaKO mice revealed a transient increase in female mice that was resolved by 8 weeks of age (FIG. 4C and FIG. 4D). However, at 8 weeks of age, both male and female βERRγKO mice were glucose-intolerant compared to ERRγ$^{lox/lox}$ (WT) and RIP-Cre (WT(RIP-Cre)) cohorts, as determined by glucose tolerance tests (GTTs) (FIG. 5A and FIG. 6A). While no significant differences in insulin sensitivity were seen, βERRγKO mice failed to increase insulin secretion in response to a glucose challenge (FIGS. 5C and 5D, and FIGS. 6C and 6D). Notably, this βERRγKO phenotype was exaggerated by metabolic stress; βERRγKO mice fed a high fat-high sucrose diet for 4 weeks from 4 weeks of age displayed more pronounced glucose intolerance and defects in insulin secretion, without any significant change in insulin sensitivity (FIG. 5B, FIG. 5E, and FIG. 6B, FIG. 6E).

Figure 6F:
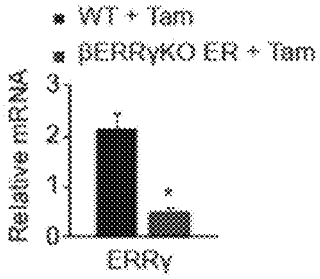
Figure 6G:
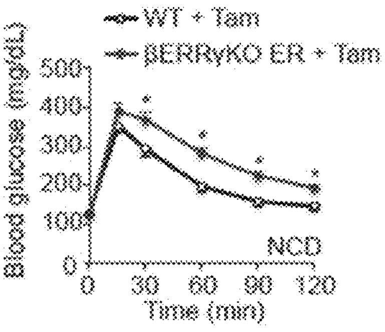
Figure 7A:
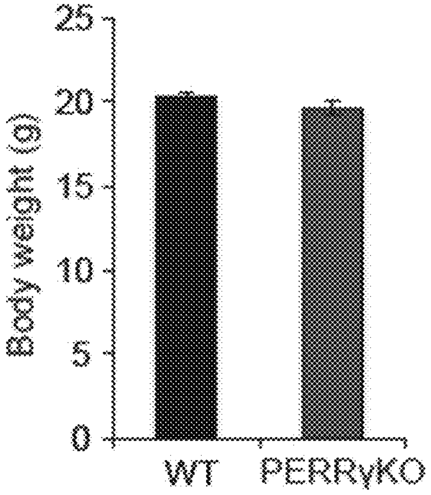
FIGS. 7A-7D show that pancreas-specific ERRgamma deletion caused glucose intolerance.
Figure 7B:
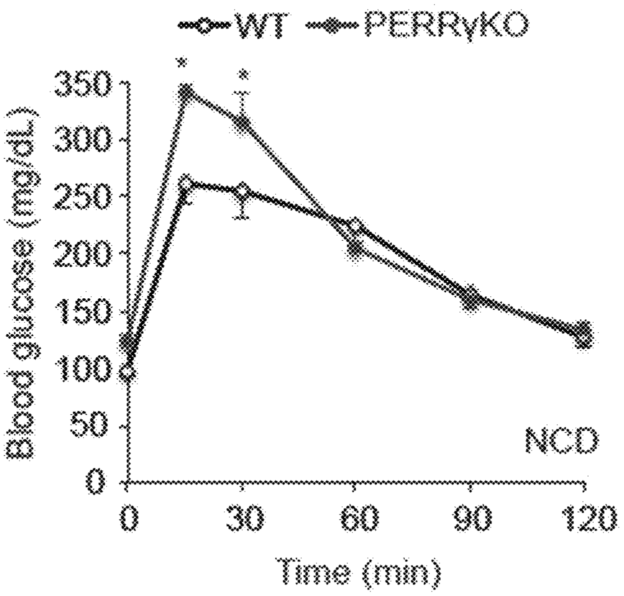
Figure 7C:
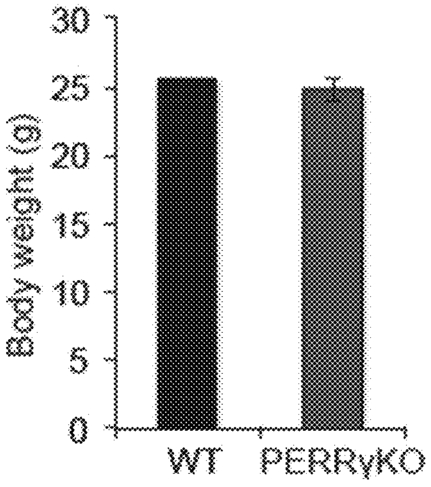
Figure 7D:
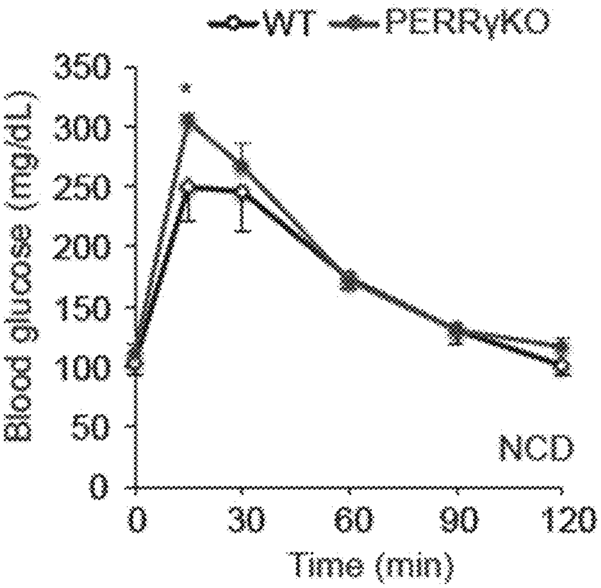

The inability of βERRγKO mice to secrete insulin in response to a glucose challenge was phenocopied in both inducible beta cell-specific deletion (βERRγKO ER+Tam) and pancreatic-specific ERRγKO (βERRγKO) mouse models. βERRγKO ER mice treated with tamoxifen (7 days sequential i.p. injection) showed a 75% reduction in islet ERRgamma expression and exhibited glucose intolerance similar to that observed in the developmental βERRγKO mice (FIGS. 6F and 6G). Furthermore, mice lacking ERRgamma in the entire pancreas, generated by crossing $ERR\gamma^{lox/lox}$ mice with PDX1-Cre mice (βERRγKO mice), displayed impaired glucose tolerance compared to WT mice (FIGS. 7A-7D). Without being bound to a particular theory, collectively these results indicate that islet ERRgamma expression is essential for proper GSIS function and whole-body glucose homeostasis when challenged with elevated blood glucose levels.

Figure 8A:
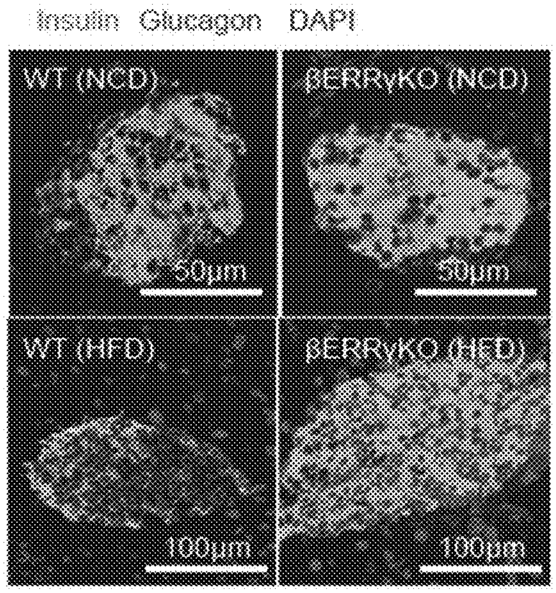
FIGS. 8A-8F show that HFD-fed βERRγKO islets were hypertrophic.
Figure 8B:
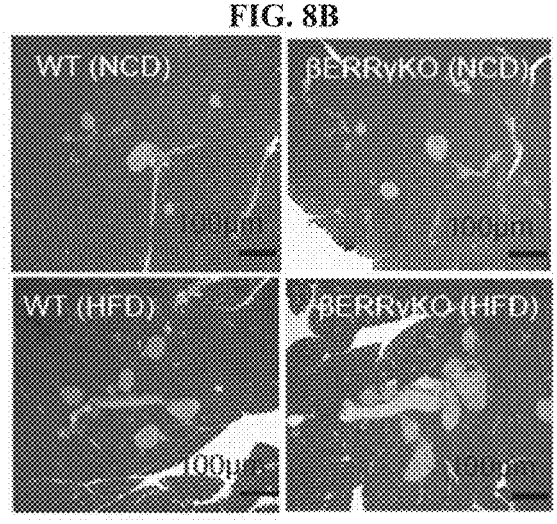
Figure 8C:
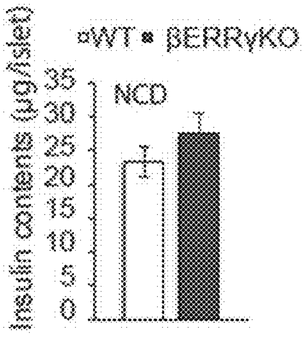
Figure 8D:
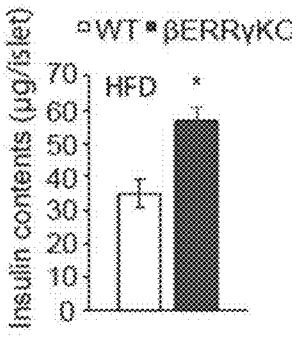
Figure 8E:
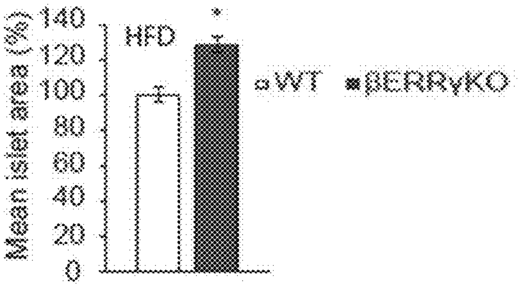
Figure 8F:
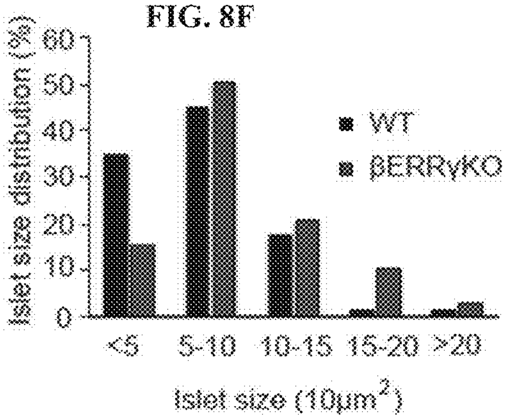
Figure 9A:
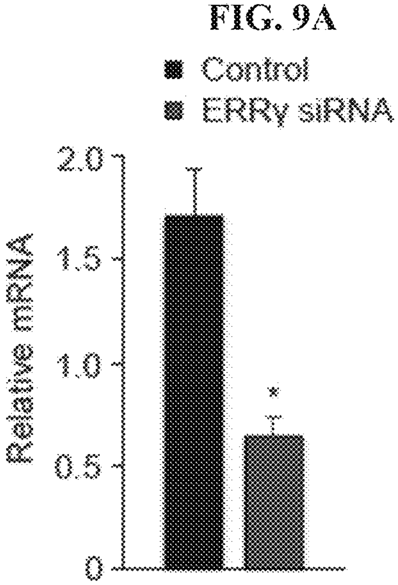
FIGS. 9A-9D show that ERRgamma affected GSIS and bioenergetics in INS-1 cells.
Figure 9B:
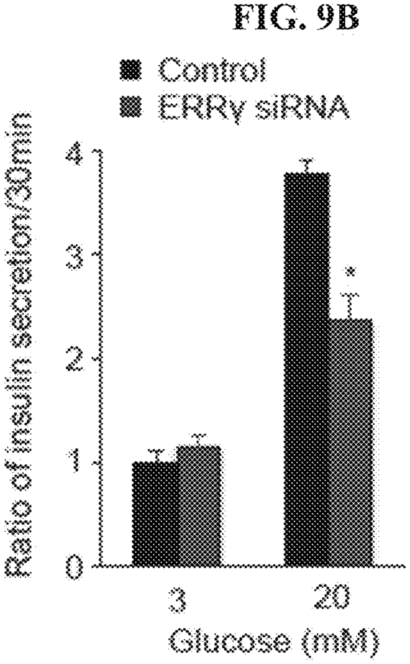
Figure 9C:
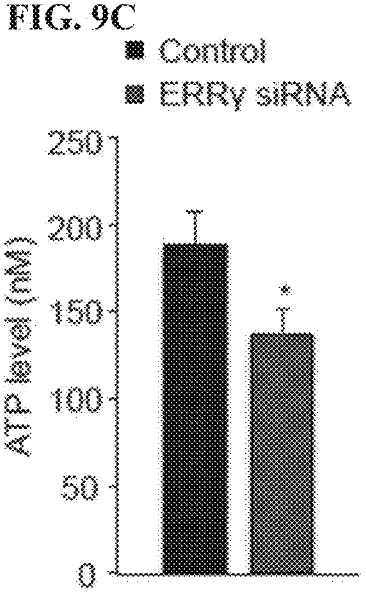
Figure 9D:
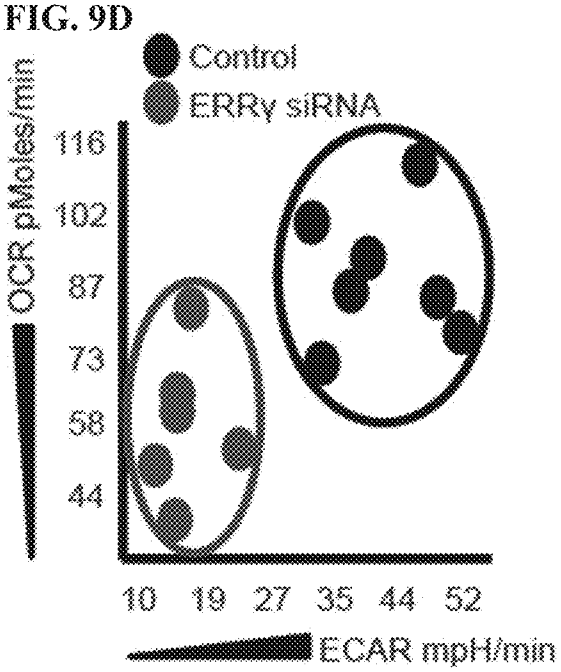

Morphologically, islets isolated from βERRγKO mice maintained on a normal chow diet were indistinguishable from control islets, based on hematoxylin and eosin (H&E) staining and immunohistochemical analysis (FIG. 8A). However, when stressed by a high fat diet (HFD), βERRγKO islets were larger with significant increases in beta cell mass, as measured by insulin content and islet size, compared to control islets (FIGS. 5F and 5G, and FIGS. 8A-8F).

Figure 5H:
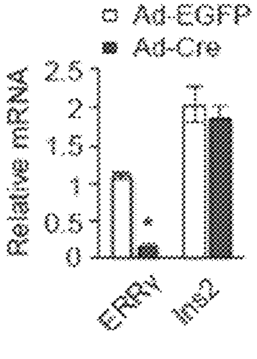
Figure 5I:
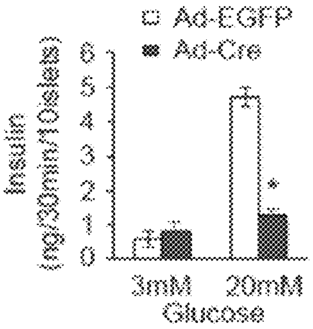
Figure 5J:
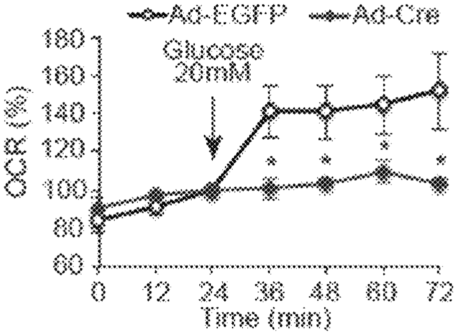
Figure 5K:
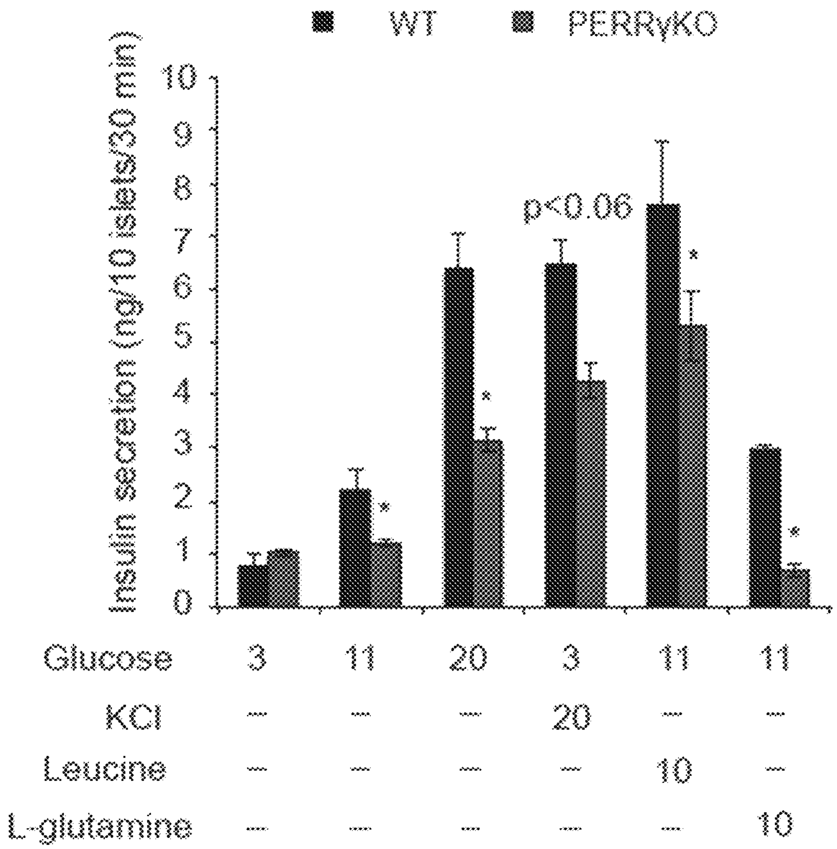

Without being bound to a particular theory, the above observations are indicative of a defect in GSIS in βERRγKO mice. To test this hypothesis, the effect of transient ERRgamma deletion ex vivo on GSIS was investigated. Adenoviral-induced Cre-recombination in $ERR\gamma^{lox/lox}$ (Ad-ERRγKO) islets reduced ERRgamma expression by ~75% compared to control adenovirus EGFP-$ERR\gamma^{lox/lox}$ (Ad-Control) islets without affecting insulin2 (Ins2) expression (FIG. 5H). Notably, the ability of Ad-ERRγKO islets to secrete insulin in response to a glucose challenge was almost totally abrogated ex vivo (FIG. 5I). Furthermore, loss of ERRγ in the entire pancreas (βERRγKO mice) reduced islet insulin secretion in response to nutrients (FIG. 5K). As ERRgamma regulates mitochondrial oxidative phosphorylation and metabolism in heart (Alaynick et al., 2007, Cell metabolism 6, 13-24; Dufour et al., 2007, Cell metabolism 5, 345-356) and skeletal muscle (Zhao et al., 1998, FEBS letters 430, 213-216), it was investigated whether ERRgamma is required for mitochondrial function in islets. Ad-Control islets responded robustly with a 2-fold increase in their oxygen consumption rate (OCR) when stimulated with 20 mM glucose. In contrast, Ad-ERRγKO islets failed to increase their OCR in response to the glucose challenge (FIG. 5J). Consistent with these results, ERRgamma knockdown in the rat clonal beta cell line INS-1 similarly reduced OCR, cellular ATP production and GSIS function in response to a glucose challenge (FIGS. 9A-9D). Without being bound to a particular theory, these results indicate that ERRgamma regulation of beta cell energy metabolism is required for GSIS.

Example 3: ERRgamma was Required for Beta Cell Metabolic Maturation

As mitochondrial function and morphology are tightly correlated (Tang et al., 2013, Cell metabolism 18, 883-895; Narkar et al., Cell metabolism 13, 283-293), it was investigated whether structural changes were detectable in βERRγKO beta cell mitochondria. Electron microscopy revealed that the insulin and proinsulin granules, and the overall mitochondrial number were not affected by ERRgamma deletion (FIGS. 10A and 10B). However, mitochondria swelling with disrupted cristae structure was seen in the ERRgamma-deficient beta cells, with significant increases in mitochondrial length, width, and volume, hallmarks of functionally defective mitochondria (FIGS. 10A-10C).

Figure 10H:
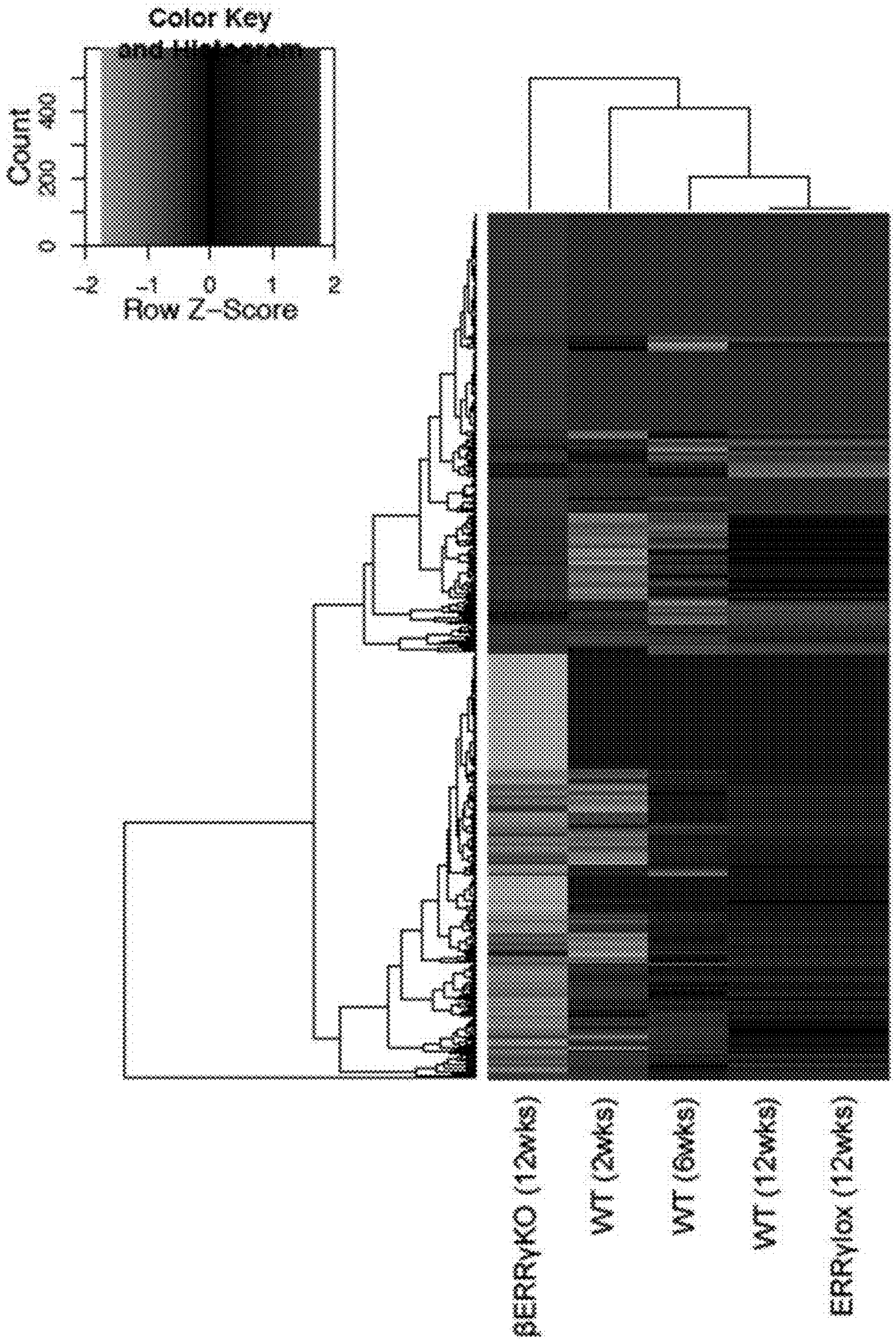
Figure 11:
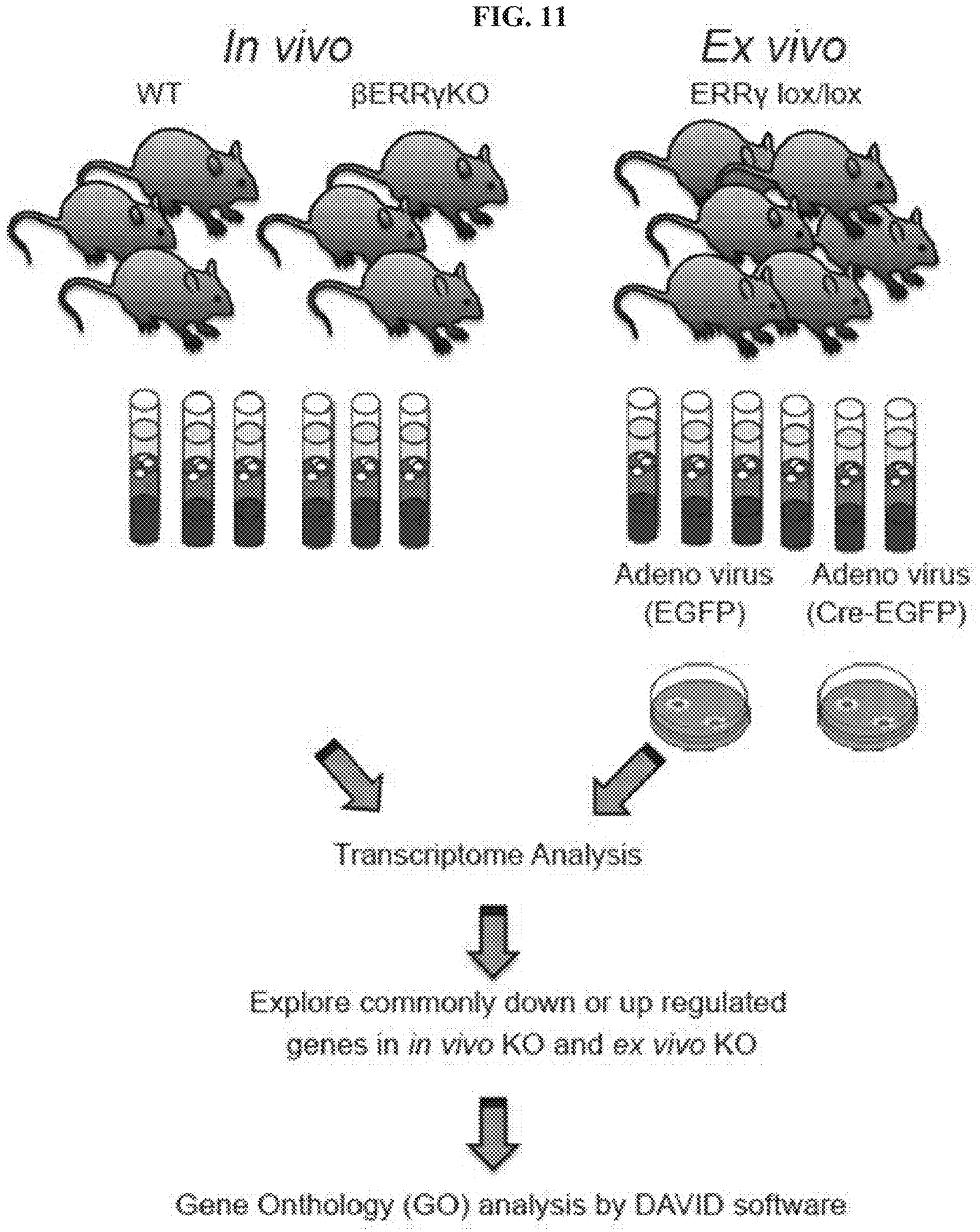
FIG. 11 is a schematic of genomic analyses of ERRγ-deleted beta cells. Transcriptional changes between islets from ERRγ$^{lox/lox}$ (WT, n=3) and βERRγKO (n=3) mice were compared to the changes between WT islets after adenoviral EGFP or Cre infection (n=10).
Figure 12A:
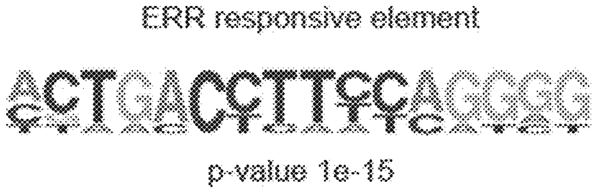
FIGS. 12A and 12B show that ERRgamma directly regulates postnatal islet maturation.
Figure 12B:
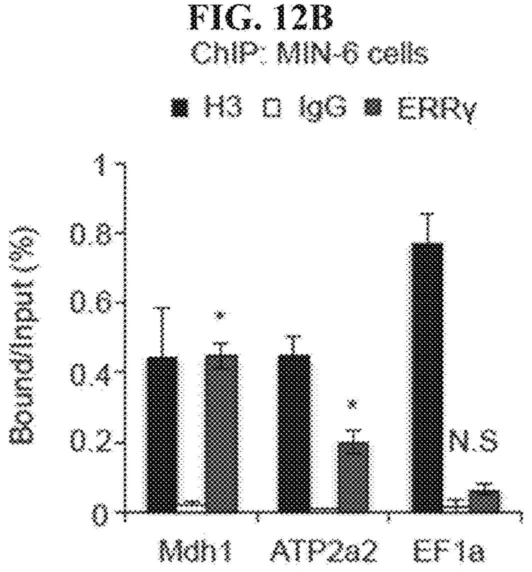

To understand the molecular role of ERRgamma in beta cell function, the transcriptional consequences of ERRgamma deletion were determined. In the developmentally-deleted βERRgammaKO islets, RNA-Seq revealed that the expression of 4189 genes was altered, with almost equal numbers of genes down- and up-regulated (2008 and 2181 genes, respectively; false discovery rate [FDR]<0.01, fold change [FC]>1.5). A similar comparison in the transiently-deleted Ad-ERRgammaKO islets by microarray analysis identified 2205 genes with altered expression, again with similar numbers of genes down- and up-regulated (1207 and 998 genes, respectively; false discovery rate [FDR]<0.01, fold change [FC]>1.25). As defects in GSIS were observed in both βERRγKO and Ad-ERRγKO islets, Gene Ontology (GO) analysis was performed on the common, differentially-expressed genes (232 down- and 239 up-regulated genes) to identify global cellular processes affected by ERRgamma deletion (FIG. 11 and FIG. 24). Consistent with the diabetic phenotype, ERRgamma-regulated genes were associated with processes important for beta cell function including ATP biosynthesis, cation transport, oxidative phosphorylation, electron transport and secretion (FIG. 10D). Furthermore, motif analyses of promoter regions identified ERR response elements (ERREs) in more than half of these differentially expressed genes (62.1% of down- and 64.6% of up-regulated genes). Without being bound to a particular theory, this indicates direct regulation by ERRgamma (FIG. 12A). In support of this notion, conventional ChIP assays, performed in the mouse insulinoma cell line MIN-6, confirmed the direct binding of ERRgamma to the promoter regions of Atp2a2 and Mdh1 (FIG. 12B). The expression changes of selected genes relevant to metabolic pathways (Mdh1, Cox6a2, Atp2a2, Ndufs2 and Atp6v0a2) were confirmed by qPCR analysis in both βERRγKO and βERRγKO islets (Table 4 and FIG. 10E, left and right panels, respectively). Without being bound to a particular theory, these results indicate that ERRgamma is a global regulator of ATP biosynthesis and metabolic genes in islet beta cells.

To further clarify the role of ERRgamma in the functional maturation of beta cells, the postnatal transcriptional changes in islets were compared with those induced by ERRgamma deletion. Notably, loss of ERRgamma abrogated a large number of the developmental changes associated with postnatal beta cell maturation (FIG. 10H). Specifically, the changes in expression of 74 genes normally up-regulated, and 35 genes normally down-regulated during maturation were lost in βERRgammaKO islets (FIG. 10F). These dysregulated genes included genes involved in energy production (ATP biosynthesis, oxidative phosphorylation and ETC) and secretory/exocytosis pathways (FIG. 10G). Without being bound to a particular theory, collectively these results indicate that ERRgamma is not only important for maintaining mitochondrial function in functionally mature beta cells, but also directly orchestrates many of the transcriptional changes that drive the postnatal maturation of these cells.

Example 4: ERRgamma Drives the Maturation of Synthetic Beta Cells

Figure 13J:
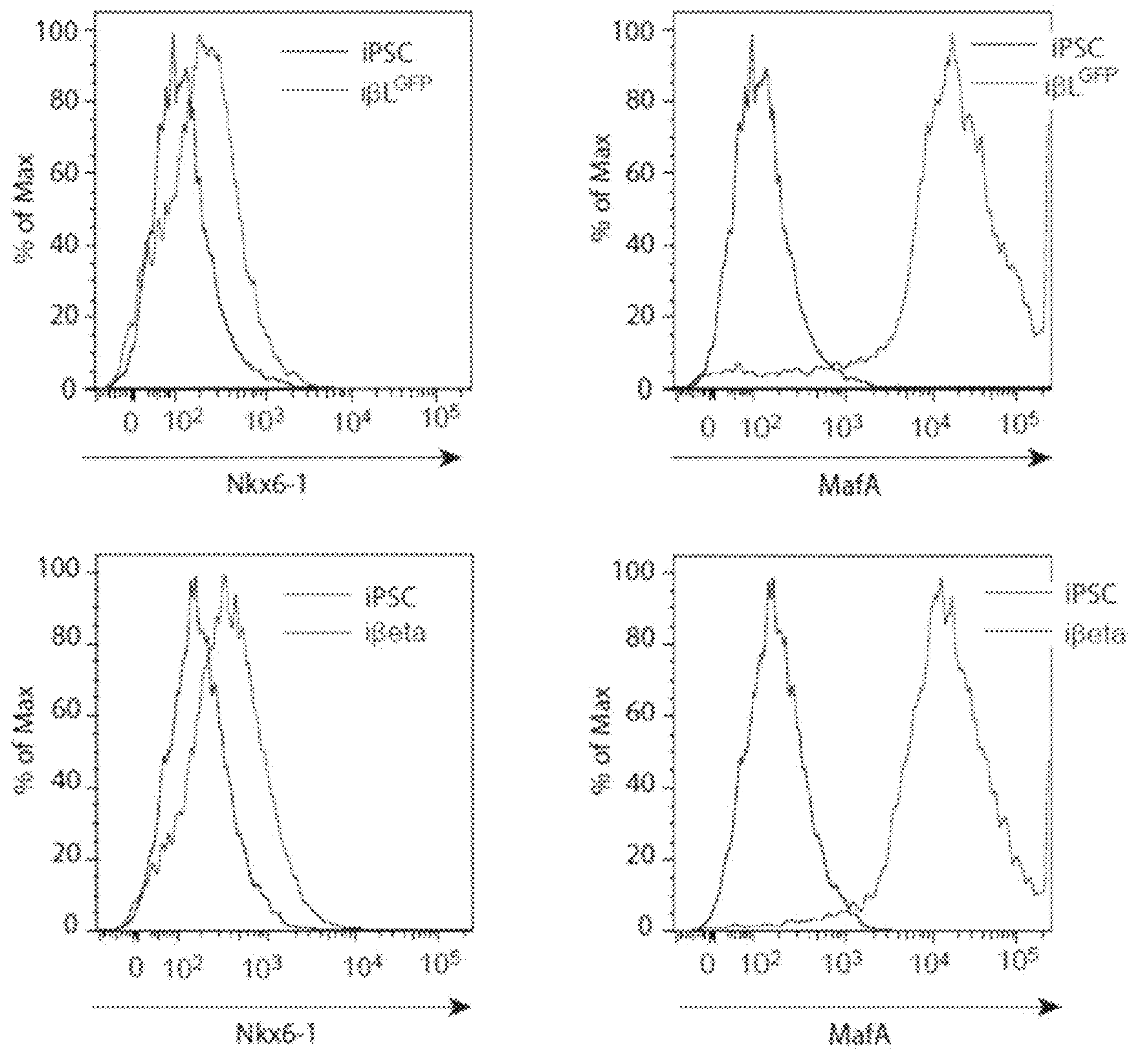
Figure 13K:
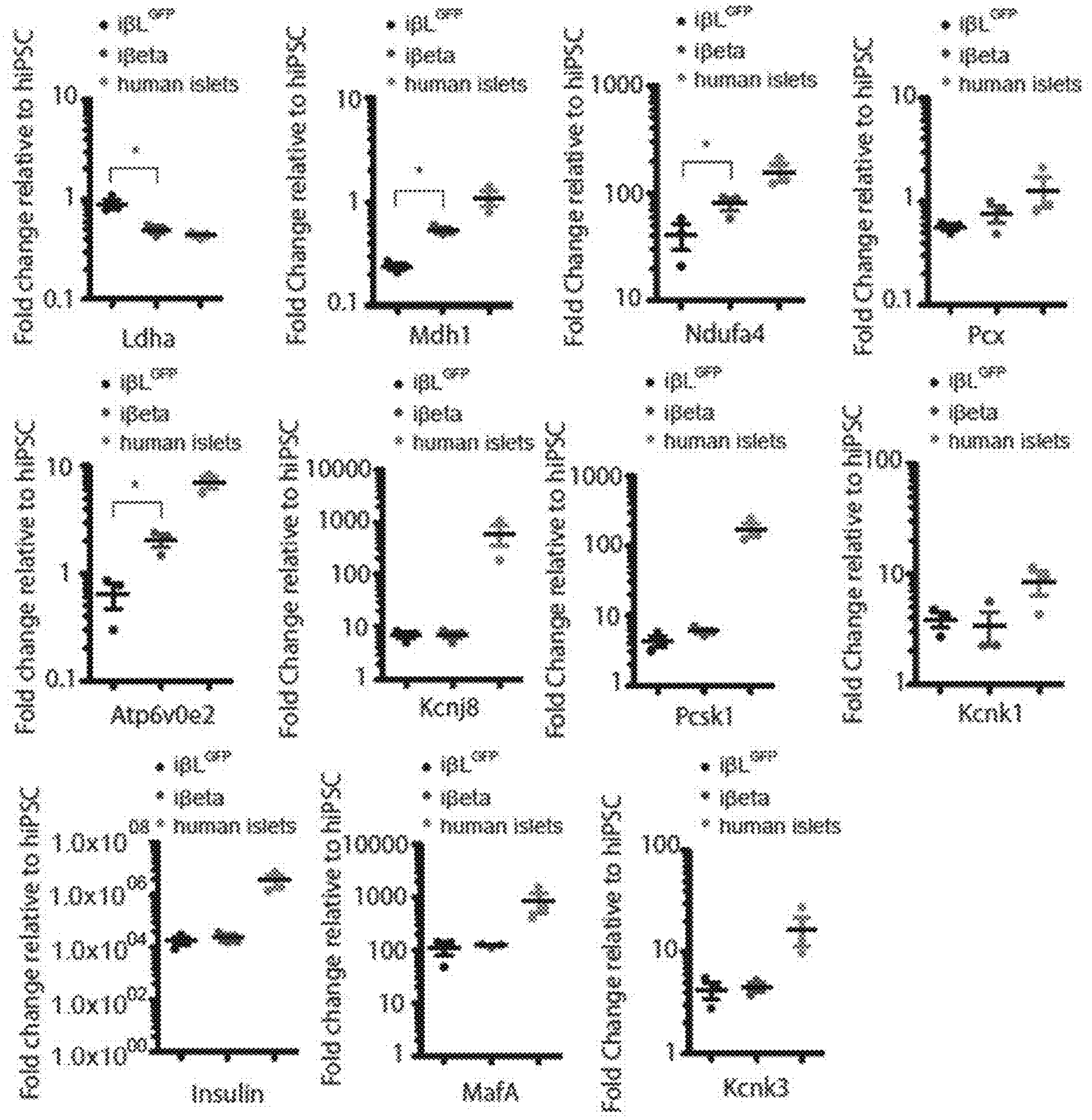
Figure 14:
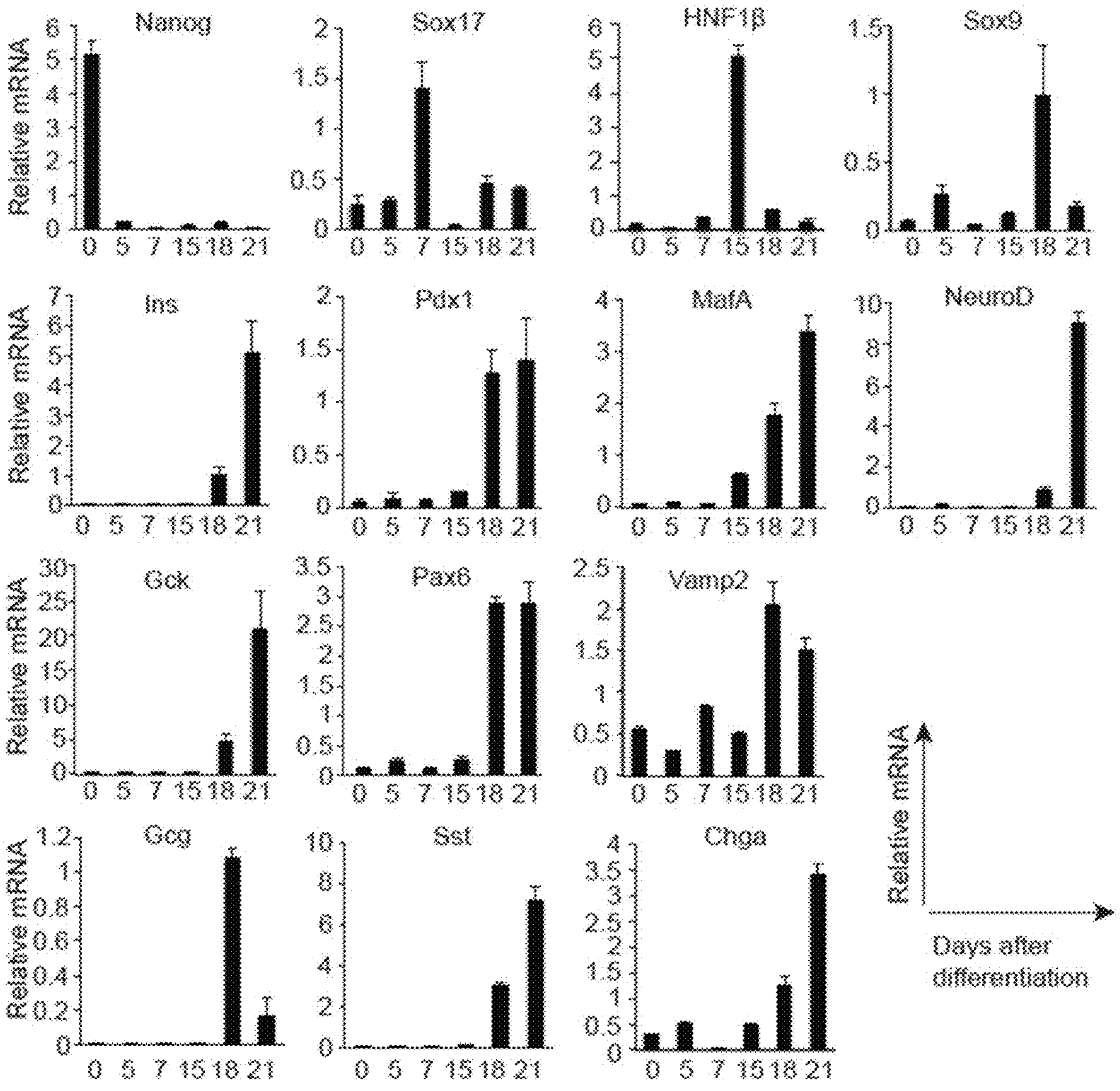
FIG. 14 is a set of bar graphs profiling expression of 14 genes in differentiating human iPSC. Relative expression of the pluripotent marker (Nanog), endoderm marker (SOX17), pancreatic progenitor marker (HNF1β), early endocrine marker (SOX9), and endocrine/beta-cell markers (Insulin, PDX1, MAFA, NEUROD, GCK, PAX6, VAMP2, GCG, SST, CHGA) in iPSCs during differentiation into beta-like cells is depicted.
Figure 15A:
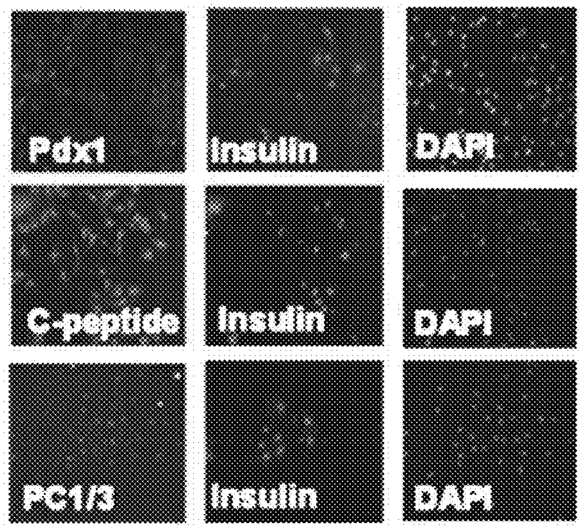
FIGS. 15A-15H depict functional characterization of iPSC-derived beta-like cells.
Figure 15B:
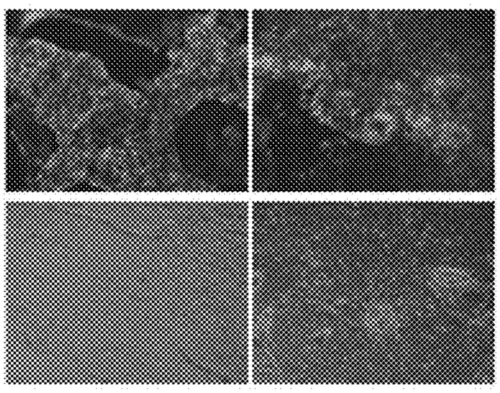
Figure 15C:
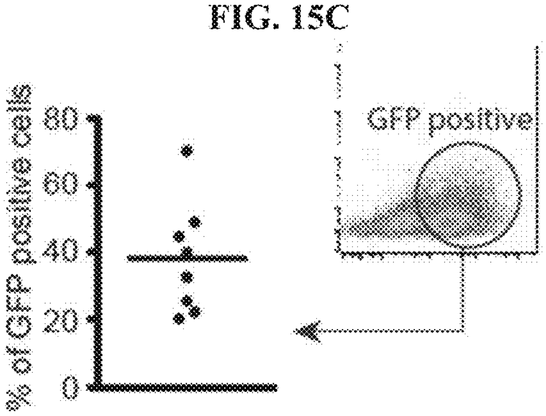
Figure 15D:
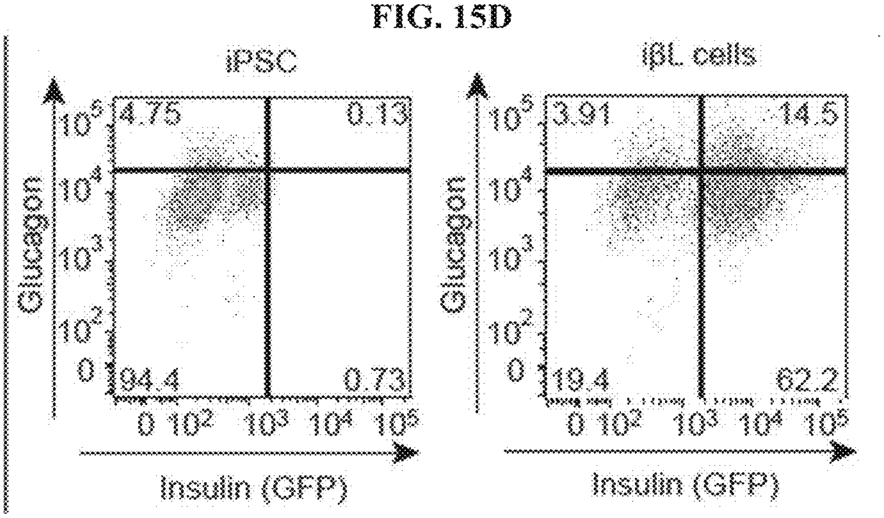
Figure 15E:
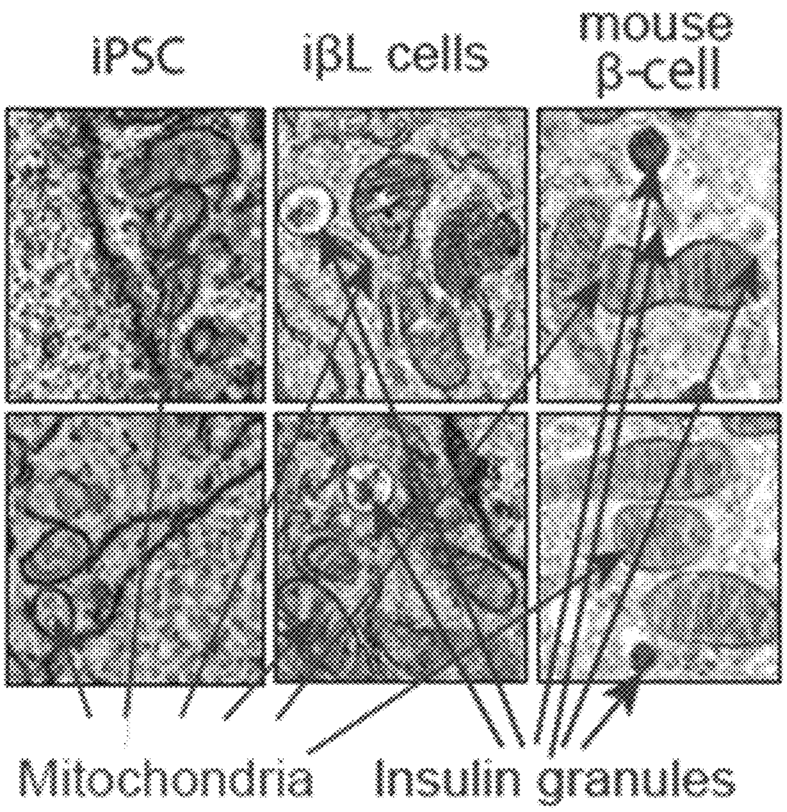
Figure 15F:
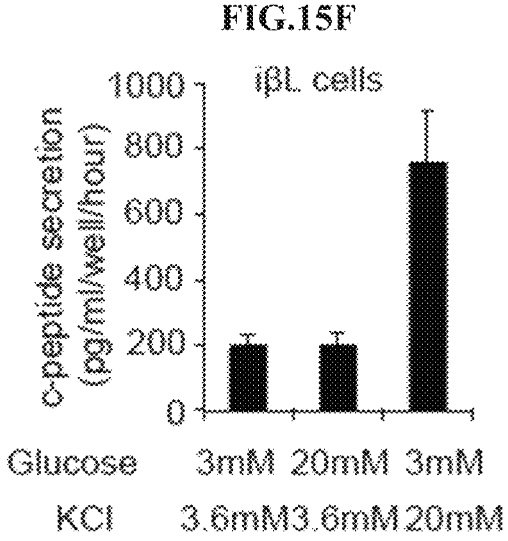
Figure 15G:
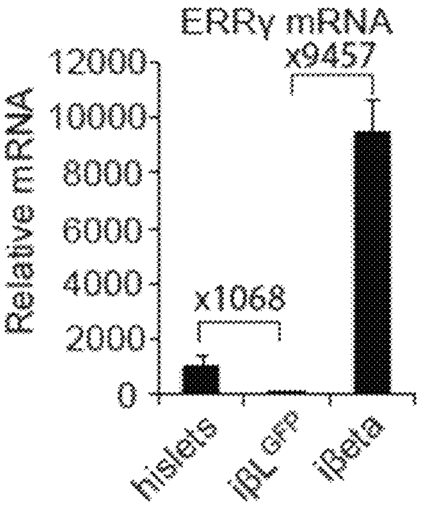
Figure 15H:
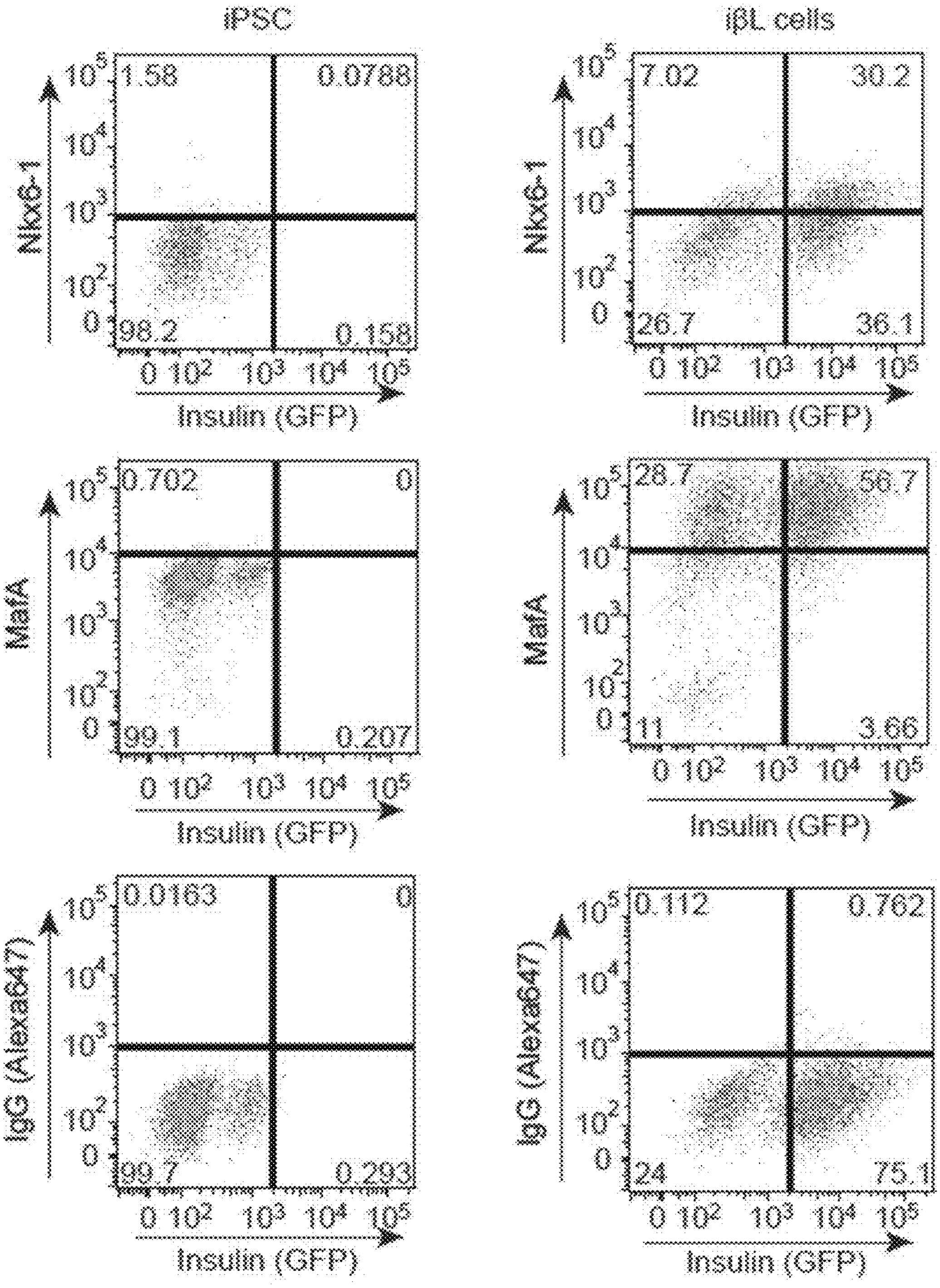
Figure 16:
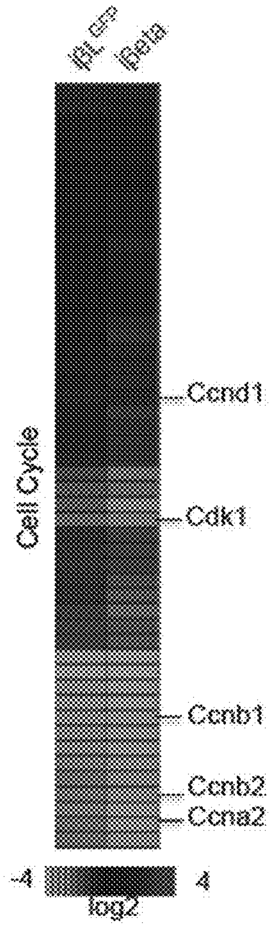
FIG. 16 depicts a table (left panel) and a heatmap (right panel) showing pathways down-regulated in iβeta cells. The table depicts functional annotation of down-regulated gene categories in iβeta cells, identified by Gene Ontology (GO). The heatmap depicts expression changes in selected genes involved in cell cycle.

Generation of transplantable beta cells from pluripotent stem cells is a major goal of stem cell therapeutics. However, current iPSC-derived beta-like cells resemble fetal cells in their inability to secrete insulin in response to a glucose challenge (Hackenbrock et al., 1966, The Journal of Cell Biology 30, 269-297; Anello et al., 2005, Diabetologia 48, 282-289; Hrvatin et al., 2014, Proc. Natl. Acad. Sci. 111(8): 3038-3043; D'Amour et al., 2006, Nature Biotechnology 24, 1392-1401; Kroon et al., 2008, Nature Biotechnology 26, 443-452; Schulz et al., 2012, PloS one 7, e37004; Xie et al., 2012, Cell Stem Cell 12, 224-237; Sneddon et al., 2012, Nature 491, 765-768). Based on a proposed regulatory role for ERRgamma in enhancing oxidative metabolism during beta cell maturation, it was investigated whether overexpression of ERRgamma could drive the maturation of human iPSC-derived beta-like cells into mature beta cells, in terms of metabolism. To address this question, the differentiation protocol was optimized for producing insulin-positive beta-like cells from human iPSCs, utilizing a human insulin promoter driven-GFP reporter for screening and isolation (Pagliuca et al., 2014, Development 140, 2472-2483; Hrvatin et al., Proceedings of the National Academy of Sciences of the United States of America; 111(8): 3038-3043). In the optimized protocol, insulin-positive cells were generated from iPSC, derived from a human endothelial cell line HUVEC, 18-21 days after initiation of differentiation (FIGS. 13A-13C and FIG. 14). Expression profiling during iPSC differentiation confirmed the generation of beta-like cells. Specifically, expression of the pluripotent marker Nanog was lost upon initiation of differentiation, while the terminal beta cell differentiation marker, insulin, appeared 18-21 days after initiation of differentiation. The definitive endoderm marker SOX17, the pancreatic progenitor marker HNF1β and endocrine progenitor marker SOX9 were transiently increased around days 7, 15 and 18, respectively (FIG. 14). Furthermore, the expression of additional beta cell markers including PDX1, MAFA, PAX6, NEUROD1, GCK, CHGA and VAMP2 were strongly induced at day 21 (FIG. 14). Immunohistochemical analyses confirmed that the optimized, 21 day differentiation protocol yielded beta-like cells that express the beta cell marker PDX1, c-peptide and prohormone carboxylase1/3 (PC1/3) (FIG. 15A). This optimized differentiation protocol reproducibly generated insulin-positive, glucagon-negative β-like cells, defined here as iβL cells, and electron microscopy revealed the presence of insulin granules (FIG. 13H and FIGS. 15B-15E). Moreover, while these iPSC-derived beta-like cells failed to secrete c-peptide in response to a glucose challenge, they were responsive to direct cellular depolarization-mediated insulin secretion by KCl (FIG. 15F). This confirmed the expression of Nkx6-1 and MafA in insulin-positive iβL cells (FIG. 15H). These results confirmed the generation of human beta-like cells. Without being bound to a particular theory, this indicated that mitochondrial function might be one reason for the defective GSIS function in β-like cells.

Figure 18A:
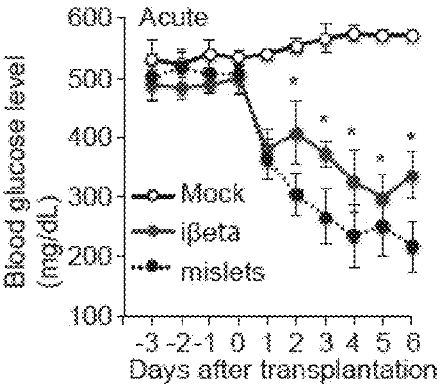
FIGS. 18A-18E show that iβeta cells restored glucose homeostasis in diabetic mice.
Figure 18B:
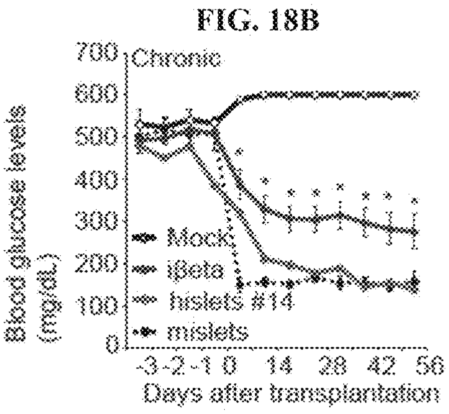
Figure 18C:
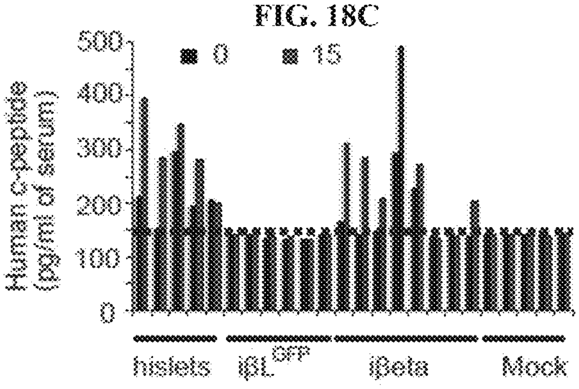
Figure 18D:
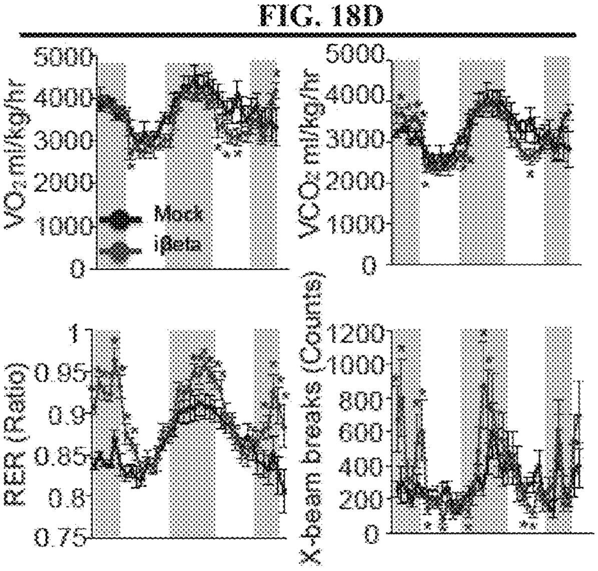
Figure 18E:
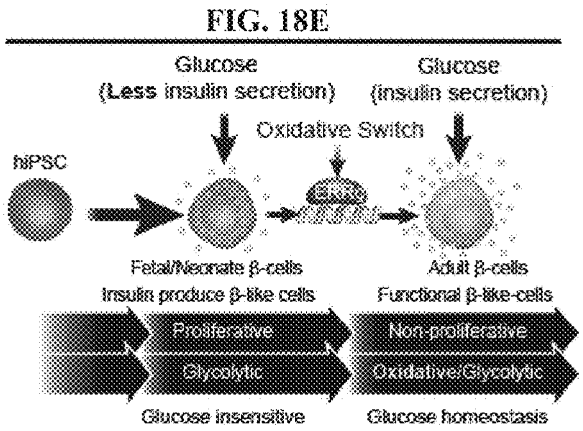

Given the role of ERRgamma in endogenous beta cell maturation, it was investigated whether overexpression of ERRgamma could rescue GSIS function in iPSC-derived beta-like cells. To address this question, iPSC-derived beta-like cells (day 22-25) were infected with adenoviral ERRgamma (Ad-ERRγ) or control (Ad-GFP) vector. Gene expression and functional analyses were performed at days 25-30. Given the widespread use of insulin in culture media, c-peptide levels were used as a surrogate measure of beta-like cell-derived insulin. It was found that Ad-ERRgamma infection successfully restored ERRgamma expression in iPSC-derived beta-like cells but did not significantly affect their intracellular c-peptide content (FIG. 13D left panel, and FIG. 15G). Encouragingly, Ad-ERRgamma infection significantly increased the c-peptide concentration in the culture media (FIG. 13D, right panel). Next the GSIS ability of Ad-ERRγ infected iPSC-derived beta-like cells was examined. Control infected iPSC-derived beta-like cells (defined as iβLG$^{FP}$ cells) were not able to secrete c-peptide in response to a glucose challenge. Remarkably, Ad-ERRγ infected iPSC-derived beta-like cells (iβeta cells) demonstrated enhanced c-peptide secretion in response to a glucose challenge, similar to that recorded for isolated human islets (FIG. 13E). Furthermore, transcriptomic analyses identified increases in iβeta cells of genes associated with the generation of precursor metabolites, oxidation reduction, electron transport chain (ETC), oxidative phosphorylation and mitochondrial organization, and decreases in genes associated with cell cycle, without significant increases in the expression of beta cell lineage-specific genes (FIG. 13F, FIG. 13G, FIG. 13J, FIG. 13K, FIG. 16, and FIG. 25). Notably, ERRgamma overexpression improved the cristae structure, as well as the respiration function of mitochondria in iβeta cells (FIGS. 13H and 13I). Thus, these results describe the generation of a synthetic glucose-responsive beta cell from iPSC. Without being bound to a particular theory, these results support the hypothesis that ERRgamma-regulated mitochondrial metabolic pathways are required for GSIS (FIG. 18E).

Figure 17:
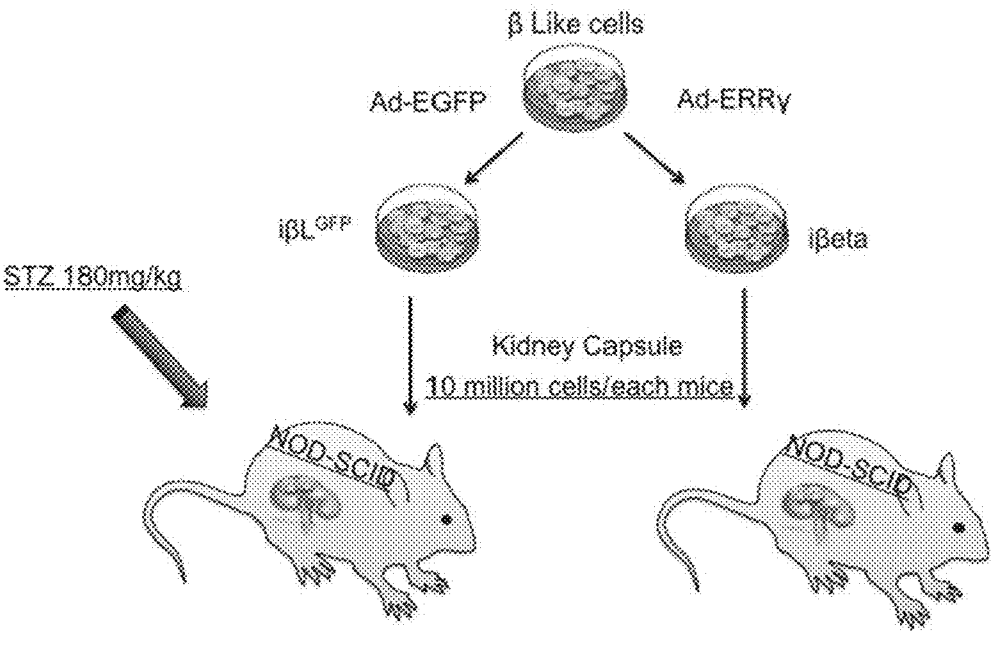
FIG. 17 is a schematic of cell transplantation experiments.
Figure 19A:
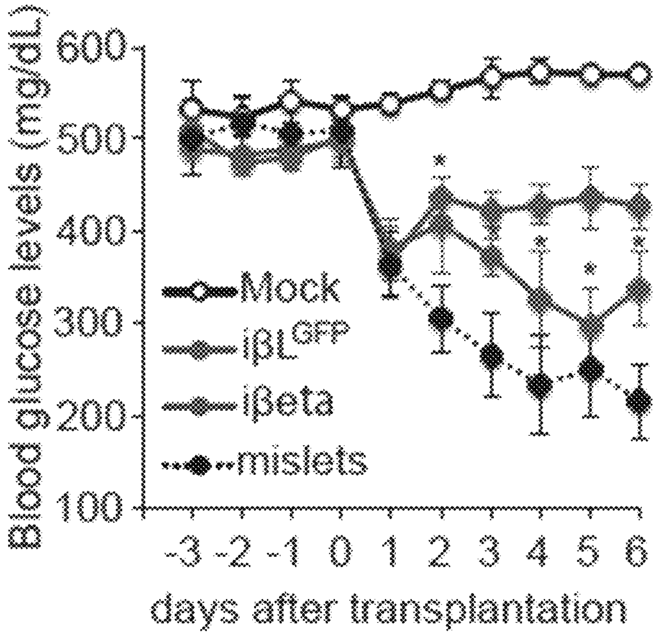
FIGS. 19A and 19B have graphs showing in vivo transplantation studies.
Figure 19B:
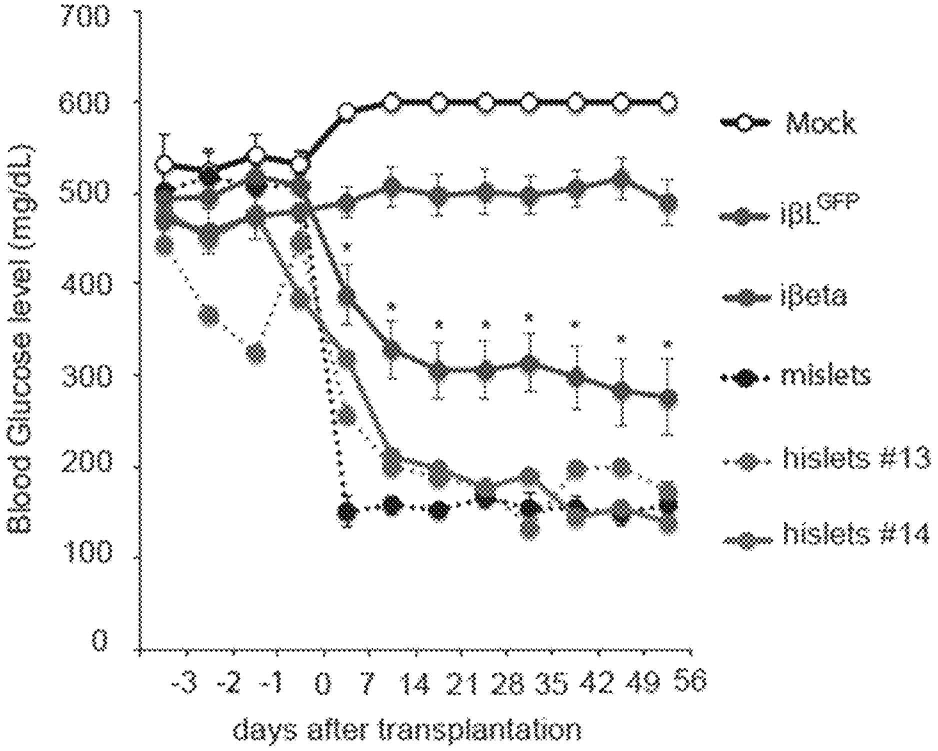
Figure 20:
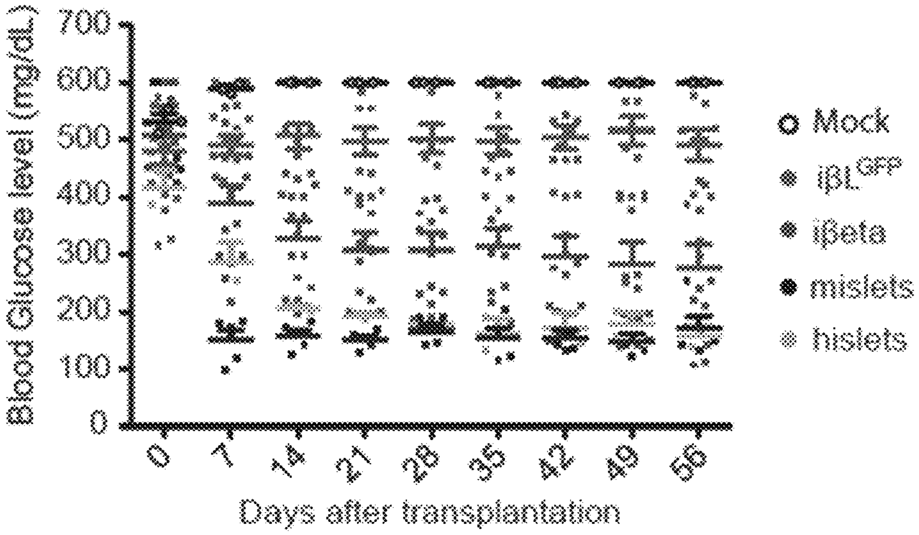
FIG. 20 is a scatter graph showing diversity of the glucose-lowering effect by iβeta cells. The graph shows blood glucose levels of individual mice described in FIG. 19B.
Figure 21:
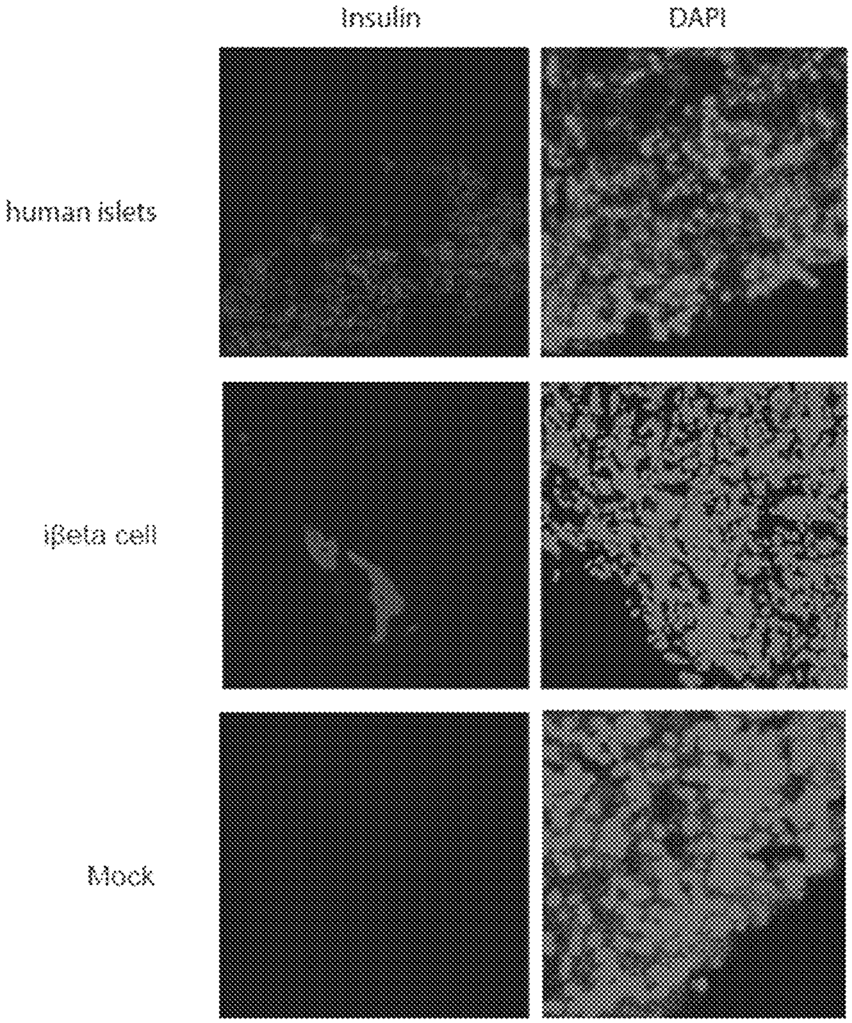
FIG. 21 shows immunohistochemistry (IHC) of kidneys in transplanted mice.

The ability to produce transplantable β cells capable of restoring glucose homeostasis in the setting of diabetes is the ultimate therapeutic goal. To determine whether iβeta cells function in vivo, a Streptozocin (STZ)-induced diabetic NOD-SCID mouse model was utilized. Blood glucose levels of NOD-SCID mice treated with STZ (180 mg/kg i.p. injection) were monitored daily to confirm hyperglycemia. Twelve (12) days after STZ injection, 10 million iPSC-derived beta-like cells infected with Ad-GFP (iβL$^{GFP}$ cells) or Ad-ERRγ(iβeta cells) were transplanted into the kidney capsule (FIG. 17). Human islets and mouse islets were similarly transplanted as positive controls. Remarkably, the blood glucose levels of mice that received the iβeta cells began to normalize within days of transplantation, similar to those receiving functional human or mouse islets (FIG. 18A and FIG. 19A). Furthermore, transplanted iβeta cells controlled blood glucose levels in recipient mice chronically (56 days, FIG. 18B, FIG. 19B and FIG. 20) and insulin-positive cells were detected in the kidney after chronic treatment (FIG. 21). Importantly, in approximately half of chronically treated iβeta cell recipient mice, the blood glucose levels were restored to non-diabetic levels (<250 mg/dL) concomitant with a glucose-responsive phenotype, as demonstrated by glucose tolerance tests, similar to mice that received human islet transplantation (FIG. 18C). Additionally, pronounced improvements in the circadian regulation of metabolism were observed in chronically treated iβeta cell recipient mice with normalized blood glucose levels (increased night time respiratory exchange ratio (RER) consistent with improved glucose utilization), and were accompanied by increased night time activity (FIG. 18D). These results demonstrate that genetically engineered ERRgamma expression might be exploited to potentiate GSIS function in beta-like-cells.

The present study shows that the estrogen-related receptor gamma (ERRγ) expression distinguishes neonatal and adult beta cells, and that ERRgamma is required for the glucose-responsive beta cells. ERRgamma is a known activator of oxidative metabolism and mitochondrial biogenesis. Without being bound to a particular theory, high energy requirements may be needed to achieve and maintain glucose responsiveness. Although it has not been previously possible to differentiate iPSCs to functional beta cells, the results described herein indicate that activation of the ERRgamma gene network has the potential to overcome this metabolic roadblock. Indeed, genome-directed metabolic maturation was an important step in transforming iPSCs-derived fetal-like cells into glucose-responsive cells in vitro. Perhaps more importantly, optimized scale up and purification shows that these converted cells can, via transplantation, effectively rescue type 1 diabetic mice. Importantly, these experiments provide proof-of-concept in vivo that stem cell transplantation is useful as a therapeutic in the treatment of type 1 and type 2 diabetes.

Here, the fundamental discovery that ERRgamma, a known regulator of oxidative mitochondrial metabolism, is required for the functional maturation of beta cells to produce glucose-responsive, transplantable iPSC-derived beta cells (iβeta cells) was exploited. Remarkably, transplantation of iβeta cells not only restored glucose homeostasis in a severe STZ-induced Type 1 diabetic mouse model, but re-established circadian metabolic rhythmicity to substrate usage.

This is important because poor glucose management is associated with long-term diabetic consequences including diabetic retinopathy, nephropathy and neuropathy. While long-acting insulin formulations and programmable delivery pumps provide therapeutic utility, they fail to fully replicate the glucose-responsiveness of pancreatic β cells. Human islet transplantations offer superior glucose management but require immuno-suppressive drug regimens and are limited by the availability and in vivo viability of the transplanted cells. Though insulin independence can be achieved via islet transplantation, more than 50% of allotransplanted patients and virtually all autotransplanted patients are back on insulin therapy after 5 years. In both situations, transplantation of a larger mass of islets may alleviate some of the limitations. Thus, patient-specific iPSC-derived β cells could resolve many of these concerns and is considered one of the central goals of stem cell replacement therapy.

How might ERRγ work? As fetal development occurs under conditions of low oxygen tension and steady maternal glucose, most physiologic systems including the pancreas are in a poised but not fully functional state at birth. In the postnatal and adult setting, oxidative metabolism becomes dominant and intermittent feeding exposes the pancreas to dramatic changes in glucose levels. Recently, it has been reported that weaning triggers a maturation step in β cells which is characterized by enhanced glucose-stimulated oxidative phosphorylation and insulin secretion (Pagliuca et al. 2014, Cell 159, 428-439). The transcriptomic analyses presented in this study indicates that the increased ERRgamma expression in beta cells served as the key driver of the oxidative metabolic gene network. Furthermore, low ERR-gamma expression in iPSC-derived beta-like cells might be limiting their ability to secrete insulin. This is consistent with observations that iβeta cells, ERRgamma expressing iPSC-derived beta-like cells, activated an oxidative metabolic program and demonstrated glucose-responsive insulin production. However, the key feature of beta cells is their ability to repeatedly secrete insulin in response to a glucose challenge in vivo and in vitro. Importantly, transplantation of iβeta cells not only restored glucose homeostasis in a severe STZ-induced Type I diabetic mouse model, but re-established circadian metabolic rhythmicity to substrate usage.

Despite recent advances, including generating functional beta cells from ES cells and the in vivo maturation of in vitro-differentiated pancreatic progenitor cells, the underlying mechanisms of beta cell maturation remain poorly understood. Whereas dynamic chromatin remodeling and sympathetic innervation stimuli are implicated, the finding that ERRgamma coordinates a transcriptional program regulating increased oxidative metabolism provides mechanistic insight into the functional maturation of beta cells (FIG. 18E). Genetic and epidemiology studies have implicated ERRgamma in the development of diabetes (http://tldbase-.org/page/AtlasHome), however its role was previously not understood. Notably, an understanding of the role of ERR-gamma in driving the metabolic maturation necessary for the generation of glucose-responsive beta cells has the potential to accelerate the development of insulin-responsive beta cells from the patient's own cells. The results described here indicate that iβata cells represent a new opportunity for stem cell-based therapy.

The experiments described above were performed with the following methods.

Animal Experiments

Beta cell-specific ERRgamma-knockout mice (βERRγKO) were generated by crossing $ERR\gamma^{lox/lox}$ and RIP-Cre (B6N.Cg-Tg(Ins2-cre)25 Mgn/J) mice on a pure C57BL/6J genetic background. Tamoxifen-inducible beta cell-specific ERRgamma-knockout mice were generated by crossing $ERR\gamma^{lox/lox}$ and RIP-CreER (STOCK Tg (Ins2-cre/Esr1)1 Dam/J) mice. Pancreas-specific ERRgamma-knockout mice (βERRγKO) were generated by crossing $ERR\gamma^{lox/lox}$ and PDX1-Cre (B6.FVB-Tg(PDX1-cre)6Tuv/J). Insulin promoter GFP (MIP-GFP) mice (Tg(Ins1-EGFP)1Hara) were purchased from Jackson Laboratory. The ERRγ-LacZ knock-in mice were described previously (Alaynick et al., 2007, Cell metabolism 6, 13-24). Glucose tolerance tests were performed before (12 week-old) and 3 weeks after treatment (16 week-old) of tamoxifen-inducible β cell-specific ERRγ-knockout mice. Male mice were given daily injections of tamoxifen (2 mg/kg in corn oil, intra-peritoneally) for 7 days.

Animals were maintained in a specific pathogen-free animal facility (SPF) on a 12-hour light-dark cycle at an ambient temperature of 23° C. Water and food were provided ad lib. All animal experiments used age- and sex-matched mice. All procedures involving animals were performed in accordance with protocols approved by the IACUC and Animal Resources Department (ARD) of the Salk Institute for Biological Studies.

Intra-Peritoneal Glucose (IP-GTT) or Insulin (IP-ITT) Tolerance Tests

IP-GTTs were performed on overnight fasted mice. Blood glucose values were assessed before and at 15, 30, 60 and 120 minutes after intra-peritoneal administration of 2 g/kg of glucose using glucose PILOT. Serum insulin levels were assessed before and at 5, 15 and 30 min after the intra-peritoneal administration of glucose using a Rat/mouse Insulin ELISA kit (Millipore). IP-ITT assays were performed on mice after a 6 hour fast with the injection of 0.75 U/kg of insulin (Humalin R, Eli Lilly).

Isolated Pancreatic Islet Studies

Mouse pancreatic islets were isolated as previously described for rats (Sutton et al., 1986, Transplantation 42, 689-691). Briefly, 0.5 mg/ml collagenase P (Roche) diluted in HBSS buffer was injected through the common bile duct, and the perfused pancreas dissected and incubated in water bath (37° C. for 21 minutes). Digested exocrine cells and intact islets were separated using Histopaque-1077 (SIGMA) with centrifugation (900 g for 15 minutes) and intact islets were handpicked. All human islets were provided by the Integrated Islets Distribution Program (IIDP)

under an approved protocol. Additional information on human islets is provided at FIG. 26.

Insulin Secretion Assay (Primary Mouse and Human Pancreatic Islets and Human iPSC-Derived Cells)

Insulin release from intact islets was monitored using batch incubation methods. Overnight-cultured isolated pancreatic islets (RPMI-1640 supplemented with 10% (v/v) fetal bovine serum and 1% (v/v) Antibiotic-Antimycotic (Gibco) were pre-cultured at 37° C. for 30 minutes (Krebs Ringer bicarbonate buffer (KRBB) containing 129.4 mM NaCl, 3.7 mM KCl, 2.7 mM $CaCl_2$, 1.3 mM $KH_2PO_4$, 1.3 mM $MgSO_4$, 24.8 mM $NaHCO_3$ (equilibrated with 5% $CO_2$, 95% $O_2$, pH7.4), 10 mM HEPES and 0.2% (v/v) BSA (fraction V, Sigma) (KRBH) with 3 mM glucose). Pancreatic islets were then incubated in KRBH buffer (500 μl/10 islets) with 3 mM or 20 mM glucose to determine insulin secretion levels. After 30 minutes, islets were pelleted by centrifugation and insulin levels determined by ELISA (Rat/mouse Insulin ELISA KIT (Millipore) and Human Insulin ELISA KIT (Millipore) for mouse and human islets, respectively). For human iPSC-derived cells, the cells ($1\times10^6$ cells/well in 24 well) were pre-cultured in 3 mM glucose KRBH buffer (500 μl/well). The cells were then incubated in KRBH buffer (200 μl/well) with 3 mM or 20 mM glucose to determine c-peptide secretion levels as indicator of insulin secretion levels. After 30 min, the cells were pelleted by centrifugation and c-peptide levels were determined by human c-peptide ELISA KIT (Millipore).

INS-1 Cell Culture, Transfection and Insulin Secretion Assay

INS-1 cells were cultured at 37° C. in 5% $CO_2$ in air in RPMI-1640 (Sigma Aldrich) supplemented with 10% (v/v) fetal bovine serum, 1% (v/v) Antibiotic-Antimycotic (Gibco) 10 mM HEPES, 2 mM glutamax, 1 mM sodium pyruvate, and 50 μM β-mercaptoethanol (RPMI for INS-1 medium). INS-1 cells were transfected with Lipofectamine2000 containing Plus Reagent (Invitrogen). INS-1 cells were transfected with ERRgamma siRNA (Qiagen) or negative control scramble siRNA (Qiagen) for 72 hours. Insulin secretion was measured in pre-incubated cells (37° C. for 30 minutes in KRBH with 3 mM glucose, as described in insulin secretion assays for primary islets) after a 30 minute glucose challenge (KRBH buffer with 3 mM or 20 mM glucose) using a Rat/mouse Insulin ELISA kit (Millipore).

Quantitative RT-PCR Analysis

Total RNA was extracted using TRIzol reagent (Invitrogen) and RNeasy KIT (Qiagen). Reverse transcription was performed with a SuperScript III First-Strand Synthesis System kit (Invitrogen) or PrimeScript RT reagent kit (TAKARA). Real time quantitative RT-PCR (qPCR) was performed using SYBR Green (Bio-Rad). PCR analyses were carried out using the oligonucleotide primers listed in FIG. 27.

Chromatin Immunoprecipitation

Chromatin was prepared from mouse insulinoma, MIN-6 cells. Briefly, MIN-6 cells were cross-linked with 1% formaldehyde for 10 minutes, followed by the addition of glycine at 125 mM. Chromatin was sheared by enzymes (CHIP IT Express Kit, Active Motif) and immuno-precipitated with 2 μg anti-H3, control mouse IgG; or anti-ERRgamma antibodies. ChIP-qPCR primers are listed in FIG. 27.

Electron Microscopy

Pancreatic samples were cut into 1 $mm^2$ sections and fixed for 36 hours at 4° C. in 0.1 mM sodium phosphate buffer (pH 7.4) containing 2% paraformaldehyde and 2% glutaraldehyde. The tissue pieces were subsequently washed and dehydrated using graded acetone, and embedded in Epon-Araldite. An ultra microtome was used to prepare ultra-thin sections. The sectioned tissues were stained with 1% toluidine blue borax solution, mounted on copper grids, and double-stained with uranyl acetate prior to examination in a JEM 100 CX-II electron microscope.

Histology (H&E Staining, Immunostaining and LacZ Staining)

H&E staining was performed by Pacific Pathology (San Diego). Immunostaining was visualized by ZEISS confocal microscopy analysis using the following antibodies on frozen sections of pancreas and 4% PFA-fixed cells: Insulin (1/100, Abcam ab7842), c-peptide (1/100, Abcam ab14182), glucagon (1/100, Abcam ab10988), somatostatin (1/100, Abcam ab103790), Prohormone Carboxylase 1/3 (1/100, Millipore AB10553), Pdx-1 (1/100, Abcam ab47267). DAPI-containing mounting media (VECTASHIELD mounting medium for fluorescence) was used for nuclear staining. Whole pancreases from ERRγ knock-in mice (Alaynick et al., 2007, Cell metabolism 6, 13-24) were fixed with paraformaldehyde and glutaraldehyde, and frozen sections stained by X-gal.

Microarray Analyses

Total RNA was extracted from Ad-GFP or Ad-Cre infected islets using Trizol reagent (Invitrogen) and its quality determined by an Agilent 2100 Bioanalyzer. 500 ng of RNA was reverse transcribed into cRNA and biotin-UTP labeled using the Illumina TotalPrep RNA Amplification Kit (Ambion). cRNA was quantified using an Agilent Bioanalyzer 2100 and hybridized to the Illumina mouseRefseq-8v2 Expression BeadChip using standard protocols (Illumina). Image data were converted into unnormalized Sample Probe Profiles using Illumina GenomeStudio. Data were analyzed by GeneSpring GX software. Briefly, per-chip normalizations were set to the $75^{th}$ percentile, and per-gene normalizations to the median and specific samples. Genes assigned as absent were eliminated from the dataset and genes with an expression difference of 2-fold more than WT were selected. Combination analyses by GO, pathway analyses and cluster analyses were performed using mainly DAVID software (Huang et al., 2009, Nature protocols 4, 44-57; Huang et al., 2009, Nucleic acids research 37, 1-13). The microarray data are deposited in the NCBI Gene Expression Omnibus and accessible through GEO Series accession number GSE56080.

RNA-Seq Library Generation

Total RNA was isolated from cell pellets treated with RNAlater using the RNA mini kit (Qiagen) and treated with DNaseI (Qiagen) for 30 min at room temperature. Sequencing libraries were prepared from 100-500 ng total RNA using the TruSeq RNA Sample Preparation Kit v2 (Illumina) according to the manufacturer's protocol. Briefly, mRNA was purified, fragmented, and used for first- and second-strand cDNA synthesis followed by adenylation of 3' ends. Samples were ligated to unique adapters and PCR amplified. Libraries were then validated using the 2100 BioAnalyzer (Agilent), normalized and pooled for sequencing.

High-Throughput Sequencing and Analysis

RNA-Seq libraries prepared from 2-3 biological replicates for each experimental condition were sequenced on the Illumina HiSeq 2500 using bar-coded multiplexing and a 100 bp read length. Image analysis and base calling were performed with Illumina CASAVA-1.8.2. This yielded a median of 29.9M usable reads per sample. Short read sequences were mapped to a UCSC mm9 reference sequence using the RNA-Seq aligner STAR (Dobin et al., 2013, Bioinformatics 29, 15-21). Known splice junctions from mm9 were supplied to the aligner and de novo junction discovery was also permitted. Differential gene expression analysis, statistical testing and annotation were performed using Cuffdiff 2 (Trapnell et al., 2013, Nature biotechnology 31, 46-53). Transcript expression was calculated as gene-level relative abundance in fragments per kilobase of exon model per million (fpkm) mapped fragments and employed correction for transcript abundance bias (Roberts et al., 2011, Bioinformatics 27, 2325-2329). RNA-Seq results for genes of interest were also explored visually using the UCSC Genome Browser. RNA-Seq data can be accessed on the NCBI Sequence Read Archive under the accessions SRP048600 and SRP048605.

Differentiation of Human Induced Pluripotent Cells (hiPSC) to Insulin-Producing Cells and Glucose-Responsive Cells Human induced pluripotent stem cells derived from Huvec (hiPSC) and embryonic stem cells (H9ES) were obtained from the Stem Cell Core (Salk Institute). Cells were maintained on matrigel (BD)-coated dishes in complete mTeSR Media. For pancreatic differentiation, hPCs were infected with a human insulin reporter lentivirus (pGreenZero lenti reporter human insulin, System Biosciences) by Spinfection (800 g, 1 hour) and then media was changed to 100 ng/ml human Activin (Sigma), 25 ng/ml recombinant human Wnt3a (Sigma) in differentiation media (800 ml DMEM/F12, 13.28 g BSA, 10 ml Glutamax, 560 mg $NaHCO_3$, 330 mg thiamine, 100 mg reduced glutathione, 3300 mg Vitamin C, 14 μg Selenium, 10 ml NEAA, 2 ml Trace Element B, 1 ml Trace Element C, 7 μl β-ME, 2 ml DLC, 2 ml GABA, 2 ml LiCl, 129.7 ug PA, Insulin 2 mg up to 1000 ml) for 2 days and then 100 ng/ml human Activin in differentiation media for another 2 days (Stage 1). Subsequently, media was replaced with differentiation media with 1μ.M dorsomorphin (Calbiochem), 2 μM Retinoic Acid (Sigma), and 1004 SB431542 for 7 days (Stage 2). Media was then replaced with differentiation media with 1004 Forskolin (Sigma), 10 dexamethasone (Stemgent), 1004 TGFβ RI Kinase inhibitor II (Calbiochem), 10 mM Nicotinamide (Sigma) for 10 days (stage 3). Media was replaced every day (stage 1), every day or every other day (stage 2) and every other day (stage 3, beta-like-cells).

At days 22-25, the expression of human insulin genes and GFP were confirmed regularly by qPCR and fluorescence microscopy. Positive cells were used in subsequent experiments. EGFP-adenovirus (Ad-GFP) or human ERRgamma adenovirus (Ad-ERRγ) were diluted in RPMI-1640 with 2% FCS, and $1\times10^8$ pfu/ml (MOI 100) used to infect beta-like cells for 2 hours. Media was changed to differentiation media containing 1004 Forskolin (Sigma), 10 μM dexamethasone (Stemgent), 1004 TGFβ RI Kinase inhibitor II (Calbiochem), 10 mM Nicotinamide (Sigma) for 3-5 days, then GFP-expressing beta-like cells (iGFP cells) and ERR-gamma expressing beta-like-cells (iβeta cells) were analyzed for RNA-Seq, EM, Seahorse and transplantation studies. Additional information for differentiation protocol is listed in FIG. 28.

OCR and ECAR Measurements

Oxygen consumption rates (OCRs) and extracellular acidification rates (ECARs) were recorded in 96-well plates using an XF96 seahorse (Seahorse Biosciences). Briefly, 70 isolated islets/well were pre-cultured with XF DMEM media (pH7.4) and 3 mM glucose for 1 hour prior to the incremental addition of glucose, up to a final concentration of 20 mM. OCRs (reported as % change compared to 3 mM glucose) were recorded during the addition of glucose. Insulin-positive beta-like cells, sorted by flow cytometry, were cultured for 3 days in 96-well plates ($1\times10^5$ cells/well) prior to infection with adenoviral EGFP or ERRgamma vectors. Infected cells were pre-cultured in XF DMEM media (pH 7.4) with 3 mM glucose for 1 hour, then the media was changed to XF DMEM media (pH 7.4) with 20 mM glucose, 1 mM sodium pyruvate, and appropriate mitochondrial stress reagents (oligomycin, Fccp, Rotenone and Antimycin A), as instructed in the Mitostress Kit (Seahorse Biosciences).

Virus Production

Lentiviruses were produced using 2nd generation or 3rd generation lentiviral systems in HEK293T cell line. Adenovirus EGFP and Cre were purchased from Illinois University and Adenovirus ERRgamma was purchased from Welgen, Inc.

NOD-SCID Mice Transplantation Study

Immunodeficient NOD-SCID mice (NOD.Cg-Prkdcscid Il2rgtm1Wjl/SzJ) were purchased from Jackson Laboratory and bred and maintained in autoclaved cages in a SPF facility at the Salk Institute. Mice were rendered diabetic by a single intra-peritoneal (i.p.) high dose of streptozotocin (STZ; 180 mg/kg) injection. 1 week after STZ injection, mice with blood glucose levels higher than 400 mg/dL were used as recipients for transplantation analyses.

Human and mouse islets (200-500 islets or 500-1000 IEQ per animal) or human iPSC-derived insulin-producing cells (iβ$L^{GFP}$ or iβeta cells; 10 million cells per animal) were resuspended in 200 ul RPMI-1640 media. Cells were loaded into laboratory tubing (SiLastic, 508-004) and centrifuged 400 g for 1-2 minutes. Cell clusters were transplanted (approximately 30-50 ul) under kidney capsules in 8-16 week old STZ-injected diabetic mice. Ketamine (80 mg/kg) and Xylazine (10 mg/kg) were used as surgical anesthetics and mice were placed on 37° C. heat pads to recover.

Metabolic Cage Analyses

Metabolic cage analyses were conducted with a Comprehensive Lab Animal Monitoring System (Columbus Instruments). $CO_2$ production, $O_2$ consumption, Respiratory Exchange Rate (RER) and ambulatory counts by x-peak were determined for 5 consecutive days and nights, with at least a 24 hour adaptation before data recording.

Statistical Methods

Results were expressed as the mean±standard error of the mean (s.e.m.). Statistical comparisons were made using Student's t-test. A statistically significant difference was defined as *P<0.05.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating and/or ameliorating type 1 or type 2 diabetes in a mammalian subject having or suspected of having type 1 or type 2 diabetes, the method comprising:

administering to the mammalian subject an effective amount of glucose-responsive mammalian adipose derived β-like cells, which overexpress recombinant estrogen-related receptor gamma (ERRγ) and pancreatic and duodenal homeobox 1 (PDX1); and reducing or normalizing blood glucose levels in the subject following administration of the glucose-responsive mammalian adipose derived β-like cells, thereby treating and/or ameliorating type 1 or type 2 diabetes in the subject.

2. The method of claim 1, wherein the glucose-responsive mammalian adipose derived β-like cells have been differentiated from human adipose-derived progenitor cells.

3. The method of claim 2, wherein the human adipose-derived progenitor cells express Pax4 and/or PGC-1α.

4. The method of claim 1, wherein the cells comprise a viral vector that overexpresses ERRγ and PDX1 in the cells.

5. The method of claim 2, wherein the human adipose-derived progenitor cells are or are not derived from the subject.

6. The method of claim 1, wherein the mammalian subject is a human subject.

7. A method of reducing elevated blood glucose levels in a mammalian subject in need thereof, the method comprising:

administering to the mammalian subject an effective amount of glucose-responsive, mammalian adipose derived β-like cells, which overexpress recombinant ERRγ and pancreatic and duodenal homeobox 1 (PDX1); thereby reducing elevated blood glucose levels in the subject.

8. The method of claim 7, wherein the glucose-responsive mammalian adipose derived β-like cells have been differentiated from human adipose-derived progenitor cells.

9. The method of claim 8, wherein the human adipose-derived progenitor cells express Pax4 and/or PGC-1α.

10. The method of claim 7, wherein the cells comprise a viral vector that overexpresses ERRγ and PDX1 in the cells.

11. The method of claim 7, wherein the glucose-responsive mammalian adipose derived β-like cells are or are not derived from the mammalian subject.

12. The method of claim 7, wherein the mammalian subject is a human subject.

13. The method of claim 4, wherein the viral vector is an adeno-associated viral vector (AAV).

14. The method of claim 10, wherein the viral vector is an adeno-associated viral vector (AAV).

15. A method of treating and/or ameliorating type 1 or type 2 diabetes in a mammalian subject having or suspected of having type 1 or type 2 diabetes; treating and/or ameliorating hyperglycemia in a mammalian subject having or suspected of having hyperglycemia; and/or reducing elevated blood glucose levels in a mammalian subject in need thereof; the method comprising:

administering to the mammalian subject an effective amount of glucose-responsive human adipose derived β-cells that have been differentiated from human adipose-derived progenitor cells to glucose-responsive adipose-derived β-cells by overexpressing in the human adipose-derived progenitor cells recombinant estrogen-related receptor γ (ERRγ) and pancreatic and duodenal homeobox 1 (PDX1); wherein the overexpression of ERRγ and PDX1 differentiates the adipose-derived progenitor cells into glucose-responsive β-cells which are capable of glucose-stimulated insulin secretion; and treating and/or ameliorating type 1 or type 2 diabetes in the mammalian subject; treating or ameliorating hyperglycemia in the mammalian subject; and/or reducing elevated blood glucose levels in the mammalian subject following administration of the glucose-responsive human adipose derived B-cells.

16. The method of claim 15, wherein the human adipose-derived progenitor cells express Pax4 and/or PGC-1α.

17. The method of claim 15, wherein the cells comprise a viral vector that overexpresses ERRγ and PDX1 in the cells.

18. The method of claim 17, wherein the viral vector is an adeno-associated viral vector (AAV).

19. The method of claim 15, wherein the glucose-responsive mammalian adipose derived β-like cells are or are not derived from the mammalian subject.

20. The method of claim 19, wherein the mammalian subject is a human subject.

* * * * *